US010765936B2

(12) United States Patent
Berme et al.

(10) Patent No.: US 10,765,936 B2
(45) Date of Patent: Sep. 8, 2020

(54) FORCE MEASUREMENT SYSTEM

(71) Applicant: Bertec Limited, Edinburgh (GB)

(72) Inventors: Necip Berme, Worthington, OH (US); Sasan Ghassab, Columbus, OH (US); Mohan Chandra Baro, Columbus, OH (US)

(73) Assignee: Bertec Limited, Edinburgh (GB)

( * ) Notice: Subject to any disclaimer, the term of this patent is extended or adjusted under 35 U.S.C. 154(b) by 0 days.

(21) Appl. No.: 16/735,411

(22) Filed: Jan. 6, 2020

(65) Prior Publication Data
US 2020/0139229 A1 May 7, 2020

Related U.S. Application Data

(63) Continuation-in-part of application No. 16/186,512, filed on Nov. 10, 2018, now Pat. No. 10,527,508, (Continued)

(51) Int. Cl.
G01L 1/00 (2006.01)
A63F 13/218 (2014.01)
(Continued)

(52) U.S. Cl.
CPC .......... A63F 13/218 (2014.09); A61B 5/1117 (2013.01); A61B 5/1128 (2013.01); (Continued)

(58) Field of Classification Search
CPC .... A63F 13/218; A63F 13/211; A63F 13/213; A63F 13/23; A63F 13/80; (Continued)

(56) References Cited

U.S. PATENT DOCUMENTS 3,693,425 A 9/1972 Starita et al.
3,927,560 A 12/1975 Farr
(Continued)

FOREIGN PATENT DOCUMENTS

CN 201302482 Y 9/2009
CN 201935729 U 8/2011
(Continued)

OTHER PUBLICATIONS

First office action on the merits (Non-Final Rejection) in U.S. Appl. No. 14/158,809, dated Jul. 18, 2014.
(Continued)

Primary Examiner — Max H Noori
(74) Attorney, Agent, or Firm — The Law Office of Patrick F. O'Reilly III, LLC

(57) ABSTRACT

A force measurement system is disclosed herein. In one embodiment, the system includes a force measurement assembly configured to receive a subject; a data processing device operatively coupled to the force measurement assembly, the data processing device configured to determine a center of pressure for the subject using output forces and/or moments from the force measurement assembly; and a mobile device configured to determine one or more parameters indicative of the body sway for the subject. In this embodiment, a fall risk of the subject is assessed based upon a combination of the center of pressure and the one or more parameters indicative of the body sway determined for the subject.

18 Claims, 78 Drawing Sheets

Related U.S. Application Data which is a continuation-in-part of application No. 15/721,951, filed on Oct. 1, 2017, now Pat. No. 10,126,186, which is a continuation-in-part of application No. 15/224,419, filed on Jul. 29, 2016, now Pat. No. 9,778,119, which is a continuation-in-part of application No. 14/714,797, filed on May 18, 2015, now Pat. No. 9,404,823, which is a continuation-in-part of application No. 14/158,809, filed on Jan. 18, 2014, now Pat. No. 9,032,817.

(60) Provisional application No. 62/957,178, filed on Jan. 4, 2020, provisional application No. 61/887,357, filed on Oct. 5, 2013.

(51) Int. Cl.

| | | |
|---|---|---|
| G01P 15/02 | (2013.01) | |
| G01L 1/22 | (2006.01) | |
| A63F 13/211 | (2014.01) | |
| A63F 13/213 | (2014.01) | |
| A63F 13/23 | (2014.01) | |
| A63F 13/80 | (2014.01) | |
| A61B 5/11 | (2006.01) | |
| A61B 5/00 | (2006.01) | |
| G01C 19/00 | (2013.01) | |

(52) U.S. Cl.
CPC .......... *A61B 5/7264* (2013.01); *A63F 13/211* (2014.09); *A63F 13/213* (2014.09); *A63F 13/23* (2014.09); *A63F 13/80* (2014.09); *G01C 19/00* (2013.01); *G01L 1/2206* (2013.01); *G01L 1/2268* (2013.01); *G01P 15/02* (2013.01); *A61B 2562/0219* (2013.01); *A61B 2562/0247* (2013.01); *A63F 2300/105* (2013.01); *A63F 2300/1025* (2013.01); *A63F 2300/1062* (2013.01); *A63F 2300/1068* (2013.01); *A63F 2300/1087* (2013.01)

(58) Field of Classification Search
CPC ........ A63F 2300/1025; A63F 2300/105; A63F 2300/1062; A63F 2300/1068; A63F 2300/1087; A61B 5/1117; A61B 5/1128; A61B 5/7264; A61B 2562/0219; A61B 2562/0247; G01C 19/00; G01L 1/2206; G01L 1/2268; G01P 15/02
USPC .......................................................... 73/760
See application file for complete search history.

(56) References Cited

U.S. PATENT DOCUMENTS

| | | | |
|---|---|---|---|
| 3,939,704 A | 2/1976 | Zipin | |
| 4,448,083 A | 5/1984 | Hayashi | |
| 4,573,362 A | 3/1986 | Amlani | |
| 4,674,339 A | 6/1987 | Hatamura et al. | |
| 4,686,440 A | 8/1987 | Hatamura et al. | |
| 4,924,708 A | 5/1990 | Solomon et al. | |
| 4,964,211 A | 10/1990 | Arao et al. | |
| 4,993,506 A | 2/1991 | Angel | |
| 5,083,466 A | 1/1992 | Holm-Kennedy et al. | |
| 5,166,571 A | 11/1992 | Konno et al. | |
| 5,166,892 A | 11/1992 | Inoue et al. | |
| 5,400,661 A | 3/1995 | Cook et al. | |
| 5,510,581 A | 4/1996 | Angel | |
| 5,512,713 A | 4/1996 | Naito et al. | |
| 5,814,740 A | 9/1998 | Cook et al. | |
| 5,889,208 A | 3/1999 | Nose | |
| 5,889,214 A | 3/1999 | Kang et al. | |
| 5,929,391 A | 7/1999 | Petrucelli et al. | |
| 6,038,488 A | 3/2000 | Barnes et al. | |
| 6,038,933 A | 3/2000 | Meyer | |
| 6,113,237 A | 9/2000 | Ober et al. | |
| 6,152,564 A | 11/2000 | Ober et al. | |
| 6,295,878 B1 | 10/2001 | Berme | |
| 6,323,840 B1 | 11/2001 | Steinbrunner | |
| 6,324,919 B1 | 12/2001 | Larsen et al. | |
| 6,353,431 B1 | 3/2002 | Poole et al. | |
| 6,354,155 B1 | 3/2002 | Berme | |
| 6,389,883 B1 | 5/2002 | Berme et al. | |
| 6,497,430 B1 | 12/2002 | Odom et al. | |
| 6,609,054 B2 | 8/2003 | Wallace | |
| 6,871,552 B2 | 3/2005 | Liu et al. | |
| 6,936,016 B2 | 8/2005 | Berme et al. | |
| 7,204,010 B2 | 4/2007 | Germanton | |
| 7,743,672 B2 | 6/2010 | Kurtz et al. | |
| 8,181,541 B2 | 5/2012 | Berme | |
| 8,186,232 B2 | 5/2012 | McDearmon et al. | |
| 8,315,822 B2 | 11/2012 | Berme et al. | |
| 8,315,823 B2 | 11/2012 | Berme et al. | |
| D689,388 S | 9/2013 | Berme | |
| D689,389 S | 9/2013 | Berme | |
| 8,543,540 B1 | 9/2013 | Wilson et al. | |
| 8,544,347 B1 | 10/2013 | Berme | |
| 8,574,080 B2 * | 11/2013 | Yamazaki ............... A63F 13/06 463/39 |
| 8,643,669 B1 | 2/2014 | Wilson et al. | |
| 8,700,569 B1 | 4/2014 | Wilson et al. | |
| 8,704,855 B1 | 4/2014 | Berme et al. | |
| 8,746,085 B2 | 6/2014 | Singh et al. | |
| 8,749,501 B2 | 6/2014 | Oda et al. | |
| 8,764,532 B1 | 7/2014 | Berme | |
| 8,844,377 B2 | 9/2014 | Yap | |
| 8,847,989 B1 | 9/2014 | Berme et al. | |
| D715,669 S | 10/2014 | Berme | |
| 8,902,249 B1 | 12/2014 | Wilson et al. | |
| 8,915,149 B1 | 12/2014 | Berme | |
| 8,943,902 B2 | 2/2015 | Bosscher et al. | |
| 9,032,817 B2 | 5/2015 | Berme et al. | |
| 9,404,823 B1 | 8/2016 | Berme et al. | |
| 9,778,119 B2 | 10/2017 | Berme et al. | |
| 10,126,186 B2 | 11/2018 | Berme et al. | |
| 10,216,262 B1 | 2/2019 | Berme et al. | |
| 10,231,662 B1 | 3/2019 | Berme et al. | |
| 10,331,324 B1 | 6/2019 | Wilson et al. | |
| 10,342,473 B1 | 7/2019 | Berme et al. | |
| 10,390,736 B1 | 8/2019 | Berme et al. | |
| 10,413,230 B1 | 9/2019 | Berme et al. | |
| 10,527,508 B2 | 1/2020 | Berme et al. | |
| 2003/0216656 A1 | 11/2003 | Berme et al. | |
| 2006/0038516 A1 | 2/2006 | Burse | |
| 2007/0064066 A1 | 3/2007 | Piatt et al. | |
| 2007/0136017 A1 | 6/2007 | Wang et al. | |
| 2008/0228110 A1 | 9/2008 | Berme | |
| 2009/0120208 A1 | 5/2009 | Meyer | |
| 2010/0031746 A1 | 2/2010 | Paros et al. | |
| 2010/0170349 A1 | 7/2010 | Hatanaka et al. | |
| 2011/0107850 A1 | 5/2011 | Kim et al. | |
| 2011/0259111 A1 | 10/2011 | Ohsato | |
| 2011/0277562 A1 | 11/2011 | Berme | |
| 2012/0234104 A1 | 9/2012 | Seibold | |
| 2012/0266648 A1 | 10/2012 | Berme et al. | |
| 2012/0271565 A1 | 10/2012 | Berme et al. | |
| 2013/0291653 A1 | 11/2013 | Kempainen et al. | |
| 2015/0096387 A1 | 4/2015 | Berme et al. | |
| 2015/0135856 A1 | 5/2015 | Kim et al. | |
| 2016/0245711 A1 | 8/2016 | Berme et al. | |
| 2016/0334288 A1 | 11/2016 | Berme et al. | |
| 2017/0055851 A1 * | 3/2017 | Al-Ali ................. A61B 5/0004 |
| 2017/0363464 A1 | 12/2017 | Shafer et al. | |
| 2018/0008168 A1 * | 1/2018 | Pearlman ............... A61B 5/002 |
| 2018/0024015 A1 | 1/2018 | Berme et al. | |
| 2019/0078951 A1 | 3/2019 | Berme et al. | |

FOREIGN PATENT DOCUMENTS

| | | |
|---|---|---|
| EP | 1707934 A1 | 10/2006 |
| GB | 2538631 B | 2/2018 |
| JP | 59094016 A | 5/1984 |

(56) References Cited

FOREIGN PATENT DOCUMENTS

OTHER PUBLICATIONS

Notice of Allowance in U.S. Appl. No. 14/158,809, dated Jan. 21, 2015.
First office action on the merits (Non-Final Rejection) in U.S. Appl. No. 14/714,797, dated Feb. 3, 2016.
Notice of Allowance in U.S. Appl. No. 14/714,797, dated Mar. 28, 2016.
Search Report from the UK Intellectual Property Office for UK Patent Appl. No. GB1608606.8, dated Jun. 8, 2016.
Examination Report from the UK Intellectual Property Office for UK Patent Appl. No. GB1608606.8, dated May 22, 2017.
First office action on the merits (Non-Final Rejection) in U.S. Appl. No. 15/224,419, dated Mar. 29, 2017.
Notice of Allowance in U.S. Appl. No. 15/224,419, dated May 19, 2017.
P. Holmberg and A. Nilsson, "The use of an adaptively temperature compensated a.c. bridge circuit for torque measurements—a robotics application", Measurement, vol. 11, issue 1, Mar. 1993, pp. 65-77.
First office action on the merits (Non-Final Rejection) in U.S. Appl. No. 15/721,951, dated Apr. 5, 2018.
Notice of Allowance in U.S. Appl. No. 15/721,951, dated Jul. 12, 2018.
First office action on the merits (Non-Final Rejection) in U.S. Appl. No. 16/186,512, dated Jul. 31, 2019.
Notice of Allowance in U.S. Appl. No. 16/186,512, dated Aug. 22, 2019.

\* cited by examiner

SECTION B-B

FORCE MEASUREMENT SYSTEM

CROSS-REFERENCE TO RELATED APPLICATIONS

This patent application claims priority to U.S. Provisional Patent Application No. 62/957,178, entitled "Body Sway Measurement System", filed on Jan. 4, 2020, and is a continuation-in-part of U.S. Nonprovisional patent application Ser. No. 16/186,512, entitled "Force Measurement System and a Method of Calibrating the Same", filed on Nov. 10, 2018; which is a continuation-in-part of U.S. Nonprovisional patent application Ser. No. 15/721,951, entitled "Load Transducer System", filed on Oct. 1, 2017, now U.S. Pat. No. 10,126,186; which is a continuation-in-part of U.S. Nonprovisional patent application Ser. No. 15/224,419, entitled "Load Transducer and Force Measurement Assembly Using the Same", filed on Jul. 29, 2016, now U.S. Pat. No. 9,778,119; which is a continuation-in-part of U.S. Nonprovisional patent application Ser. No. 14/714,797, entitled "Load Transducer and Force Measurement Assembly Using the Same", filed on May 18, 2015, now U.S. Pat. No. 9,404,823; which is a continuation-in-part of U.S. Nonprovisional patent application Ser. No. 14/158,809, entitled "Low Profile Load Transducer", filed on Jan. 18, 2014, now U.S. Pat. No. 9,032,817; and further claims the benefit of U.S. Provisional Patent Application No. 61/887,357, entitled "Low Profile Load Transducer", filed on Oct. 5, 2013, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a force measurement system and a method of calibrating the same. More particularly, the invention relates to a force measurement system and a method of calibrating the same that is capable of more accurately determining an applied load.

2. Background and Related Art

The use of strain gages in load transducers to measure forces and moments is a known art. A transducer can incorporate one or more load channels. Each load channel measures one of the load components, and is comprised of one or more strain gages mounted to one or more elastic elements that deform under the applied load. An appropriate circuitry relates the resistance change in each set of gages to the applied force or moment. Strain gages have many industrial, medical, and electrical applications due to their small size, low production cost, flexibility in installation and use, and high precision.

A typical low profile, small, multi-component load transducer only functions correctly when the axial (i.e. vertical) force acts relatively central to the transducer. Specifications of such transducers indicate a maximum allowable offset for the force being approximately half the diameter of the transducer. Technical specifications of transducers are given as the allowable force and moment ratings, where the moment rating is obtained by multiplying the maximum allowable force with the maximum allowable offset of the force.

Transducers can be used to measure forces and moments in linkages such as those found in a robotic arm, where the links are connected by joints, and the magnitude and offset of the forces transmitted by these joints are used to control the linkage. In such applications, it is desirable to have a transducer which has significantly higher moment capacity than those available in the market. Accordingly, there is a need for an improved multi-component, low profile load transducer with high moment capacity.

When conventional load transducers are utilized in conjunction with force plates, unique load transducers must be designed and fabricated for force plates having a particular footprint size. Consequently, in order to fit force plates with varying footprint sizes, many different custom load transducers are required. These custom load transducers significantly increase the material costs associated with the fabrication of a force plate. Also, conventional load transducers often span the full length or width of the force plate component to which they are mounted, thereby resulting in elongate load transducers that utilize an excessive amount of stock material.

Therefore, what is needed is a load transducer that is capable of being interchangeably used with a myriad of different force plate sizes so that load transducers that are specifically tailored for a particular force plate size are unnecessary. Moreover, there is a need for a universal load transducer that is compact and uses less stock material than conventional load transducers, thereby resulting in lower material costs. Furthermore, there is a need for a force measurement assembly that utilizes the compact and universal load transducer thereon so as to result in a more lightweight and portable force measurement assembly.

Also, certain strain gages or strain gage pairs of a typical multi-component load transducer are configured to be sensitive to a particular component of the applied load (i.e., to a particular one of the force or moment components being measured). However, because the body portion of a typical load transducer has unavoidable machining imperfections, and the strain gages are not perfectly positioned on the body of the load transducer, there is some crosstalk between the channels of the load transducer. For example, a channel that is intended to be sensitive only to the x-component of the force may also emit a non-zero output signal when only a vertical force is applied to the load transducer (i.e., when the z-component of the force is applied). Thus, in such a typical load transducer, there is undesirable crosstalk between the channels.

Moreover, the output of a typical multi-component load transducer is also undesirably affected by the ambient temperature of the environment in which the load transducer is disposed. For example, the accuracy of a load output signal of a load transducer that is disposed in a space having a high ambient temperature (e.g., a space with a temperature of 140 degrees or more) will be adversely affected by the high ambient temperature. That is, high ambient temperature will introduce inaccuracies in the load output signal.

Furthermore, the position of the applied load may also adversely affect the accuracy of the output signal of a typical multi-component load transducer. For example, when the load is applied at a location that is near the periphery of the measurement surface of the load measurement device in which the load transducer is installed, the load output of the load transducer is often less accurate than when the load is applied proximate to the center of the measurement surface of the load measurement device. As such, the measurement accuracy of a typical load measurement device undesirably varies depending upon the position of the load applied thereto.

Therefore, what is also needed is a load transducer system that is capable of correcting the output signal of a load transducer so as to reduce or eliminate the effects of cross-talk among the channels of the load transducer. In addition, there is a need for a load transducer system that is capable of correcting the output signal of a load transducer so as to reduce or eliminate the effects of changes in temperature on the output of the load transducer. Further, there is a need for a load transducer system that is capable of accurately determining the applied load regardless of the location of the applied load being measured by the load transducer.

Further, force plates historically have been calibrated by applying known loads at known locations and using the collected data to form a calibration matrix. This unique calibration matrix, stored on the force plate, converts the raw signal input into a calibrated force output. This methodology provides a global calibration for the force plate. However, the global calibration of the force plate can result in unacceptable errors for certain regions of the force plate (e.g., near the edges of the force plate), and can also result in unacceptable errors for force plates having non-standard shapes (e.g., force plates with top plate components having shapes other than a rectangular shape).

Therefore, what is additionally needed is a force measurement system that allows for more versatile transducer designs and minimizes measurement errors. Moreover, a force measurement system is needed that is capable of correcting for load measurement errors resulting from loads applied near the periphery of the force measurement assembly. Furthermore, a need exists for a load calibration process for a force measurement system that results in more accurate load measurements by correcting the computed load based upon the applied position of the load. In addition, a force measurement system is needed that is capable of assessing the fall risk of a subject based upon a combination of balance parameters.

BRIEF SUMMARY OF EMBODIMENTS OF THE INVENTION

Accordingly, the present invention is directed to a force measurement system that substantially obviates one or more problems resulting from the limitations and deficiencies of the related art.

In accordance with one or more embodiments of the present invention, there is provided a force measurement system that comprises a force measurement assembly configured to receive a subject, the force measurement assembly includes a top surface for receiving at least one portion of the body of the subject; and at least one force transducer, the at least one force transducer configured to sense one or more measured quantities and output one or more signals that are representative of forces and/or moments being applied to the top surface of the force measurement assembly by the subject; a data processing device operatively coupled to the force measurement assembly, the data processing device configured to receive the one or more signals that are representative of the forces and/or moments being applied to the top surface of the force measurement assembly by the subject, and to convert the one or more signals into output forces and/or moments, the data processing device further configured to determine a center of pressure for the subject using the output forces and/or moments from the force measurement assembly; and a mobile device configured to determine one or more parameters indicative of the body sway for the subject. In these one or more embodiments, a fall risk of the subject is assessed based upon a combination of the center of pressure and the one or more parameters indicative of the body sway determined for the subject.

In a further embodiment of the present invention, the mobile device is selected from the group consisting of: (i) a smartphone, (ii) a tablet computing device, (iii) a laptop computing device, and (iv) a smartwatch.

In yet a further embodiment, the data processing device and/or the mobile device is programmed to determine a mathematical relationship between the center of pressure and the one or more parameters indicative of the body sway for the subject over a predetermined time period, and the data processing device and/or the mobile device is further programmed to determine the fall risk of the subject based upon the mathematical relationship between the center of pressure and the one or more parameters indicative of the body sway over the predetermined time period.

In still a further embodiment, the output forces and/or moments determined by the data processing device from the force measurement assembly include a shear force in a fore/aft direction of the subject, and the data processing device and/or the mobile device is further programmed to determine the fall risk of the subject based upon a relationship between the one or more parameters indicative of the body sway for the subject and the shear force in the fore/aft direction of the subject.

In yet a further embodiment, the force measurement system further comprises a visual display device having an output screen, the visual display device operatively coupled to the data processing device and/or the mobile device. In this further embodiment, the data processing device and/or the mobile device is programmed to control the movement of at least one manipulatable element of an interactive game displayed on the visual display device by using the center of pressure and the one or more parameters indicative of the body sway for the subject, and the data processing device and/or the mobile device is further programmed to determine the fall risk of the subject based upon the performance of the subject while playing the interactive game.

In still a further embodiment, the center of pressure for the subject determined by the data processing device is independently computed from the one or more parameters indicative of the body sway for the subject determined by the mobile device.

In yet a further embodiment, the at least one force transducer of the force measurement assembly comprises a force transducer beam with at least one load cell and at least one foot member disposed near an end of the force transducer beam, the at least one load cell configured to measure at least one component of the forces and/or moments being applied to the top surface of the force measurement assembly by the subject, and the at least one load cell being located a predetermined distance from the at least one foot member so that the measurement is not affected by a stress concentration on the force transducer beam.

In still a further embodiment, the mobile device further comprises a camera, and the mobile device is configured to determine the one or more parameters indicative of the body sway for the subject based upon output data from the camera.

In yet a further embodiment, the data processor is configured to determine the one or more parameters indicative of the body sway of the subject by using a convolutional neural network (CNN) to process the output data from the camera of the mobile device.

In still a further embodiment, the mobile device further comprises an inertial measurement unit, and the mobile device is configured to determine the one or more parameters indicative of the body sway for the subject based upon output data from the inertial measurement unit.

In yet a further embodiment, the inertial measurement unit of the mobile device comprises at least one of an accelerometer configured to detect linear acceleration and a gyroscope configured to detect angular velocity.

In still a further embodiment, the one or more parameters indicative of the body sway of the subject determined by the mobile device are selected from the group consisting of: (i) a sway angle of the subject, (ii) sway coordinates of the subject, (iii) a sway envelope of the subject.

In accordance with one or more other embodiments of the present invention, there is provided a force measurement system that comprises a force measurement assembly configured to receive a subject, the force measurement assembly includes a top surface for receiving at least one portion of the body of the subject; and at least one force transducer, the at least one force transducer configured to sense one or more measured quantities and output one or more signals that are representative of forces and/or moments being applied to the top surface of the force measurement assembly by the subject; a data processing device operatively coupled to the force measurement assembly, the data processing device configured to receive the one or more signals that are representative of the forces and/or moments being applied to the top surface of the force measurement assembly by the subject, and to convert the one or more signals into output forces and/or moments, the data processing device further configured to determine a center of pressure for the subject using the output forces and/or moments from the force measurement assembly; an inertial measurement unit or camera configured to generate output data for determining one or more parameters indicative of the body sway of the subject; and a computing device having a data processor, the data processor including at least one hardware component, the data processor being operatively coupled to the inertial measurement unit or camera, the data processor configured to receive the output data from the inertial measurement unit or camera, and to determine the one or more parameters indicative of the body sway of the subject. In these one or more other embodiments, a fall risk of the subject is assessed based upon a combination of the center of pressure and the one or more parameters indicative of the body sway determined for the subject.

In a further embodiment of the present invention, the inertial measurement unit configured to generate the output data for determining the one or more parameters indicative of the body sway of the subject is located remotely from the computing device, and the data processor of the computing device is configured to determine the one or more parameters indicative of the body sway of the subject based upon the output data from the remotely located inertial measurement unit.

In yet a further embodiment, the data processor of the computing device is operatively coupled to the remotely located inertial measurement unit by a wireless connection.

In still a further embodiment, the camera configured to generate the output data for determining the one or more parameters indicative of the body sway of the subject is located remotely from the computing device; and the data processor of the computing device is configured to determine the one or more parameters indicative of the body sway of the subject based upon the output data from the remotely located camera.

In yet a further embodiment, the data processor of the computing device is operatively coupled to the remotely located camera by a wireless connection.

In accordance with one or more other embodiments of the present invention, there is provided a force measurement system that comprises a force measurement assembly configured to receive a subject, the force measurement assembly includes a top surface for receiving at least one portion of the body of the subject; and at least one force transducer, the at least one force transducer configured to sense one or more measured quantities and output one or more signals that are representative of forces and/or moments being applied to the top surface of the force measurement assembly by the subject; and a data processing device operatively coupled to the force measurement assembly, the data processing device configured to receive the one or more signals that are representative of the forces and/or moments being applied to the top surface of the force measurement assembly by the subject, and to convert the one or more signals into output forces and/or moments, the output forces and/or moments determined by the data processing device from the force measurement assembly including a shear force in a fore/aft direction of the subject, the data processing device further configured to determine a center of pressure for the subject using the output forces and/or moments from the force measurement assembly, and the data processing device additionally configured to determine the fall risk of the subject based upon a combination of the center of pressure and the shear force in the fore/aft direction of the subject.

It is to be understood that the foregoing summary and the following detailed description of the present invention are merely exemplary and explanatory in nature. As such, the foregoing summary and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Figure 1:
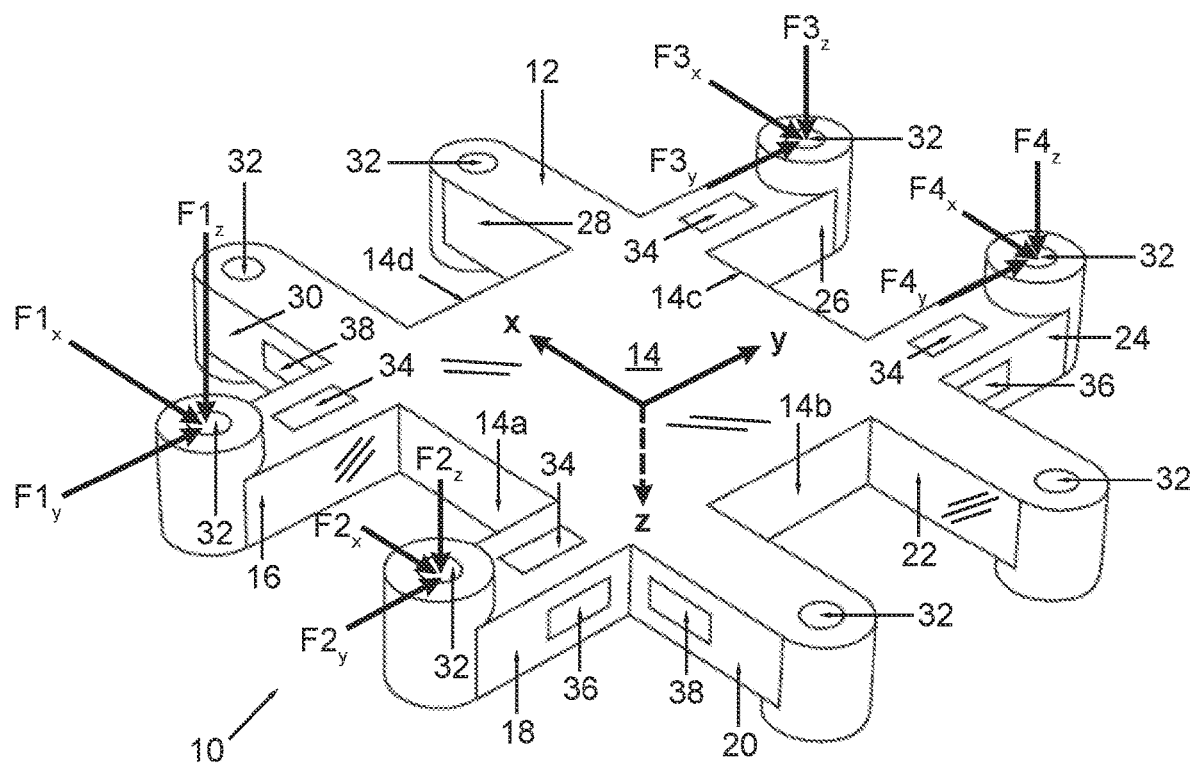
FIG. 1 is a perspective view of a low profile load transducer, according to a first embodiment of the invention.
Figure 2:
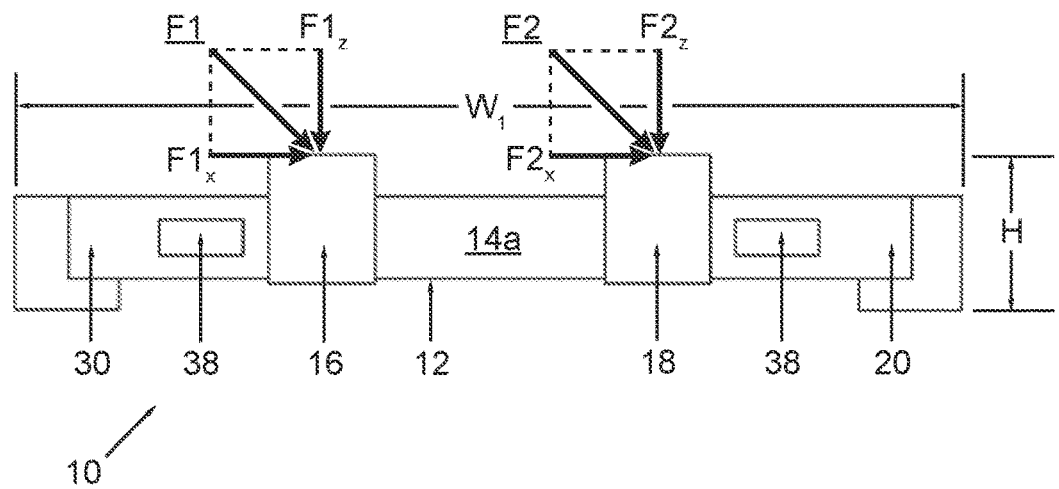
FIG. 2 is a first side view of the low profile load transducer of FIG. 1, according to the first embodiment of the invention.
Figure 3:
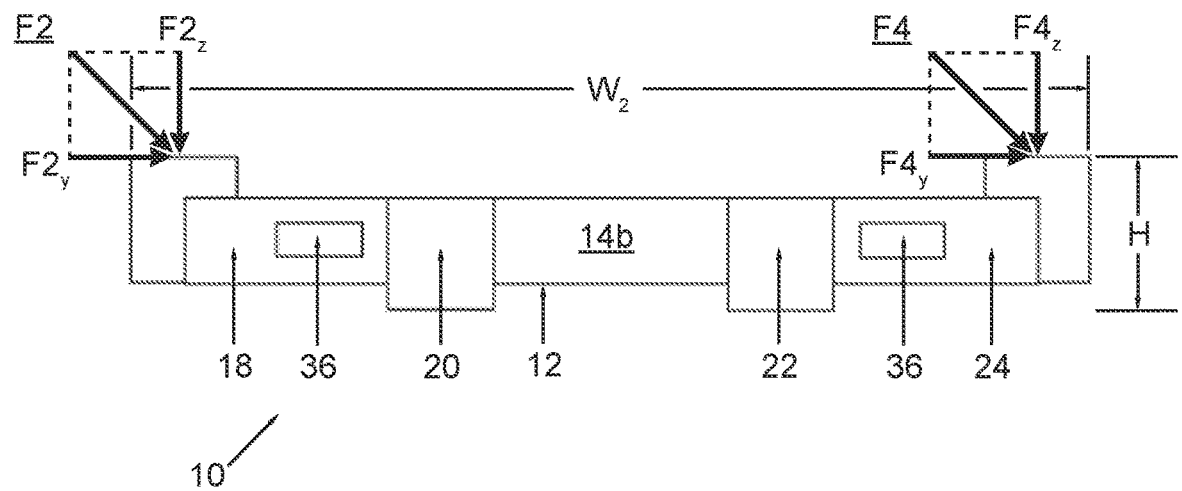
FIG. 3 is a second side view of the low profile load transducer of FIG. 1, according to the first embodiment of the invention.

It should be understood that the appended drawings are not necessarily to scale, presenting a somewhat simplified representation of various preferred features illustrative of the basic principles of the invention. The specific design features of the load transducers and the force measurement systems as disclosed herein, including, for example, specific dimensions, orientations, locations, and shapes of the various components, will be determined in part by the particular intended application and use environment. Certain features of the illustrated embodiments have been enlarged or distorted relative to others to facilitate visualization and clear understanding. In particular, thin features may be thickened, for example, for clarity or illustration. All references to direction and position, unless otherwise indicated, refer to the orientation of the load transducers illustrated in the drawings. In general, up or upward generally refers to an upward direction within the plane of the paper in FIG. 1 and down or downward generally refers to a downward direction within the plane of the paper in FIG. 1.

DETAILED DESCRIPTION OF EMBODIMENTS OF THE INVENTION

It will be apparent to those skilled in the art, that is, to those who have knowledge or experience in this area of technology, that many uses and design variations are possible for the improved load transducers and force measurement systems disclosed herein. The following detailed discussion of various alternative and preferred embodiments will illustrate the general principles of the invention. Other embodiments suitable for other applications will be apparent to those skilled in the art given the benefit of this disclosure.

Referring now to the drawings, FIGS. 1-4 illustrate a load transducer 10 according to a first exemplary embodiment of the present invention. This load transducer 10 is designed to have a low profile, small size, trivial weight, high sensitivity, and easy manufacturability. The load transducer 10 generally includes a one-piece compact transducer frame 12 having a central body portion 14 and a plurality of beams 16, 18, 20, 22, 24, 26, 28, 30 extending outwardly from the central body portion 14. As best illustrated in the perspective view of FIG. 1, each of the beams 16, 18, 20, 22, 24, 26, 28, 30 comprises a respective load cell or transducer element for measuring forces and/or moments. For example, the load cells of beams 16, 18, 24, 26 are configured to respectively measure the forces F1, F2, F3, F4 with force vector components $F1_x$, $F1_y$, $F1_z$, $F2_x$, $F2_y$, $F2_z$, $F3_x$, $F3_y$, $F3_z$, $F4_x$, $F4_y$, $F4_z$. In addition to forces, the output of the load cells can also be used to determine moments and the point of application of a force (i.e., its center of pressure). Referring again to FIG. 1, it can be seen that the illustrated load transducer 10 comprises eight single or multi-axis load cells that are mounted to a common structure or body portion 14.

The illustrated transducer frame 12 is shown in FIGS. 1-4. The illustrated transducer frame 12 includes the central body portion 14 and a plurality of beams 16, 18, 20, 22, 24, 26, 28, 30 extending outwardly therefrom. In the illustrated embodiment, the transducer frame 12 is milled as one solid and continuous piece of a single material. That is, the transducer frame 12 is of unitary or one-piece construction with the body portion 14 and the beams 16, 18, 20, 22, 24, 26, 28, 30 integrally formed together. The transducer frame 12 is preferably machined in one piece from aluminum, titanium, steel, or any other suitable material that meets strength and weight requirements. Alternatively, the beams 16, 18, 20, 22, 24, 26, 28, 30 can be formed separately and attached to the body portion 14 in any suitable manner.

With reference to FIG. 1, it can be seen that the illustrated central body portion 14 is generally in the form of rectangular prism (i.e., a square prism) with substantially planar top, bottom, and side surfaces. In FIG. 1, it can be seen that the body portion 14 comprises a first pair of opposed sides 14a, 14c and a second pair of opposed sides 14b, 14d. The side 14a is disposed generally parallel to the side 14c, while the side 14b is disposed generally parallel to the side 14d. Each of the sides 14a, 14b, 14c, 14d is disposed generally perpendicular to the planar top and bottom surfaces. Also, each of the first pair of opposed sides 14a, 14c is disposed generally perpendicular to each of the second pair of opposed sides 14b, 14d. While not explicitly shown in FIGS. 1-4, the central body portion 14 may comprise one or more apertures disposed therethrough for accommodating fasteners (e.g., screws) that attach electronics or circuitry to the body portion 14. In addition to fasteners, it is noted that any other suitable means for attachment of the electronics or circuitry can alternatively be utilized (e.g., suitable adhesives, etc.). While the illustrated body portion 14 is generally in the form of a square prism, it is to be understood that the body portion 14 can alternatively have other suitable shapes.

As shown in FIGS. 1-4, the illustrated beams 16, 18, 20, 22, 24, 26, 28, 30 are each attached to one of the sides 14a, 14b, 14c, 14d of the body portion 14, and extend generally horizontally outward therefrom. In particular, beams 16, 18 extend generally horizontally outward from side 14a of the body portion 14, beams 20, 22 extend generally horizontally outward from side 14b of the body portion 14, beams 24, 26 extend generally horizontally outward from side 14c of the body portion 14, and beams 28, 30 extend generally horizontally outward from side 14d of the body portion 14. In addition, each of the illustrated beams 16, 18, 20, 22, 24, 26, 28, 30 extend substantially parallel to the top and bottom surfaces of the body portion 14. Each of the illustrated beams 16, 18, 20, 22, 24, 26, 28, 30 has a cantilevered end relative to the body portion 14 that allows for deflection of the ends of the beams 16, 18, 20, 22, 24, 26, 28, 30 in the vertical direction.

Figure 4:
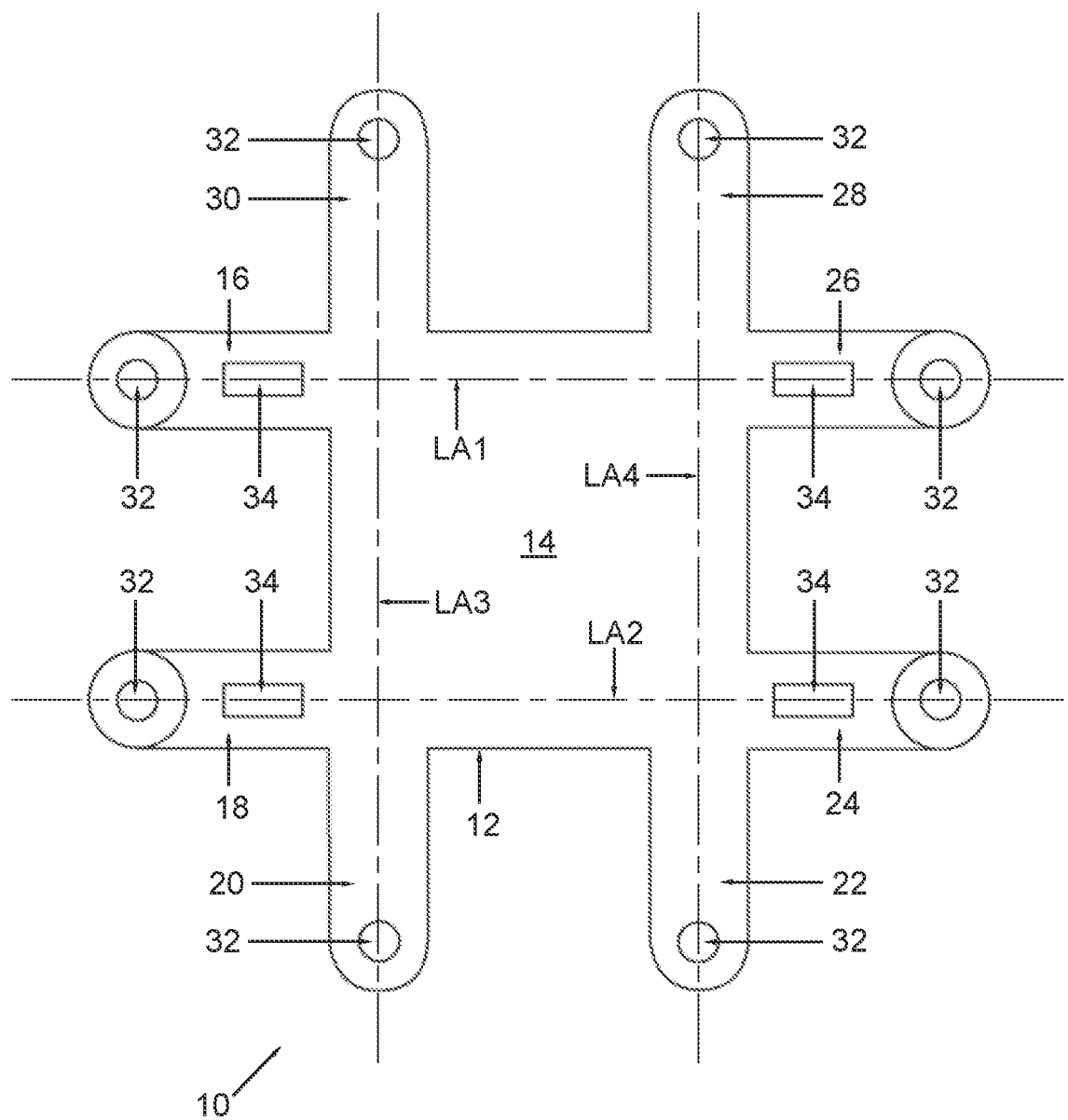
FIG. 4 is a top view of the low profile load transducer of FIG. 1, according to the first embodiment of the invention.

With particular reference to FIGS. 1 and 4, it can be seen that the beams 16, 18 extending from side 14a are substantially parallel to one another, and laterally spaced apart from one another by a gap. Opposed beams 24, 26, which extend from side 14c, also are substantially parallel to one another, and laterally spaced apart from one another by a gap. Beam 16 extends in a longitudinal direction that is generally co-linear with, but opposite to the extending direction of beam 26 (i.e., both beams 16 and 26 are aligned along central longitudinal axis LA1). Similarly, beam 18 extends in a longitudinal direction that is generally co-linear with, but opposite to the extending direction of beam 24 (i.e., both beams 18 and 24 are aligned along central longitudinal axis LA2). The beams 20, 22 extending from side 14b are substantially parallel to one another, and laterally spaced apart from one another by a gap. Opposed beams 28, 30, which extend from side 14d, also are substantially parallel to one another, and laterally spaced apart from one another by a gap. Beam 20 extends in a longitudinal direction that is generally co-linear with, but opposite to the extending direction of beam 30 (i.e., both beams 20 and 30 are aligned along central longitudinal axis LA3). Similarly, beam 22 extends in a longitudinal direction that is generally co-linear with, but opposite to the extending direction of beam 28 (i.e., both beams 22 and 28 are aligned along central longitudinal axis LA4). The illustrated beams 16, 18, 20, 22, 24, 26, 28, 30 are provided with generally vertically extending apertures 32 near their ends for accommodating fasteners that are used to secure the load transducer 10 to additional structures. Although, it is noted that any other suitable means for attachment of the load transducer 10 can alternatively be utilized (e.g., a suitable adhesive for attaching metallic components to one another).

The main body portions of illustrated beams 16, 18, 20, 22, 24, 26, 28, 30 have a rectangular-shaped cross section to form generally planar, opposed top and bottom surfaces, and generally planar, opposed side surfaces for attachment of load cell components as described hereinafter. The illustrated beams 16, 18, 20, 22, 24, 26, 28, 30 have generally cylindrical end portions, which include the fastener apertures 32. As best shown in FIG. 1, the illustrated top planar surfaces of the beam main body portions of beams 16, 18, 24, 26 are recessed below the top surfaces of the beam cylindrical end portions to protect the load cell components from engagement with the structure to which the load transducer 10 is attached, while the illustrated bottom planar surfaces of the beam main body portions of beams 20, 22, 28, 30 are recessed above the bottom surfaces of the beam cylindrical end portions to protect the load cell components from engagement with the structure to which the load transducer 10 is attached. In other words, as shown in FIG. 1, the cylindrical end portions of beams 16, 18, 24, 26 are provided with a top standoff portion (i.e., a cylindrical portion protruding from the top of each beam having the aperture 32), while the cylindrical end portions of beams 20, 22, 28, 30 are provided with a bottom standoff portion (i.e., a cylindrical portion protruding from the bottom of each beam having the aperture 32). While not explicitly shown in the figures, beams 16, 18, 20, 22, 24, 26, 28, 30 may also include apertures disposed therethrough for increasing the deflectability of the beams 16, 18, 20, 22, 24, 26, 28, 30 as desired (e.g., the apertures could be disposed below, or adjacent to each of the strain gages 34, 36, 38). In order to accommodate these apertures, the length of each beam 16, 18, 20, 22, 24, 26, 28, 30 could be extended so that multiple strain gages 34, 36 on a common beam could be spaced apart from one another along a length of the beam (i.e., each strain gage 34, 36 would occupy a dedicated, respective segment of the beam). It is noted that these apertures can be of any suitable size and shape as needed and also can be eliminated if desired. It is further noted that the beams 16, 18, 20, 22, 24, 26, 28, 30 can alternatively have other cross-sectional shapes depending on whether it is desired to have planar surfaces at the top and/or bottom or left and/or right sides for the load cell components but the illustrated rectangular shape is particularly desirable because the same frame can be used for multiple configurations of the transducer load cells.

The illustrated one-piece frame 12 has a low profile or is compact. The terms "low profile" and "compact" are used in this specification and the claims to mean that the height is substantially smaller than the footprint dimensions so that the load transducer 10 can be utilized in a mechanical joint without significant changes to the mechanical joint. The illustrated one piece frame 12 has a height H that is about 20% its footprint width $W_1$ or $W_2$ (see FIGS. 2, 3, 7, and 8). As a result, the load transducer 10 has a low profile or is compact and has a height H that is about 20% its footprint width $W_1$ or $W_2$. The term "load cell" is used in the specification and claims to mean a load sensing element of the load transducer that is capable of sensing one or more load components of the applied load.

As best shown in FIG. 1, the illustrated load cells are located on beams 16, 18, 20, 24, 26, and 30. In the illustrated embodiment, beams 22, 28 do not contain any load cells, but, in other embodiments, may contain load cells with strain gages 38 similar to beams 20, 30. Beams 16, 26 also may contain strain gages 36, similar to beams 18, 24, in other embodiments. In a preferred embodiment, each load cell comprises one or more strain gages 34, 36, 38. Specifically, in the illustrated embodiment, beams 16, 18, 24, 26 each comprise a strain gage 34 disposed on the top surface thereof that is sensitive to the vertical force component (i.e., a $F_Z$ strain gage). Opposed beams 18, 24 also each comprise a strain gage 36 disposed on a side surface thereof that is sensitive to a first shear force component (i.e., a $F_X$ strain gage). Opposed beams 20, 30 each comprise a strain gage 38 disposed on a side surface thereof that is sensitive to a second shear force component (i.e., a $F_Y$ strain gage). All eight (8) of the strain gages 34, 36, 38 are measuring a difference in the bending moments in the beams. If the applied shears to each of the two parallel beams 18, 24 or 20, 30 are equal (which is most likely the case), this is an optimal number of strain gages for a six-component load transducer (i.e., for a load transducer that is capable of measuring the three (3) force components $F_X$, $F_Y$, $F_Z$ and the three (3) moment components $M_X$, $M_Y$, $M_Z$). Shear web gages can also be used in lieu of one or more of the illustrated strain gages 34, 36, 38. Also, in other preferred embodiments alternate load and/or moment sensors may be utilized as required or desired as long as they do not interfere with the advantages of the design as a whole. For example, piezoelectric gages or Hall-effect sensors are possible alternatives to the strain gages 34, 36, 38.

As best shown in FIG. 1, the illustrated load cells are configured as bending beam load cells. The illustrated strain gages 34, 36, 38 are mounted to either top or side surfaces of the beams 16, 18, 20, 24, 26, 30 between their attachment locations to the body portion 14 and the cylindrical end portions thereof. Alternatively, the strain gages 34 can be mounted to the bottom surfaces of the beams 16, 18, 24, 26 between their attachment locations to the body portion 14 and the cylindrical end portions thereof, while the strain gages 36, 38 can be mounted to the opposite side surfaces of the beams 18, 20, 24, 30 between their attachment locations to the body portion 14 and the cylindrical end portions thereof. That is, the strain gages 34, 36, 38 are mounted to surfaces generally normal to the direction of applied vertical and/or shear forces (i.e., $F_X$, $F_Y$, $F_Z$). It is also noted that alternatively, the strain gages 34 can be mounted at both the top surface and the bottom surface of the beams 16, 18, 24, 26, and/or the strain gages 36, 38 can be mounted at both opposed side surfaces of the beams 18, 20, 24, 30. These strain gages 34, 36, 38 measure force either by bending moment or difference of bending moments at two cross sections. As force is applied to the ends of the beams (e.g., forces F1, F2, F3, F4 with force vector components $F1_x$, $F1_y$, $F1_z$, $F2_x$, $F2_y$, $F2_z$, $F3_x$, $F3_y$, $F3_z$, $F4_x$, $F4_y$, $F4_z$ applied to the ends of respective beams 16, 18, 24, 26), the beams 16, 18, 20, 24, 26, 30 with strain gages attached thereto bend. This bending either stretches or compresses the strain gages 34, 36, 38, in turn changing the resistances of the electrical currents passing therethrough. The amount of change in the electrical voltage or current is proportional to the magnitude of the applied force (e.g., forces F1, F2, F3, F4 with force vector components $F1_x$, $F1_y$, $F1_z$, $F2_x$, $F2_y$, $F2_z$, $F3_x$, $F3_y$, $F3_z$, $F4_x$, $F4_y$, $F4_z$ applied to the ends of respective beams 16, 18, 24, 26.

Alternatively, the load cells can be configured as shear-web load cells. In this configuration, the strain gages are mounted to either one of the lateral side surfaces of the beams between their attachment locations to the body portion 14 and the cylindrical end portions thereof. It is noted that alternatively, the strain gages can be mounted at both of the lateral side surfaces of the beams. Mounted in these positions, the strain gages directly measure shear as force is applied to the end of the beam.

As best shown in FIG. 1, the load transducer 10 measures applied forces (e.g., forces F1, F2, F3, F4 with force vector components $F1_x$, $F1_y$, $F1_z$, $F2_x$, $F2_y$, $F2_z$, $F3_x$, $F3_y$, $F3_z$, $F4_x$, $F4_y$, $F4_z$ applied to the ends of respective beams 16, 18, 24, 26) at each of the load cells. The sum of the forces is the force being applied to any assembly attached to the top of the load transducer 10. The load cells of the beams 16, 26 measure the force being applied to one lateral side of the load transducer 10; whereas, load cells of the beams 18, 24 measure the force being applied to the other lateral side of the load transducer 10. The various moments are determined by subtracting the sum total of the forces acting on one pair of load cells from the sum total acting upon the opposite pair. For example, subtracting the sum total of the forces acting on load cell of beam 16 and load cell of beam 18 from the sum total of the forces acting on load cell of beam 24 and load cell of beam 26, subtracting the sum total of load cells of beams 18, 24 from the sum total of load cells of beams 16, 26.

Figure 5:
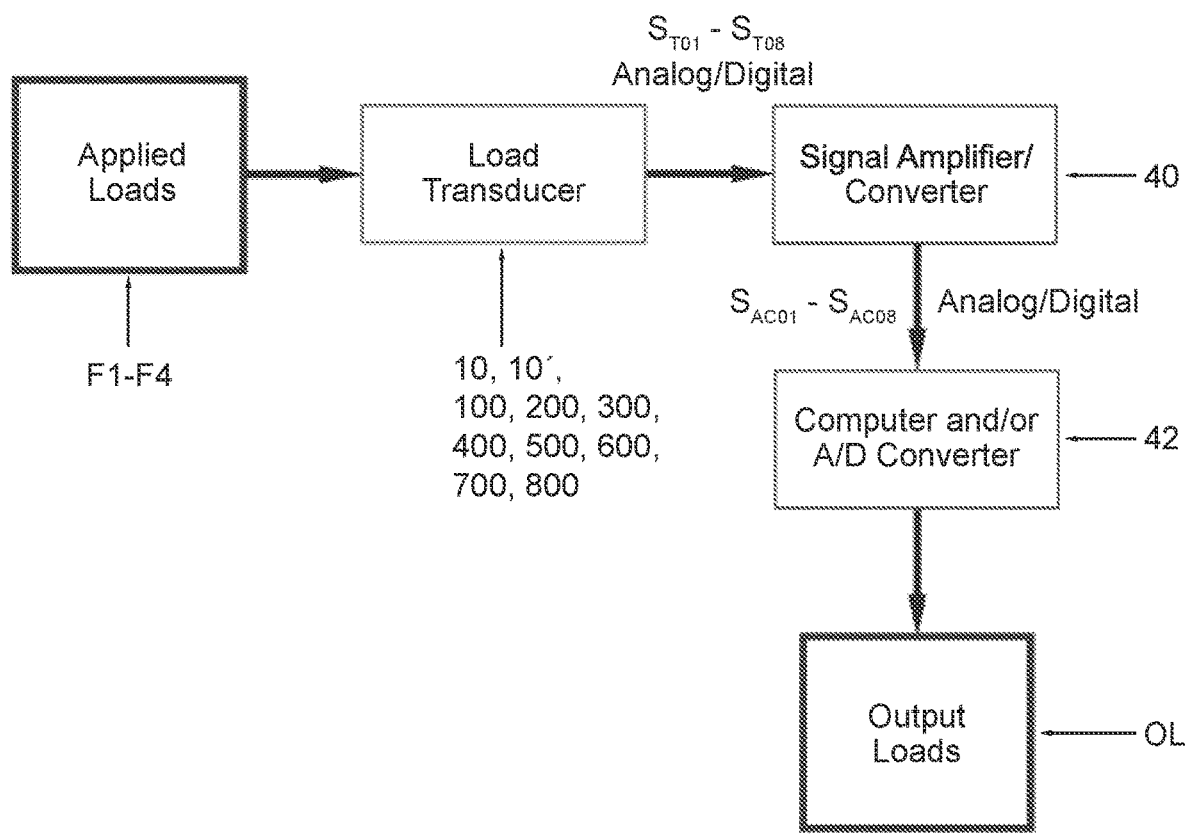
FIG. 5 is a block diagram illustrating data manipulation operations carried out by the load transducer data processing system, according to an embodiment of the invention.

The sensory information from the strain gages 34, 36, 38 is transmitted to a microprocessor which could then be used to control the assembly to which the load transducer is a part of such as a robotic assembly. As best shown in FIG. 1, the planar central body portion 14 of the transducer frame 12 provides an area where associated electronics and/or circuitry can be mounted. Alternatively, the electronics and/or circuitry can be mounted at any other suitable location. FIG. 5 schematically illustrates exemplary electronic components that can be included in the load transducer data processing system. The strain gages 34, 36, 38 of load transducer 10 may be electrically connected to a signal amplifier/converter 40, which in turn, is electrically connected to a computer 42 (i.e., a data acquisition and processing device or a data processing device with a microprocessor). The components 10, 40, 42 of the system may be connected either by wiring, or wirelessly to one another.

FIG. 5 graphically illustrates the acquisition and processing of the load data carried out by the exemplary load transducer data processing system. Initially, as shown in FIG. 5, external forces F1-F4 and/or moments are applied to the load transducer 10. When the electrical resistance of each strain gage 34, 36, 38 is altered by the application of the applied forces and/or moments, the change in the electrical resistance of the strain gages brings about a consequential change in the output voltage of the strain gage bridge circuit (e.g., a Wheatstone bridge circuit). Thus, in one embodiment, the eight (8) strain gages 34, 36, 38 output a total of eight (8) analog output voltages (signals). In some embodiments, the eight (8) analog output voltages from the eight (8) strain gages 34, 36, 38 are then transmitted to a preamplifier board (not shown) for preconditioning. The preamplifier board is used to increase the magnitudes of the analog voltage signals, and preferably, to convert the analog voltage signals into digital voltage signals as well. After which, the load transducer 10 transmits the output signals $S_{TO1}$-$S_{TO8}$ to a main signal amplifier/converter 40. Depending on whether the preamplifier board also includes an analog-to-digital (A/D) converter, the output signals $S_{TO1}$-$S_{TO8}$ could be either in the form of analog signals or digital signals. The main signal amplifier/converter 40 further magnifies the transducer output signals $S_{TO1}$-$S_{TO8}$, and if the signals $S_{TO1}$-$S_{TO8}$ are of the analog-type (for a case where the preamplifier board did not include an analog-to-digital (A/D) converter), it may also convert the analog signals to digital signals. Then, the signal amplifier/converter 40 transmits either the digital or analog signals $S_{ACO1}$-$S_{ACO8}$ to the data acquisition/data processing device 42 (computer 42) so that the forces and/or moments that are being applied to the load transducer 10 can be transformed into output load values OL. The computer or data acquisition/data processing device 42 may further comprise an analog-to-digital (A/D) converter if the signals $S_{ACO1}$-$S_{ACO8}$ are in the form of analog signals. In such a case, the analog-to-digital converter will convert the analog signals into digital signals for processing by the microprocessor of the computer 42.

When the computer or data acquisition/data processing device 42 receives the voltage signals $S_{ACO1}$-$S_{ACO8}$, it initially transforms the signals into output forces and/or moments by multiplying the voltage signals $S_{ACO1}$-$S_{ACO8}$ by a calibration matrix. After which, the force components $F_X$, $F_Y$, $F_Z$ and the moment components $M_X$, $M_Y$, $M_Z$ applied to the load transducer 10 are determined by the computer or data acquisition/data processing device 42. Also, the center of pressure (i.e., the x and y coordinates of the point of application of the force applied to the load transducer 10) can be determined by the computer or data acquisition/data processing device 42.

FIGS. 6-9 illustrate a load transducer 10' according to a second exemplary embodiment of the present invention. With reference to these figures, it can be seen that, in some respects, the second exemplary embodiment is similar to that of the first embodiment. Moreover, some parts are common to both such embodiments. For the sake of brevity, the parts that the second embodiment of the load transducer has in common with the first embodiment will only be briefly mentioned, if at all, because these components have already been explained in detail above. Furthermore, in the interest of clarity, these components will be denoted using the same reference characters that were used in the first embodiment.

Figure 6:
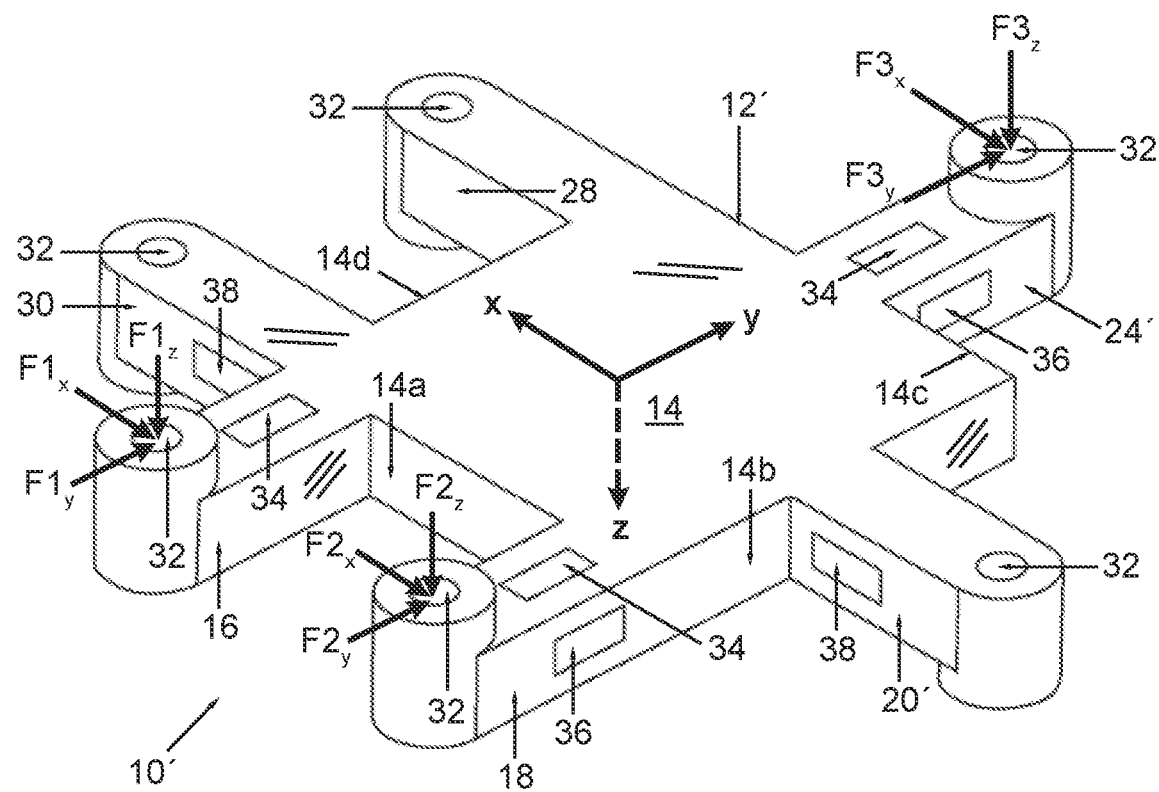
FIG. 6 is a perspective view of a low profile load transducer, according to a second embodiment of the invention.
Figure 7:
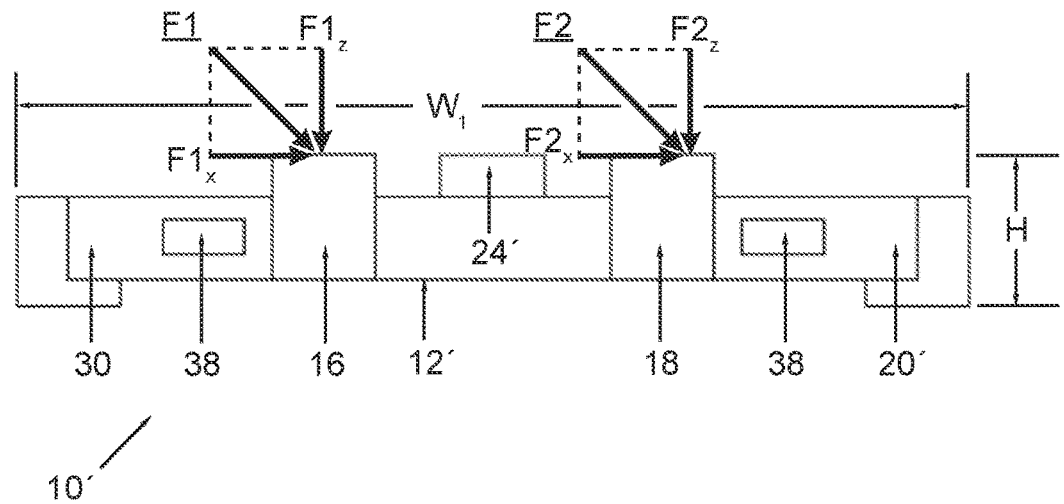
FIG. 7 is a first side view of the low profile load transducer of FIG. 6, according to the second embodiment of the invention.
Figure 8:
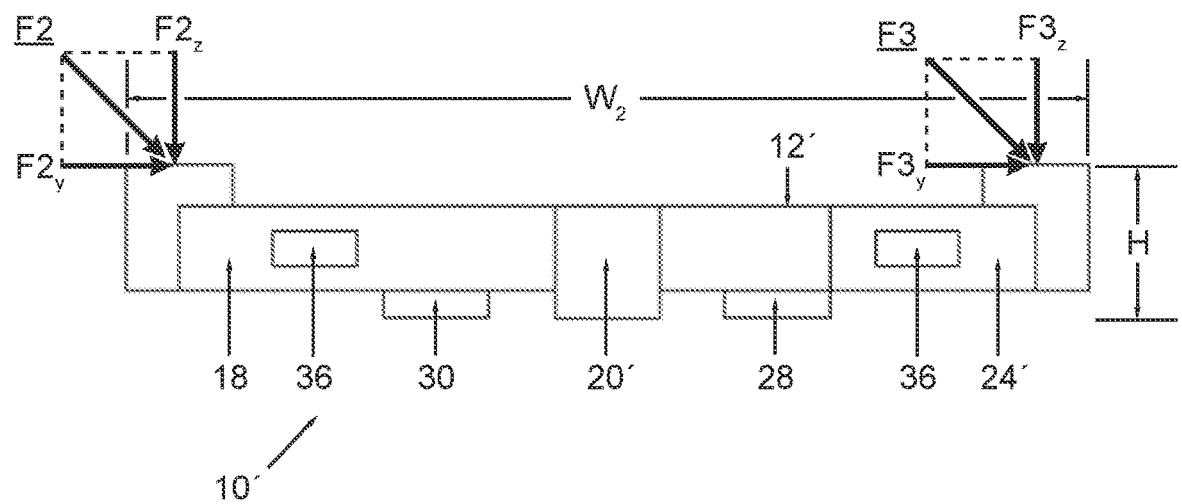
FIG. 8 is a second side view of the low profile load transducer of FIG. 6, according to the second embodiment of the invention.

Initially, referring to the perspective view of FIG. 6, it can be seen that, like the first exemplary embodiment, the transducer frame 12' of the second embodiment includes a central body portion 14 and a plurality of beams 16, 18, 20', 24', 28, 30 extending outwardly therefrom. Although, unlike the first exemplary embodiment of the load transducer, the side 14b of the body portion 14 of the load transducer 10' contains only a single beam 20' extending therefrom, rather two beams 20, 22 (see FIG. 1). Similarly, unlike the load transducer 10 of the first embodiment, the side 14c of the body portion 14 of the load transducer 10' contains only a single beam 24' extending therefrom, rather two beams 24, 26 (refer to FIG. 1). Also, unlike the load transducer 10 of the first embodiment, the load transducer 10' includes only three strain gages 34 that are sensitive to the vertical force component (i.e., three $F_Z$ strain gages), rather than four strain gages.

In particular, in the second embodiment, beams 16, 18, 24' each comprise a strain gage 34 disposed on the top surface thereof that is sensitive to the vertical force component (i.e., a $F_Z$ strain gage). Beams 18, 24' also each comprise a strain gage 36 disposed on a side surface thereof that is sensitive to a first shear force component (i.e., a $F_X$ strain gage), while beams 20', 30 each comprise a strain gage 38 disposed on a side surface thereof that is sensitive to a second shear force component (i.e., a $F_Y$ strain gage). The load transducer 10' of the second embodiment is capable of measuring the three force components ($F_X$, $F_Y$, $F_Z$) and the three moment components ($M_X$, $M_Y$, $M_Z$) with a minimum of six beams 16, 18, 20', 24', 28, 30 (i.e., three input beams and three output beams) and a minimum of seven strain gages 34, 36, 38.

Figure 9:
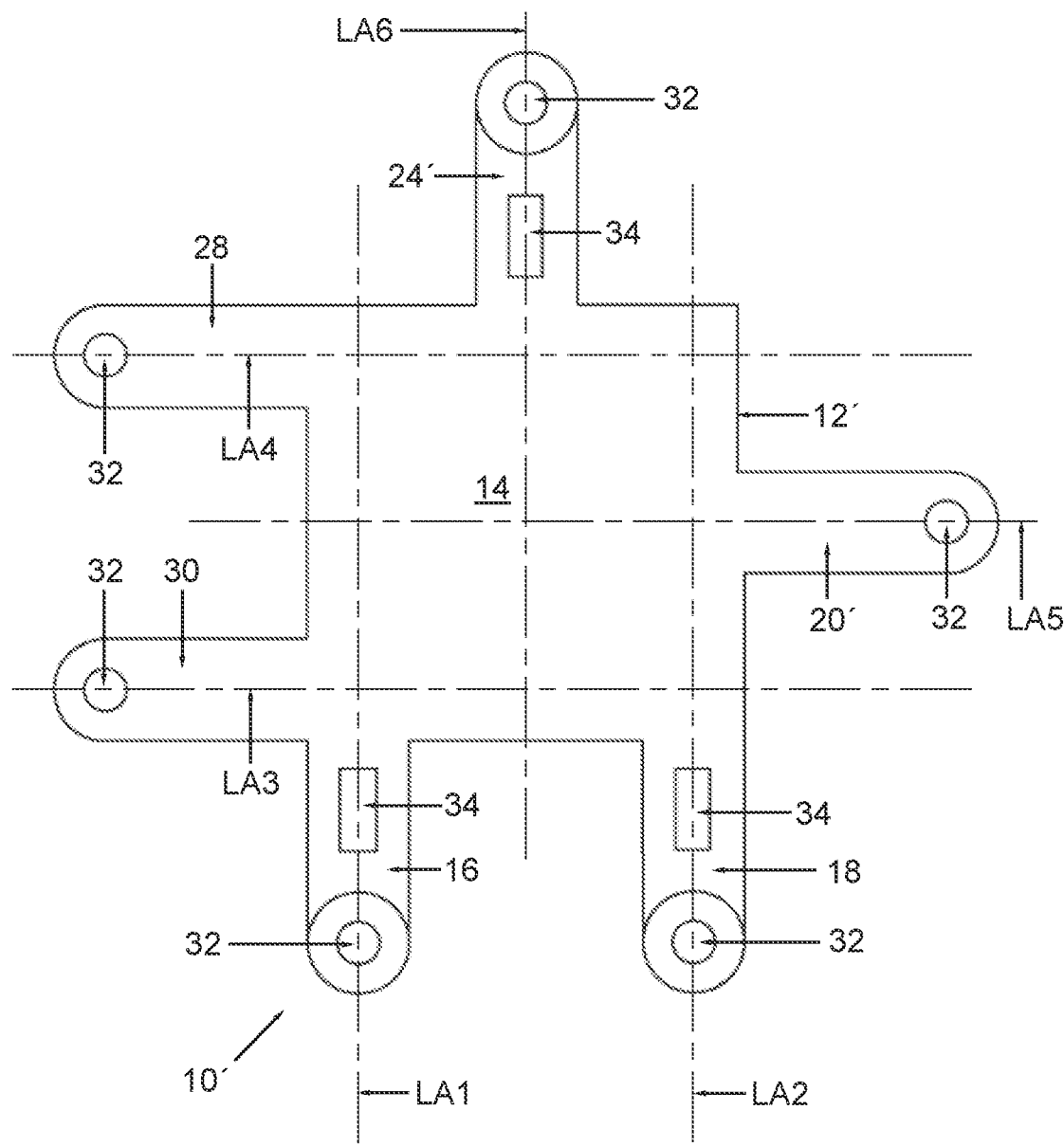
FIG. 9 is a top view of the low profile load transducer of FIG. 6, according to the second embodiment of the invention.

Now, with reference to the top view illustrated in FIG. 9, it can be seen that the central longitudinal axis LA5 of the beam 20', which extends from side 14b of the body portion 14, is generally equally spaced apart from the central longitudinal axis LA3 and LA4 (i.e., the central longitudinal axis LA5 of the beam 20' is generally centered between the central longitudinal axis LA3 of beam 30 and the central longitudinal axis LA4 of beam 28). Similarly, as shown in FIG. 9, the longitudinal axis LA6 of the beam 24', which extends from side 14c of the body portion 14, is generally equally spaced apart from the central longitudinal axis LA1 and LA2 (i.e., the central longitudinal axis LA6 of the beam 24' is generally centered between the central longitudinal axis LA1 of beam 16 and the central longitudinal axis LA2 of beam 18). The other features of the load transducer 10' are similar to that of the load transducer 10, and thus, need not be reiterated herein.

Figure 10:
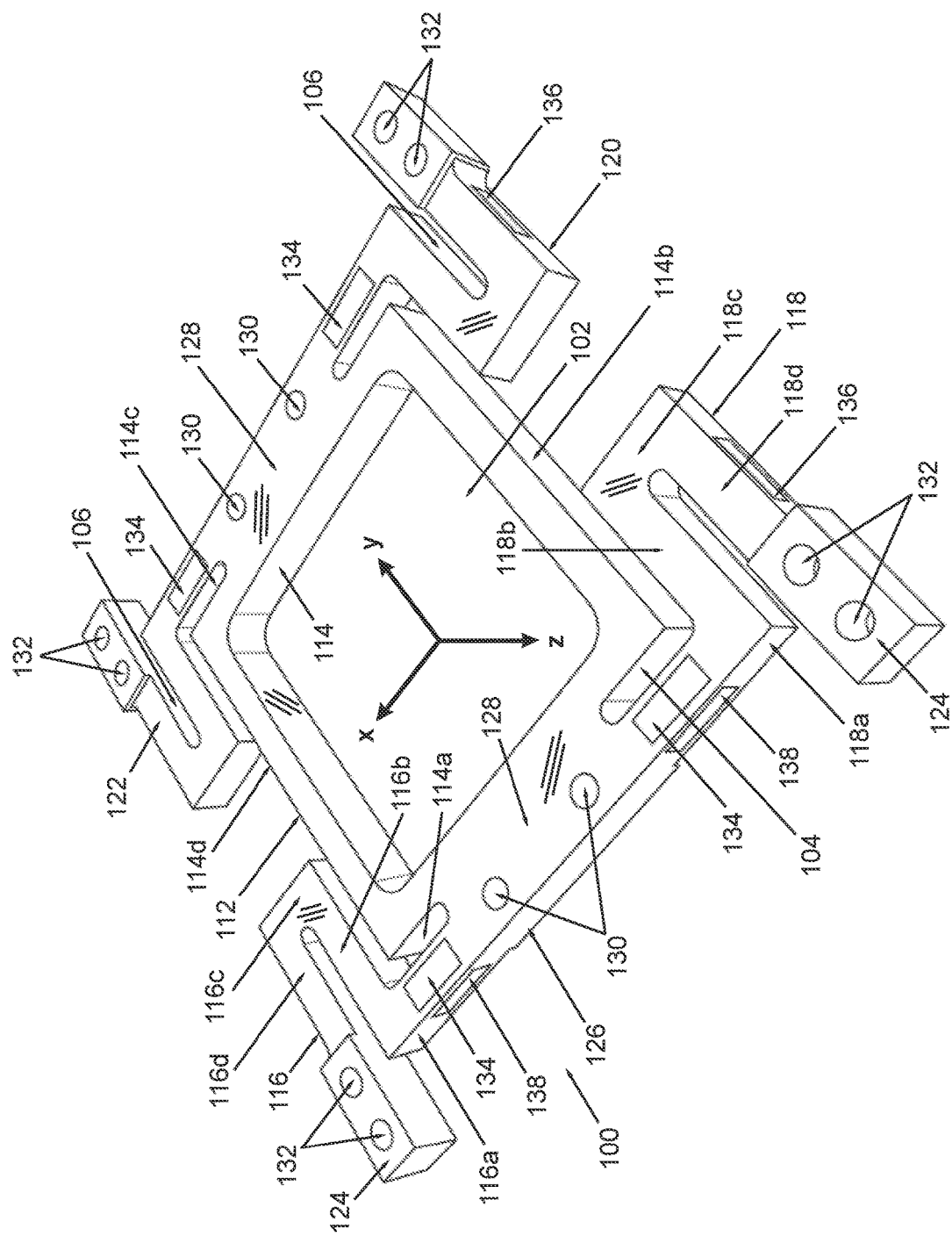
FIG. 10 is a perspective view of a low profile load transducer, according to a third embodiment of the invention.
Figure 11:
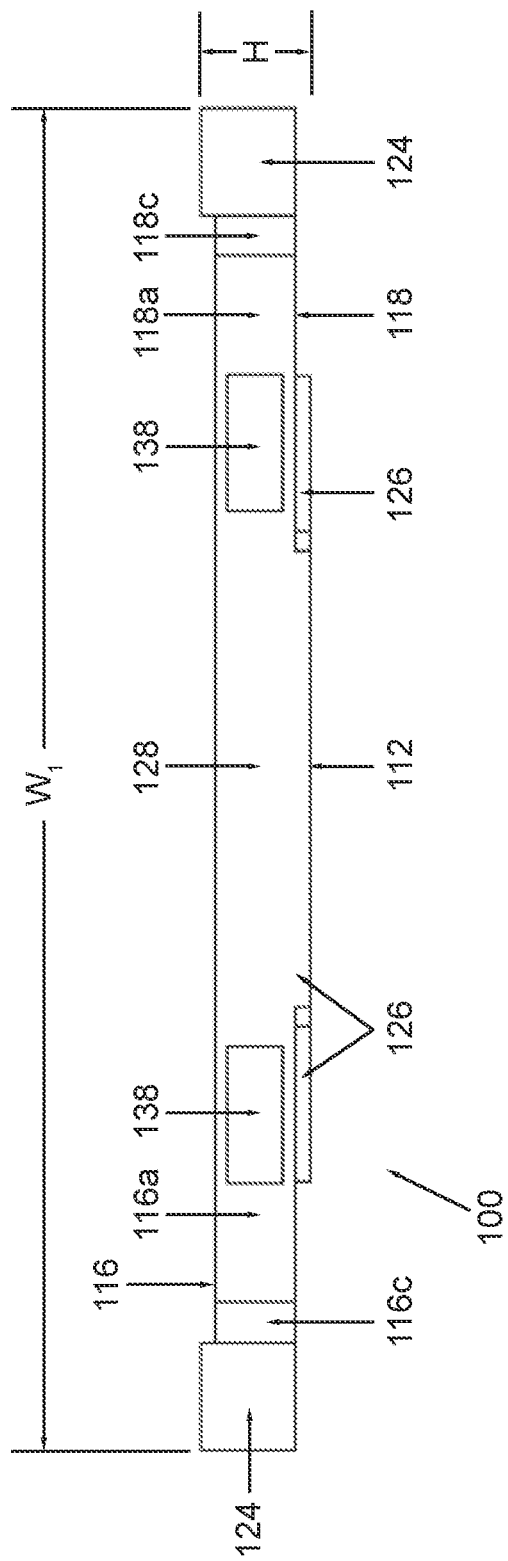
FIG. 11 is a first side view of the low profile load transducer of FIG. 10, according to the third embodiment of the invention.
Figure 12:
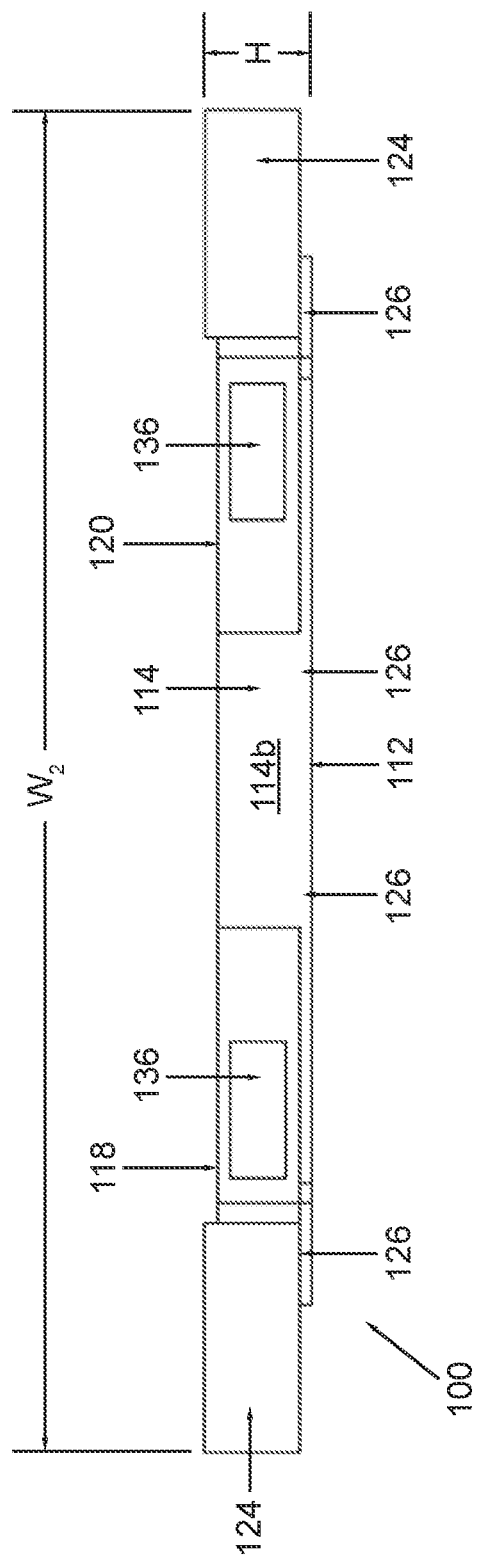
FIG. 12 is a second side view of the low profile load transducer of FIG. 10, according to the third embodiment of the invention.

FIGS. 10-14 illustrate a load transducer 100 according to a third exemplary embodiment of the present invention. Referring initially to the perspective view of FIG. 10, it can be seen that the load transducer 100 generally includes a one-piece compact transducer frame 112 having a central body portion 114 and a plurality of generally U-shaped transducer beams 116, 118, 120, 122 extending outwardly from the central body portion 114. As best illustrated in FIG. 10, each of the beams 116, 118, 120, 122 comprises a plurality of load cells or transducer elements for measuring forces and/or moments.

With reference again to FIG. 10, it can be seen that the illustrated central body portion 114 is generally in the form of square band-shaped element with a central opening 102 disposed therethrough. In FIG. 10, it can be seen that the body portion 114 comprises a first pair of opposed sides 114a, 114c and a second pair of opposed sides 114b, 114d. The side 114a is disposed generally parallel to the side 114c, while the side 114b is disposed generally parallel to the side 114d. Each of the sides 114a, 114b, 114c, 114d is disposed generally perpendicular to the planar top and bottom surfaces of the body portion 114. Also, each of the first pair of opposed sides 114a, 114c is disposed generally perpendicular to each of the second pair of opposed sides 114b, 114d. In addition, as shown in FIG. 10, each of the opposed sides 114a, 114c comprises a beam connecting portion 128 extending outward therefrom. In the illustrated embodiment, it can be seen that each of the beam connecting portions 128 comprises a plurality of apertures 130 (e.g., two apertures 130) disposed therethrough for accommodating fasteners (e.g., screws) that attach the load transducer 100 to another object, such as a robotic arm, etc. Also, as depicted in the side views of FIGS. 11 and 12 and the bottom view of FIG.

14, the bottom surface of the central body portion 114 comprises a raised portion or standoff portion 126 for elevating the transducer beams 116, 118, 120, 122 above the object (e.g., robotic arm) to which the load transducer 100 is attached so that forces and/or moments are capable of being accurately measured by the load transducer 100. In one or more embodiments, the structural components to which the load transducer 100 is mounted are connected only to the top standoff portions 124 and the bottom standoff 126 so as to ensure that the total load applied to the load transducer 100 is transmitted through the transducer beams 116, 118, 120, 122.

As shown in FIGS. 10-14, the illustrated generally U-shaped transducer beams 116, 118, 120, 122 are each attached to one of the sides 114a, 114b, 114c, 114d of the body portion 114 via a connecting portion 128, and extend generally horizontally outward therefrom. In particular, beams 116, 118 extend generally horizontally outward from opposed sides of the beam connecting portion 128 attached to side 114a of the body portion 114, while the beams 120, 122 extend generally horizontally outward from opposed sides of the beam connecting portion 128 attached to side 114c of the body portion 114. As best shown in FIG. 10, the top and bottom surfaces of each of the illustrated beams 116, 118, 120, 122 are disposed substantially co-planar with the top and bottom surfaces of the body portion 114. Each of the illustrated beams 116, 118, 120, 122 has a U-shaped cantilevered end relative to the body portion 114 that allows for deflection of the ends of the beams in multiple directions.

Figure 13:
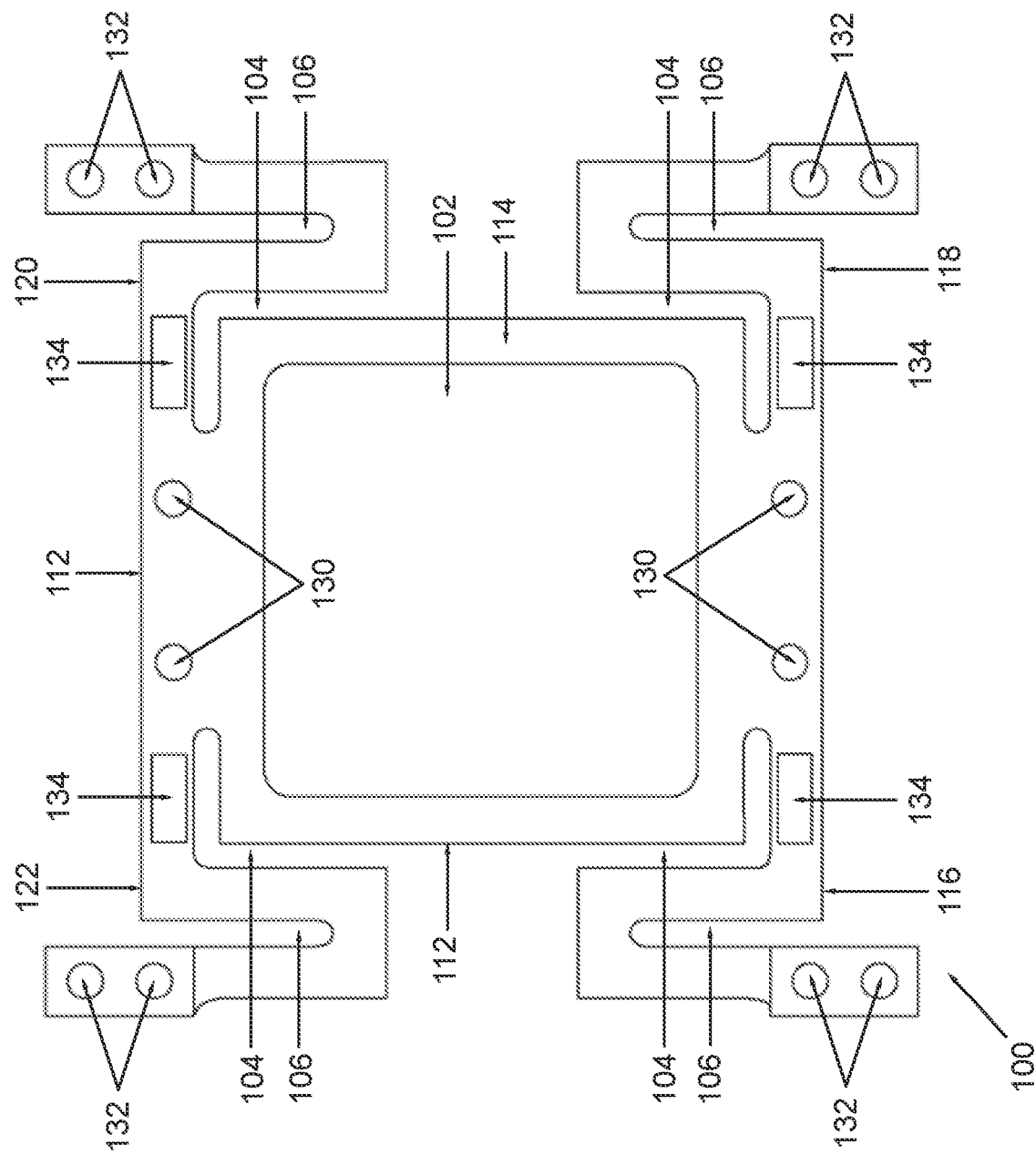
FIG. 13 is a top view of the low profile load transducer of FIG. 10, according to the third embodiment of the invention.
Figure 14:
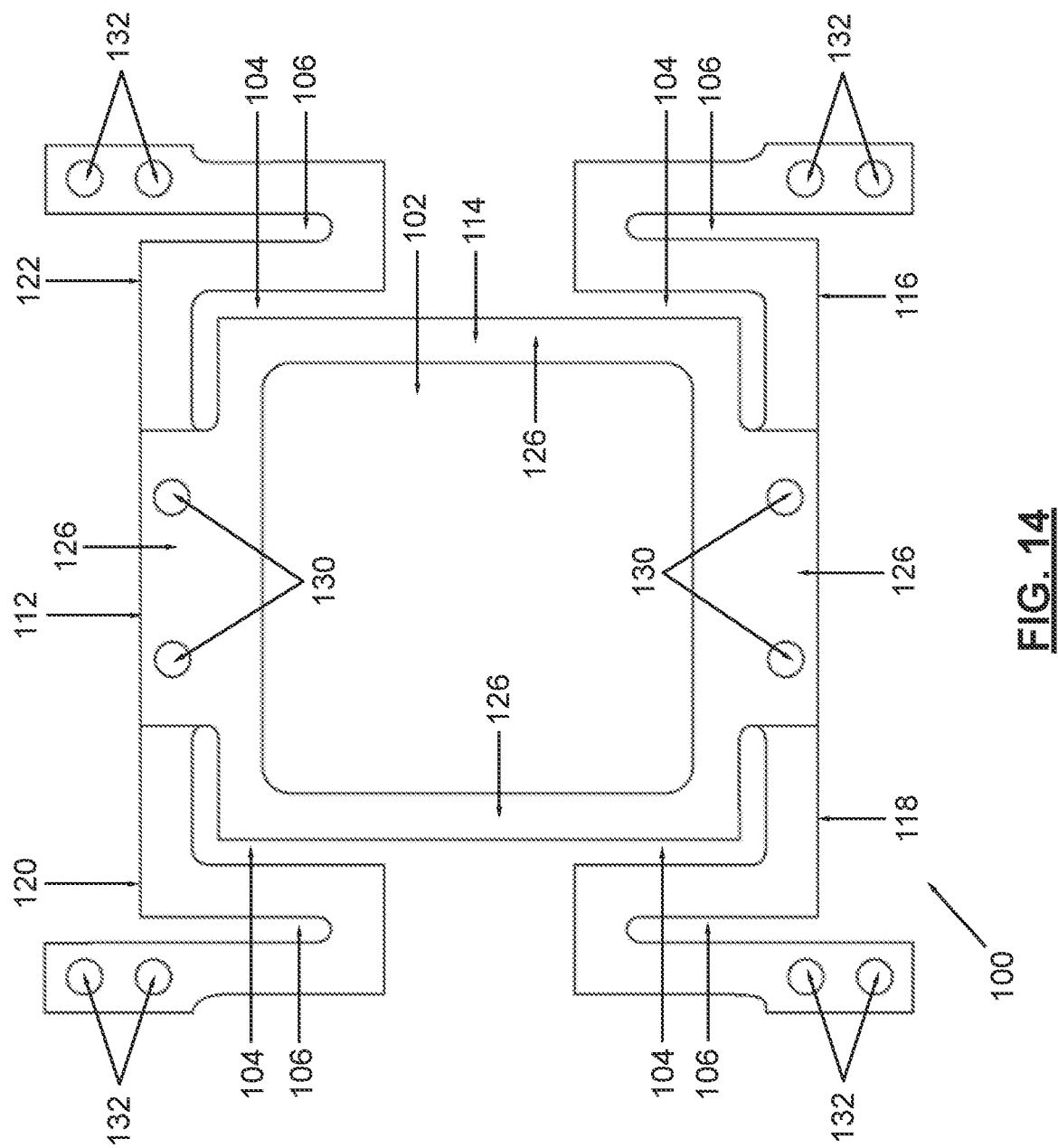
FIG. 14 is a bottom view of the low profile load transducer of FIG. 10, according to the third embodiment of the invention.

With particular reference to FIGS. 10, 13, and 14, it can be seen that each of the generally U-shaped beams 116, 118, 120, 122 comprises a plurality of segmental beam portions, wherein each of the successive beam portions are disposed substantially perpendicular to the immediately preceding beam portion. For example, as shown in FIG. 10, the first generally U-shaped transducer beam 116 comprises a first beam portion 116a extending from a first side of the beam connecting portion 128, a second beam portion 116b connected to the first beam portion 116a and disposed substantially perpendicular thereto, a third beam portion 116c connected to the second beam portion 116b and disposed substantially perpendicular thereto, and a fourth beam portion 116d connected to the third beam portion 116c and disposed substantially perpendicular thereto. Similarly, the second generally U-shaped transducer beam 118 comprises a first beam portion 118a extending from a second side of the beam connecting portion 128 (which is generally opposite to the first side of the beam connecting portion 128 from which the first beam portion 116a extends), a second beam portion 118b connected to the first beam portion 118a and disposed substantially perpendicular thereto, a third beam portion 118c connected to the second beam portion 118b and disposed substantially perpendicular thereto, and a fourth beam portion 118d connected to the third beam portion 118c and disposed substantially perpendicular thereto. With reference to FIGS. 10, 13, and 14, it can be seen that the generally U-shaped transducer beams 120, 122 are generally mirror images of the generally U-shaped transducer beams 116, 118, and thus, have the same structure as the generally U-shaped transducer beams 116, 118. Referring again to FIGS. 10, 13, and 14, it can be seen that the fourth beam portion of each of the generally U-shaped transducer beams 116, 118, 120, 122 comprises a raised portion or standoff portion 124 with mounting apertures 132 (e.g., two apertures 132) disposed therethrough for accommodating fasteners (e.g., screws) that attach the load transducer 100 to another object, such as a robotic arm, etc. In addition, as shown in FIGS. 10 and 13, each generally U-shaped transducer beam 116, 118, 120, 122 comprises a central beam gap 106, which is bounded by the second, third, and fourth beam portions. Also, it can be seen that the first and second beam portions of each transducer beam 116, 118, 120, 122 are separated from the opposing sides of the central body portion 114 by an L-shaped gap 104. That is, the sides of the central body portion 114, which face the sides of the first and second beam portions in an opposing relationship, are separated from the sides of the first and second beam portions by the L-shaped gap 104.

As best shown in the perspective view of FIG. 10, the illustrated load cells are located on the transducer beams 116, 118, 120, 122. In the illustrated embodiment, each load cell comprises a plurality of strain gages 134, 136, 138. Specifically, in the illustrated embodiment, each of the first portions (e.g., 116a, 118a) of the transducer beams 116, 118, 120, 122 comprise a strain gage 134 disposed on the top surface thereof that is sensitive to the vertical force component (i.e., a $F_Z$ strain gage). The first portions (e.g., 116a, 118a) of the transducer beams 116, 118, 120, 122 also each comprise a strain gage 138 disposed on a side surface thereof that is sensitive to a first shear force component (i.e., a $F_Y$ strain gage). Also, in the illustrated embodiment, each of the fourth portions (e.g., 116d, 118d) of the transducer beams 116, 118, 120, 122 comprise a strain gage 136 disposed on a side surface thereof that is sensitive to a second shear force component (i.e., a $F_X$ strain gage).

As best shown in FIG. 10, the illustrated load cells are configured as bending beam load cells. The illustrated strain gages 134, 136, 138 are mounted to either top or side surfaces of the beams 116, 118, 120, 122 between their attachment locations to the beam connecting portions 128 and the raised end portions 124 thereof. Alternatively, the strain gages 134 can be mounted to the bottom surfaces of the first beam portions (e.g., 116a, 118a) of the transducer beams 116, 118, 120, 122, while the strain gages 138 can be mounted to the opposite side surfaces of the first beam portions (e.g., 116a, 118a) of the transducer beams 116, 118, 120, 122. Similarly, the strain gages 136 can be mounted to the opposite side surfaces of the fourth beam portions (e.g., 116d, 118d) of the transducer beams 116, 118, 120, 122. In general, the strain gages 134, 136, 138 are mounted to surfaces generally normal to the direction of applied vertical and/or shear forces (i.e., $F_X$, $F_Y$, $F_Z$). It is also noted that alternatively, the strain gages 134 can be mounted at both the top surface and the bottom surface of the first beam portions of the beams 116, 118, 120, 122, the strain gages 138 can be mounted at both opposed side surfaces of first beam portions of the beams 116, 118, 120, 122, and/or the strain gages 136 can be mounted at both opposed side surfaces of the beams 116, 118, 120, 122. These strain gages 134, 136, 138 measure force either by bending moment or difference of bending moments at two cross sections. As force is applied to the ends of the beams, the beams 116, 118, 120, 122 bend. This bending either stretches or compresses the strain gages 134, 136, 138, which in turn changes the resistance of the electrical current passing therethrough. The amount of change in the electrical voltage or current is proportional to the magnitude of the applied force, as applied to the ends of respective beams 116, 118, 120, 122.

Figure 15:
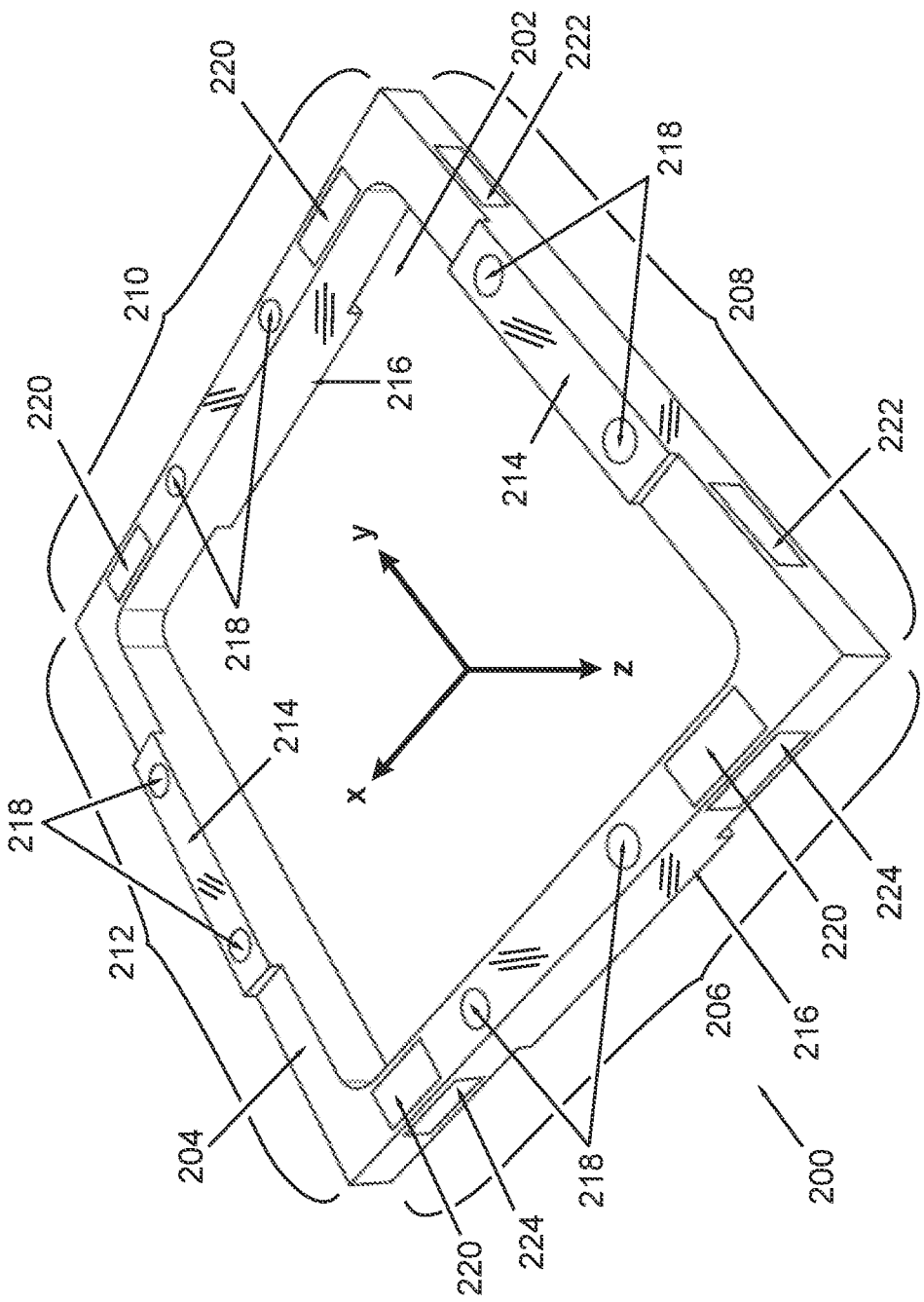
FIG. 15 is a perspective view of a low profile load transducer, according to a fourth embodiment of the invention.
Figure 16:
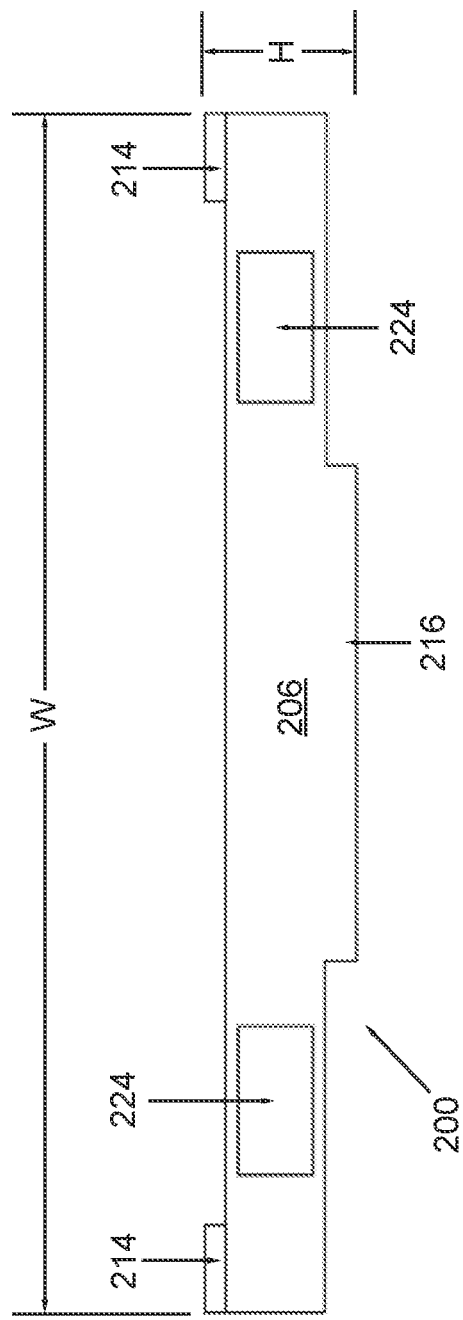
FIG. 16 is a first side view of the low profile load transducer of FIG. 15, according to the fourth embodiment of the invention.

Next, referring to FIGS. 15-18, a load transducer 200 according to a fourth exemplary embodiment of the present invention will be described. Referring initially to the perspective view of FIG. 15, it can be seen that the load transducer 200 generally includes a one-piece compact transducer frame 204 that is generally in the form of square band-shaped element with a central opening 202 disposed therethrough. As best illustrated in FIGS. 15 and 18, the square band-shaped transducer frame 204 comprises a first transducer beam side portion 206, a second transducer beam side portion 208, a third transducer beam side portion 210, and a fourth transducer beam side portion 212. Also, as shown in FIG. 15, the transducer beam side portions 206, 208, 210, 212 comprise a plurality of load cells or transducer elements for measuring forces and/or moments. The transducer frame 204 of the load transducer 200 is similar to the other transducers (e.g., transducers 300, 400) that will be described hereinafter, except that the central body portion of these transducers (e.g., 300, 400) has been removed in the load transducer 200.

Figure 17:
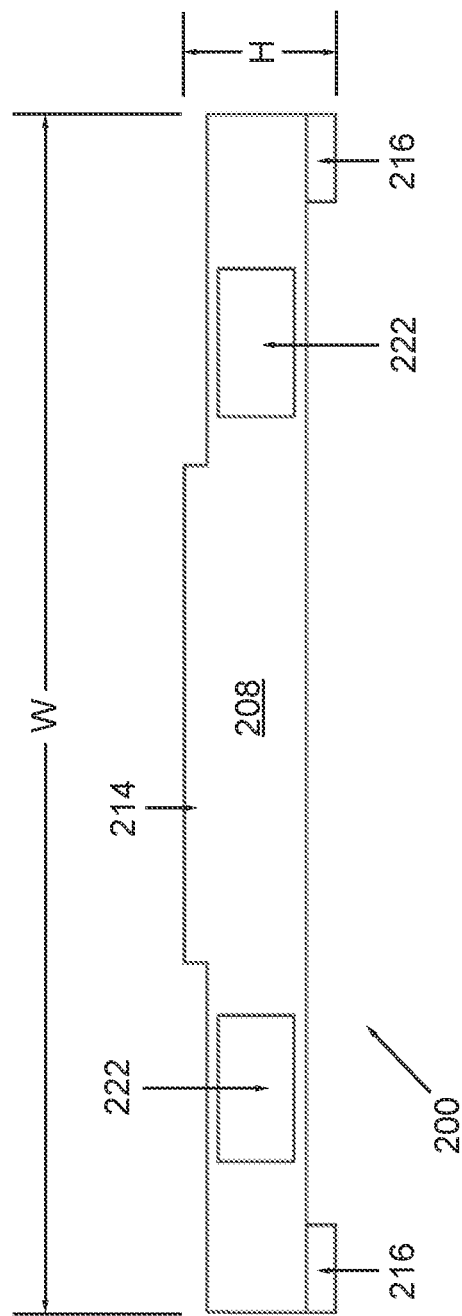
FIG. 17 is a second side view of the low profile load transducer of FIG. 15, according to the fourth embodiment of the invention.
Figure 18:
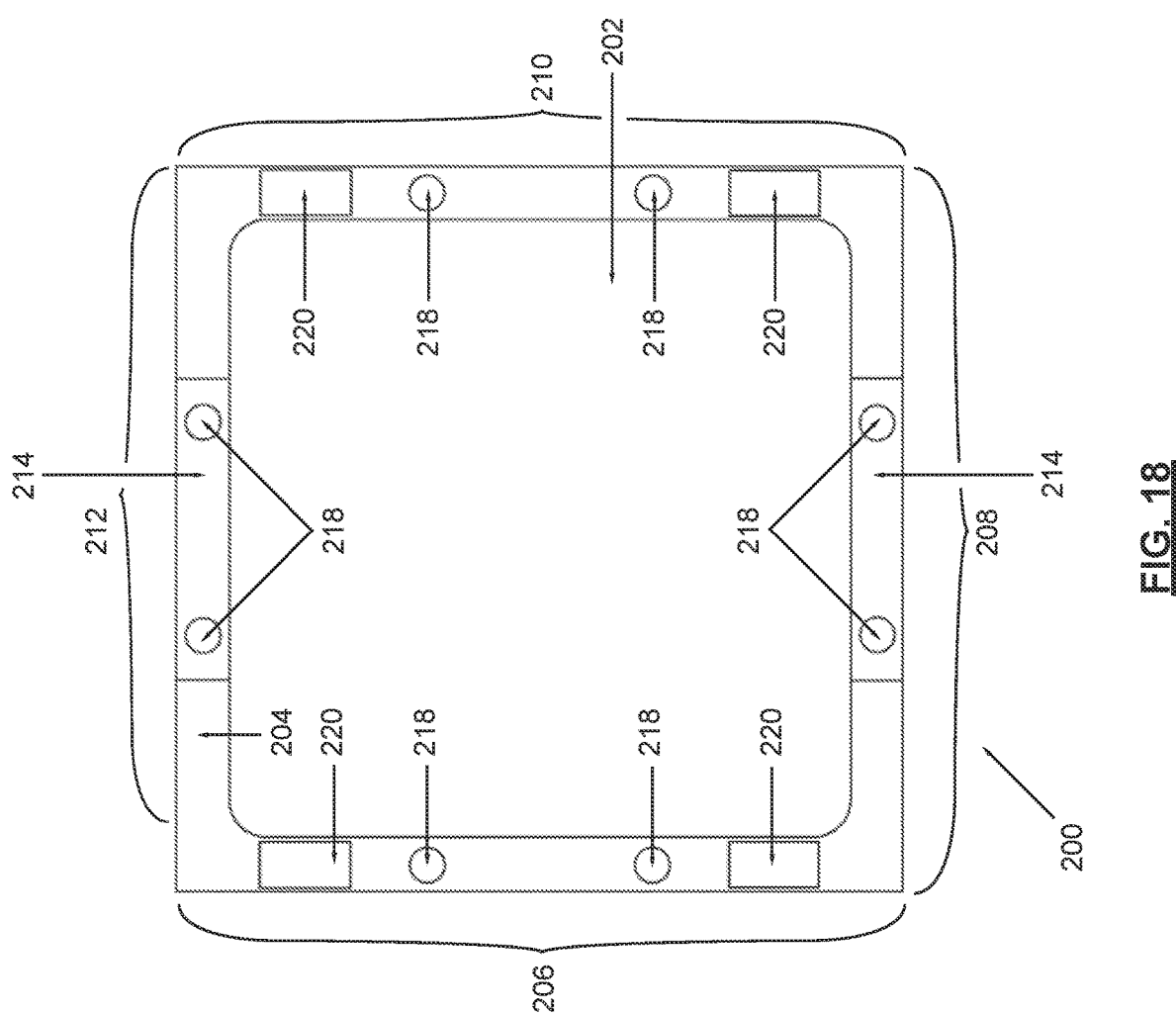
FIG. 18 is a top view of the low profile load transducer of FIG. 15, according to the fourth embodiment of the invention.

As shown in FIGS. 15-18, the illustrated transducer beam side portions 206, 208, 210, 212 of the transducer frame 204 are arranged in a generally square configuration. In particular, with reference to FIGS. 15 and 18, the first transducer beam side portion 206 is connected to the second transducer beam side portion 208 on one of its longitudinal ends, and the fourth transducer beam side portion 212 on the other one of its longitudinal ends, and the first transducer beam side portion 206 is disposed generally perpendicular to each of the second and fourth transducer beam side portions 208, 212. The second transducer beam side portion 208 is connected to the first transducer beam side portion 206 on one of its longitudinal ends, and the third transducer beam side portion 210 on the other one of its longitudinal ends, and the second transducer beam side portion 208 is disposed generally perpendicular to each of the first and third transducer beam side portions 206, 210. The third transducer beam side portion 210 is connected to the second transducer beam side portion 208 on one of its longitudinal ends, and the fourth transducer beam side portion 212 on the other one of its longitudinal ends, and the third transducer beam side portion 210 is disposed generally perpendicular to each of the second and fourth transducer beam side portions 208, 212. The fourth transducer beam side portion 212 is connected to the third transducer beam side portion 210 on one of its longitudinal ends, and the first transducer beam side portion 206 on the other one of its longitudinal ends, and the fourth transducer beam side portion 212 is disposed generally perpendicular to each of the first and third transducer beam side portions 206, 210. Referring to FIGS. 15, 17, and 18, it can be seen that the top surface of the second transducer beam side portion 208 and the top surface of the fourth transducer beam side portion 212 each comprises a central raised portion or standoff portion 214 with spaced apart mounting apertures 218 (e.g., two spaced apart apertures 218) disposed therethrough for accommodating fasteners (e.g., screws) that attach the load transducer 200 to another object, such as a robotic arm, etc. Similarly, with reference to FIGS. 15 and 16, it can be seen that the bottom surface of the first transducer beam side portion 206 and the bottom surface of the third transducer beam side portion 210 each comprises a central raised portion or standoff portion 216 with spaced apart mounting apertures 218 (e.g., two spaced apart apertures 218) disposed therethrough for accommodating fasteners (e.g., screws) that attach the load transducer 200 to another object, such as a robotic arm, etc.

As best shown in the perspective view of FIG. 15, the illustrated load cells are located on the transducer beam side portions 206, 208, 210, 212. In the illustrated embodiment, each load cell comprises one or more strain gages 220, 222, 224. Specifically, in the illustrated embodiment, the first transducer beam side portion 206 and the third transducer beam side portion 210 each comprise a plurality of spaced apart strain gages 220 (e.g., two spaced apart strain gages 220) disposed on the top surface thereof that is sensitive to the vertical force component (i.e., a $F_Z$ strain gage). The second transducer beam side portion 208 and the fourth transducer beam side portion 212 also each comprise a plurality of spaced apart strain gages 222 (e.g., two spaced apart strain gages 222) disposed on a side surface thereof that is sensitive to a first shear force component (i.e., a $F_X$ strain gage). Also, in the illustrated embodiment, the first transducer beam side portion 206 and the third transducer beam side portion 210 also each comprise a plurality of spaced apart strain gages 224 (e.g., two spaced apart strain gages 224) disposed on a side surface thereof that is sensitive to a second shear force component (i.e., a $F_Y$ strain gage).

As best shown in FIG. 15, the illustrated load cells are configured as bending beam load cells. The illustrated strain gages 220, 222, 224 are mounted to either top or side surfaces of the transducer beam side portions 206, 208, 210, 212 between the opposed longitudinal ends thereof. Alternatively, the strain gages 220 can be mounted to the bottom surfaces of the first and third transducer beam side portions 206, 210, while the strain gages 222 can be mounted to the opposite side surfaces of the second and fourth transducer beam side portions 208, 212. Similarly, the strain gages 224 can be mounted to the opposite side surfaces of the first and third transducer beam side portions 206, 210. In general, the strain gages 220, 222, 224 are mounted to surfaces generally normal to the direction of applied vertical and/or shear forces (i.e., $F_X$, $F_Y$, $F_Z$). It is also noted that alternatively, the strain gages 220 can be mounted at both the top surface and the bottom surface of the first and third transducer beam side portions 206, 210, the strain gages 222 can be mounted at both opposed side surfaces of second and fourth transducer beam side portions 208, 212, and/or the strain gages 224 can be mounted at both opposed side surfaces of the first and third transducer beam side portions 206, 210. These strain gages 220, 222, 224 measure force either by bending moment or difference of bending moments at two cross sections. As force is applied to the beams, the beams 206, 208, 210, 212 bend. This bending either stretches or compresses the strain gages 220, 222, 224, which in turn changes the resistance of the electrical current passing therethrough. The amount of change in the electrical voltage or current is proportional to the magnitude of the applied force, as transferred through the end portions of respective beams 206, 208, 210, 212.

Figure 25:
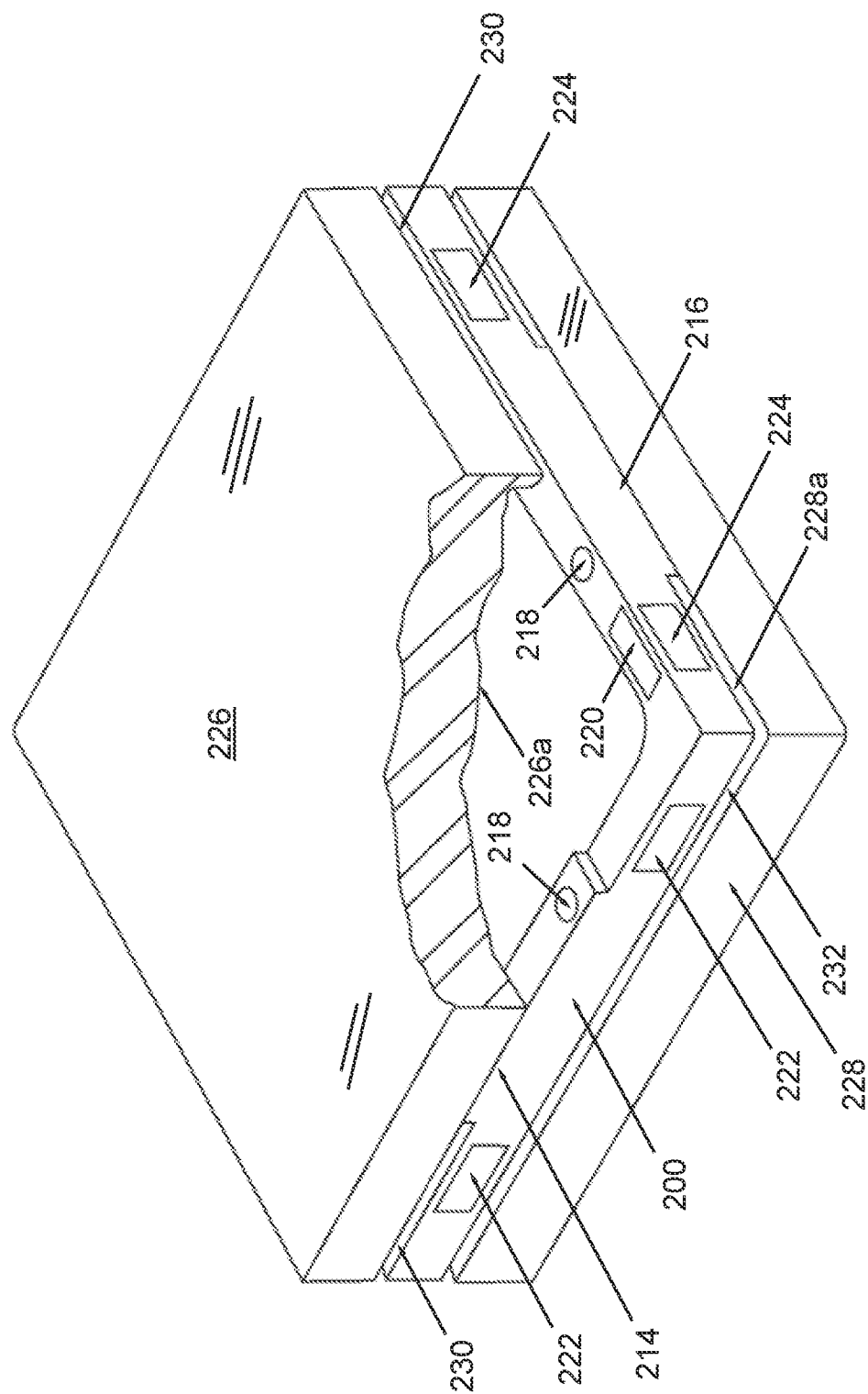
FIG. 25 is a perspective view of an exemplary mounting arrangement for the low profile load transducer illustrated in FIGS. 15-18.

An exemplary mounting arrangement for the load transducer 200 is illustrated in FIG. 25. As depicted in the perspective view of FIG. 25, the load transducer 200 is mounted between a top plate member 226 and a bottom plate member 228. Specifically, in this mounting arrangement, the bottom surface 226a of the top plate member 226 abuts the top surfaces of the standoff portions 214 on the second and fourth transducer beam side portions 208, 212, while the top surface 228a of the bottom plate member 228 abuts the bottom surfaces of the standoff portions 216 on the first and third transducer beam side portions 206, 210. As such, in this mounting arrangement, an upper gap 230 is formed between the top surfaces of the load transducer 200 and the bottom surface 226a of the top plate member 226 by the two spaced apart top standoff portions 214. Similarly, a lower gap 232 is formed between the bottom surfaces of the load transducer 200 and the top surface 228a of the bottom plate member 228 by the two spaced apart bottom standoff portions 216. Thus, as result of the mounting arrangement illustrated in FIG. 25, the entire load exerted on the load transducer 200 by the top and bottom plate members 226, 228 is transferred through the corner portions of the transducer frame 204, which are instrumented with the strain gages 220, 222, 224 and are spaced apart from the top and bottom plate members 226, 228 by the standoff portions 214, 216.

While the exemplary mounting arrangement is illustrated in FIG. 25 using the load transducer 200, it is to be understood that each of the other load transducers 10, 10', 100, 300, 400, 500, 600, 700, 800 described herein are mounted in generally the same manner to adjoining structures (e.g., plate members 226, 228 or components of a robotic arm). That is, the standoff portions described on the load transducers 10, 10', 100, 300, 400, 500, 600, 700, 800 perform the same functions as those described in conjunction with the load transducer 200 above. In particular, the adjoining structures to which the transducers are mounted are only connected to the top standoff portions and the bottom standoff portions of each load transducer 10, 10', 100, 300, 400, 500, 600, 700, 800 so as to ensure that the total loads applied to the load transducers 10, 10', 100, 300, 400, 500, 600, 700, 800 are transmitted through the instrumented portions of the transducer beams of the transducers.

Figure 19:
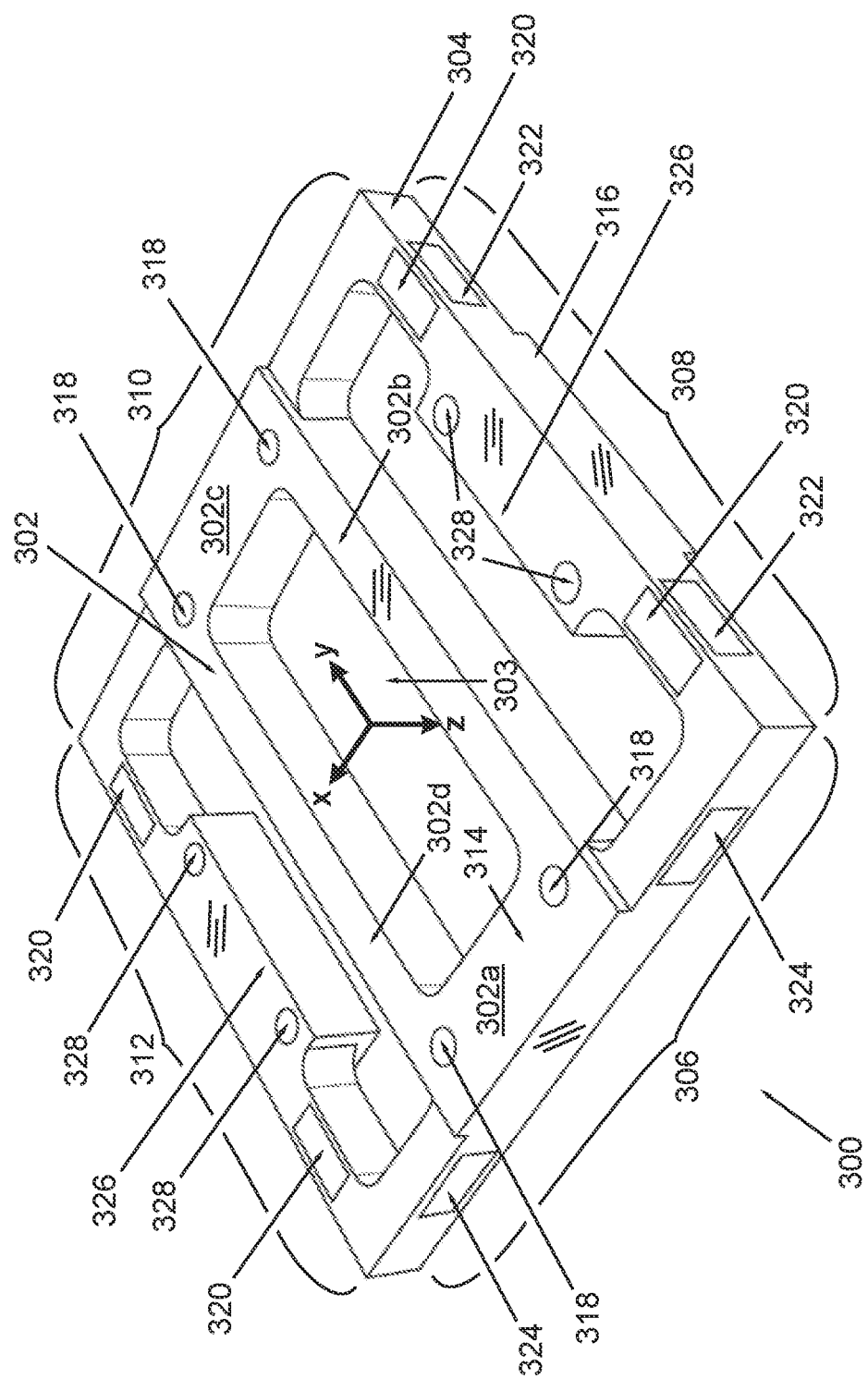
FIG. 19 is a perspective view of a low profile load transducer, according to a fifth embodiment of the invention.

FIG. 19 illustrates a load transducer 300 according to a fifth exemplary embodiment of the present invention. With reference to this figure, it can be seen that, in some respects, the fifth exemplary embodiment is similar to that of the fourth embodiment. Moreover, some parts are common to both such embodiments. For the sake of brevity, the parts that the fifth embodiment of the load transducer has in common with the fourth embodiment will only be briefly mentioned because these components have already been explained in detail above.

Initially, referring to the perspective view of FIG. 19, it can be seen that, unlike the fourth exemplary embodiment of the load transducer, the load transducer 300 comprises a central body portion 302. Also, unlike the load transducer 200 of the fourth embodiment, the second and fourth transducer beam side portions 308, 312 have side projecting portions 326 extending from the inner sides thereof towards the central body portion 302. As shown in FIG. 19, the load transducer 300 generally includes a one-piece compact transducer frame 304 with a central body portion 302 and a plurality of transducer beam side portions 306, 308, 310, 312.

With reference again to FIG. 19, it can be seen that the illustrated central body portion 302 is generally in the form of rectangular band-shaped element with a central opening 303 disposed therethrough. In FIG. 19, it can be seen that the body portion 302 comprises a first pair of opposed side portions 302a, 302c and a second pair of opposed side portions 302b, 302d. The side portion 302a is disposed generally parallel to the side portion 302c, while the side portion 302b is disposed generally parallel to the side portion 302d. Each of the side surfaces of the side portions 302a, 302b, 302c, 302d is disposed generally perpendicular to the planar top and bottom surfaces thereof. Also, each of the first pair of opposed side portions 302a, 302c is disposed generally perpendicular to each of the second pair of opposed sides portions 302b, 302d. In addition, as shown in FIG. 19, each of the opposed side portions 302a, 302c forms a middle portion of the first and third transducer beam side portions 306, 310. In the illustrated embodiment, it can be seen that each of the opposed side portions 302a, 302c comprises a plurality of apertures 318 (e.g., two apertures 318) disposed therethrough for accommodating fasteners (e.g., screws) that attach the load transducer 300 to another object, such as a robotic arm, etc. Also, as depicted in the FIG. 19, the central body portion 302 comprises a raised top portion or top standoff portion 314 for spacing the transducer beam side portions 306, 308, 310, 312 apart from the object (e.g., robotic arm) to which the load transducer 300 is attached so that forces and/or moments are capable of being accurately measured by the load transducer 300.

As shown in FIG. 19, the illustrated transducer beam side portions 306, 308, 310, 312 of the transducer frame 304 are arranged in a generally square configuration. In particular, with reference to FIG. 19, the first transducer beam side portion 306 is connected to the second transducer beam side portion 308 on one of its longitudinal ends, and the fourth transducer beam side portion 312 on the other one of its longitudinal ends, and the first transducer beam side portion 306 is disposed generally perpendicular to each of the second and fourth transducer beam side portions 308, 312. The second transducer beam side portion 308 is connected to the first transducer beam side portion 306 on one of its longitudinal ends, and the third transducer beam side portion 310 on the other one of its longitudinal ends, and the second transducer beam side portion 308 is disposed generally perpendicular to each of the first and third transducer beam side portions 306, 310. The third transducer beam side portion 310 is connected to the second transducer beam side portion 308 on one of its longitudinal ends, and the fourth transducer beam side portion 312 on the other one of its longitudinal ends, and the third transducer beam side portion 310 is disposed generally perpendicular to each of the second and fourth transducer beam side portions 308, 312. The fourth transducer beam side portion 312 is connected to the third transducer beam side portion 310 on one of its longitudinal ends, and the first transducer beam side portion 306 on the other one of its longitudinal ends, and the fourth transducer beam side portion 312 is disposed generally perpendicular to each of the first and third transducer beam side portions 306, 310. Referring to FIG. 19, it can be seen that the bottom surface of the second transducer beam side portion 308 and the bottom surface of the fourth transducer beam side portion 312 each comprises a central standoff portion 316, which is connected to the side projecting portion 326 on each of the transducer beam side portions 308, 312. The side projecting portions 326 each comprise spaced apart mounting apertures 328 (e.g., two spaced apart apertures 328) disposed therethrough for accommodating fasteners (e.g., screws) that attach the load transducer 300 to another object, such as a robotic arm, etc.

As best shown in the perspective view of FIG. 19, the illustrated load cells are located on the transducer beam side portions 306, 308, 310, 312. In the illustrated embodiment, each load cell comprises one or more strain gages 320, 322, 324. Specifically, in the illustrated embodiment, the second transducer beam side portion 308 and the fourth transducer beam side portion 312 each comprise a plurality of spaced apart strain gages 320 (e.g., two spaced apart strain gages 320) disposed on the top surface thereof that is sensitive to the vertical force component (i.e., a $F_Z$ strain gage). The second transducer beam side portion 308 and fourth transducer beam side portion 312 also each comprise a plurality of spaced apart strain gages 322 (e.g., two spaced apart strain gages 322) disposed on a side surface thereof that is sensitive to a first shear force component (i.e., a $F_X$ strain gage). Also, in the illustrated embodiment, the first transducer beam side portion 306 and the third transducer beam side portion 310 also each comprise a plurality of spaced apart strain gages 324 (e.g., two spaced apart strain gages 324) disposed on a side surface thereof that is sensitive to a second shear force component (i.e., a $F_Y$ strain gage).

Figure 20:
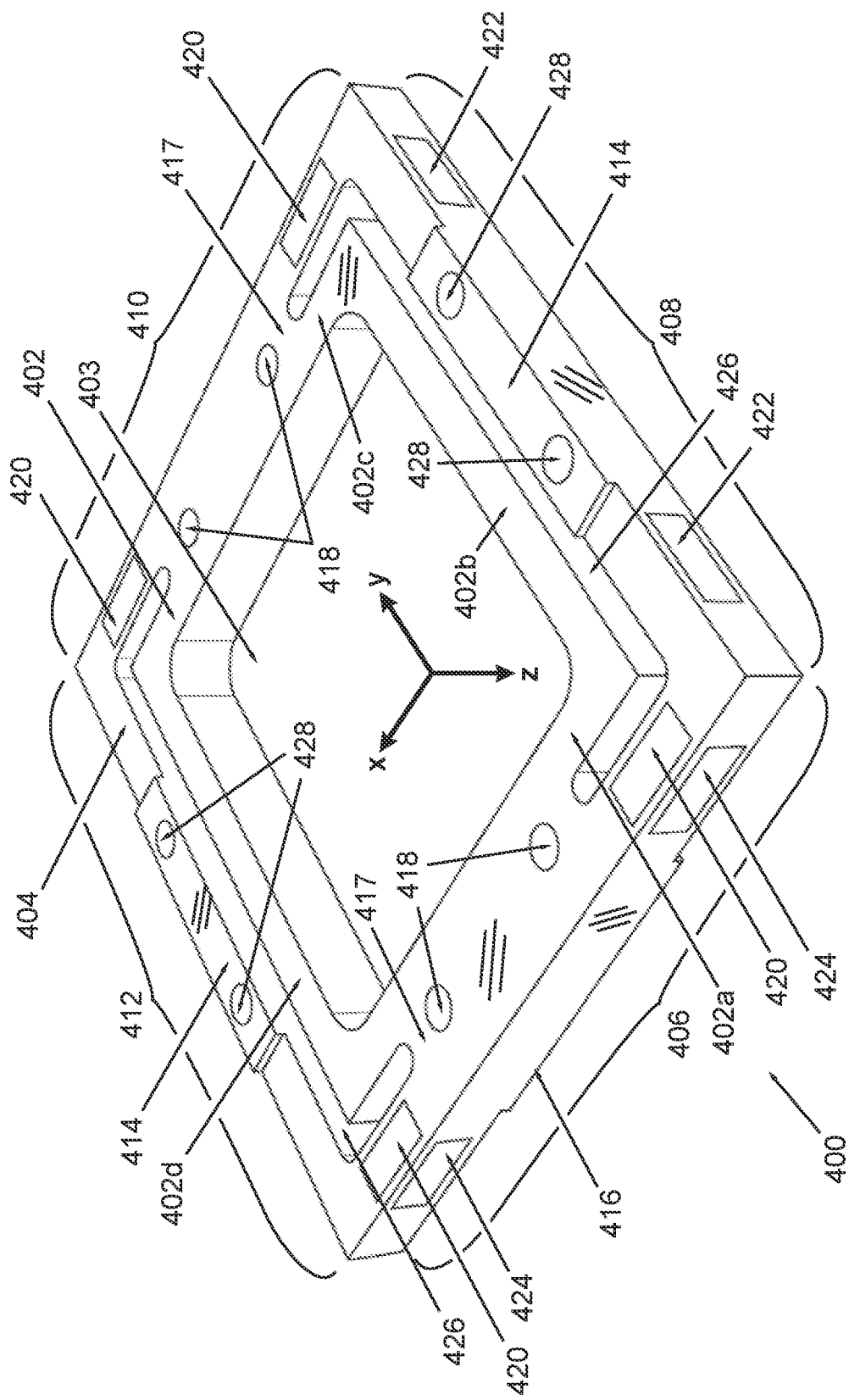
FIG. 20 is a perspective view of a low profile load transducer, according to a sixth embodiment of the invention.

FIG. 20 illustrates a load transducer 400 according to a sixth exemplary embodiment of the present invention. With reference to this figure, it can be seen that, in some respects, the sixth exemplary embodiment is similar to that of the fifth embodiment. Moreover, some parts are common to both such embodiments. For the sake of brevity, the parts that the sixth embodiment of the load transducer has in common with the fifth embodiment will only be briefly mentioned because these components have already been explained in detail above.

Initially, referring to the perspective view of FIG. 20, it can be seen that, unlike the fifth exemplary embodiment of the load transducer, all four sides of the central body portion 402 of the load transducer 400 are spaced apart from the transducer beam side portions 406, 408, 410, 412. In particular, the central body portion 402 is spaced apart from the transducer beam side portions 406, 408, 410, 412 by the two C-shaped gaps 426. Also, unlike the load transducer 300 of the fifth embodiment, the first and third transducer beam side portions 406, 410 of the load transducer 400 are connected to the central body portion 402 by the beam connecting portions 417. Although, like the load transducer 300, the load transducer 400 generally includes a one-piece compact transducer frame 404 with a central body portion 402 and a plurality of transducer beam side portions 406, 408, 410, 412.

With reference again to FIG. 20, it can be seen that the illustrated central body portion 402 is generally in the form of rectangular band-shaped element with a central opening 403 disposed therethrough. In FIG. 20, it can be seen that the body portion 402 comprises a first pair of opposed side portions 402a, 402c and a second pair of opposed side portions 402b, 402d. The side portion 402a is disposed generally parallel to the side portion 402c, while the side portion 402b is disposed generally parallel to the side portion 402d. Each of the side surfaces of the side portions 402a, 402b, 402c, 402d is disposed generally perpendicular to the planar top and bottom surfaces thereof. Also, each of the first pair of opposed side portions 402a, 402c is disposed generally perpendicular to each of the second pair of opposed sides portions 402b, 402d. In addition, as shown in FIG. 20, each of the opposed side portions 402a, 402c is connected to the first and third transducer beam side portions 406, 410 by beam connecting portions 417. In the illustrated embodiment, it can be seen that each of the beam connecting portions 417 comprises a plurality of apertures 418 (e.g., two apertures 418) disposed therethrough for accommodating fasteners (e.g., screws) that attach the load transducer 400 to another object, such as a robotic arm, etc.

As shown in FIG. 20, the illustrated transducer beam side portions 406, 408, 410, 412 of the transducer frame 404 are arranged in a generally square configuration. In particular, with reference to FIG. 20, the first transducer beam side portion 406 is connected to the second transducer beam side portion 408 on one of its longitudinal ends, and the fourth transducer beam side portion 412 on the other one of its longitudinal ends, and the first transducer beam side portion 406 is disposed generally perpendicular to each of the second and fourth transducer beam side portions 408, 412. The second transducer beam side portion 408 is connected to the first transducer beam side portion 406 on one of its longitudinal ends, and the third transducer beam side portion 410 on the other one of its longitudinal ends, and the second transducer beam side portion 408 is disposed generally perpendicular to each of the first and third transducer beam side portions 406, 410. The third transducer beam side portion 410 is connected to the second transducer beam side portion 408 on one of its longitudinal ends, and the fourth transducer beam side portion 412 on the other one of its longitudinal ends, and the third transducer beam side portion 410 is disposed generally perpendicular to each of the second and fourth transducer beam side portions 408, 412. The fourth transducer beam side portion 412 is connected to the third transducer beam side portion 410 on one of its longitudinal ends, and the first transducer beam side portion 406 on the other one of its longitudinal ends, and the fourth transducer beam side portion 412 is disposed generally perpendicular to each of the first and third transducer beam side portions 406, 410. Referring to FIG. 20, it can be seen that the top surface of the second transducer beam side portion 408 and the top surface of the fourth transducer beam side portion 412 each comprises a central raised portion or standoff portion 414 with spaced apart mounting apertures 428 (e.g., two spaced apart apertures 428) disposed therethrough for accommodating fasteners (e.g., screws) that attach the load transducer 400 to another object, such as a robotic arm, etc. Similarly, with reference to FIG. 20, it can be seen that the bottom surface of the first transducer beam side portion 406 and the bottom surface of the third transducer beam side portion 410 each comprises a central raised portion or standoff portion 416.

As best shown in the perspective view of FIG. 20, the illustrated load cells are located on the transducer beam side portions 406, 408, 410, 412. In the illustrated embodiment, each load cell comprises one or more strain gages 420, 422, 424. Specifically, in the illustrated embodiment, the first transducer beam side portion 406 and the third transducer beam side portion 410 each comprise a plurality of spaced apart strain gages 420 (e.g., two spaced apart strain gages 420) disposed on the top surface thereof that is sensitive to the vertical force component (i.e., a $F_Z$ strain gage). The second transducer beam side portion 408 and fourth transducer beam side portion 412 also each comprise a plurality of spaced apart strain gages 422 (e.g., two spaced apart strain gages 422) disposed on a side surface thereof that is sensitive to a first shear force component (i.e., a $F_X$ strain gage). Also, in the illustrated embodiment, the first transducer beam side portion 406 and the third transducer beam side portion 410 also each comprise a plurality of spaced apart strain gages 424 (e.g., two spaced apart strain gages 424) disposed on a side surface thereof that is sensitive to a second shear force component (i.e., a $F_Y$ strain gage).

Figure 21:
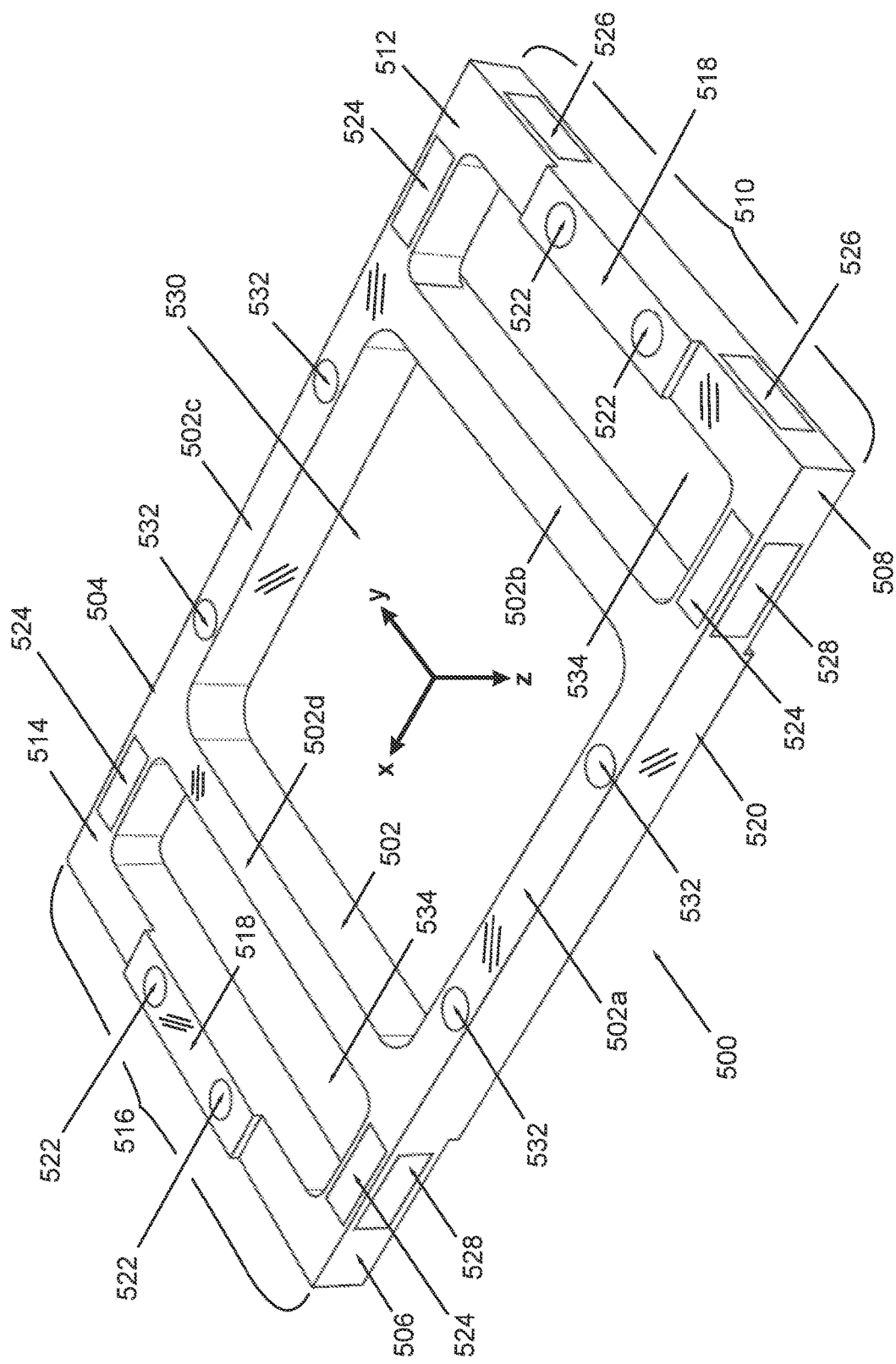
FIG. 21 is a perspective view of a low profile load transducer, according to a seventh embodiment of the invention.

FIG. 21 illustrates a load transducer 500 according to a seventh exemplary embodiment of the present invention. With reference to this figure, it can be seen that, in some respects, the seventh exemplary embodiment is similar to that of the fifth embodiment. Moreover, some parts are common to both such embodiments. For the sake of brevity, the parts that the seventh embodiment of the load transducer has in common with the fifth embodiment will only be briefly mentioned because these components have already been explained in detail above.

Initially, referring to the perspective view of FIG. 21, it can be seen that, like the fifth embodiment described above, the load transducer 500 generally includes a one-piece compact transducer frame 504 with a central body portion 502 and a plurality of transducer beam side portions 506, 508, 510, 512, 514, 516. Although, the central body portion 502 of the load transducer 500 is considerably wider than the central body portion 302 of the load transducer 300.

With reference again to FIG. 21, it can be seen that the illustrated central body portion 502 is generally in the form of square band-shaped element with a central opening 530 disposed therethrough. In FIG. 21, it can be seen that the body portion 502 comprises a first pair of opposed side portions 502a, 502c and a second pair of opposed side portions 502b, 502d. The side portion 502a is disposed generally parallel to the side portion 502c, while the side portion 502b is disposed generally parallel to the side portion 502d. Each of the side surfaces of the side portions 502a, 502b, 502c, 502d is disposed generally perpendicular to the planar top and bottom surfaces thereof. Also, each of the first pair of opposed side portions 502a, 502c is disposed generally perpendicular to each of the second pair of opposed sides portions 502b, 502d. In addition, as shown in FIG. 21, each of the opposed side portions 502a, 502c is disposed between a respective pair of transducer beam side portions 506, 508 and 512, 514. In the illustrated embodiment, it can be seen that each of the opposed side portions 502a, 502c comprises a plurality of apertures 532 (e.g., two apertures 532) disposed therethrough for accommodating fasteners (e.g., screws) that attach the load transducer 500 to another object, such as a robotic arm, etc. Also, as depicted in the FIG. 21, the central body portion 502 comprises a raised bottom portion or bottom standoff portion 520 for spacing the transducer beam side portions 506, 508, 510, 512, 514, 516 apart from the object (e.g., robotic arm) to which the load transducer 500 is attached so that forces and/or moments are capable of being accurately measured by the load transducer 500.

As shown in FIG. 21, the first set of illustrated transducer beam side portions 506, 514, 516 of the transducer frame 504 are arranged in a generally C-shaped configuration on a first side of the central body portion 502. A first side aperture 534 is formed between the side portion 502d of the central body portion 502 and the first set of transducer beam side portions 506, 514, 516. Referring again to FIG. 21, it can be seen that the first transducer beam side portion 506 is connected to the sixth transducer beam side portion 516 on one of its longitudinal ends, and the side portion 502d of the central body portion 502 on the other one of its longitudinal ends, and the first transducer beam side portion 506 is disposed generally perpendicular to the side portion 502d of the central body portion 502 and to sixth transducer beam side portion 516. Similarly, the fifth transducer beam side portion 514 is connected to the sixth transducer beam side portion 516 on one of its longitudinal ends, and the side portion 502d of the central body portion 502 on the other one of its longitudinal ends, and the fifth transducer beam side portion 514 is disposed generally perpendicular to the side portion 502d of the central body portion 502 and to sixth transducer beam side portion 516. The sixth transducer beam side portion 516 is connected to the first transducer beam side portion 506 on one of its longitudinal ends, and the fifth transducer beam side portion 514 on the other one of its longitudinal ends, and the sixth transducer beam side portion 516 is disposed generally perpendicular to each of the first and fifth transducer beam side portions 506, 514. Turning again to FIG. 21, it can be seen that the second set of transducer beam side portions 508, 510, 512 of the transducer frame 504 is arranged in a generally C-shaped configuration on a second side of the central body portion 502, which is opposite to the first side of the central body portion 502. A second side aperture 534 is formed between the side portion 502b of the central body portion 502 and the second set of transducer beam side portions 508, 510, 512. In FIG. 21, it can be seen that the second transducer beam side portion 508 is connected to the third transducer beam side portion 510 on one of its longitudinal ends, and the side portion 502b of the central body portion 502 on the other one of its longitudinal ends, and the second transducer beam side portion 508 is disposed generally perpendicular to the side portion 502b of the central body portion 502 and to third transducer beam side portion 510. Similarly, the fourth transducer beam side portion 512 is connected to the third transducer beam side portion 510 on one of its longitudinal ends, and the side portion 502b of the central body portion 502 on the other one of its longitudinal ends, and the fourth transducer beam side portion 512 is disposed generally perpendicular to the side portion 502b of the central body portion 502 and to third transducer beam side portion 510. The third transducer beam side portion 510 is connected to the second transducer beam side portion 508 on one of its longitudinal ends, and the fourth transducer beam side portion 512 on the other one of its longitudinal ends, and the third transducer beam side portion 510 is disposed generally perpendicular to each of the second and fourth transducer beam side portions 508, 512. Also, as shown in FIG. 21, it can be seen that the top surface of the third transducer beam side portion 510 and the top surface of the sixth transducer beam side portion 516 each comprises a central standoff portion 518. The central standoff portions 518 each comprise spaced apart mounting apertures 522 (e.g., two spaced apart apertures 522) disposed therethrough for accommodating fasteners (e.g., screws) that attach the load transducer 500 to another object, such as a robotic arm, etc.

As best shown in the perspective view of FIG. 21, the illustrated load cells are located on the transducer beam side portions 506, 508, 510, 512, 514, 516. In the illustrated embodiment, each load cell comprises one or more strain gages 524, 526, 528. Specifically, in the illustrated embodiment, the first transducer beam side portion 506, the second transducer beam side portion 508, the fourth transducer beam side portion 512, and the fifth transducer beam side portion 514 each comprise a strain gage 524 disposed on the top surface thereof that is sensitive to the vertical force component (i.e., a $F_Z$ strain gage). The third transducer beam side portion 510 and the sixth transducer beam side portion 516 also each comprise a plurality of spaced apart strain gages 526 (e.g., two spaced apart strain gages 526) disposed on a side surface thereof that is sensitive to a first shear force component (i.e., a $F_X$ strain gage). Also, in the illustrated embodiment, the first transducer beam side portion 506, the second transducer beam side portion 508, the fourth transducer beam side portion 512, and the fifth transducer beam side portion 514 each comprises a strain gage 528 disposed on an outer side surface thereof that is sensitive to a second shear force component (i.e., a $F_Y$ strain gage).

Figure 22:
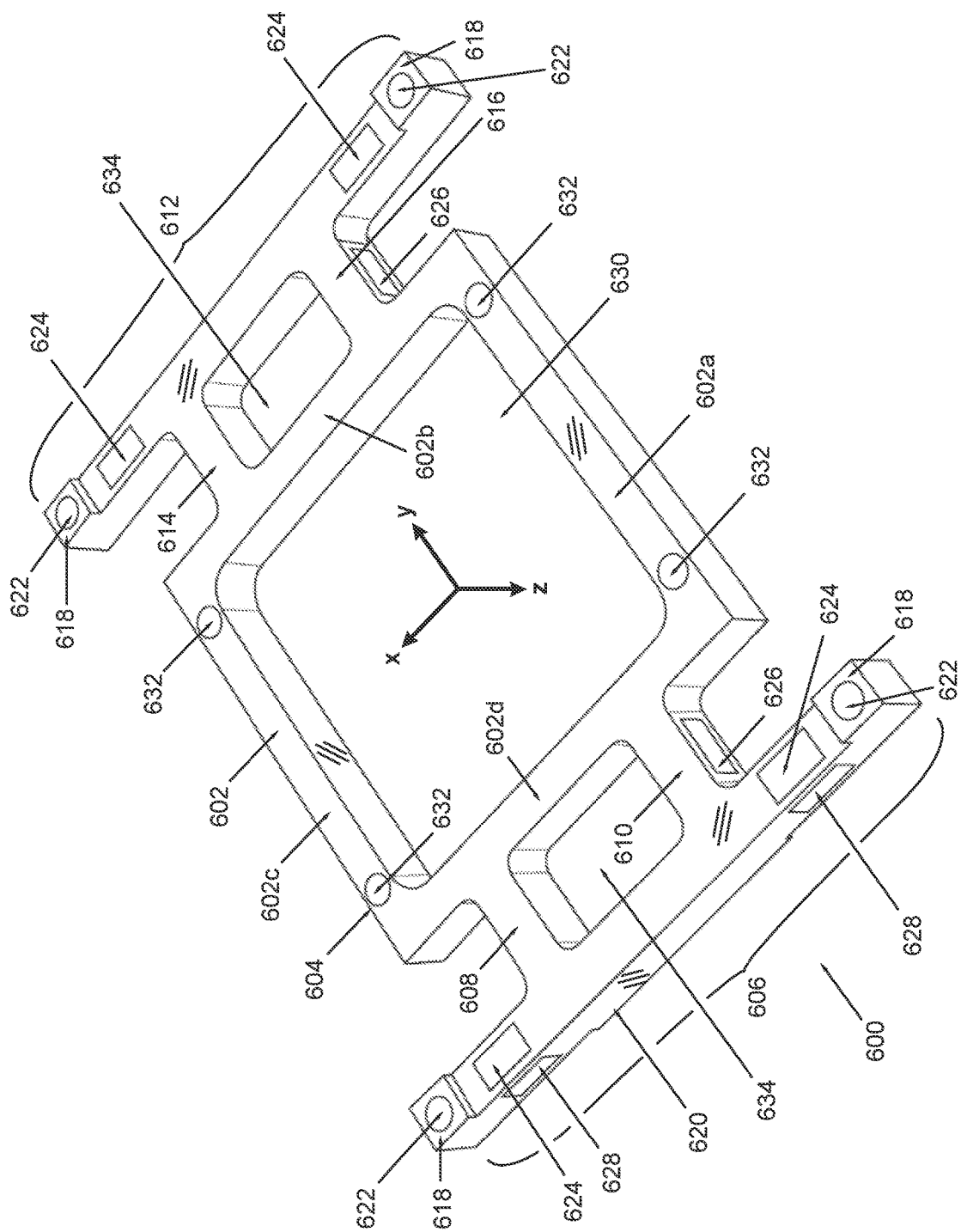
FIG. 22 is a perspective view of a low profile load transducer, according to an eighth embodiment of the invention.

FIG. 22 illustrates a load transducer 600 according to an eighth exemplary embodiment of the present invention. With reference to this figure, it can be seen that, in some respects, the eighth exemplary embodiment is similar to that of the preceding embodiments. Moreover, some parts are common to all of the embodiments. For the sake of brevity, the parts that the eighth embodiment of the load transducer has in common with the preceding embodiments will only be briefly mentioned because these components have already been explained in detail above.

Initially, referring to the perspective view of FIG. 22, it can be seen that, like the preceding embodiments described above, the load transducer 600 generally includes a one-piece compact transducer frame 604 with a central body portion 602 and a plurality of transducer beams 606, 608, 610, 612, 614, 616 connected thereto. Although, the transducer beams 606, 608, 610, 612, 614, 616 are arranged in a different configuration than that which was described for the preceding embodiments.

With reference again to FIG. 22, it can be seen that the illustrated central body portion 602 is generally in the form of square band-shaped element with a central opening 630 disposed therethrough. In FIG. 22, it can be seen that the body portion 602 comprises a first pair of opposed side portions 602a, 602c and a second pair of opposed side portions 602b, 602d. The side portion 602a is disposed generally parallel to the side portion 602c, while the side portion 602b is disposed generally parallel to the side portion 602d. Each of the side surfaces of the side portions 602a, 602b, 602c, 602d is disposed generally perpendicular to the planar top and bottom surfaces thereof. Also, each of the first pair of opposed side portions 602a, 602c is disposed generally perpendicular to each of the second pair of opposed sides portions 602b, 602d. In addition, as shown in FIG. 22, each of the opposed side portions 602b, 602d is connected to a respective set of transducer beams 606, 608, 610 and 612, 614, 616. In the illustrated embodiment, it can be seen that each of the opposed side portions 602a, 602c comprises a plurality of apertures 632 (e.g., two apertures 632) disposed therethrough for accommodating fasteners (e.g., screws) that attach the load transducer 600 to another object, such as a robotic arm, etc.

As shown in FIG. 22, the first set of illustrated transducer beams 606, 608, 610 of the transducer frame 604 is arranged in a generally T-shaped configuration on a first side of the central body portion 602. A first side aperture 634 is formed between the side portion 602d of the central body portion 602 and the first set of transducer beam side portions 606, 608, 610. Referring again to FIG. 22, it can be seen that the first transducer beam 606 is connected to the side portion 602d of the central body portion 602 by means of two spaced apart connecting transducer beams 608, 610. Specifically, the second transducer beam 608 is connected to an inner side of the first transducer beam 606 on one of its longitudinal ends, and the side portion 602d of the central body portion 602 on the other one of its longitudinal ends, and the second transducer beam 608 is disposed generally perpendicular to the side portion 602d of the central body portion 602 and to first transducer beam 606. Similarly, the third transducer beam 610 is connected to the inner side of the first transducer beam 606 on one of its longitudinal ends, and the side portion 602d of the central body portion 602 on the other one of its longitudinal ends, and the third transducer beam 610 is disposed generally perpendicular to the side portion 602d of the central body portion 602 and to first transducer beam 606. Turning again to FIG. 22, it can be seen that the second set of transducer beams 612, 614, 616 of the transducer frame 604 is arranged in a generally T-shaped configuration on a second side of the central body portion 602, which is opposite to the first side of the central body portion 602. A second side aperture 634 is formed between the side portion 602b of the central body portion 602 and the second set of transducer beam side portions 612, 614, 616. In FIG. 22, similar to the first transducer beam 606, it can be seen that the fourth transducer beam 612 is connected to the side portion 602b of the central body portion 602 by means of two spaced apart connecting transducer beams 614, 616. Specifically, the fifth transducer beam 614 is connected to an inner side of the fourth transducer beam 612 on one of its longitudinal ends, and the side portion 602b of the central body portion 602 on the other one of its longitudinal ends, and the fifth transducer beam 614 is disposed generally perpendicular to the side portion 602b of the central body portion 602 and to fourth transducer beam 612. Similarly, the sixth transducer beam 616 is connected to the inner side of the fourth transducer beam 612 on one of its longitudinal ends, and the side portion 602b of the central body portion 602 on the other one of its longitudinal ends, and the sixth transducer beam 616 is disposed generally perpendicular to the side portion 602b of the central body portion 602 and to fourth transducer beam 612. Also, as shown in FIG. 22, it can be seen that the bottom surface of the first transducer beam 606 and the bottom surface of the fourth transducer beam 612 each comprises a central standoff portion 620. In addition, it can be seen that the opposed longitudinal ends of the first transducer beam 606 and the fourth transducer beam 612 are each provided with raised standoff portions 618. Each raised standoff portion 618 is provided with a mounting aperture 622 disposed therethrough for accommodating a respective fastener (e.g., a screw) that attaches the load transducer 600 to another object, such as a robotic arm, etc.

As best shown in the perspective view of FIG. 22, the illustrated load cells are located on the transducer beams 606, 608, 610, 612, 614, 616. In the illustrated embodiment, each load cell comprises one or more strain gages 624, 626, 628. Specifically, in the illustrated embodiment, the first transducer beam 606 and the fourth transducer beam 612 each comprise a pair of spaced apart strain gages 624 disposed on the top surfaces thereof that are sensitive to the vertical force component (i.e., $F_Z$ strain gages). In FIG. 22, it can be seen that each of the strain gages 624 is disposed near the raised standoff portions 618 at the opposed ends of the beams 606, 612. Also, in the illustrated embodiment, the second transducer beam 608, the third transducer beam 610, the fifth transducer beam 614, and the sixth transducer beam 616 each comprise a strain gage 626 disposed on an outer side surface thereof that is sensitive to a first shear force component (i.e., a $F_X$ strain gage). The first transducer beam 606 and the fourth transducer beam 612 also each comprise a plurality of spaced apart strain gages 628 (e.g., two spaced apart strain gages 628) disposed on an outer side surface thereof that is sensitive to a second shear force component (i.e., a $F_Y$ strain gage).

Figure 23:
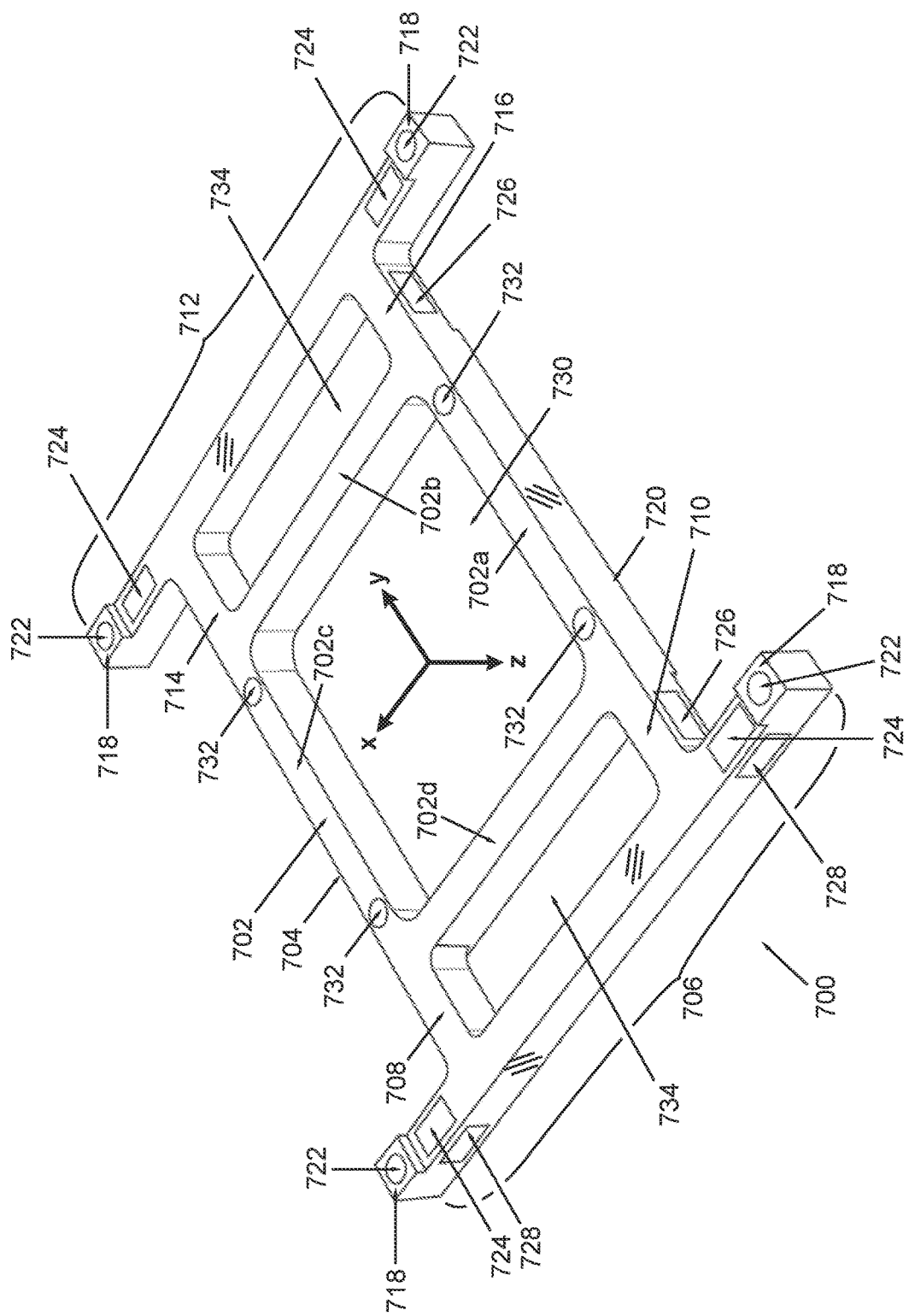
FIG. 23 is a perspective view of a low profile load transducer, according to a ninth embodiment of the invention.

FIG. 23 illustrates a load transducer 700 according to a ninth exemplary embodiment of the present invention. With reference to this figure, it can be seen that, in some respects, the ninth exemplary embodiment is similar to that of the eighth embodiment. Moreover, some parts are common to all of the embodiments. For the sake of brevity, the parts that the ninth embodiment of the load transducer has in common with the eighth embodiment will only be briefly mentioned because these components have already been explained in detail above.

Initially, referring to the perspective view of FIG. 23, it can be seen that, like the eighth embodiment described above, the load transducer 700 generally includes a one-piece compact transducer frame 704 with a central body portion 702 and a plurality of transducer beams 706, 708, 710, 712, 714, 716 connected thereto. Although, each of connecting transducer beams 708, 710, and each of connecting transducer beams 714, 716, are spaced considerably further apart from one another as compared to the connecting transducer beams 608, 610, 614, 616 of the load transducer 600 such that the connecting beams 708, 710, 714, 716 are generally axially aligned with the side portions 702a, 702c of the central body portion 702.

With reference again to FIG. 23, it can be seen that the illustrated central body portion 702 is generally in the form of square band-shaped element with a central opening 730 disposed therethrough. In FIG. 23, it can be seen that the body portion 702 comprises a first pair of opposed side portions 702a, 702c and a second pair of opposed side portions 702b, 702d. The side portion 702a is disposed generally parallel to the side portion 702c, while the side portion 702b is disposed generally parallel to the side portion 702d. Each of the side surfaces of the side portions 702a, 702b, 702c, 702d is disposed generally perpendicular to the planar top and bottom surfaces thereof. Also, each of the first pair of opposed side portions 702a, 702c is disposed generally perpendicular to each of the second pair of opposed sides portions 702b, 702d. In addition, as shown in FIG. 23, each of the opposed side portions 702b, 702d is connected to a respective set of transducer beams 706, 708, 710 and 712, 714, 716. In the illustrated embodiment, it can be seen that each of the opposed side portions 702a, 702c comprises a plurality of apertures 732 (e.g., two apertures 732) disposed therethrough for accommodating fasteners (e.g., screws) that attach the load transducer 700 to another object, such as a robotic arm, etc. Also, as depicted in the FIG. 23, the central body portion 702 comprises a raised bottom portion or bottom standoff portion 720 for spacing the transducer beams 706, 708, 710, 712, 714, 716 apart from an object (e.g., robotic arm) to which the load transducer 700 is attached so that forces and/or moments are capable of being accurately measured by the load transducer 700.

As shown in FIG. 23, the first set of illustrated transducer beams 706, 708, 710 of the transducer frame 704 is arranged in a generally T-shaped configuration on a first side of the central body portion 702 (with the wide base of the T-shaped arrangement being formed by the connecting beam transducers 708, 710). A first side aperture 734 is formed between the side portion 702d of the central body portion 702 and the first set of transducer beam side portions 706, 708, 710. Referring again to FIG. 23, it can be seen that the first transducer beam 706 is connected to the side portion 702d of the central body portion 702 by means of two spaced apart connecting transducer beams 708, 710. Specifically, the second transducer beam 708 is connected to an inner side of the first transducer beam 706 on one of its longitudinal ends, and the side portion 702d of the central body portion 702 on the other one of its longitudinal ends, and the second transducer beam 708 is disposed generally perpendicular to the side portion 702d of the central body portion 702 and to first transducer beam 706. Similarly, the third transducer beam 710 is connected to the inner side of the first transducer beam 706 on one of its longitudinal ends, and the side portion 702d of the central body portion 702 on the other one of its longitudinal ends, and the third transducer beam 710 is disposed generally perpendicular to the side portion 702d of the central body portion 702 and to first transducer beam 706. Turning again to FIG. 23, it can be seen that the second set of transducer beams 712, 714, 716 of the transducer frame 704 is arranged in a generally T-shaped configuration on a second side of the central body portion 702, which is opposite to the first side of the central body portion 702 (with the wide base of the T-shaped arrangement being formed by the connecting beam transducers 714, 716). A second side aperture 734 is formed between the side portion 702b of the central body portion 702 and the second set of transducer beam side portions 712, 714, 716. In FIG. 23, similar to the first transducer beam 706, it can be seen that the fourth transducer beam 712 is connected to the side portion 702b of the central body portion 702 by means of two spaced apart connecting transducer beams 714, 716. Specifically, the fifth transducer beam 714 is connected to an inner side of the fourth transducer beam 712 on one of its longitudinal ends, and the side portion 702b of the central body portion 702 on the other one of its longitudinal ends, and the fifth transducer beam 714 is disposed generally perpendicular to the side portion 702b of the central body portion 702 and to fourth transducer beam 712. Similarly, the sixth transducer beam 716 is connected to the inner side of the fourth transducer beam 712 on one of its longitudinal ends, and the side portion 702b of the central body portion 702 on the other one of its longitudinal ends, and the sixth transducer beam 716 is disposed generally perpendicular to the side portion 702b of the central body portion 702 and to fourth transducer beam 712. Also, in FIG. 23, it can be seen that the opposed longitudinal ends of the first transducer beam 706 and the fourth transducer beam 712 are each provided with raised standoff portions 718. Each raised standoff portion 718 is provided with a mounting aperture 722 disposed therethrough for accommodating a respective fastener (e.g., a screw) that attaches the load transducer 700 to another object, such as a robotic arm, etc.

As best shown in the perspective view of FIG. 23, the illustrated load cells are located on the transducer beams 706, 708, 710, 712, 714, 716. In the illustrated embodiment, each load cell comprises one or more strain gages 724, 726, 728. Specifically, in the illustrated embodiment, the first transducer beam 706 and the fourth transducer beam 712 each comprise a pair of spaced apart strain gages 724 disposed on the top surfaces thereof that are sensitive to the vertical force component (i.e., $F_Z$ strain gages). In FIG. 23, it can be seen that each of the strain gages 724 is disposed near the raised standoff portions 718 at the opposed ends of the beams 706, 712. Also, in the illustrated embodiment, the second transducer beam 708, the third transducer beam 710, the fifth transducer beam 714, and the sixth transducer beam 716 each comprise a strain gage 726 disposed on an outer side surface thereof that is sensitive to a first shear force component (i.e., a $F_X$ strain gage). The first transducer beam 706 and the fourth transducer beam 712 also each comprise a plurality of spaced apart strain gages 728 (e.g., two spaced apart strain gages 728) disposed on an outer side surface thereof that is sensitive to a second shear force component (i.e., a $F_Y$ strain gage).

Figure 24:
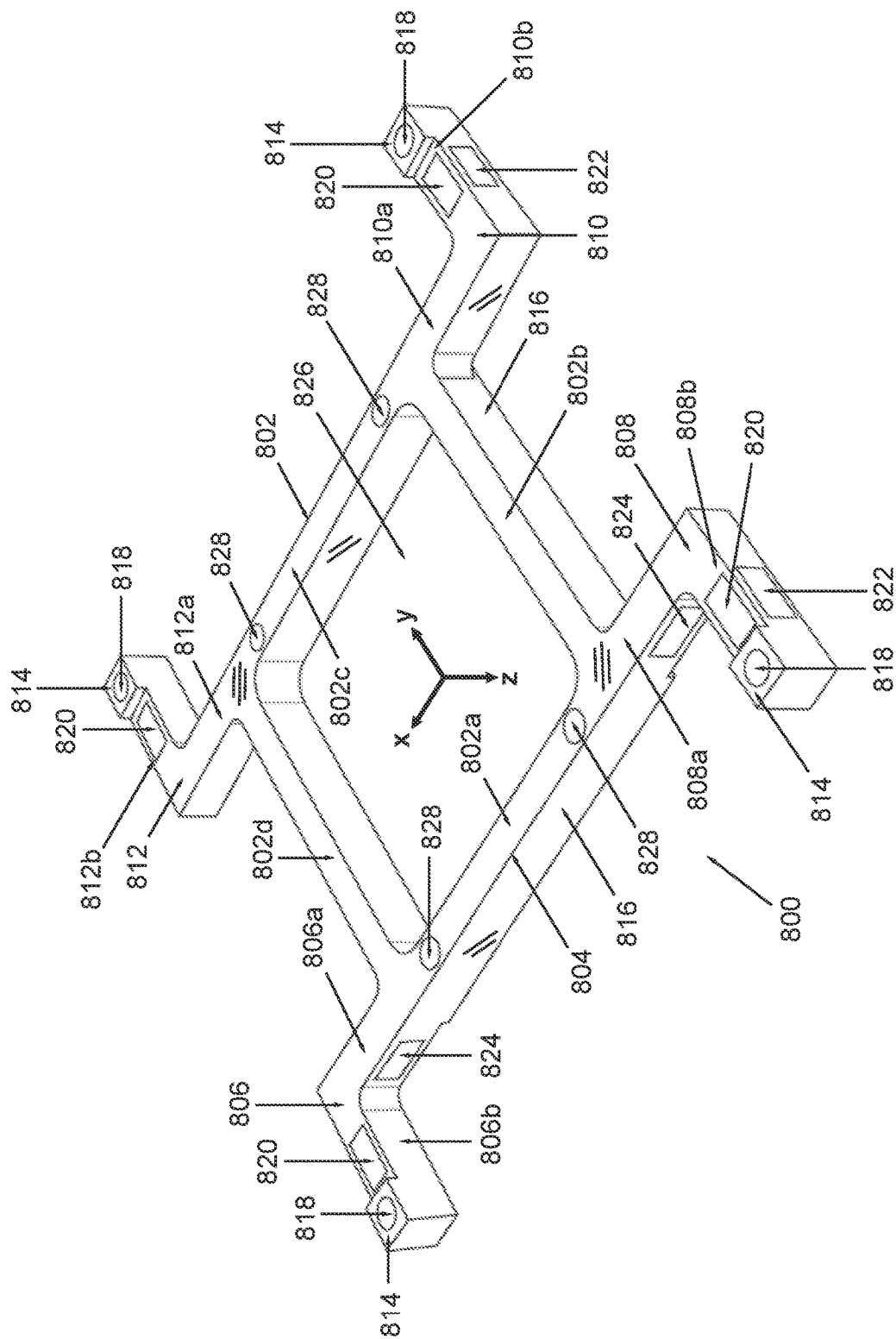
FIG. 24 is a perspective view of a low profile load transducer, according to a tenth embodiment of the invention.

FIG. 24 illustrates a load transducer 800 according to a tenth exemplary embodiment of the present invention. With reference to this figure, it can be seen that, in some respects, the tenth exemplary embodiment is similar to that of the preceding embodiments. Moreover, some parts are common to all of the embodiments. For the sake of brevity, the parts that the tenth embodiment of the load transducer has in common with the preceding embodiments will only be briefly mentioned because these components have already been explained in detail above.

Initially, referring to the perspective view of FIG. 24, it can be seen that the load transducer 800 generally includes a one-piece compact transducer frame 804 with a central body portion 802 and a plurality of L-shaped transducer beams 806, 808, 810, 812 connected thereto. As shown in FIG. 24, each of the L-shaped transducer beams 806, 808, 810, 812 is generally disposed at a respective corner of the central body portion 802.

With reference again to FIG. 24, it can be seen that the illustrated central body portion 802 is generally in the form of square band-shaped element with a central opening 826 disposed therethrough. In FIG. 24, it can be seen that the body portion 802 comprises a first pair of opposed side portions 802a, 802c and a second pair of opposed side portions 802b, 802d. The side portion 802a is disposed generally parallel to the side portion 802c, while the side portion 802b is disposed generally parallel to the side portion 802d. Each of the side surfaces of the side portions 802a, 802b, 802c, 802d is disposed generally perpendicular to the planar top and bottom surfaces thereof. Also, each of the first pair of opposed side portions 802a, 802c is disposed generally perpendicular to each of the second pair of opposed sides portions 802b, 802d. In addition, as shown in FIG. 24, each of the corners of the central body portion 802 is connected to a respective L-shaped transducer beam 806, 808, 810, 812. In the illustrated embodiment, it can be seen that each of the opposed side portions 802a, 802c comprises a plurality of apertures 828 (e.g., two apertures 828) disposed therethrough for accommodating fasteners (e.g., screws) that attach the load transducer 800 to another object, such as a robotic arm, etc. Also, as depicted in the FIG. 24, the central body portion 802 comprises a raised bottom portion or bottom standoff portion 816 for spacing the L-shaped transducer beams 806, 808, 810, 812 apart from an object (e.g., robotic arm) to which the load transducer 800 is attached so that forces and/or moments are capable of being accurately measured by the load transducer 800.

As shown in FIG. 24, the first generally L-shaped transducer beam 806 comprises a first beam portion 806a and a second beam portion 806b, wherein the first beam portion 806a is disposed generally perpendicular to the second beam portion 806b. Similarly, the second generally L-shaped transducer beam 808 comprises a first beam portion 808a and a second beam portion 808b, wherein the first beam portion 808a is disposed generally perpendicular to the second beam portion 808b. Also, it can be seen in FIG. 24 that the first beam portion 806a of the first generally L-shaped transducer beam 806 and the first beam portion 808a of the second generally L-shaped transducer beam 808 are both generally axially aligned with the side portion 802a of the central body portion 802 (i.e., the longitudinal axes of the beam portions 806a, 808a are generally aligned with the longitudinal axis of the side portion 802a). With reference again to FIG. 24, the third generally L-shaped transducer beam 810 comprises a first beam portion 810a and a second beam portion 810b, wherein the first beam portion 810a is disposed generally perpendicular to the second beam portion 810b. Similarly, the fourth generally L-shaped transducer beam 812 comprises a first beam portion 812a and a second beam portion 812b, wherein the first beam portion 812a is disposed generally perpendicular to the second beam portion 812b. Also, it can be seen in FIG. 24 that the first beam portion 810a of the third generally L-shaped transducer beam 810 and the first beam portion 812a of the fourth generally L-shaped transducer beam 812 are both generally axially aligned with the side portion 802c of the central body portion 802 (i.e., the longitudinal axes of the beam portions 810a, 812a are generally aligned with the longitudinal axis of the side portion 802c). Also, in FIG. 24, it can be seen that the free ends of the second beam portions 806b, 808b, 810b, 812b of the L-shaped transducer beams 806, 808, 810, 812 are each provided with raised standoff portions 814. Each raised standoff portion 814 is provided with a mounting aperture 818 disposed therethrough for accommodating a respective fastener (e.g., a screw) that attaches the load transducer 800 to another object, such as a robotic arm, etc.

As best shown in the perspective view of FIG. 24, the illustrated load cells are located on the L-shaped transducer beams 806, 808, 810, 812. In the illustrated embodiment, each load cell comprises one or more strain gages 820, 822, 824. Specifically, in the illustrated embodiment, the second beam portions 806b, 808b, 810b, 812b of the L-shaped transducer beams 806, 808, 810, 812 are each provided with a strain gage 820 disposed on the top surface thereof that is sensitive to the vertical force component (i.e., an $F_Z$ strain gage). In FIG. 24, it can be seen that each of the strain gages 820 is disposed near the raised standoff portions 818 of the second beam portions 806b, 808b, 810b, 812b. Also, in the illustrated embodiment, the second beam portions 806b, 808b, 810b, 812b of the L-shaped transducer beams 806, 808, 810, 812 each comprise a strain gage 822 disposed on an outer side surface thereof that is sensitive to a first shear force component (i.e., a $F_X$ strain gage). The first beam portions 806a, 808a, 810a, 812a of the L-shaped transducer beams 806, 808, 810, 812 each comprise a strain gage 824 disposed on an outer side surface thereof that is sensitive to a second shear force component (i.e., a $F_Y$ strain gage).

In the illustrated embodiments of the present invention, the transducer beams do not extend from a top or upper surface of the central body portion. As such, there is no gap formed between the top or upper surface of the central body portion and a bottom or lower surface of one or more of the transducer beams. Rather, in the exemplary embodiments comprising a central body portion, the transducer beams extend outwardly from a side or lateral surface of the central body portion so as to minimize the overall height of the transducer profile (i.e., because the transducer beams are not required to be disposed above the central body portion). Also, in the illustrated embodiments discussed above, the transducer beams are not in the form of generally linear beams, and are not in the form of generally linear beams with generally symmetrical end portions. Rather, the transducer beams of the exemplary embodiments generally either emanate from a central body portion and have only one cantilevered end or are arranged in a continuous band-like configuration. In addition, it can be seen that, except for the top and bottom standoff portions on either the transducer beams or the central body portions, the top and bottom surfaces of the transducer beams of the exemplary embodiments are generally co-planar with the respective top and bottom surfaces of the central body portion. Similarly, in the exemplary embodiments having a band-like configuration of transducer beams, the top surfaces of each of the looped transducer beams are generally co-planar with one another, while the bottom surfaces of each of the looped transducer beams are also generally co-planar with one another.

FIGS. 26-29 illustrate a load transducer 900 according to an eleventh exemplary embodiment of the present invention. Referring initially to the top perspective view of FIG. 26, it can be seen that the load transducer 900 generally includes a one-piece compact transducer frame 902 having a plurality of transducer beam portions 904, 906, 908, 910, 912 connected to one another in succession. As best shown in the perspective views of FIGS. 26 and 29, the plurality of transducer beam portions 904, 906, 908, 910, 912 are arranged in a circumscribing pattern whereby a central one of the plurality of transducer beam portions (i.e., transducer beam portion 904) is at least partially circumscribed by one or more outer ones of the plurality of beam portions (i.e., transducer beam portions 906, 908, 910, 912). In other words, the plurality of transducer beam portions 904, 906, 908, 910, 912 forming the load transducer 900 are arranged in a looped configuration whereby a central one of the plurality of beam portions (i.e., transducer beam portion 904) emanates from a generally central location within a footprint of the load transducer 900 and outer ones of the plurality of beam portions (i.e., transducer beam portions 906, 908, 910, 912) are wrapped around the central one of the plurality of beam portions. As best illustrated in the perspective views of FIGS. 26 and 29, each of the beam portions 908, 910, 912 comprise one or more load cells or transducer elements for measuring forces and/or moments.

Figure 26:
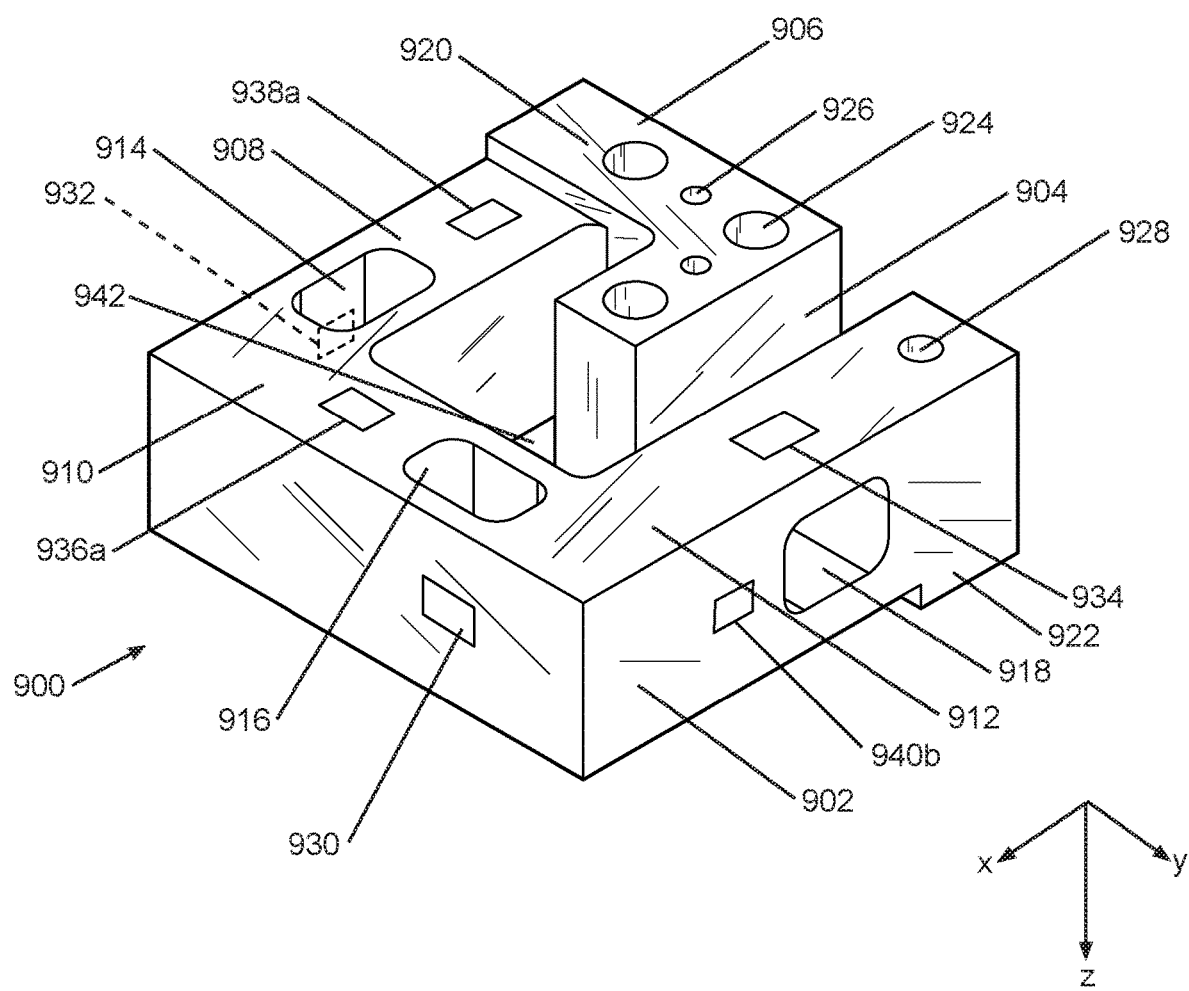
FIG. 26 is a top perspective view of a load transducer, according to an eleventh embodiment of the invention.
Figure 27:
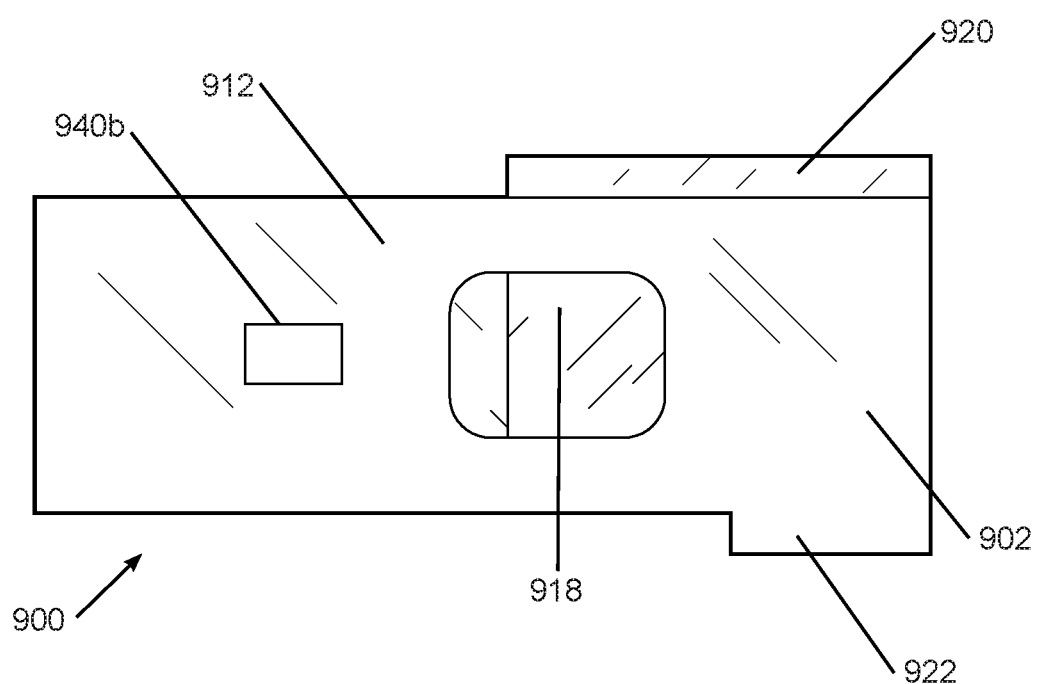
FIG. 27 is a first side view of the load transducer of FIG. 26, according to the eleventh embodiment of the invention.
Figure 28:
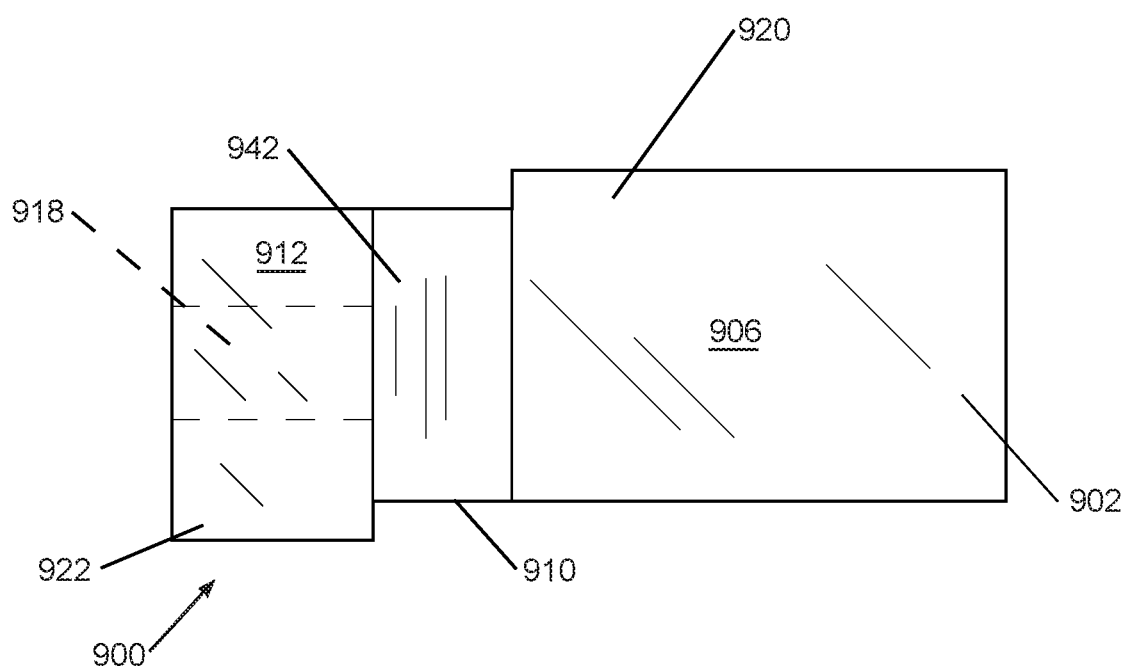
FIG. 28 is a second side view of the load transducer of FIG. 26, according to the eleventh embodiment of the invention.
Figure 29:
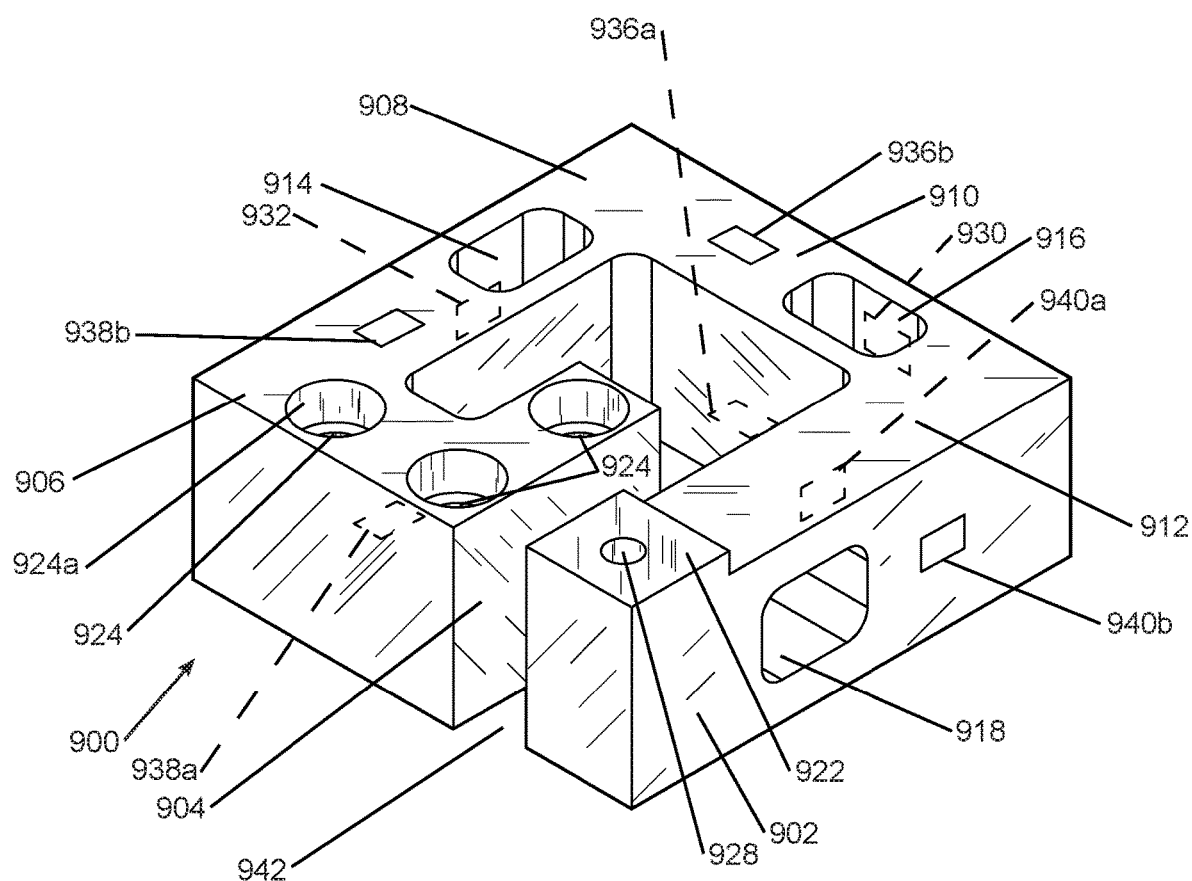
FIG. 29 is a bottom perspective view of the load transducer of FIG. 26, according to the eleventh embodiment of the invention.

As shown in FIGS. 26-29, the illustrated transducer beam portions 904, 906, 908, 910, 912 are arranged in a generally spiral-shaped pattern that emanates from the centrally located transducer beam portion 904. The pattern in which the transducer beam portions 904, 906, 908, 910, 912 are arranged is also generally G-shaped (refer to FIGS. 26 and 29). With particular reference to the perspective views of FIGS. 26 and 29, it can be seen that the transducer beam portions 904, 906, 908, 910, 912 of the load transducer 900 are arranged in such a configuration that each of the successive transducer beam portions are disposed substantially perpendicular to the immediately preceding transducer beam portion. For example, referring to FIG. 26, the first transducer beam portion 904 is disposed at the approximate center of the transducer footprint, the second transducer beam portion 906 is connected to the first transducer beam portion 904 and is disposed substantially perpendicular thereto, the third transducer beam portion 908 is connected to the second transducer beam portion 906 and is disposed substantially perpendicular thereto, the fourth transducer beam portion 910 is connected to the third transducer beam portion 908 and is disposed substantially perpendicular thereto, and the fifth transducer beam portion 912 is connected to the fourth transducer beam portion 910 and is disposed substantially perpendicular thereto. In FIGS. 26 and 29, it can be seen that the transducer beam portions 904, 906, 908, 910, 912 of the load transducer 900 are spaced apart from one another by a generally U-shaped, central gap 942, which is bounded by each of the transducer beam portions 904, 906, 908, 910, 912. In particular, the first transducer beam portion 904 and the third transducer beam portion 908, which are disposed generally parallel to one another, are laterally spaced apart by the gap 942. Similarly, the second transducer beam portion 906 and the fourth transducer beam portion 910, which are disposed generally parallel to one another, are laterally spaced apart by the gap 942. Also, the first transducer beam portion 904 and the fifth transducer beam portion 912, which are disposed generally parallel to one another, are laterally spaced apart by the gap 942. The third transducer beam portion 908 and the fifth transducer beam portion 912, which are disposed generally parallel to one another, are laterally spaced apart by the gap 942 and a segment of the first transducer beam portion 904.

Referring again to the top perspective view of FIG. 26, it can be seen that the first and second transducer beam portions 904, 906 of the load transducer 900 together comprise an L-shaped raised portion or standoff portion 920 with mounting apertures 924 (e.g., three apertures 924) disposed therethrough for accommodating fasteners (e.g., screws) that attach the load transducer 900 to another object, such as a plate component of a force plate or force measurement assembly. The mounting apertures 924 pass completely through the first and second transducer beam portions 904, 906, and are provided with respective bottom bore portions 924a of increased diameter (see FIG. 29) in order to accommodate fasteners (e.g., screws) with fillister heads that have a larger outer diameter than the threaded portions of the fasteners. In addition, with reference again to FIG. 26, it can be seen that the elevated L-shaped top surface of the first and second transducer beam portions 904, 906 is provided with pin locating bores 926 (e.g., two bores 926) formed therein for receiving locating pins that ensure the proper positioning of the load transducer 900 on the object to which it is mounted, such as a plate component of a force plate or force measurement assembly. The locating pins are received within the pin locating bores 926 on the load transducer 900 and within corresponding pin locating bores provided on the object (e.g., the force plate or force measurement assembly). As depicted in the bottom perspective view of FIG. 29, the fifth transducer beam portion 912 of the load transducer 900 comprises a generally rectangular or square raised portion or standoff portion 922 with a mounting aperture 928 (e.g., a single aperture 928) disposed therethrough for accommodating a fastener (e.g., a screw) that attaches the load transducer 900 to another object, such as a mounting foot of a force plate or force measurement assembly. Advantageously, the standoff portions 920, 922 on the top and bottom of the load transducer 900 elevate the transducer beam portions 904, 906, 908, 910, 912 above the object(s) to which the load transducer 900 is attached so that forces and/or moments are capable of being accurately measured by the load transducer 900. In one or more embodiments, the structural components to which the load transducer 900 is mounted are connected only to the top standoff portion 920 and the bottom standoff 922 so as to ensure that the total load applied to the load transducer 900 is transmitted through the transducer beam portions 904, 906, 908, 910, 912.

In the illustrative embodiment, the third, fourth, and fifth transducer beam portions 908, 910, 912 have a top surface that is disposed at a first elevation relative to a bottom surface of the load transducer 900, whereas the L-shaped raised portion 920 of the first and second transducer beam portions 904, 906 has a top surface that is disposed at a second elevation relative to the bottom surface of the load transducer 900. As best shown in FIGS. 26-28, the second elevation is greater than the first elevation such that a recessed area is created by the difference in elevation between the second elevation and the first elevation. In the illustrated embodiment, the recessed area is used to accommodate electrical components of the transducer load cells (e.g., strain gages 934, 936a, 938a).

In the illustrative embodiment of FIGS. 26-29, each of the transducer beam portions 908, 910, 912 is provided with a respective aperture 914, 916, 918 disposed therethrough. In particular, the third transducer beam portion 908 is provided with a generally rectangular aperture 914 disposed vertically through the beam portion. Similarly, the fourth transducer beam portion 910 is provided with a generally rectangular aperture 916 disposed vertically through the beam portion. The fifth transducer beam portion 912 is provided with a generally rectangular aperture 918 disposed horizontally through the beam portion. The apertures 914, 916, 918, which are disposed through the respective transducer beam portions 908, 910, 912, significantly increase the sensitivity of the load transducer 900 when a load is applied thereto by reducing the cross-sectional area of the transducer beam portions 908, 910, 912 at the locations of the apertures 914, 916, 918.

As best shown in the perspective views of FIGS. 26 and 29, the illustrated load cells are located on the transducer beam portions 908, 910, 912. In the illustrated embodiment, each load cell comprises one or more strain gages 930, 932, 934, 936a, 936b, 938a, 938b, 940a, and 940b. Specifically, in the illustrated embodiment, the third transducer beam portion 908 of the load transducer 900 comprises a strain gage 932 disposed on a side surface thereof that is sensitive to a first shear force component (i.e., a $F_Y$ strain gage) and substantially centered on the aperture 914. The third transducer beam portion 908 also comprises a set of strain gages 938a, 938b that are sensitive to a first moment component (i.e., a $M_Y$ strain gages). The strain gages 938a, 938b are disposed on opposed side surfaces (e.g., top and bottom surfaces) of the third transducer beam portion 908, and are substantially vertically aligned with one another. Turning again to FIGS. 26 and 29, in the illustrated embodiment, the fourth transducer beam portion 910 of the load transducer 900 comprises a strain gage 930 disposed on a side surface thereof that is sensitive to a second shear force component (i.e., a $F_X$ strain gage) and substantially centered on the aperture 916. The fourth transducer beam portion 910 also comprises a set of strain gages 936a, 936b that are sensitive to a second moment component (i.e., a $M_X$ strain gages). Like the strain gages 938a, 938b, the strain gages 936a, 936b are disposed on opposed side surfaces (e.g., top and bottom surfaces) of the fourth transducer beam portion 910, and are substantially vertically aligned with one another. With reference again to FIGS. 26 and 29, in the illustrated embodiment, the fifth transducer beam portion 912 of the load transducer 900 comprises a strain gage 934 disposed on the top surface thereof that is sensitive to a vertical force component (i.e., a $F_Z$ strain gage) and substantially centered on the aperture 918. The fifth transducer beam portion 912 also comprises a set of strain gages 940a, 940b that are sensitive to a third moment component (i.e., a $M_Z$ strain gages). Like the strain gages 936a, 936b and 938a, 938b, the strain gages 940a, 940b are disposed on opposed side surfaces (e.g., first and second lateral surfaces) of the fifth transducer beam portion 912, and are substantially horizontally aligned with one another. In the illustrated embodiment, the first shear force component is generally perpendicular to the second shear force component, and each of the first and second shear force components are generally perpendicular to the vertical force component.

In the illustrated embodiment, the strain gages 930, 932, 934 are disposed on respective outer surfaces of the transducer beam portions 910, 908, 912. The outer surfaces of the transducer beam portions 910, 908, 912 on which the strain gages 930, 932, 934 are disposed are generally opposite to the inner surfaces of the respective apertures 916, 914, 918.

As best shown in FIGS. 26 and 29, the illustrated load cells are mounted on top, bottom, or side surfaces of the transducer beam portions 908, 910, 912 between the standoff portions 920, 922 of the load transducer 900. Alternatively, the strain gages 932, 930 can be mounted to the inner side surfaces of the respective third and fourth transducer beam portions 908, 910, rather than to the outer side surfaces of the respective third and fourth transducer beam portions 908, 910 as illustrated in FIGS. 26 and 29. Similarly, the strain gage 934 can be mounted to the bottom surface of the fifth transducer beam portion 912, rather than to the top of the transducer beam portion 912 as illustrated in FIG. 26. In general, the strain gages 930, 932, 934 are mounted to surfaces generally normal to the direction of applied vertical and/or shear forces (i.e., $F_X$, $F_Y$, $F_Z$). It is also noted that alternatively, strain gages 930 can be mounted at both opposed side surfaces of fourth transducer beam portion 910 and/or strain gages 932 can be mounted at both opposed side surfaces of the third transducer beam portion 908. Similarly, strain gages 934 can be mounted at both the top surface and the bottom surface of the fifth transducer beam portion 912. These strain gages 930, 932, 934 measure force either by bending moment or difference of bending moments at two cross sections. As force is applied to the ends of the load transducer 900, the transducer beam portions bend. This bending either stretches or compresses the strain gages 930, 932, 934, which in turn changes the resistance of the electrical current passing therethrough. The amount of change in the electrical voltage or current is proportional to the magnitude of the applied force, as applied to the L-shaped standoff portion 920.

In the illustrated embodiment, each of the strain gages 930, 932, 934 comprises a full-bridge strain gage configuration (i.e., four (4) active strain gage elements wired in a Wheatstone bridge configuration), while each of the strain gages 936a, 936b, 938a, 938b, 940a, and 940b comprises a half-bridge strain gage configuration (i.e., two (2) active strain gage elements). Also, in the illustrative embodiment, the pair of strain gages 936a, 936b are wired together in one Wheatstone bridge configuration (i.e., with a total of four (4) active strain gage elements), the pair of strain gages 938a, 938b are wired together in another Wheatstone bridge configuration (i.e., with a total of four (4) active strain gage elements), and the pair of strain gages 940a, 940b are wired together in yet another Wheatstone bridge configuration (i.e., with a total of four (4) active strain gage elements).

FIGS. 30-33 illustrate a load transducer 1000 according to a twelfth exemplary embodiment of the present invention. With reference to these figures, it can be seen that the load transducer 1000 is similar in many respects to the load transducer 900 of the eleventh embodiment described above. However, unlike the aforedescribed load transducer 900, the load transducer 1000 only measures the force components of a load (i.e., $F_X$, $F_Y$, $F_Z$), rather than both the force and moment components of a load as explained above with regard to the load transducer 1000.

Figure 30:
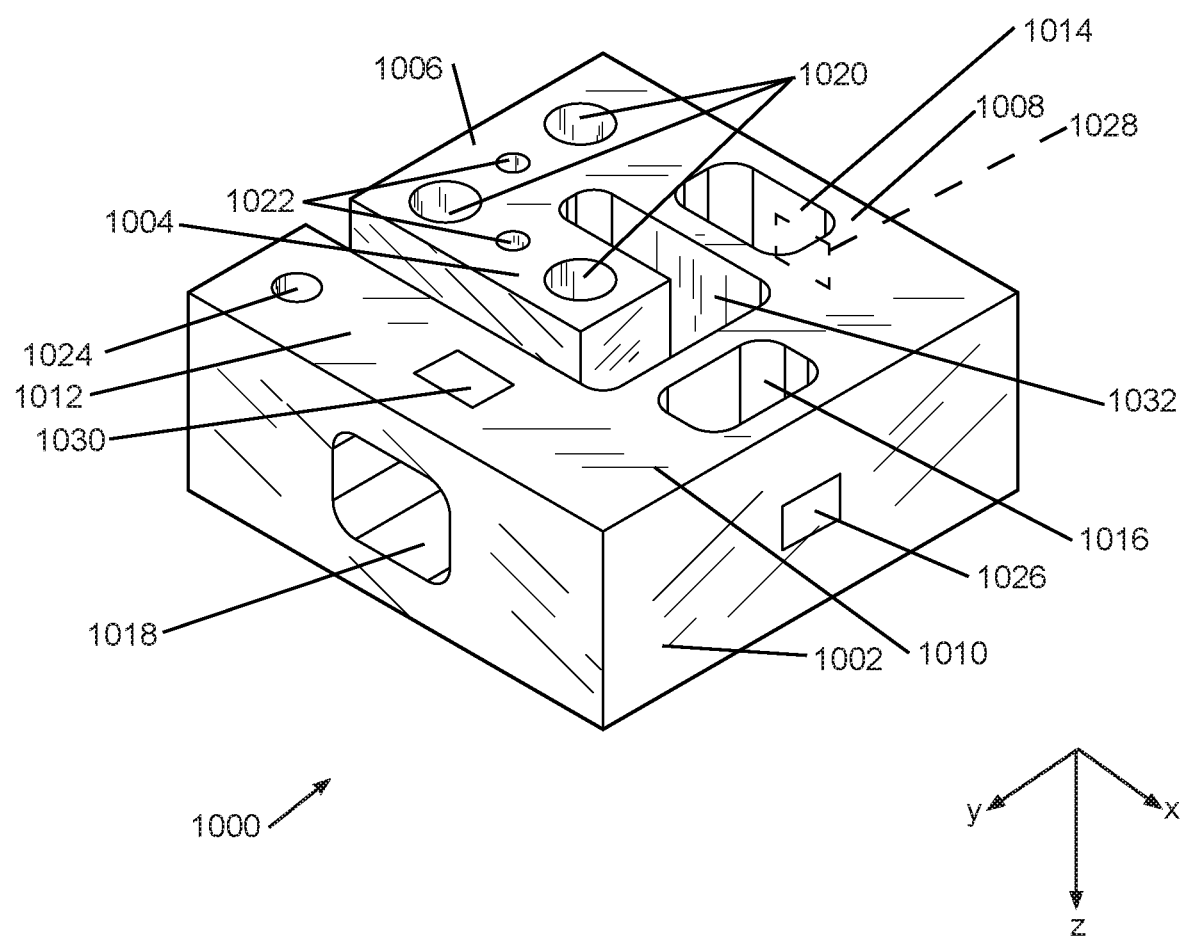
FIG. 30 is a top perspective view of a load transducer, according to a twelfth embodiment of the invention.
Figure 31:
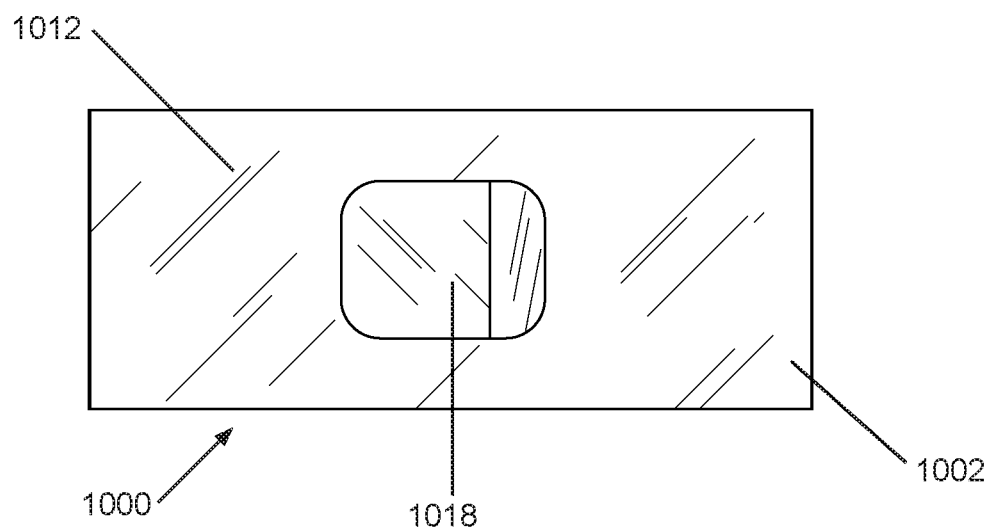
FIG. 31 is a first side view of the load transducer of FIG. 30, according to the twelfth embodiment of the invention.
Figure 32:
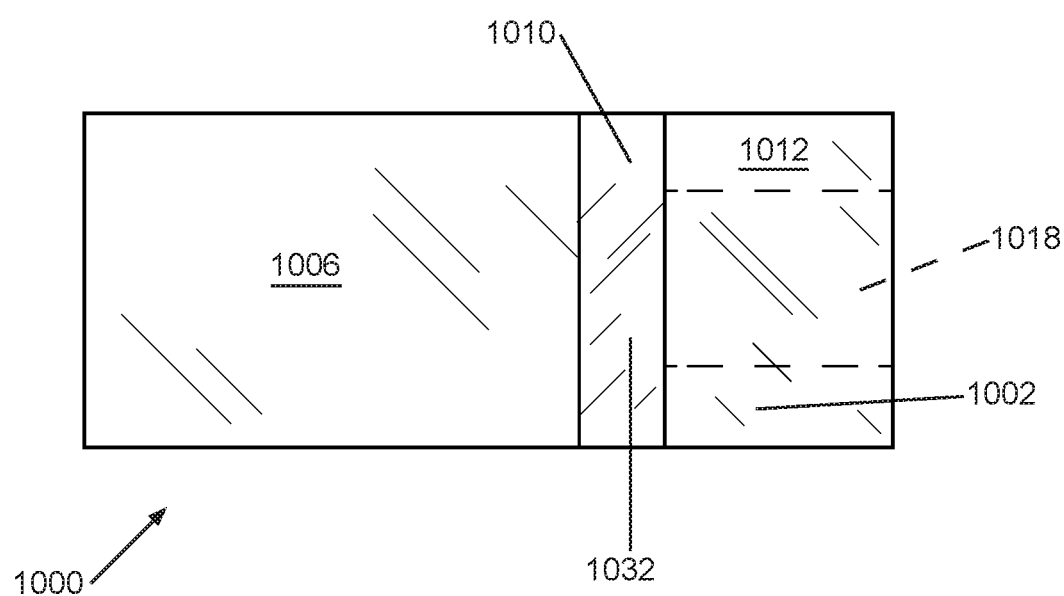
FIG. 32 is a second side view of the load transducer of FIG. 30, according to the twelfth embodiment of the invention.

Initially, referring to the top perspective view of FIG. 30, it can be seen that the load transducer 1000 generally includes a one-piece compact transducer frame 1002 having a plurality of transducer beam portions 1004, 1006, 1008, 1010, 1012 connected to one another in succession. As best shown in the perspective views of FIGS. 30 and 33, the plurality of transducer beam portions 1004, 1006, 1008, 1010, 1012 are arranged in a circumscribing pattern whereby a central one of the plurality of transducer beam portions (i.e., transducer beam portion 1004) is at least partially circumscribed by one or more outer ones of the plurality of beam portions (i.e., transducer beam portions 1006, 1008, 1010, 1012). In other words, the plurality of transducer beam portions 1004, 1006, 1008, 1010, 1012 forming the load transducer 1000 are arranged in a looped configuration whereby a central one of the plurality of beam portions (i.e., transducer beam portion 1004) emanates from a generally central location within a footprint of the load transducer 1000 and outer ones of the plurality of beam portions (i.e., transducer beam portions 1006, 1008, 1010, 1012) are wrapped around the central one of the plurality of beam portions. As best illustrated in the perspective views of FIGS. 30 and 33, each of the beam portions 1008, 1010, 1012 comprise one or more load cells or transducer elements for measuring the various components of an applied force.

Figure 33:
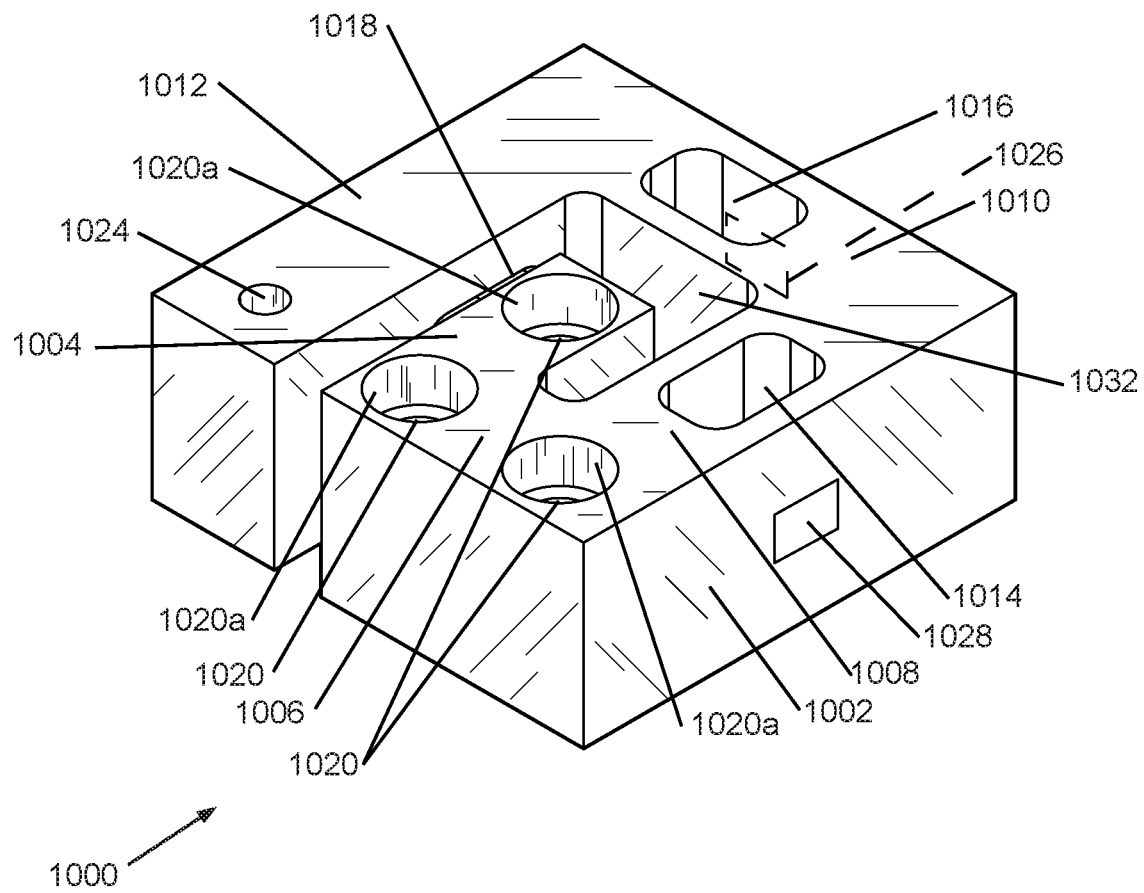
FIG. 33 is a bottom perspective view of the load transducer of FIG. 30, according to the twelfth embodiment of the invention.

As shown in FIGS. 30-33, the illustrated transducer beam portions 1004, 1006, 1008, 1010, 1012 are arranged in a generally spiral-shaped pattern that emanates from the centrally located transducer beam portion 1004. The pattern in which the transducer beam portions 1004, 1006, 1008, 1010, 1012 are arranged is also generally G-shaped (refer to FIGS. 30 and 33). With particular reference to the perspective views of FIGS. 30 and 33, it can be seen that the transducer beam portions 1004, 1006, 1008, 1010, 1012 of the load transducer 1000 are arranged in such a configuration that each of the successive transducer beam portions are disposed substantially perpendicular to the immediately preceding transducer beam portion. For example, referring to FIG. 30, the first transducer beam portion 1004 is disposed at the approximate center of the transducer footprint, the second transducer beam portion 1006 is connected to the first transducer beam portion 1004 and is disposed substantially perpendicular thereto, the third transducer beam portion 1008 is connected to the second transducer beam portion 1006 and is disposed substantially perpendicular thereto, the fourth transducer beam portion 1010 is connected to the third transducer beam portion 1008 and is disposed substantially perpendicular thereto, and the fifth transducer beam portion 1012 is connected to the fourth transducer beam portion 1010 and is disposed substantially perpendicular thereto. In FIGS. 30 and 33, it can be seen that the transducer beam portions 1004, 1006, 1008, 1010, 1012 of the load transducer 1000 are spaced apart from one another by a generally U-shaped, central gap 1032, which is bounded by each of the transducer beam portions 1004, 1006, 1008, 1010, 1012. In particular, the first transducer beam portion 1004 and the third transducer beam portion 1008, which are disposed generally parallel to one another, are laterally spaced apart by the gap 1032. Similarly, the second transducer beam portion 1006 and the fourth transducer beam portion 1010, which are disposed generally parallel to one another, are laterally spaced apart by the gap 1032. Also, the first transducer beam portion 1004 and the fifth transducer beam portion 1012, which are disposed generally parallel to one another, are laterally spaced apart by the gap 1032. The third transducer beam portion 1008 and the fifth transducer beam portion 1012, which are disposed generally parallel to one another, are laterally spaced apart by the gap 1032 and a segment of the first transducer beam portion 1004.

Referring again to the top perspective view of FIG. 30, it can be seen that the first and second transducer beam portions 1004, 1006 of the load transducer 1000 comprise an L-shaped arrangement of mounting apertures 1020 (e.g., three (3) apertures 1020) disposed therethrough for accommodating fasteners (e.g., screws) that attach the load transducer 1000 to another object, such as a plate component of a force plate or force measurement assembly. The mounting apertures 1020 pass completely through the first and second transducer beam portions 1004, 1006, and are provided with respective bottom bore portions 1020a of increased diameter (see FIG. 33) in order to accommodate fasteners (e.g., screws) with fillister heads that have a larger outer diameter than the threaded portions of the fasteners. In addition, with reference again to FIG. 30, it can be seen that the L-shaped portion of the load transducer 1000 that is formed by the first and second transducer beam portions 1004, 1006 is provided with pin locating bores 1022 (e.g., two (2) bores 1022) formed therein for receiving locating pins that ensure the proper positioning of the load transducer 1000 on the object to which it is mounted, such as a plate component of a force plate or force measurement assembly. The locating pins are received within the pin locating bores 1022 on the load transducer 1000 and within corresponding pin locating apertures provided on the object (e.g., the force plate or force measurement assembly). As depicted in the perspective views of FIGS. 30 and 33, the fifth transducer beam portion 1012 of the load transducer 1000 comprises a mounting aperture 1024 (e.g., a single aperture 1024 proximate to the free end thereof) disposed therethrough for accommodating a fastener (e.g., a screw) that attaches the load transducer 1000 to another object, such as a mounting foot of a force plate or force measurement assembly. In one or more embodiments, the load transducer 1000 is connected to one or more objects in such a manner that the total load applied to the load transducer 1000 is transmitted through the transducer beam portions 1004, 1006, 1008, 1010, 1012.

In the illustrative embodiment of FIGS. 30-33, each of the transducer beam portions 1008, 1010, 1012 is provided with a respective aperture 1014, 1016, 1018 disposed therethrough. In particular, the third transducer beam portion 1008 is provided with a generally rectangular aperture 1014 disposed vertically through the beam portion. Similarly, the fourth transducer beam portion 1010 is provided with a generally rectangular aperture 1016 disposed vertically through the beam portion. The fifth transducer beam portion 1012 is provided with a generally rectangular aperture 1018 disposed horizontally through the beam portion. The apertures 1014, 1016, 1018, which are disposed through the respective transducer beam portions 1008, 1010, 1012, significantly increase the sensitivity of the load transducer 1000 when a load is applied thereto by reducing the cross-sectional area of the transducer beam portions 1008, 1010, 1012 at the locations of the apertures 1014, 1016, 1018.

As best shown in the perspective views of FIGS. 30 and 33, the illustrated load cells are located on the transducer beam portions 1008, 1010, 1012. In the illustrated embodiment, each load cell comprises one or more strain gages 1026, 1028, and 1030. Specifically, in the illustrated embodiment, the third transducer beam portion 1008 of the load transducer 1000 comprises a strain gage 1028 disposed on a side surface thereof that is sensitive to a first shear force component (i.e., a $F_Y$ strain gage) and substantially centered on the aperture 1014. Turning again to FIGS. 30 and 33, in the illustrated embodiment, the fourth transducer beam portion 1010 of the load transducer 1000 comprises a strain gage 1026 disposed on a side surface thereof that is sensitive to a second shear force component (i.e., a $F_X$ strain gage) and substantially centered on the aperture 1016. With reference again to FIGS. 30 and 33, in the illustrated embodiment, the fifth transducer beam portion 1012 of the load transducer 1000 comprises a strain gage 1030 disposed on the top surface thereof that is sensitive to a vertical force component (i.e., a $F_Z$ strain gage) and substantially centered on the aperture 1018. In the illustrated embodiment, the first shear force component is generally perpendicular to the second shear force component, and each of the first and second shear force components are generally perpendicular to the vertical force component.

In the illustrated embodiment, the strain gages 1026, 1028, 1030 are disposed on respective outer surfaces of the transducer beam portions 1010, 1008, 1012. The outer surfaces of the transducer beam portions 1010, 1008, 1012 on which the strain gages 1026, 1028, 1030 are disposed are generally opposite to the inner surfaces of the respective apertures 1016, 1014, 1018.

As best shown in FIGS. 30 and 33, the illustrated load cells are mounted on top or side surfaces of the transducer beam portions 1008, 1010, 1012 between the ends of the load transducer 1000. Alternatively, the strain gages 1028, 1026 can be mounted to the inner side surfaces of the respective third and fourth transducer beam portions 1008, 1010, rather than to the outer side surfaces of the respective third and fourth transducer beam portions 1008, 1010 as illustrated in FIGS. 30 and 33. Similarly, the strain gage 1030 can be mounted to the bottom surface of the fifth transducer beam portion 1012, rather than to the top of the transducer beam portion 1012 as illustrated in FIG. 30. In general, the strain gages 1026, 1028, 1030 are mounted to surfaces generally normal to the direction of applied vertical and/or shear forces (i.e., $F_X$, $F_Y$, $F_Z$). It is also noted that alternatively, strain gages 1026 can be mounted at both opposed side surfaces of fourth transducer beam portion 1010 and/or strain gages 1028 can be mounted at both opposed side surfaces of the third transducer beam portion 1008. Similarly, strain gages 1030 can be mounted at both the top surface and the bottom surface of the fifth transducer beam portion 1012. These strain gages 1026, 1028, 1030 measure force either by bending moment or difference of bending moments at two cross sections. As force is applied to the ends of the load transducer 1000, the transducer beam portions bend. This bending either stretches or compresses the strain gages 1026, 1028, 1030, which in turn changes the resistance of the electrical current passing therethrough. The amount of change in the electrical voltage or current is proportional to the magnitude of the applied force, as applied to the load transducer 1000.

In the illustrated embodiment, each of the strain gages 1026, 1028, 1030 comprises a full-bridge strain gage configuration (i.e., four (4) active strain gage elements wired in a Wheatstone bridge configuration) for measuring the applied vertical and shear forces.

Figure 34:
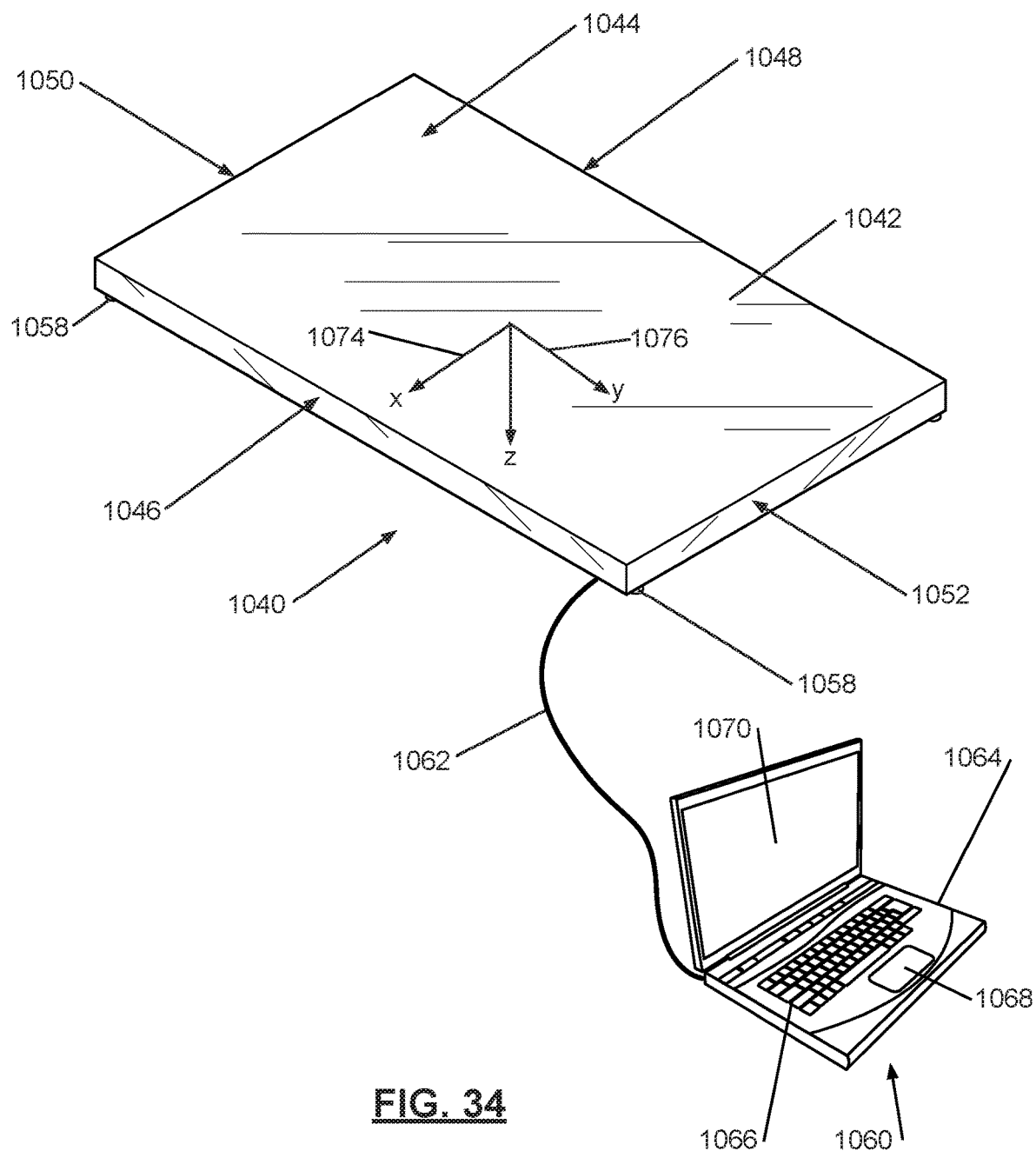
FIG. 34 is a perspective view of a force measurement system that utilizes the load transducer of FIG. 30, according to an embodiment of the invention.
Figure 35:
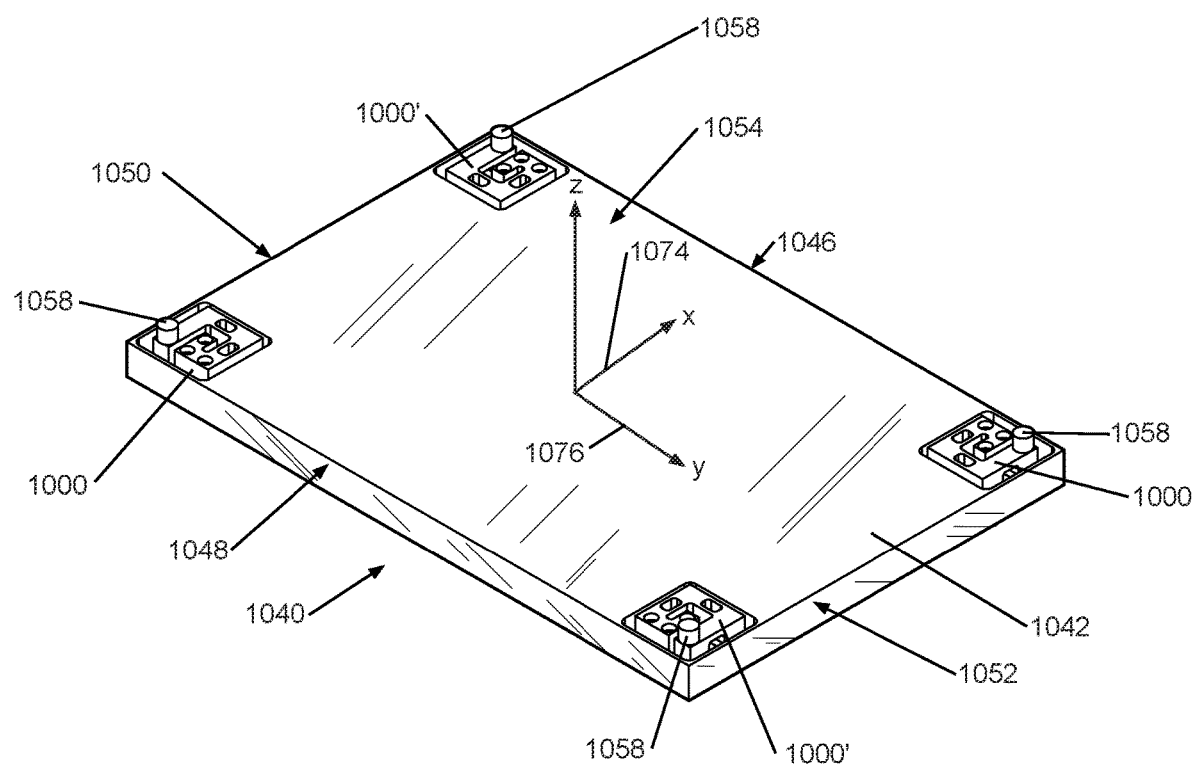
FIG. 35 is a bottom, assembled perspective view of the force measurement assembly of the force measurement system of FIG. 34.
Figure 36:
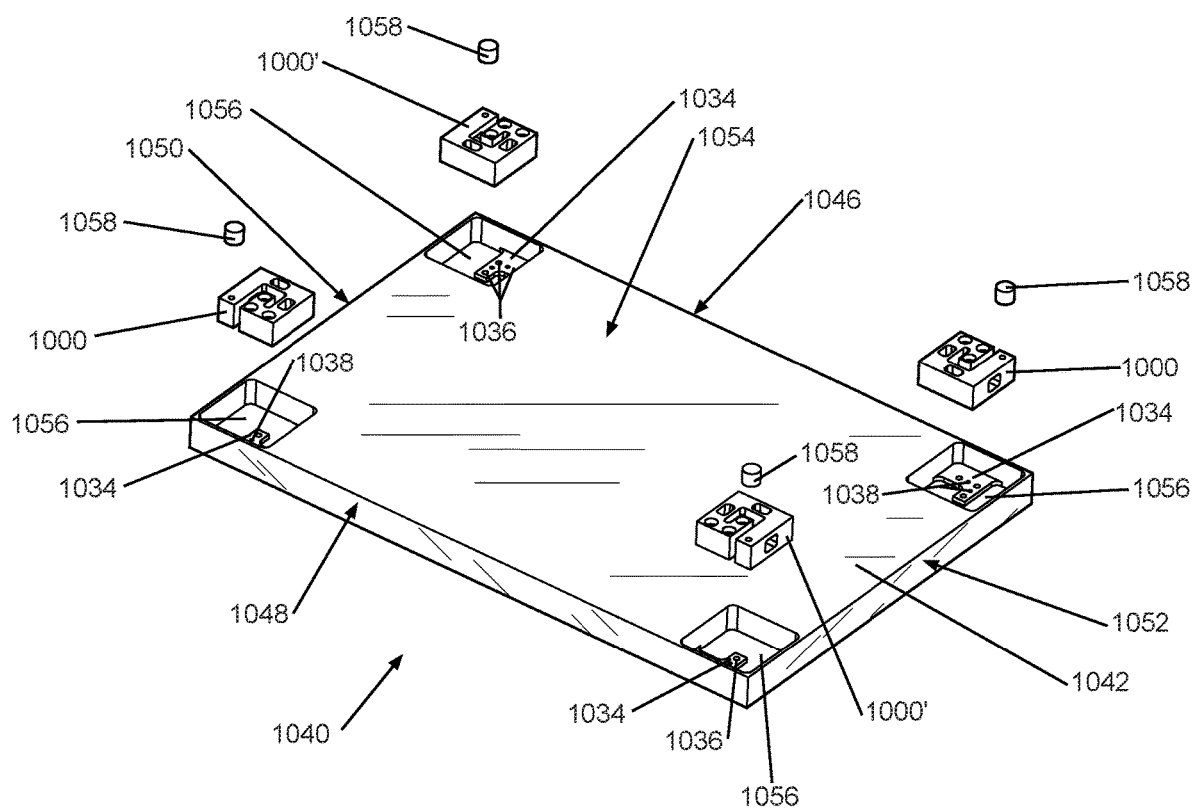
FIG. 36 is a bottom, partially exploded perspective view of the force measurement assembly of the force measurement system of FIG. 34.

An exemplary embodiment of a force measurement system is illustrated in FIGS. 34-37. In the illustrative embodiment, the force measurement system generally comprises a force measurement assembly 1040 (i.e., a force plate) that is operatively coupled to a data acquisition/data processing device 1060 (i.e., a data acquisition and processing device or computing device that is capable of collecting, storing, and processing data). The force measurement assembly 1040 illustrated in FIGS. 34-36 is configured to receive a subject thereon, and is capable of measuring the forces and/or moments applied to its measurement surface by the subject.

As shown in FIG. 34, the data acquisition and processing device 1060 (e.g., in the form of a laptop digital computer) generally includes a base portion 1064 with a central processing unit (CPU) disposed therein for collecting and processing the data that is received from the force measurement assembly 1040, and a plurality of devices 1066-1070 operatively coupled to the central processing unit (CPU) in the base portion 1064. Preferably, the devices that are operatively coupled to the central processing unit (CPU) comprise user input devices 1066, 1068 in the form of a keyboard 1066 and a touchpad 1068, as well as a graphical user interface in the form of a laptop LCD screen 1070. While a laptop type computing system is depicted in the embodiment of FIG. 34, one of ordinary skill in the art will appreciate that another type of data acquisition and processing device 1060 can be substituted for the laptop computing system such as, but not limited to, a palmtop computing device (i.e., a PDA) or a desktop type computing system having a plurality of separate, operatively coupled components (e.g., a desktop type computing system including a main housing with a central processing unit (CPU) and data storage devices, a remote monitor, a remote keyboard, and a remote mouse).

As illustrated in FIG. 34, force measurement assembly 1040 is operatively coupled to the data acquisition/data processing device 1060 by virtue of an electrical cable 1062. In one embodiment of the invention, the electrical cable 1062 is used for data transmission, as well as for providing power to the force measurement assembly 1040. Various types of data transmission cables can be used for cable 1062. For example, the cable 1062 can be a Universal Serial Bus (USB) cable or an Ethernet cable. Preferably, the electrical cable 1062 contains a plurality of electrical wires bundled together, with at least one wire being used for power and at least another wire being used for transmitting data. The bundling of the power and data transmission wires into a single electrical cable 1062 advantageously creates a simpler and more efficient design. In addition, it enhances the safety of the testing environment when human subjects are being tested on the force measurement assembly 1040. However, it is to be understood that the force measurement assembly 1040 can be operatively coupled to the data acquisition/data processing device 1040 using other signal transmission means, such as a wireless data transmission system. If a wireless data transmission system is employed, it is preferable to provide the force measurement assembly 1040 with a separate power supply in the form of an internal power supply or a dedicated external power supply.

Referring again to FIG. 34, it can be seen that the force measurement assembly 1040 of the illustrated embodiment is in the form of a force plate assembly with a single, continuous measurement surface. The force plate assembly includes a plate component 1042 supported on a plurality of load transducers 1000, 1000'. As shown in FIGS. 34 and 35, the plate component 1042 comprises a top measurement surface 1044, a bottom surface 1054 disposed generally opposite to the top measurement surface 1044, and a plurality of side surfaces 1046, 1048, 1050, 1052 disposed between the top and bottom surfaces 1044, 1054. In the illustrated embodiment, the first side surface 1046 of the plate component 1042 is disposed generally parallel to the second side surface 1048, and is disposed generally perpendicular to both the third side surface 1050 and the fourth side surface 1052. The third side surface 1050 of the plate component 1042 is disposed generally parallel to the fourth side surface 1052, and is disposed generally perpendicular to both the first side surface 1046 and the second side surface 1048. Turning to the exploded view of FIG. 36, it can be seen that the bottom surface 1054 of the plate component 1042 comprises a plurality of transducer mounting recesses 1056 for accommodating respective ones of the load transducers 1000, 1000'. Also, as shown in FIG. 36, it can be seen that an L-shaped transducer standoff plate 1034 is provided in each of the transducer mounting recesses 1056 for spacing the top surfaces of the load transducers 1000, 1000' from the mounting surfaces of the recesses 1056. Referring again to the bottom perspective view of FIG. 36, it can be seen that each L-shaped transducer standoff plate 1034 comprises a plurality of mounting apertures 1036 (e.g., three (3) apertures 1036) disposed therethrough for accommodating fasteners (e.g., screws) that attach the plate component 1042 of the force measurement assembly 1040 to either the load transducer 1000 or the load transducer 1000'. As such, the mounting apertures 1036 in each L-shaped transducer standoff plate 1034 are substantially aligned with the mounting apertures 1020 in the load transducers 1000, 1000' such that they correspond thereto. In addition, with reference again to FIG. 36, it can be seen that each L-shaped transducer standoff plate 1034 further comprises pin locating apertures 1038 (e.g., two (2) apertures 1038) formed therein for receiving locating pins that ensure the proper positioning of the load transducers 1000, 1000' on the plate component 1042 of the force measurement assembly 1040. Thus, the pin locating apertures 1038 in each L-shaped transducer standoff plate 1034 are substantially aligned with the pin locating bores 1022 in the load transducers 1000, 1000' such that they correspond thereto. The pin locating apertures 1038 in the L-shaped transducer standoff plates 1034, and the pin locating bores 1022 in the load transducers 1000, 1000', collectively receive locating pins that ensure the proper positioning of the load transducers 1000, 1000' on the plate component 1042 of the force measurement assembly 1040.

In illustrated embodiment of FIGS. 34-36, the force measurement assembly 1040 comprises a total of four (4) load transducers 1000, 1000' that are disposed underneath, and near each of the respective four corners (4) of the plate component 1042. The load transducers 1000' are generally the same as the load transducers 1000, expect that they are configured as a mirror image of the load transducers 1000. Advantageously, because the load transducers 1000, 1000' are compact, none of the plurality of load transducers 1000, 1000' extend substantially an entire length or width of the plate component 1042 of the force measurement assembly 1040. The compact construction of the load transducers 1000, 1000' not only reduces material costs because less material is used to form the load transducers 1000, 1000', but it also allows the load transducers 1000, 1000' to be universally used on force plates having a myriad of different lengths and widths because it is not necessary for the load transducers 1000, 1000' to conform to the footprint size of the force plate.

In an alternative embodiment, rather than using the load transducers 1000, 1000' on the force measurement assembly 1040, the load transducers 900 described above could be provided on the force measurement assembly 1040. Using the load transducers 900 in lieu of the load transducers 1000, 1000' would enable the moment components of the load applied to the plate component 1042 to be measured in addition to the force components of the load.

In other embodiments of the invention, rather than using a force measurement assembly 1040 having a plate component 1042 with a single measurement surface 1044, it is to be understood that a force measurement assembly in the form of a dual force plate may be alternatively employed. Unlike the single force plate assembly 1040 illustrated in FIGS. 34-36, the dual force plate comprises two separate plate components, each of which is configured to accommodate a respective one of a subject's feet thereon (i.e., the left plate component accommodates the subject's left foot, whereas the right plate component accommodates the subject's right foot). In these alternative embodiments, each of the two plate components of the dual force plate are supported on four (4) load transducers 1000, 1000' (i.e., a load transducer 1000, 1000' is disposed in each of the respective four (4) corners of each of the two plate components). As such, the dual force plate comprises a total of eight (8) load transducers 1000, 1000' (i.e., four (4) load transducers 1000, 1000' under each of the two plate components).

Also, as shown in FIGS. 34-36, the force measurement assembly 1040 is provided with a plurality of support feet 1058 disposed thereunder. Preferably, each of the four (4) corners of the force measurement assembly 1040 is provided with a support foot 1058 (e.g., mounted on the bottom of each load transducer 1000, 1000'). In particular, in the illustrated embodiment, each support foot 1058 is attached to an aperture 1024 in a respective one of the load transducers 1000, 1000' by means of a fastener (e.g., a screw). In one embodiment, at least one of the support feet 1058 is adjustable so as to facilitate the leveling of the force measurement assembly 1040 on an uneven floor surface.

Figure 37:
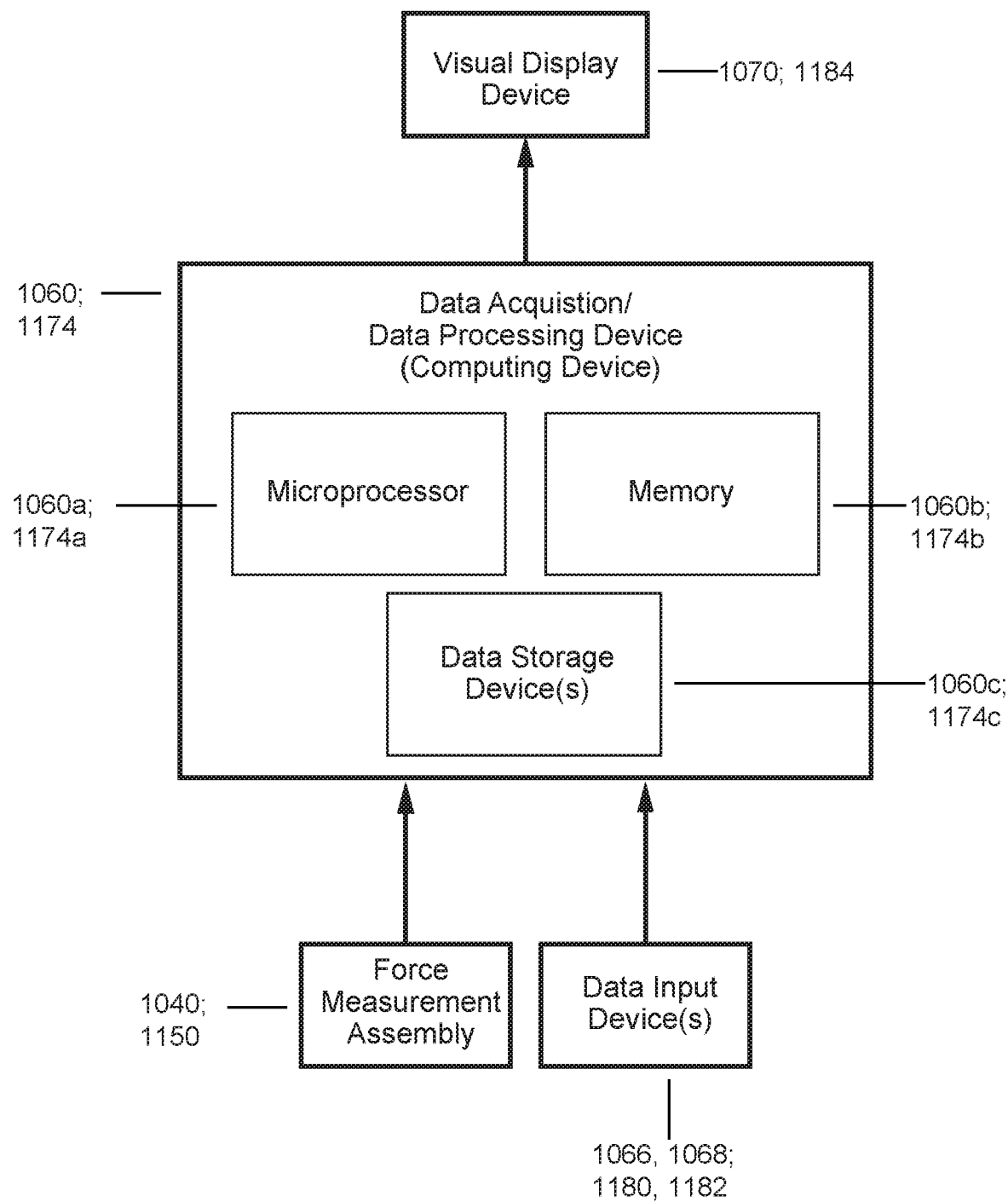
FIG. 37 is a block diagram of constituent components of the force measurement systems of FIGS. 34 and 42.

Now, turning to FIG. 37, it can be seen that the data acquisition/data processing device 1060 (i.e., the laptop computing device) of the force measurement system comprises a microprocessor 1060a for processing data, memory 1060b (e.g., random access memory or RAM) for storing data during the processing thereof, and data storage device(s) 1060c, such as one or more hard drives, compact disk drives, floppy disk drives, flash drives, or any combination thereof. As shown in FIG. 37, the force measurement assembly 1040 and the visual display device 1070 are operatively coupled to the core components 1060a, 1060b, 1060c of the data acquisition/data processing device 1060 such that data is capable of being transferred between these devices 1040, 1060a, 1060b, 1060c, and 1070. Also, as illustrated in FIG. 37, a plurality of data input devices 1066, 1068 such as the keyboard 1066 and mouse 1068 shown in FIG. 34, are operatively coupled to the core components 1060a, 1060b, 1060c of the data acquisition/data processing device 1060 so that a user is able to enter data into the data acquisition/data processing device 1060. In some embodiments, the data acquisition/data processing device 1060 can be in the form of a laptop computer, while in other embodiments, the data acquisition/data processing device 1060 can be embodied as a desktop computer.

Figure 38:
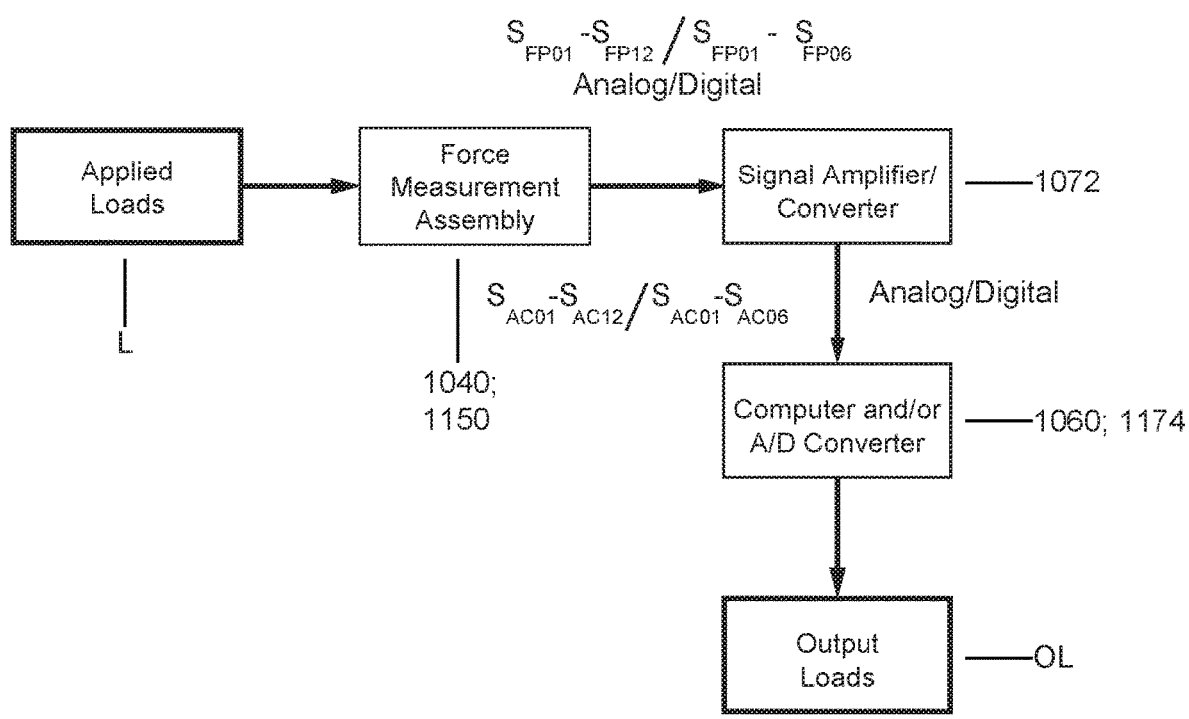
FIG. 38 is a block diagram illustrating data manipulation operations carried out by the force measurement systems of FIGS. 34 and 42.

FIG. 38 graphically illustrates the acquisition and processing of the load data carried out by the exemplary force measurement system of FIG. 34. Initially, as shown in FIG. 38, a load L is applied to the force measurement assembly 1040 (e.g., by a subject disposed thereon). The load is transmitted from the plate component 1042 to the load transducers 1000, 1000' disposed in each of its four (4) corners. As described above, in the illustrated embodiment, each of the load transducers 1000, 1000' includes a plurality of strain gages 1026, 1028, 1030 wired in one or more Wheatstone bridge configurations, wherein the electrical resistance of each strain gage is altered when the associated beam portion of the load transducer 1000, 1000' undergoes deformation resulting from the load (i.e., forces and/or moments) acting on the plate component 1042. For each plurality of strain gages disposed on the load transducers 1000, 1000', the change in the electrical resistance of the strain gages brings about a consequential change in the output voltage of the Wheatstone bridge (i.e., a quantity representative of the load being applied to the measurement surface 1044). Thus, in one embodiment, the four (4) load transducers 1000, 1000' disposed under the plate component 1042 output a total of twelve (12) analog output voltages (signals). In some embodiments, the twelve (12) analog output voltages from load transducers 1000, 1000' disposed under the plate component 1042 are then transmitted to a preamplifier board (not shown) for preconditioning. The preamplifier board is used to increase the magnitudes of the transducer analog voltages, and preferably, to convert the analog voltage signals into digital voltage signals as well. After which, the force measurement assembly 1040 transmits the force plate output signals $S_{FPO1}$-$S_{FP12}$ to a main signal amplifier/converter 1072. Depending on whether the preamplifier board also includes an analog-to-digital (A/D) converter, the force plate output signals $S_{FPO1}$-$S_{FP12}$ could be either in the form of analog signals or digital signals. The main signal amplifier/converter 1072 further magnifies the force plate output signals $S_{FPO1}$-$S_{FP12}$, and if the signals $S_{FPO1}$-$S_{FP12}$ are of the analog-type (for a case where the preamplifier board did not include an analog-to-digital (A/D) converter), it may also convert the analog signals to digital signals. Then, the signal amplifier/converter 1072 transmits either the digital or analog signals $S_{ACO1}$-$S_{AC12}$ to the data acquisition/data processing device 1060 (computer 1060) so that the forces and/or moments that are being applied to the measurement surface 1044 of the force measurement assembly 1040 can be transformed into output load values OL. In addition to the components 1060a, 1060b, 1060c, the data acquisition/data processing device 1060 may further comprise an analog-to-digital (A/D) converter if the signals $S_{ACO1}$-$S_{AC12}$ are in the form of analog signals. In such a case, the analog-to-digital converter will convert the analog signals into digital signals for processing by the microprocessor 1060a.

When the data acquisition/data processing device 1060 receives the voltage signals $S_{ACO1}$-$S_{AC12}$, it initially transforms the signals into output forces by multiplying the voltage signals $S_{AC01}$-$S_{AC12}$ by a calibration matrix. If the load transducer 900 is used in conjunction with the force measurement assembly 1040, the data acquisition/data processing device 1060 may additionally transform the signals into output moments by multiplying the voltage signals by the calibration matrix. After which, the force exerted on the surface 1044 of the force measurement assembly 1040, and the center of pressure of the applied force (i.e., the x and y coordinates of the point of application of the force applied to the measurement surface 1044) is determined by the data acquisition/data processing device 1060. Referring to the perspective view of FIG. 34, it can be seen that the center of pressure coordinates ($x_{P_L}$, $y_{P_L}$) for the plate component 1042 of the force measurement assembly 1040 are determined in accordance with x and y coordinate axes 1074, 1076.

In one exemplary embodiment, the data acquisition/data processing device 1060 determines all three (3) orthogonal components of the resultant forces acting on the plate component 1042 of the force measurement assembly 1040 (i.e., $F_X$, $F_Y$, $F_Z$). In yet other embodiments of the invention, all three (3) orthogonal components of the resultant forces and moments acting on the plate component 1042 of the force measurement assembly 1040 (i.e., $F_X$, $F_Y$, $F_Z$, $M_X$, $M_Y$, $M_Z$) may be determined (i.e., when the load transducer 900 is used in lieu of the load transducers 1000, 1000').

Figure 39:
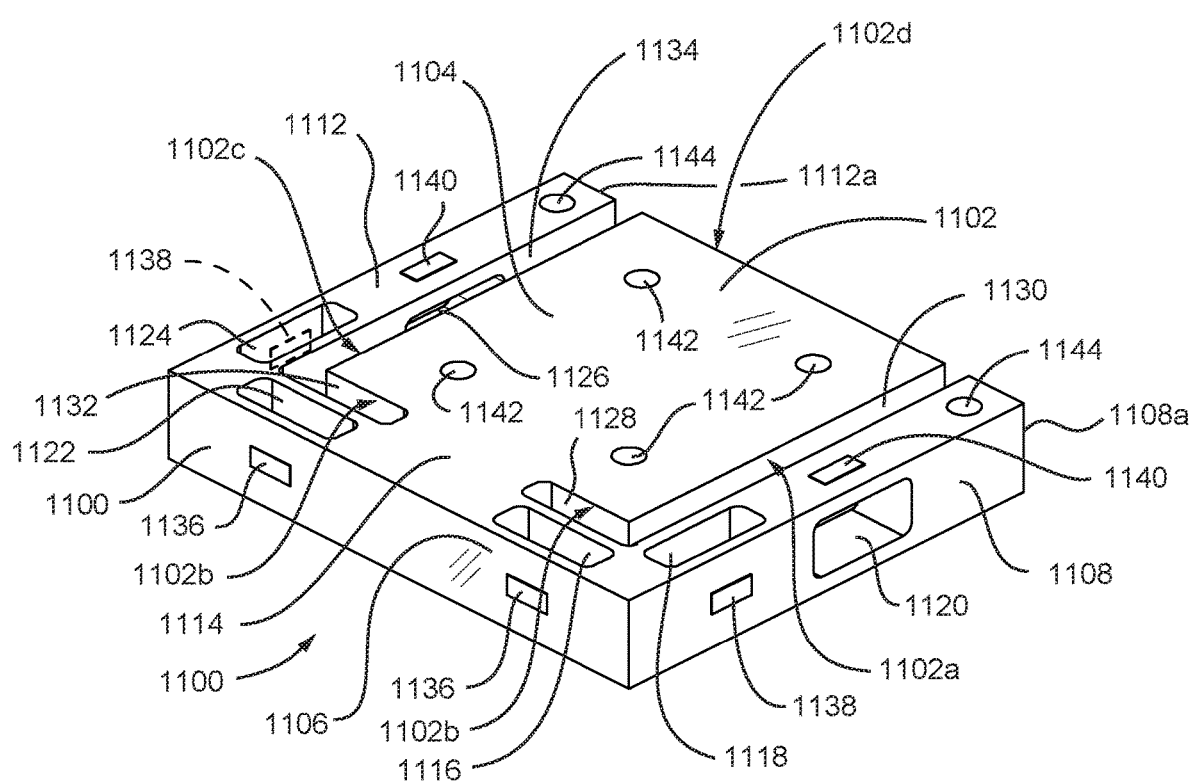
FIG. 39 is a top perspective view of a load transducer, according to a thirteenth embodiment of the invention.
Figure 40:
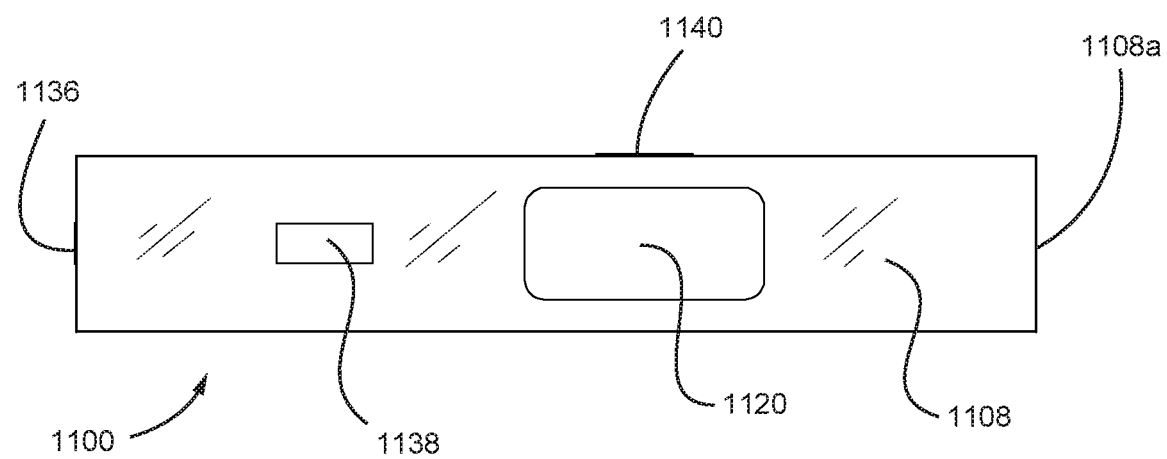
FIG. 40 is a side view of the load transducer of FIG. 39, according to the thirteenth embodiment of the invention.
Figure 41:
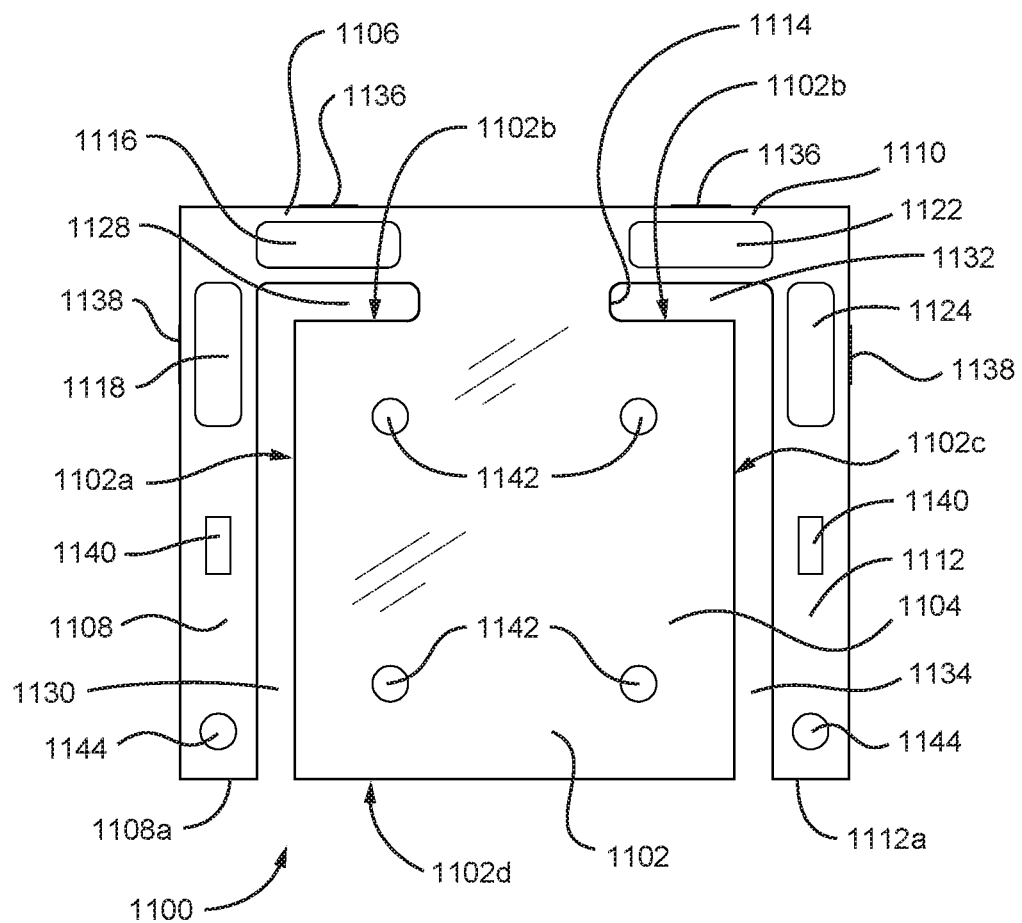
FIG. 41 is a top plan view of the load transducer of FIG. 39, according to the thirteenth embodiment of the invention.

FIGS. 39-41 illustrate a load transducer 1100 according to a thirteenth exemplary embodiment of the present invention. Referring initially to the perspective view of FIG. 39, it can be seen that the load transducer 1100 generally includes a one-piece compact transducer frame 1104 having a central body portion 1102 and a plurality of beam portions 1106, 1108, 1110, 1112 extending along sides 1102a, 1102b, 1102c of the central body portion 1102. As best illustrated in the perspective view of FIG. 39, each of the beam portions 1106, 1108, 1110, 1112 comprises one or more load cells or transducer elements for measuring forces and/or moments.

With reference again to FIG. 39, it can be seen that the illustrated central body portion 1102 is generally in the form of a square prism with substantially right angle corners (i.e., substantially 90 degree corners). In FIG. 39, it can be seen that the body portion 1102 comprises a first pair of opposed sides 1102a, 1102c and a second pair of opposed sides 1102b, 1102d. The side 1102a is disposed generally parallel to the side 1102c, while the side 1102b is disposed generally parallel to the side 1102d. Each of the sides 1102a, 1102b, 1102c, 1102d is disposed generally perpendicular to the planar top and bottom surfaces of the body portion 1102. Also, each of the first pair of opposed sides 1102a, 1102c is disposed generally perpendicular to each of the second pair of opposed sides 1102b, 1102d. In addition, as shown in FIG. 39, the second side 1102b comprises a beam connecting portion 1114 extending outward therefrom. In the illustrated embodiment, it can be seen that the beam connecting portion 1114 connects the beam portions 1106 and 1110 to the second side 1102b of the central body portion 1102. In the illustrated embodiment, the total load applied to the load transducer 1100 is transmitted through the beam portions 1106, 1108, 1110, 1112.

As best shown in FIGS. 39 and 41, the proximal end of the first beam portion 1106 is rigidly connected to the central body portion 1102 by means of the beam connecting portion 1114, and the distal end of the first beam portion 1106 is rigidly connected to the proximal end of the second beam portion 1108. As depicted in these figures, the first beam portion 1106 extends along the second side 1102b of the central body portion 1102, and the second beam portion 1108 extends along the first side 1102a of the central body portion 1102. More particularly, in the illustrative embodiment, the longitudinal axis of the first beam portion 1106 is disposed generally parallel to the second side 1102b of the central body portion 1102, and the longitudinal axis of the second beam portion 1108 is disposed generally parallel to the first side 1102a of the central body portion 1102. As best shown in the perspective view of FIG. 39, the top and bottom surfaces of each of the first and second beam portions 1106, 1108 are disposed substantially co-planar with the top and bottom surfaces of the central body portion 1102. Also, in the illustrative embodiment, with reference again to FIGS. 39 and 41, the first beam portion 1106 is generally perpendicular, or perpendicular to the second beam portion 1108 (i.e., together the first and second beam portions 1106, 1108 form an overall L-shaped beam arm). In addition, as shown in these figures, the first beam portion 1106 is spaced apart from the second side 1102b of the central body portion 1102 by a first gap 1128, and the second beam portion 1108 is spaced apart from the first side 1102a of the central body portion 1102 by a second gap 1130. In the illustrative embodiment, together the first gap 1128 and the second gap 1130 form an overall L-shaped gap (i.e., the first gap 1128 is disposed perpendicular to the second gap 1130).

Also, referring again to FIGS. 39 and 41, it can be seen that the proximal end of the third beam portion 1110 is rigidly connected to the central body portion 1102 by means of the beam connecting portion 1114, and the distal end of the third beam portion 1110 is rigidly connected to the proximal end of the fourth beam portion 1112. As depicted in these figures, the third beam portion 1110 extends along the second side 1102b of the central body portion 1102, and the fourth beam portion 1112 extends along the third side 1102c of the central body portion 1102. More particularly, in the illustrative embodiment, the longitudinal axis of the third beam portion 1110 is disposed generally parallel to the second side 1102b of the central body portion 1102, and the longitudinal axis of the fourth beam portion 1112 is disposed generally parallel to the third side 1102c of the central body portion 1102. As best shown in the perspective view of FIG. 39, the top and bottom surfaces of each of the third and fourth beam portions 1110, 1112 are disposed substantially co-planar with the top and bottom surfaces of the central body portion 1102. Also, in the illustrative embodiment, with reference again to FIGS. 39 and 41, the third beam portion 1110 is generally perpendicular, or perpendicular to the fourth beam portion 1112 (i.e., together the third and fourth beam portions 1110, 1112 form an overall L-shaped beam arm). In addition, as shown in these figures, the third beam portion 1110 is spaced apart from the second side 1102b of the central body portion 1102 by a third gap 1132, and the fourth beam portion 1112 is spaced apart from the third side 1102c of the central body portion 1102 by a fourth gap 1134. In the illustrative embodiment, together the third gap 1132 and the fourth gap 1134 form an overall L-shaped gap (i.e., the third gap 1132 is disposed perpendicular to the fourth gap 1134).

In the illustrative embodiment of FIGS. 39 and 41, it can be seen that the free end 1108a of the second beam portion 1108 is generally aligned, or aligned with the fourth side 1102d of the central body portion 1102 (i.e., the end face of the second beam portion 1108 is co-planar with the fourth side 1102d of the central body portion 1102). Also, as shown in FIGS. 39 and 41, the free end 1112a of the fourth beam portion 1112 is generally aligned, or aligned with the fourth side 1102d of the central body portion 1102 (i.e., the end face of the fourth beam portion 1112 is co-planar with the fourth side 1102d of the central body portion 1102).

In the illustrative embodiment of FIGS. 39-41, the first beam portion 1106 is provided with an aperture 1116 disposed therethrough, the second beam portion 1108 is provided with apertures 1118, 1120 disposed therethrough, the third beam portion 1110 is provided with an aperture 1122 disposed therethrough, and the fourth beam portion 1112 is provided with apertures 1124, 1126 disposed therethrough. In particular, the first and third transducer beam portions 1106, 1110 are provided with respective generally rectangular apertures 1116, 1122 disposed vertically through the beam portions 1106, 1110. The second transducer beam portion 1108 is provided with a first generally rectangular aperture 1118 disposed vertically through the beam portion 1108 and a second generally rectangular aperture 1120 disposed horizontally through the beam portion 1108. As such, the vertically extending aperture 1118 of the second beam portion 1108 extends in a direction that is generally perpendicular, or perpendicular to the extending direction of the horizontally extending aperture 1120. Similarly, the fourth transducer beam portion 1112 is provided with a first generally rectangular aperture 1124 disposed vertically through the beam portion 1112 and a second generally rectangular aperture 1126 disposed horizontally through the beam portion 1112. As such, the vertically extending aperture 1124 of the fourth beam portion 1112 extends in a direction that is generally perpendicular, or perpendicular to the extending direction of the horizontally extending aperture 1126. The apertures 1116, 1118, 1120, 1122, 1124, 1126, which are disposed through the transducer beam portions 1106, 1108, 1110, 1112, significantly increase the sensitivity of the load transducer 1100 when a load is applied thereto by reducing the cross-sectional area of the transducer beam portions 1106, 1108, 1110, 1112 at the locations of the apertures 1116, 1118, 1120, 1122, 1124, 1126.

As best shown in the perspective view of FIG. 39, the illustrated load cells are located on the transducer beam portions 1106, 1108, 1110, 1112. In the illustrated embodiment, each load cell comprises one or more strain gages 1136, 1138, 1140. Specifically, in the illustrated embodiment, the first transducer beam portion 1106 of the load transducer 1100 comprises a strain gage 1136 disposed on a side surface thereof that is sensitive to a first shear force component (i.e., a $F_Y$ strain gage) and substantially centered on the aperture 1116. In the illustrated embodiment, the second transducer beam portion 1108 of the load transducer 1100 comprises a strain gage 1138 disposed on a side surface thereof that is sensitive to a second shear force component (i.e., a $F_X$ strain gage) and substantially centered on the aperture 1118. The second transducer beam portion 1108 also comprises a strain gage 1140 disposed on a top surface thereof that is sensitive to a vertical force component (i.e., a $F_Z$ strain gage) and substantially centered on the aperture 1120. Also, in the illustrative embodiment, the third transducer beam portion 1110 of the load transducer 1100 comprises a strain gage 1136 disposed on a side surface thereof that is sensitive to the first shear force component (i.e., a $F_Y$ strain gage) and substantially centered on the aperture 1122. The fourth transducer beam portion 1112 of the load transducer 1100 comprises a strain gage 1138 disposed on a side surface thereof that is sensitive to a second shear force component (i.e., a $F_X$ strain gage) and substantially centered on the aperture 1124. The fourth transducer beam portion 1112 also comprises a strain gage 1140 disposed on a top surface thereof that is sensitive to a vertical force component (i.e., a $F_Z$ strain gage) and substantially centered on the aperture 1126. In the illustrated embodiment, the first shear force component is generally perpendicular to the second shear force component, and each of the first and second shear force components are generally perpendicular to the vertical force component.

In the illustrated embodiment, the strain gages 1136, 1138, 1140 are disposed on respective outer surfaces of the transducer beam portions 1106, 1108, 1110, 1112. The outer surfaces of the transducer beam portions 1106, 1108, 1110, 1112 on which the strain gages 1136, 1138, 1140 are disposed are generally opposite to the inner surfaces of the respective apertures 1116, 1118, 1120, 1122, 1124, 1126.

As best shown in FIGS. 39-41, the illustrated load cells are mounted on the top and outer side surfaces of the transducer beam portions 1106, 1108, 1110, 1112 of the load transducer 1100. Alternatively, the strain gages 1136, 1138 can be mounted to the inner side surfaces of the respective first and second transducer beam portions 1106, 1108, rather than to the outer side surfaces of the respective first and second transducer beam portions 1106, 1108 as illustrated in FIGS. 39 and 40. Similarly, the strain gages 1136, 1138 can be mounted to the inner side surfaces of the respective third and fourth transducer beam portions 1110, 1112, rather than to the outer side surfaces of the respective third and fourth transducer beam portions 1110, 1112 as illustrated in FIGS. 39 and 41. In addition, the strain gages 1140 can be mounted to the bottom surfaces of the second and fourth transducer beam portions 1108, 1112, rather than to the top of the transducer beam portions 1108, 1112 as illustrated in FIGS. 39 and 41. In general, the strain gages 1136, 1138, 1140 are mounted to surfaces generally normal to the direction of applied vertical and/or shear forces (i.e., $F_X$, $F_Y$, $F_Z$). It is also noted that alternatively, strain gages 1136 can be mounted at both opposed side surfaces of first and third transducer beam portions 1106, 1110 and/or strain gages 1138 can be mounted at both opposed side surfaces of the second and fourth transducer beam portions 1108, 1112. Similarly, strain gages 1140 can be mounted at both the top surface and the bottom surface of the second and fourth transducer beam portions 1108, 1112. These strain gages 1136, 1138, 1140 measure force either by bending moment or difference of bending moments at two cross sections. As force is applied to the central body portion 1102 of the load transducer 1100, the transducer beam portions bend. This bending either stretches or compresses the strain gages 1136, 1138, 1140, which in turn changes the resistance of the electrical current passing therethrough. The amount of change in the electrical voltage or current is proportional to the magnitude of the applied force, as applied to the central body portion 1102 of the load transducer 1100. In the illustrated embodiment, each of the strain gages 1136, 1138, 1140 comprises a full-bridge strain gage configuration (i.e., four (4) active strain gage elements wired in a Wheatstone bridge configuration). In an alternative embodiment, each of the strain gages 1136, 1138, 1140 may comprise a half-bridge strain gage configuration (i.e., two (2) active strain gage elements wired in a Wheatstone bridge configuration).

Figure 42:
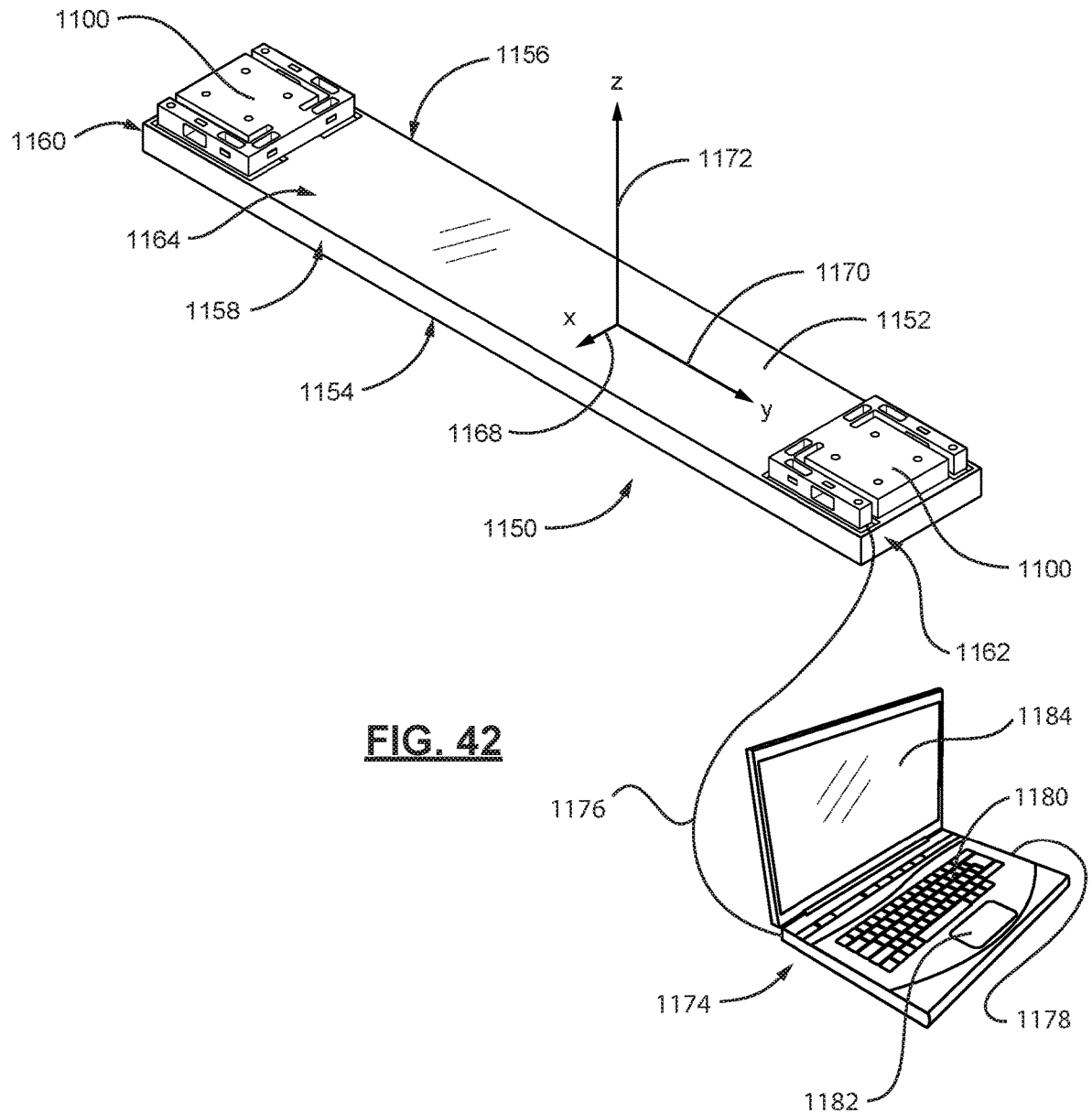
FIG. 42 is a bottom, assembled perspective view of a force measurement system that utilizes the load transducer of FIG. 39, according to an embodiment of the invention.
Figure 43:
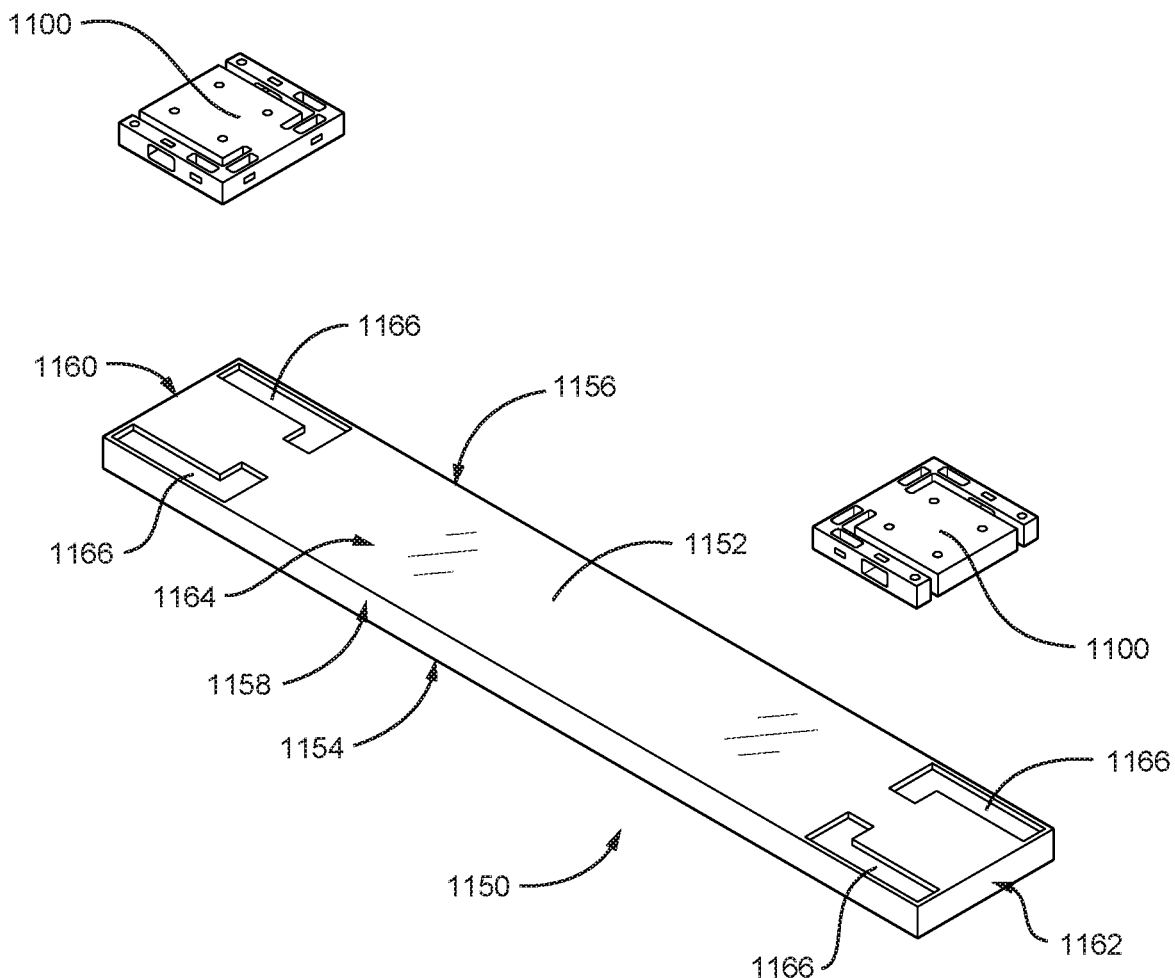
FIG. 43 is a bottom, partially exploded perspective view of the force measurement assembly of the force measurement system of FIG. 42.

Turning again to FIGS. 39 and 41 of the illustrated embodiment, it can be seen that the central body portion 1102 of the load transducer 1100 comprises a plurality of mounting apertures 1142 (e.g., four apertures 1142 arranged in 2×2 array) disposed therethrough for accommodating fasteners (e.g., screws) that attach the load transducer 1100 to a first object, such as a plate component of a force plate or force measurement assembly (e.g., plate component 1152 in FIGS. 42 and 43). Also, as depicted in FIGS. 39 and 41, the second and fourth transducer beam portions 1108, 1112 of the load transducer 1100 each comprise a mounting aperture 1144 (e.g., a single aperture 1144) disposed therethrough near the respective free ends 1108*a*, 1112*a* for accommodating a fastener (e.g., a screw) that attaches the load transducer 1100 to a second object, such as a mounting foot of a force plate or force measurement assembly. The load applied to the load transducer 1100 is conveyed through the plurality of beam portions 1106, 1108, 1110, 1112 of the load transducer 1100 from the first object (e.g., the plate component 1152 in FIGS. 42 and 43) to the second object (e.g., the mounting foot of the force measurement assembly).

In the illustrative embodiment of FIGS. 39-41, it can be seen that the central body portion 1102 of the load transducer 1100 comprises no other apertures besides the mounting apertures 1142. That is, the central body portion 1102 is completely solid, except for the mounting apertures 1142. Advantageously, the solid central body portion 1102 of the load transducer 1100 is structurally robust enough to support the load being applied to the object to which the load transducer 1100 is mounted (e.g., plate component 1152—see FIGS. 42 and 43) without undergoing excessive deformation (i.e., without undergoing non-elastic deformation).

An exemplary embodiment of a force measurement system is illustrated in FIGS. 42 and 43. In the illustrative embodiment, referring to FIG. 42, the force measurement system generally comprises a force measurement assembly 1150 (i.e., a force plate) that is operatively coupled to a data acquisition/data processing device 1174 (i.e., a data acquisition and processing device or computing device that is capable of collecting, storing, and processing data). The force measurement assembly 1150 illustrated in FIGS. 42 and 43 is configured to receive a subject thereon, and is capable of measuring the forces and/or moments applied to its measurement surface by the subject.

As shown in FIG. 42, the data acquisition and processing device 1174 (e.g., in the form of a laptop digital computer) generally includes a base portion 1178 with a central processing unit (CPU) disposed therein for collecting and processing the data that is received from the force measurement assembly 1150, and a plurality of devices 1180-1184 operatively coupled to the central processing unit (CPU) in the base portion 1178. Preferably, the devices that are operatively coupled to the central processing unit (CPU) comprise user input devices 1180, 1182 in the form of a keyboard 1180 and a touchpad 1182, as well as a graphical user interface in the form of a laptop LCD screen 1184. While a laptop type computing system is depicted in the embodiment of FIG. 42, one of ordinary skill in the art will appreciate that another type of data acquisition and processing device 1174 can be substituted for the laptop computing system such as, but not limited to, a palmtop computing device (i.e., a PDA) or a desktop type computing system having a plurality of separate, operatively coupled components (e.g., a desktop type computing system including a main housing with a central processing unit (CPU) and data storage devices, a remote monitor, a remote keyboard, and a remote mouse).

As illustrated in FIG. 42, force measurement assembly 1150 is operatively coupled to the data acquisition/data processing device 1174 by virtue of an electrical cable 1176. In one embodiment of the invention, the electrical cable 1176 is used for data transmission, as well as for providing power to the force measurement assembly 1150. Various types of data transmission cables can be used for cable 1176. For example, the cable 1176 can be a Universal Serial Bus (USB) cable or an Ethernet cable. Preferably, the electrical cable 1176 contains a plurality of electrical wires bundled together, with at least one wire being used for power and at least another wire being used for transmitting data. The bundling of the power and data transmission wires into a single electrical cable 1176 advantageously creates a simpler and more efficient design. In addition, it enhances the safety of the testing environment when human subjects are being tested on the force measurement assembly 1150. However, it is to be understood that the force measurement assembly 1150 can be operatively coupled to the data acquisition/data processing device 1176 using other signal transmission means, such as a wireless data transmission system. If a wireless data transmission system is employed, it is preferable to provide the force measurement assembly 1150 with a separate power supply in the form of an internal power supply or a dedicated external power supply.

Referring again to FIG. 42, it can be seen that the force measurement assembly 1150 of the illustrated embodiment is in the form of a force plate assembly with a single, continuous measurement surface. The force plate assembly includes a plate component 1152 supported on a plurality of load transducers 1100. As shown in FIGS. 42 and 43, the plate component 1152 comprises a top measurement surface 1154 (i.e., a planar top surface), a bottom surface 1164 disposed generally opposite to the top measurement surface 1154, and a plurality of side surfaces 1156, 1158, 1160, 1162 disposed between the top and bottom surfaces 1154, 1164. In the illustrated embodiment, the first side surface 1156 of the plate component 1152 is disposed generally parallel to the second side surface 1158, and is disposed generally perpendicular to both the third side surface 1160 and the fourth side surface 1162. The third side surface 1160 of the plate component 1152 is disposed generally parallel to the fourth side surface 1162, and is disposed generally perpendicular to both the first side surface 1156 and the second side surface 1158. Turning to the exploded view of FIG. 43, it can be seen that the bottom surface 1164 of the plate component 1152 comprises a plurality of L-shaped transducer recesses 1166 formed therein. Each of the plurality of transducer recesses 1166 corresponding to a footprint of either first and second beam portions 1106, 1108 or third and fourth beam portions 1110, 1112 of one of the plurality of load transducers 1100 so that the load measuring portions of the transducer beam portions 1106, 1108, 1110, 1112 with strain gages 1136, 1138, 1140 are spaced apart from bottom surface of the plate component 1152 (i.e., so that the entire load is transferred through the transducer beam portions 1106, 1108, 1110, 1112). Advantageously, the compact footprint of the load transducer 1100 enables the narrow force plate 1150 to be capable of measuring all three components of the force (i.e., $F_X$, $F_Y$, $F_Z$) applied to the plate component 1152 thereof.

In illustrated embodiment of FIGS. 42 and 43, the force measurement assembly 1150 comprises two (2) load transducers that are disposed underneath, and near opposite ends of the plate component 1152. Advantageously, because the load transducers 1100 are compact, neither of the load transducers 1100 extends substantially an entire length of the plate component 1152 of the force measurement assembly 1150. The compact construction of the load transducers 1100 not only reduces material costs because less material is used to form the load transducers 1100, but it also allows the load transducers 1100 to be universally used on force plates having a myriad of different lengths because it is not necessary for the load transducers 1100 to conform to the footprint size of the force plate.

In other embodiments of the invention, rather than using a force measurement assembly 1150 having a plate component 1152 with a single measurement surface 1154, it is to be understood that a force measurement assembly in the form of a dual force plate may be alternatively employed. Unlike the single force plate assembly 1150 illustrated in FIGS. 42 and 43, the dual force plate comprises two separate plate components, each of which is configured to accommodate a respective one of a subject's feet thereon (i.e., the left plate component accommodates the subject's left foot, whereas the right plate component accommodates the subject's right foot). In these alternative embodiments, each of the two plate components of the dual force plate are supported on two (2) load transducers 1100 (i.e., load transducers 1100 are disposed at opposite ends of each of the two plate components). As such, the dual force plate comprises a total of four (4) load transducers 1100 (i.e., two (2) load transducers 1100 under each of the two plate components).

Now, turning to FIG. 37, it can be seen that the data acquisition/data processing device 1174 (i.e., the laptop computing device) of the force measurement system comprises a microprocessor 1174a for processing data, memory 1174b (e.g., random access memory or RAM) for storing data during the processing thereof, and data storage device(s) 1174c, such as one or more hard drives, compact disk drives, floppy disk drives, flash drives, or any combination thereof. As shown in FIG. 37, the force measurement assembly 1150 and the visual display device 1184 are operatively coupled to the core components 1174a, 1174b, 1174c of the data acquisition/data processing device 1174 such that data is capable of being transferred between these devices 1150, 1174a, 1174b, 1174c, and 1184. Also, as illustrated in FIG. 37, a plurality of data input devices 1180, 1182 such as the keyboard 1180 and mouse 1182 shown in FIG. 42, are operatively coupled to the core components 1174a, 1174b, 1174c of the data acquisition/data processing device 1174 so that a user is able to enter data into the data acquisition/data processing device 1174. In some embodiments, the data acquisition/data processing device 1174 can be in the form of a laptop computer, while in other embodiments, the data acquisition/data processing device 1174 can be embodied as a desktop computer.

FIG. 38 graphically illustrates the acquisition and processing of the load data carried out by the exemplary force measurement system of FIG. 42. Initially, as shown in FIG. 38, a load L is applied to the force measurement assembly 1150 (e.g., by a subject disposed thereon). The load is transmitted from the plate component 1152 to the load transducers 1100 disposed at each of the opposed ends of the plate component 1152. As described above, in the illustrated embodiment, each of the load transducers 1100 includes a plurality of strain gages 1136, 1138, 1140 wired in one or more Wheatstone bridge configurations, wherein the electrical resistance of each strain gage is altered when the associated beam portion of the load transducer 1100 undergoes deformation resulting from the load (i.e., forces and/or moments) acting on the plate component 1152. For each plurality of strain gages disposed on the load transducers 1100, the change in the electrical resistance of the strain gages brings about a consequential change in the output voltage of the Wheatstone bridge (i.e., a quantity representative of the load being applied to the measurement surface 1154). Thus, in one embodiment, the two (2) load transducers 1100 disposed under the plate component 1152 output a total of six (6) analog output voltages (signals). In some embodiments, the six (6) analog output voltages from load transducers 1100 disposed under the plate component 1152 are then transmitted to a preamplifier board (not shown) for preconditioning. The preamplifier board is used to increase the magnitudes of the transducer analog voltages, and preferably, to convert the analog voltage signals into digital voltage signals as well. After which, the force measurement assembly 1150 transmits the force plate output signals $S_{FP01}$-$S_{FP06}$ to a main signal amplifier/converter 1072. Depending on whether the preamplifier board also includes an analog-to-digital (A/D) converter, the force plate output signals $S_{FP01}$-$S_{FP06}$ could be either in the form of analog signals or digital signals. The main signal amplifier/converter 1072 further magnifies the force plate output signals $S_{FP01}$-$S_{FP06}$, and if the signals $S_{FP01}$-$S_{FP06}$ are of the analog-type (for a case where the preamplifier board did not include an analog-to-digital (A/D) converter), it may also convert the analog signals to digital signals. Then, the signal amplifier/converter 1072 transmits either the digital or analog signals $S_{AC01}$-$S_{AC06}$ to the data acquisition/data processing device 1174 (computer 1174) so that the forces and/or moments that are being applied to the measurement surface 1154 of the force measurement assembly 1150 can be transformed into output load values OL. In addition to the components 1174a, 1174b, 1174c, the data acquisition/data processing device 1174 may further comprise an analog-to-digital (A/D) converter if the signals $S_{AC01}$-$S_{AC06}$ are in the form of analog signals. In such a case, the analog-to-digital converter will convert the analog signals into digital signals for processing by the microprocessor 1174a.

When the data acquisition/data processing device 1174 receives the voltage signals $S_{AC01}$-$S_{AC06}$, it initially transforms the signals into output forces by multiplying the voltage signals $S_{AC01}$-$S_{AC06}$ by a calibration matrix. If a load transducer having moment strain gages (as shown in FIGS. 51-54) is used in conjunction with the force measurement assembly 1150, the data acquisition/data processing device may additionally transform the signals into output moments by multiplying the voltage signals by the calibration matrix. After which, the force exerted on the surface 1154 of the force measurement assembly 1150, and the center of pressure of the applied force (i.e., the x and y coordinates of the point of application of the force applied to the measurement surface 1154) is determined by the data acquisition/data processing device 1174. Referring to the perspective view of FIG. 42, it can be seen that the center of pressure coordinates ($x_{P_L}$, $y_{P_L}$) for the plate component 1152 of the force measurement assembly 1150 are determined in accordance with x and y coordinate axes 1168, 1170. In FIG. 42, the vertical component of the force ($F_Z$) is defined by the z coordinate axis 1172.

In one exemplary embodiment, the data acquisition/data processing device 1174 determines all three (3) orthogonal components of the resultant forces acting on the plate component 1152 of the force measurement assembly 1150 (i.e., $F_X$, $F_Y$, $F_Z$). In yet other embodiments of the invention, all three (3) orthogonal components of the resultant forces and moments acting on the plate component 1152 of the force measurement assembly 1150 (i.e., $F_X$, $F_Y$, $F_Z$, $M_X$, $M_Y$, $M_Z$) may be determined (i.e., when the load transducer 1400 is used in lieu of the load transducers 1100).

Figure 44:
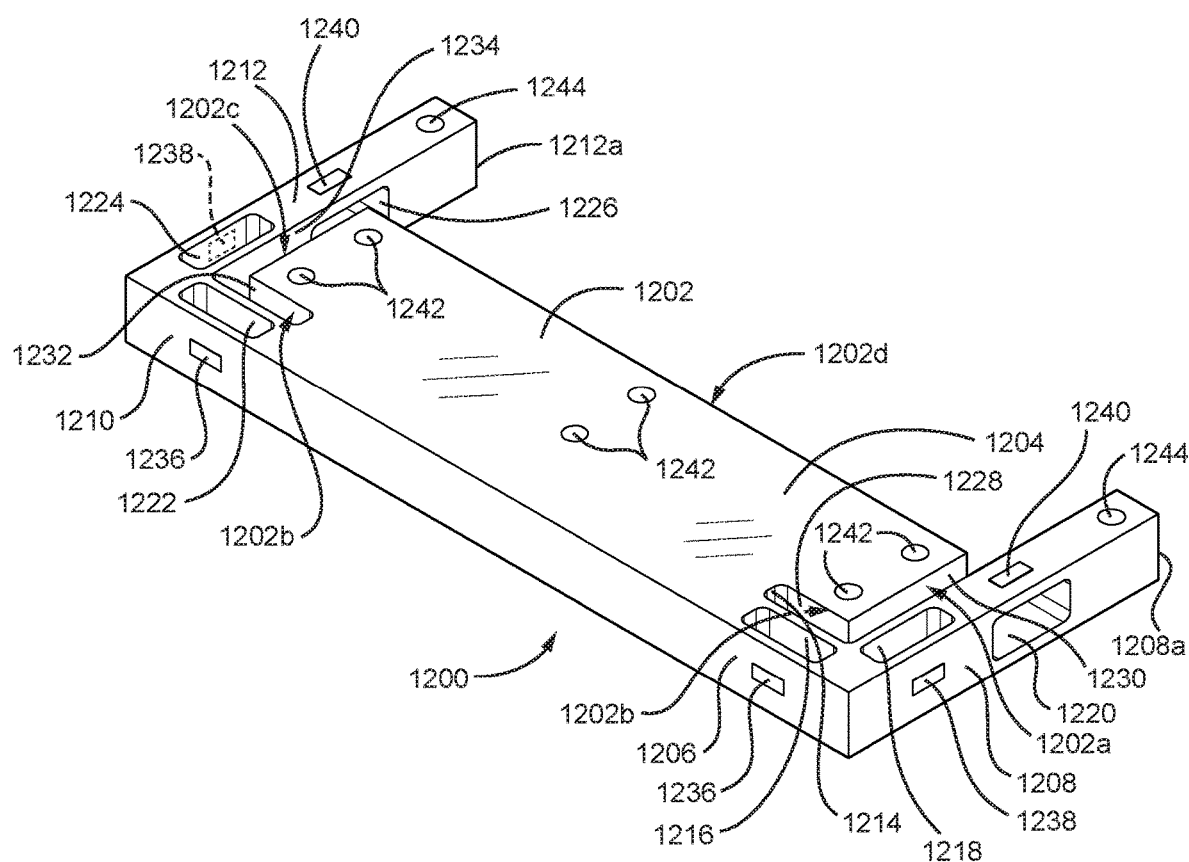
FIG. 44 is a top perspective view of a load transducer, according to a fourteenth embodiment of the invention.
Figure 45:
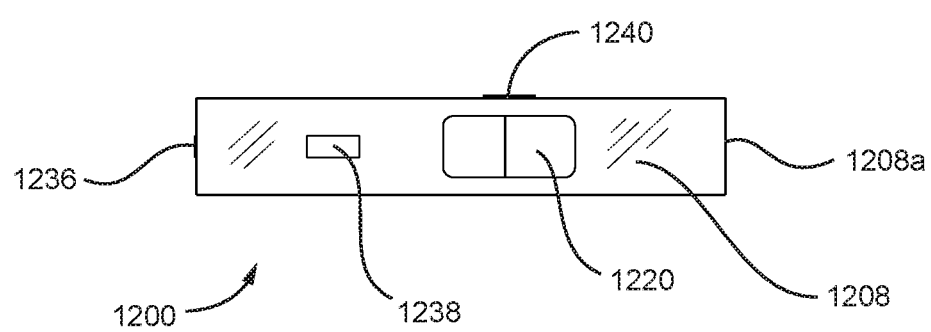
FIG. 45 is a side view of the load transducer of FIG. 44, according to the fourteenth embodiment of the invention.
Figure 46:
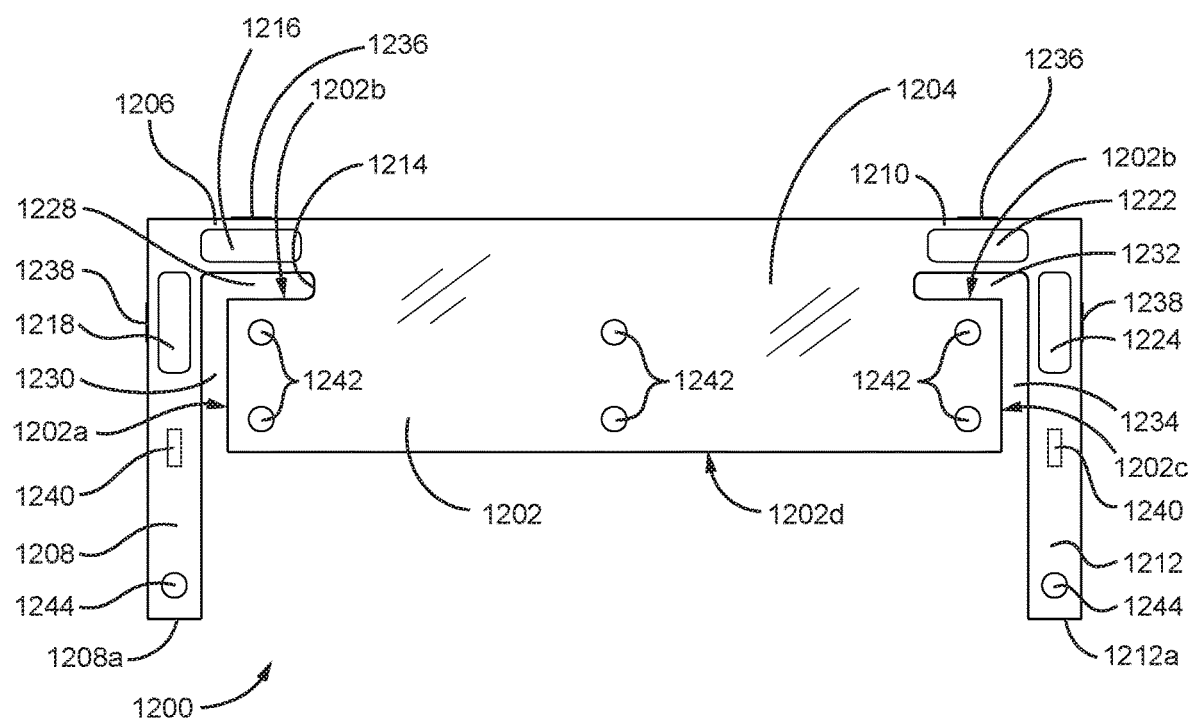
FIG. 46 is a top plan view of the load transducer of FIG. 44, according to the fourteenth embodiment of the invention.

FIGS. 44-46 illustrate a load transducer 1200 according to a fourteenth exemplary embodiment of the present invention. Referring initially to the perspective view of FIG. 44, it can be seen that the load transducer 1200 generally includes a one-piece compact transducer frame 1204 having a central body portion 1202 and a plurality of beam portions 1206, 1208, 1210, 1212 extending along sides 1202a, 1202b, 1202c of the central body portion 1202. As best illustrated in the perspective view of FIG. 44, each of the beam portions 1206, 1208, 1210, 1212 comprises one or more load cells or transducer elements for measuring forces and/or moments.

With reference again to FIG. 44, it can be seen that the illustrated central body portion 1202 is generally in the form of a rectangular prism with substantially right angle corners (i.e., substantially 90 degree corners). In FIG. 44, it can be seen that the body portion 1202 comprises a first pair of opposed sides 1202a, 1202c and a second pair of opposed sides 1202b, 1202d. The side 1202a is disposed generally parallel to the side 1202c, while the side 1202b is disposed generally parallel to the side 1202d. Each of the sides 1202a, 1202b, 1202c, 1202d is disposed generally perpendicular to the planar top and bottom surfaces of the body portion 1202. Also, each of the first pair of opposed sides 1202a, 1202c is disposed generally perpendicular to each of the second pair of opposed sides 1202b, 1202d. In addition, as shown in FIG. 44, the second side 1202b comprises a beam connecting portion 1214 extending outward therefrom. In the illustrated embodiment, it can be seen that the beam connecting portion 1214 connects the beam portions 1206 and 1210 to the second side 1202b of the central body portion 1202. In the illustrated embodiment, the total load applied to the load transducer 1200 is transmitted through the beam portions 1206, 1208, 1210, 1212.

As best shown in FIGS. 44 and 46, the proximal end of the first beam portion 1206 is rigidly connected to the central body portion 1202 by means of the beam connecting portion 1214, and the distal end of the first beam portion 1206 is rigidly connected to the proximal end of the second beam portion 1208. As depicted in these figures, the first beam portion 1206 extends along the second side 1202b of the central body portion 1202, and the second beam portion 1208 extends along the first side 1202a of the central body portion 1202. More particularly, in the illustrative embodiment, the longitudinal axis of the first beam portion 1206 is disposed generally parallel to the second side 1202b of the central body portion 1202, and the longitudinal axis of the second beam portion 1208 is disposed generally parallel to the first side 1202a of the central body portion 1202. As best shown in the perspective view of FIG. 44, the top and bottom surfaces of each of the first and second beam portions 1206, 1208 are disposed substantially co-planar with the top and bottom surfaces of the central body portion 1202. Also, in the illustrative embodiment, with reference again to FIGS. 44 and 46, the first beam portion 1206 is generally perpendicular, or perpendicular to the second beam portion 1208 (i.e., together the first and second beam portions 1206, 1208 form an overall L-shaped beam arm). In addition, as shown in these figures, the first beam portion 1206 is spaced apart from the second side 1202b of the central body portion 1202 by a first gap 1228, and the second beam portion 1208 is spaced apart from the first side 1202a of the central body portion 1202 by a second gap 1230. In the illustrative embodiment, together the first gap 1228 and the second gap 1230 form an overall L-shaped gap (i.e., the first gap 1228 is disposed perpendicular to the second gap 1230).

Also, referring again to FIGS. 44 and 46, it can be seen that the proximal end of the third beam portion 1210 is rigidly connected to the central body portion 1202 by means of the beam connecting portion 1214, and the distal end of the third beam portion 1210 is rigidly connected to the proximal end of the fourth beam portion 1212. As depicted in these figures, the third beam portion 1210 extends along the second side 1202b of the central body portion 1202, and the fourth beam portion 1212 extends along the third side 1202c of the central body portion 1202. More particularly, in the illustrative embodiment, the longitudinal axis of the third beam portion 1210 is disposed generally parallel to the second side 1202b of the central body portion 1202, and the longitudinal axis of the fourth beam portion 1212 is disposed generally parallel to the third side 1202c of the central body portion 1202. As best shown in the perspective view of FIG. 44, the top and bottom surfaces of each of the third and fourth beam portions 1210, 1212 are disposed substantially co-planar with the top and bottom surfaces of the central body portion 1202. Also, in the illustrative embodiment, with reference again to FIGS. 44 and 46, the third beam portion 1210 is generally perpendicular, or perpendicular to the fourth beam portion 1212 (i.e., together the third and fourth beam portions 1210, 1212 form an overall L-shaped beam arm). In addition, as shown in these figures, the third beam portion 1210 is spaced apart from the second side 1202b of the central body portion 1202 by a third gap 1232, and the fourth beam portion 1212 is spaced apart from the third side 1202c of the central body portion 1202 by a fourth gap 1234. In the illustrative embodiment, together the third gap 1232 and the fourth gap 1234 form an overall L-shaped gap (i.e., the third gap 1232 is disposed perpendicular to the fourth gap 1234).

In the illustrative embodiment of FIGS. 44 and 46, unlike the embodiment of FIGS. 39-41, it can be seen that the free end 1208a of the second beam portion 1208 is spaced apart from the fourth side 1202d of the central body portion 1202 (i.e., the second beam portion 1208 extends beyond the fourth side 1202d of the central body portion 1202). Also, as shown in FIGS. 44 and 46, the free end 1212a of the fourth beam portion 1212 is spaced apart from the fourth side 1202d of the central body portion 1202 (i.e., the fourth beam portion 1212 extends beyond the fourth side 1202d of the central body portion 1202).

In the illustrative embodiment of FIGS. 44-46, the first beam portion 1206 is provided with an aperture 1216 disposed therethrough, the second beam portion 1208 is provided with apertures 1218, 1220 disposed therethrough, the third beam portion 1210 is provided with an aperture 1222 disposed therethrough, and the fourth beam portion 1212 is provided with apertures 1224, 1226 disposed therethrough. In particular, the first and third transducer beam portions 1206, 1210 are provided with respective generally rectangular apertures 1216, 1222 disposed vertically through the beam portions 1206, 1210. The second transducer beam portion 1208 is provided with a first generally rectangular aperture 1218 disposed vertically through the beam portion 1208 and a second generally rectangular aperture 1220 disposed horizontally through the beam portion 1208. As such, the vertically extending aperture 1218 of the second beam portion 1208 extends in a direction that is generally perpendicular, or perpendicular to the extending direction of the horizontally extending aperture 1220. Similarly, the fourth transducer beam portion 1212 is provided with a first generally rectangular aperture 1224 disposed vertically through the beam portion 1212 and a second generally rectangular aperture 1226 disposed horizontally through the beam portion 1212. As such, the vertically extending aperture 1224 of the fourth beam portion 1212 extends in a direction that is generally perpendicular, or perpendicular to the extending direction of the horizontally extending aperture 1226. The apertures 1216, 1218, 1220, 1222, 1224, 1226, which are disposed through the transducer beam portions 1206, 1208, 1210, 1212, significantly increase the sensitivity of the load transducer 1200 when a load is applied thereto by reducing the cross-sectional area of the transducer beam portions 1206, 1208, 1210, 1212 at the locations of the apertures 1216, 1218, 1220, 1222, 1224, 1226.

As best shown in the perspective view of FIG. 44, the illustrated load cells are located on the transducer beam portions 1206, 1208, 1210, 1212. In the illustrated embodiment, each load cell comprises one or more strain gages 1236, 1238, 1240. Specifically, in the illustrated embodiment, the first transducer beam portion 1206 of the load transducer 1200 comprises a strain gage 1236 disposed on a side surface thereof that is sensitive to a first shear force component (i.e., a $F_Y$ strain gage) and substantially centered on the aperture 1216. In the illustrated embodiment, the second transducer beam portion 1208 of the load transducer 1200 comprises a strain gage 1238 disposed on a side surface thereof that is sensitive to a second shear force component (i.e., a $F_X$ strain gage) and substantially centered on the aperture 1218. The second transducer beam portion 1208 also comprises a strain gage 1240 disposed on a top surface thereof that is sensitive to a vertical force component (i.e., a $F_Z$ strain gage) and substantially centered on the aperture 1220. Also, in the illustrative embodiment, the third transducer beam portion 1210 of the load transducer 1200 comprises a strain gage 1236 disposed on a side surface thereof that is sensitive to the first shear force component (i.e., a $F_Y$ strain gage) and substantially centered on the aperture 1222. The fourth transducer beam portion 1212 of the load transducer 1200 comprises a strain gage 1238 disposed on a side surface thereof that is sensitive to a second shear force component (i.e., a $F_X$ strain gage) and substantially centered on the aperture 1224. The fourth transducer beam portion 1212 also comprises a strain gage 1240 disposed on a top surface thereof that is sensitive to a vertical force component (i.e., a $F_Z$ strain gage) and substantially centered on the aperture 1226. In the illustrated embodiment, the first shear force component is generally perpendicular to the second shear force component, and each of the first and second shear force components are generally perpendicular to the vertical force component.

In the illustrated embodiment, the strain gages 1236, 1238, 1240 are disposed on respective outer surfaces of the transducer beam portions 1206, 1208, 1210, 1212. The outer surfaces of the transducer beam portions 1206, 1208, 1210, 1212 on which the strain gages 1236, 1238, 1240 are disposed are generally opposite to the inner surfaces of the respective apertures 1216, 1218, 1220, 1222, 1224, 1226.

As best shown in FIGS. 44-46, the illustrated load cells are mounted on the top and outer side surfaces of the transducer beam portions 1206, 1208, 1210, 1212 of the load transducer 1200. Alternatively, the strain gages 1236, 1238 can be mounted to the inner side surfaces of the respective first and second transducer beam portions 1206, 1208, rather than to the outer side surfaces of the respective first and second transducer beam portions 1206, 1208 as illustrated in FIGS. 44 and 45. Similarly, the strain gages 1236, 1238 can be mounted to the inner side surfaces of the respective third and fourth transducer beam portions 1210, 1212, rather than to the outer side surfaces of the respective third and fourth transducer beam portions 1210, 1212 as illustrated in FIGS. 44 and 46. In addition, the strain gages 1240 can be mounted to the bottom surfaces of the second and fourth transducer beam portions 1208, 1212, rather than to the top of the transducer beam portions 1208, 1212 as illustrated in FIGS. 44 and 45. In general, the strain gages 1236, 1238, 1240 are mounted to surfaces generally normal to the direction of applied vertical and/or shear forces (i.e., $F_X$, $F_Y$, $F_Z$). It is also noted that alternatively, strain gages 1236 can be mounted at both opposed side surfaces of first and third transducer beam portions 1206, 1210 and/or strain gages 1238 can be mounted at both opposed side surfaces of the second and fourth transducer beam portions 1208, 1212. Similarly, strain gages 1240 can be mounted at both the top surface and the bottom surface of the second and fourth transducer beam portions 1208, 1212. These strain gages 1236, 1238, 1240 measure force either by bending moment or difference of bending moments at two cross sections. As force is applied to the central body portion 1202 of the load transducer 1200, the transducer beam portions bend. This bending either stretches or compresses the strain gages 1236, 1238, 1240, which in turn changes the resistance of the electrical current passing therethrough. The amount of change in the electrical voltage or current is proportional to the magnitude of the applied force, as applied to the central body portion 1202 of the load transducer 1200. In the illustrated embodiment, each of the strain gages 1236, 1238, 1240 comprises a full-bridge strain gage configuration (i.e., four (4) active strain gage elements wired in a Wheatstone bridge configuration). In an alternative embodiment, each of the strain gages 1236, 1238, 1240 may comprise a half-bridge strain gage configuration (i.e., two (2) active strain gage elements wired in a Wheatstone bridge configuration).

Turning again to FIGS. 44 and 46 of the illustrated embodiment, it can be seen that the central body portion 1202 of the load transducer 1200 comprises a plurality of mounting apertures 1242 (e.g., six apertures 1242 arranged in 3×2 array) disposed therethrough for accommodating fasteners (e.g., screws) that attach the load transducer 1200 to a first object, such as a plate component of a force plate or force measurement assembly (e.g., plate component 1152 in FIGS. 42 and 43). Also, as depicted in FIGS. 44 and 46, the second and fourth transducer beam portions 1208, 1212 of the load transducer 1200 each comprise a mounting aperture 1244 (e.g., a single aperture 1244) disposed therethrough near the respective free ends 1208a, 1212a for accommodating a fastener (e.g., a screw) that attaches the load transducer 1200 to a second object, such as a mounting foot of a force plate or force measurement assembly. The load applied to the load transducer 1200 is conveyed through the plurality of beam portions 1206, 1208, 1210, 1212 of the load transducer 1200 from the first object (e.g., the plate component 1152 in FIGS. 42 and 43) to the second object (e.g., the mounting foot of the force measurement assembly).

In the illustrative embodiment of FIGS. 44-46, it can be seen that the central body portion 1202 of the load transducer 1200 comprises no other apertures besides the mounting apertures 1242. That is, the central body portion 1202 is completely solid, except for the mounting apertures 1242. Advantageously, the solid central body portion 1202 of the load transducer 1200 is structurally robust enough to support the load being applied to the object to which the load transducer 1100 is mounted (e.g., plate component of a force measurement assembly) without undergoing excessive deformation (i.e., without undergoing non-elastic deformation).

Figure 47:
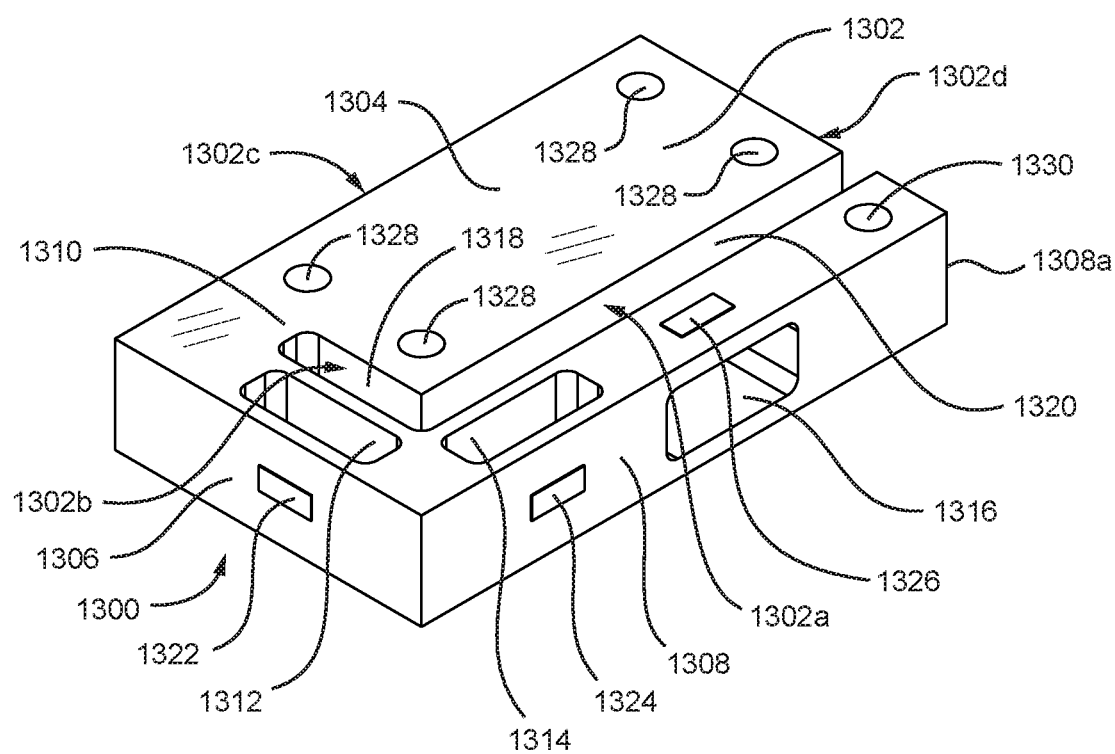
FIG. 47 is a top perspective view of a load transducer, according to a fifteenth embodiment of the invention, wherein the load transducer of FIG. 47 is configured for a left side mounting arrangement on the force measurement assembly.
Figure 48:
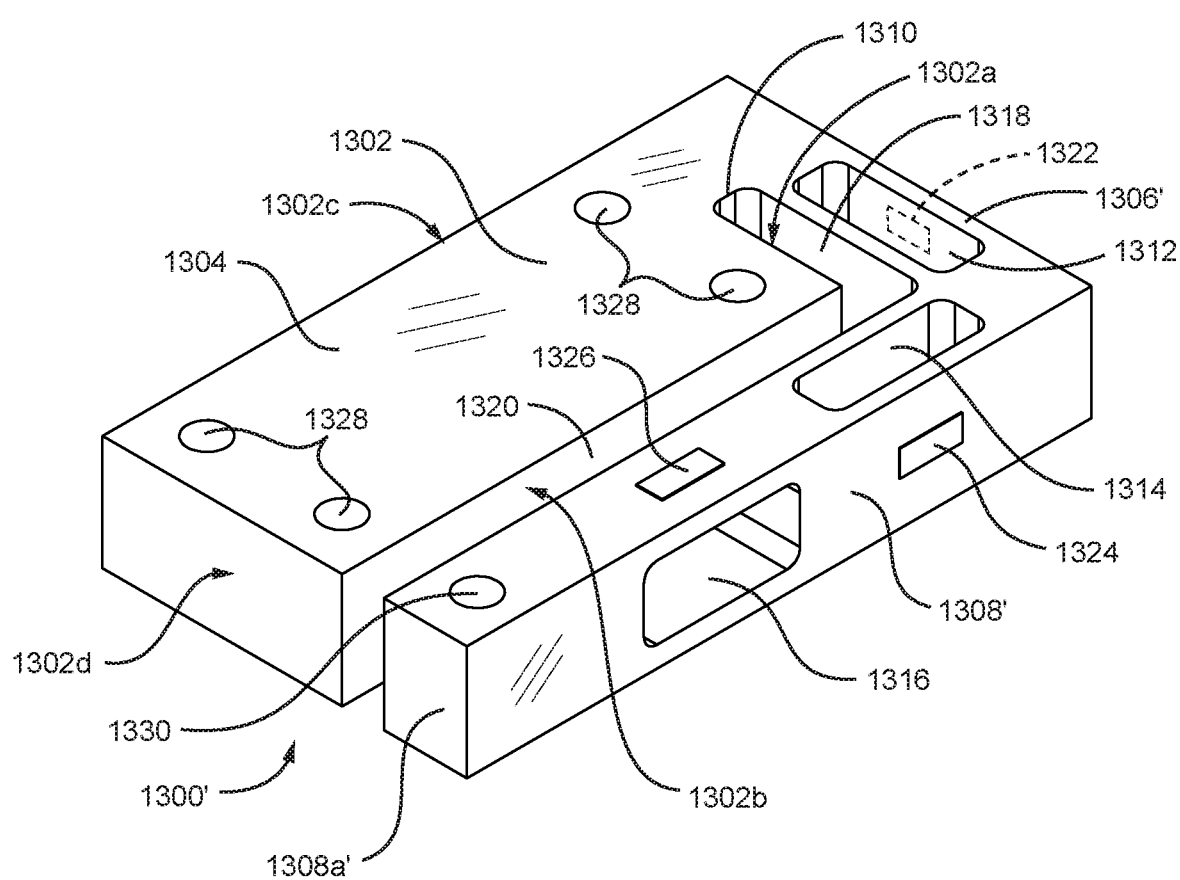
FIG. 48 is a top perspective view of a load transducer that is generally similar to the load transducer of FIG. 47, except that the load transducer of FIG. 48 is configured for a right side mounting arrangement on the force measurement assembly rather than a left side mounting arrangement.

FIGS. 47 and 48 illustrate a load transducer 1300, 1300' according to a fifteenth exemplary embodiment of the present invention. Referring to the perspective view of FIG. 47, it can be seen that the load transducer 1300 generally includes a one-piece compact transducer frame 1304 having a central body portion 1302 and a plurality of beam portions 1306, 1308 extending along sides 1302a, 1302b of the central body portion 1302. As best illustrated in the perspective view of FIG. 47, each of the beam portions 1306, 1308 comprises one or more load cells or transducer elements for measuring forces and/or moments. The load transducer 1300 in FIG. 47 is configured for a left side mounting arrangement on a force measurement assembly (e.g., the force measurement assembly 1340 in FIGS. 49 and 50), whereas the load transducer 1300' in FIG. 48 is configured for a right side mounting arrangement on a force measurement assembly (e.g., the force measurement assembly 1340 in FIGS. 49 and 50). Other than being configured for mounting on different sides of a force measurement assembly, the load transducers 1300, 1300' in FIGS. 47 and 48 are generally the same.

With reference again to FIG. 47, it can be seen that the illustrated central body portion 1302 is generally in the form of a rectangular prism with substantially right angle corners (i.e., substantially 90 degree corners). In FIG. 47, it can be seen that the body portion 1302 comprises a first pair of opposed sides 1302$a$, 1302$c$ and a second pair of opposed sides 1302$b$, 1302$d$. The side 1302$a$ is disposed generally parallel to the side 1302$c$, while the side 1302$b$ is disposed generally parallel to the side 1302$d$. Each of the sides 1302$a$, 1302$b$, 1302$c$, 1302$d$ is disposed generally perpendicular to the planar top and bottom surfaces of the body portion 1302. Also, each of the first pair of opposed sides 1302$a$, 1302$c$ is disposed generally perpendicular to each of the second pair of opposed sides 1302$b$, 1302$d$. In addition, as shown in FIG. 47, the second side 1302$b$ comprises a beam connecting portion 1310 extending outward therefrom. In the illustrated embodiment, it can be seen that the beam connecting portion 1310 connects the first beam portion 1306 to the second side 1302$b$ of the central body portion 1302. In the illustrated embodiment, the total load applied to the load transducer 1300 is transmitted through the beam portions 1306, 1308.

As best shown in FIG. 47, the proximal end of the first beam portion 1306 is rigidly connected to the central body portion 1302 by means of the beam connecting portion 1310, and the distal end of the first beam portion 1306 is rigidly connected to the proximal end of the second beam portion 1308. As depicted in these figures, the first beam portion 1306 extends along the second side 1302$b$ of the central body portion 1302, and the second beam portion 1308 extends along the first side 1302$a$ of the central body portion 1302. More particularly, in the illustrative embodiment, the longitudinal axis of the first beam portion 1306 is disposed generally parallel to the second side 1302$b$ of the central body portion 1302, and the longitudinal axis of the second beam portion 1308 is disposed generally parallel to the first side 1302$a$ of the central body portion 1302. As best shown in the perspective view of FIG. 47, the top and bottom surfaces of each of the first and second beam portions 1306, 1308 are disposed substantially co-planar with the top and bottom surfaces of the central body portion 1302. Also, in the illustrative embodiment, with reference again to FIG. 47, the first beam portion 1306 is generally perpendicular, or perpendicular to the second beam portion 1308 (i.e., together the first and second beam portions 1306, 1308 form an overall L-shaped beam arm). In addition, as shown in this figure, the first beam portion 1306 is spaced apart from the second side 1302$b$ of the central body portion 1302 by a first gap 1318, and the second beam portion 1308 is spaced apart from the first side 1302$a$ of the central body portion 1302 by a second gap 1320. In the illustrative embodiment, together the first gap 1318 and the second gap 1320 form an overall L-shaped gap (i.e., the first gap 1318 is disposed perpendicular to the second gap 1320). As shown in FIG. 48, the first and second beam portions 1306', 1308' have the same configuration as the first and second beam portions 1306, 1308, except that the beam portions 1306', 1308' of the load transducer 1300' are configured for a right side mounting arrangement on a force measurement assembly, rather than the left side mounting arrangement of the load transducer 1300.

In the illustrative embodiment of FIG. 47, like the embodiment of FIGS. 39-41, it can be seen that the free end 1308$a$ of the second beam portion 1308 is generally aligned, or aligned with the fourth side 1302$d$ of the central body portion 1302 (i.e., the end face of the second beam portion 1308 is co-planar with the fourth side 1302$d$ of the central body portion 1302). Similarly, as shown in FIG. 48, the free end 1308$a'$ of the second beam portion 1308' of the load transducer 1300' is generally aligned, or aligned with the fourth side 1302$d$ of the central body portion 1302 (i.e., the end face of the second beam portion 1308' is co-planar with the fourth side 1302$d$ of the central body portion 1302).

In the illustrative embodiment of FIG. 47, the first beam portion 1306 is provided with an aperture 1312 disposed therethrough, and the second beam portion 1308 is provided with apertures 1314, 1316 disposed therethrough. In particular, the first transducer beam portion 1306 is provided with a generally rectangular aperture 1312 disposed vertically through the beam portion 1306. The second transducer beam portion 1308 is provided with a first generally rectangular aperture 1314 disposed vertically through the beam portion 1308 and a second generally rectangular aperture 1316 disposed horizontally through the beam portion 1308. As such, the vertically extending aperture 1314 of the second beam portion 1308 extends in a direction that is generally perpendicular, or perpendicular to the extending direction of the horizontally extending aperture 1316. The apertures 1312, 1314, 1316, which are disposed through the transducer beam portions 1306, 1308, significantly increase the sensitivity of the load transducer 1300 when a load is applied thereto by reducing the cross-sectional area of the transducer beam portions 1306, 1308 at the locations of the apertures 1312, 1314, 1316.

As best shown in the perspective view of FIG. 47, the illustrated load cells are located on the transducer beam portions 1306, 1308. In the illustrated embodiment, each load cell comprises one or more strain gages 1322, 1324, 1326. Specifically, in the illustrated embodiment, the first transducer beam portion 1306 of the load transducer 1300 comprises a strain gage 1322 disposed on a side surface thereof that is sensitive to a first shear force component (i.e., a $F_Y$ strain gage) and substantially centered on the aperture 1312. In the illustrated embodiment, the second transducer beam portion 1308 of the load transducer 1300 comprises a strain gage 1324 disposed on a side surface thereof that is sensitive to a second shear force component (i.e., a $F_X$ strain gage) and substantially centered on the aperture 1314. The second transducer beam portion 1308 also comprises a strain gage 1326 disposed on a top surface thereof that is sensitive to a vertical force component (i.e., a $F_Z$ strain gage) and substantially centered on the aperture 1316. In the illustrated embodiment, the first shear force component is generally perpendicular to the second shear force component, and each of the first and second shear force components are generally perpendicular to the vertical force component.

In the illustrated embodiment, the strain gages 1322, 1324, 1326 are disposed on respective outer surfaces of the transducer beam portions 1306, 1308. The outer surfaces of the transducer beam portions 1306, 1308 on which the strain gages 1322, 1324, 1326 are disposed are generally opposite to the inner surfaces of the respective apertures 1312, 1314, 1316.

As best shown in FIG. 47, the illustrated load cells are mounted on the top and outer side surfaces of the transducer beam portions 1306, 1308 of the load transducer 1300. Alternatively, the strain gages 1322, 1324 can be mounted to the inner side surfaces of the respective first and second transducer beam portions 1306, 1308, rather than to the outer side surfaces of the respective first and second transducer beam portions 1306, 1308 as illustrated in FIG. 47. In addition, the strain gage 1326 can be mounted to the bottom surface of the second transducer beam portion 1308, rather than to the top of the transducer beam portion 1308 as illustrated in FIG. 47. In general, the strain gages 1322, 1324, 1326 are mounted to surfaces generally normal to the direction of applied vertical and/or shear forces (i.e., $F_X$, $F_Y$, $F_Z$). It is also noted that alternatively, strain gages 1322 can be mounted at both opposed side surfaces of first transducer beam portion 1306 and/or strain gages 1324 can be mounted at both opposed side surfaces of the second transducer beam portion 1308. Similarly, strain gages 1326 can be mounted at both the top surface and the bottom surface of the second transducer beam portion 1308. These strain gages 1322, 1324, 1326 measure force either by bending moment or difference of bending moments at two cross sections. As force is applied to the central body portion 1302 of the load transducer 1300, the transducer beam portions bend. This bending either stretches or compresses the strain gages 1322, 1324, 1326, which in turn changes the resistance of the electrical current passing therethrough. The amount of change in the electrical voltage or current is proportional to the magnitude of the applied force, as applied to the central body portion 1302 of the load transducer 1300. In the illustrated embodiment, each of the strain gages 1322, 1324, 1326 comprises a full-bridge strain gage configuration (i.e., four (4) active strain gage elements wired in a Wheatstone bridge configuration). In an alternative embodiment, each of the strain gages 1322, 1324, 1326 may comprise a half-bridge strain gage configuration (i.e., two (2) active strain gage elements wired in a Wheatstone bridge configuration).

Figure 49:
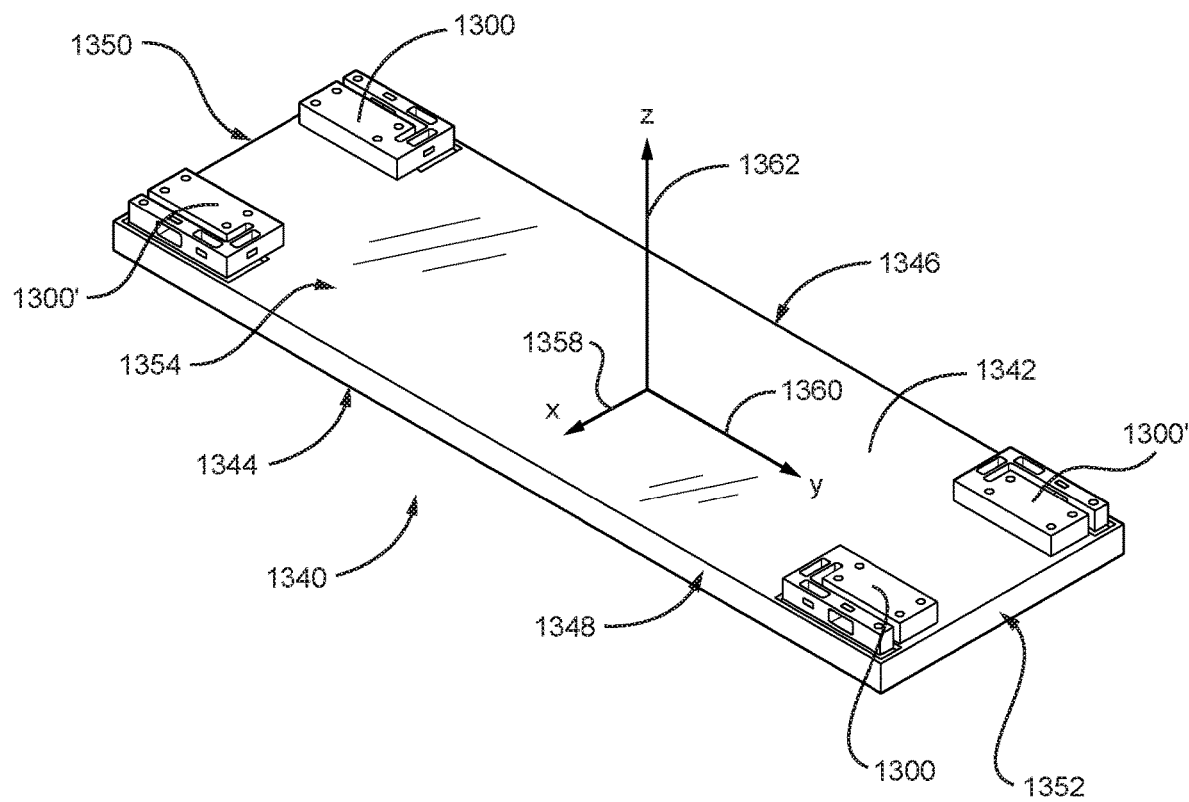
FIG. 49 is a bottom, assembled perspective view of a force measurement assembly that utilizes the load transducers of FIGS. 47 and 48, according to another embodiment of the invention.
Figure 50:
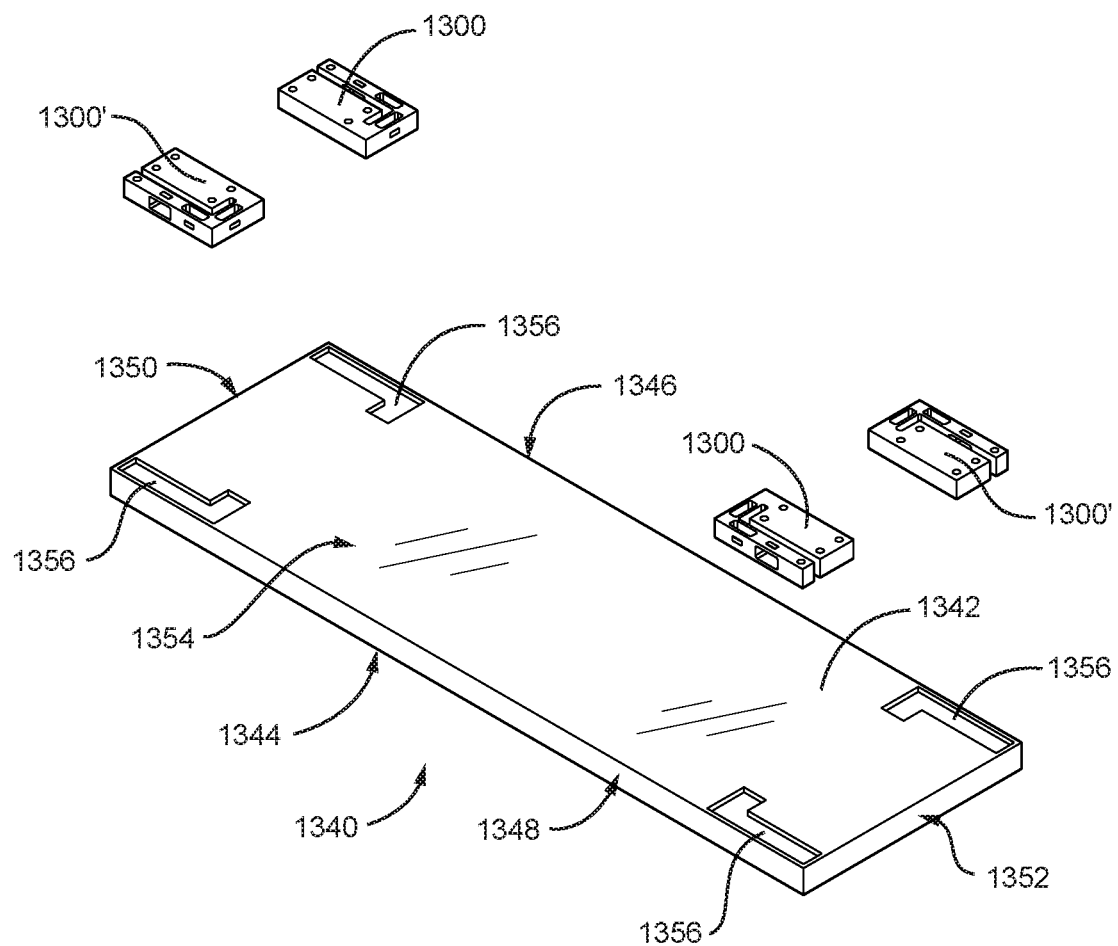
FIG. 50 is a bottom, partially exploded perspective view of the force measurement assembly of FIG. 49.

Turning again to FIG. 47 of the illustrated embodiment, it can be seen that the central body portion 1302 of the load transducer 1300 comprises a plurality of mounting apertures 1328 (e.g., four apertures 1328 arranged in 2×2 array) disposed therethrough for accommodating fasteners (e.g., screws) that attach the load transducer 1300 to a first object, such as a plate component of a force plate or force measurement assembly (e.g., plate component 1342 in FIGS. 49 and 50). Also, as depicted in FIG. 47, the second transducer beam portion 1308 of the load transducer 1300 comprises a mounting aperture 1330 (e.g., a single aperture 1330) disposed therethrough near the free end 1308a thereof for accommodating a fastener (e.g., a screw) that attaches the load transducer 1300 to a second object, such as a mounting foot of a force plate or force measurement assembly. The load applied to the load transducer 1300 is conveyed through the plurality of beam portions 1306, 1308 of the load transducer 1300 from the first object (e.g., the plate component 1342 in FIGS. 49 and 50) to the second object (e.g., the mounting foot of the force measurement assembly).

In the illustrative embodiments of FIGS. 47 and 48, it can be seen that the central body portions 1302 of the load transducers 1300, 1300' comprise no other apertures besides the mounting apertures 1328. That is, the central body portion 1302 is completely solid, except for the mounting apertures 1328. Advantageously, the solid central body portion 1302 of the load transducer 1300, 1300' is structurally robust enough to support the load being applied to the object to which the load transducer 1300, 1300' is mounted (e.g., plate component 1342—see FIGS. 49 and 50) without undergoing excessive deformation (i.e., without undergoing non-elastic deformation).

An exemplary embodiment of a force measurement assembly 1340 is illustrated in FIGS. 49 and 50. In the illustrative embodiment, the force measurement assembly 1340 of FIGS. 49 and 50 may be provided as part of a force measurement system, and thus may be operatively coupled to a data acquisition/data processing device (i.e., the data acquisition/data processing device 1174 described in conjunction with FIG. 42 above). The functionality of the force measurement system comprising the force measurement assembly 1340 and the data acquisition/data processing device would be generally the same as that described above for the embodiment of FIGS. 42 and 43, and thus need not be reiterated in conjunction with the description of the force measurement assembly 1340 of FIGS. 49 and 50. Also, like the force measurement assembly 1150 described above, the force measurement assembly 1340 illustrated in FIGS. 49 and 50 is configured to receive a subject thereon, and is capable of measuring the forces and/or moments applied to its measurement surface by the subject.

Referring again to FIG. 49, it can be seen that the force measurement assembly 1340 of the illustrated embodiment is in the form of a force plate assembly with a single, continuous measurement surface. The force plate assembly includes a plate component 1342 supported on a plurality of load transducers 1300, 1300'. As shown in FIGS. 49 and 50, the plate component 1342 comprises a top measurement surface 1344 (i.e., a planar top surface), a bottom surface 1354 disposed generally opposite to the top measurement surface 1344, and a plurality of side surfaces 1346, 1348, 1350, 1352 disposed between the top and bottom surfaces 1344, 1354. In the illustrated embodiment, the first side surface 1346 of the plate component 1342 is disposed generally parallel to the second side surface 1348, and is disposed generally perpendicular to both the third side surface 1350 and the fourth side surface 1352. The third side surface 1350 of the plate component 1342 is disposed generally parallel to the fourth side surface 1352, and is disposed generally perpendicular to both the first side surface 1346 and the second side surface 1348. Turning to the exploded view of FIG. 50, it can be seen that the bottom surface 1354 of the plate component 1342 comprises a plurality of L-shaped transducer recesses 1356 formed therein. Each of the plurality of transducer recesses 1356 corresponds to a footprint of the first and second beam portions 1306, 1308 of one of the plurality of load transducers 1300, 1300' so that the load measuring portions of the transducer beam portions 1306, 1308 with strain gages 1322, 1324, 1326 are spaced apart from a bottom surface of the plate component 1342 (i.e., so that the entire load is transferred through the transducer beam portions 1306, 1308).

In illustrated embodiment of FIGS. 49 and 50, the force measurement assembly 1340 comprises a total of four (4) load transducers 1300, 1300' that are disposed underneath, and near each of the respective four corners (4) of the plate component 1342. As explained above, the load transducers 1300' are generally the same as the load transducers 1300, expect that they are configured as a mirror image of the load transducers 1300. Advantageously, because the load transducers 1300, 1300' are compact, none of the plurality of load transducers 1300, 1300' extend substantially an entire length or width of the plate component 1342 of the force measurement assembly 1340. The compact construction of the load transducers 1300, 1300' not only reduces material costs because less material is used to form the load transducers 1300, 1300', but it also allows the load transducers 1300, 1300' to be universally used on force plates having a myriad of different lengths and widths because it is not necessary for the load transducers 1300, 1300' to conform to the footprint size of the force plate.

In other embodiments of the invention, rather than using a force measurement assembly 1340 having a plate component 1342 with a single measurement surface 1344, it is to be understood that a force measurement assembly in the form of a dual force plate may be alternatively employed. Unlike the single force plate assembly 1340 illustrated in FIGS. 49 and 50, the dual force plate comprises two separate plate components, each of which is configured to accommodate a respective one of a subject's feet thereon (i.e., the left plate component accommodates the subject's left foot, whereas the right plate component accommodates the subject's right foot). In these alternative embodiments, each of the two plate components of the dual force plate are supported on four (4) load transducers 1300, 1300' (i.e., a load transducer 1300, 1300' is disposed in each of the respective four (4) corners of each of the two plate components). As such, the dual force plate comprises a total of eight (8) load transducers 1300, 1300' (i.e., four (4) load transducers 1300, 1300' under each of the two plate components).

Similar to that described above for the force measurement assembly 1150, the force measurement assembly 1340 of FIGS. 49 and 50 is capable of measuring all three (3) orthogonal components of the resultant forces acting on the plate component 1342 of the force measurement assembly 1340 (i.e., $F_X$, $F_Y$, $F_Z$). In yet other embodiments of the invention, all three (3) orthogonal components of the resultant forces and moments acting on the plate component 1342 of the force measurement assembly 1340 (i.e., $F_X$, $F_Y$, $F_Z$, $M_X$, $M_Y$, $M_Z$) may be determined (i.e., when the load transducer 1400 is used in lieu of the load transducers 1300, 1300'). Also, referring to the perspective view of FIG. 49, it can be seen that the center of pressure coordinates ($x_{P_L}$, $y_{P_L}$) for the plate component 1342 of the force measurement assembly 1340 may be determined in accordance with x and y coordinate axes 1358, 1360. In FIG. 49, the vertical component of the force ($F_Z$) is defined by the z coordinate axis 1362.

FIGS. 51-54 illustrate a load transducer 1400 according to a sixteenth exemplary embodiment of the present invention. Referring initially to the perspective view of FIG. 51, it can be seen that the load transducer 1400 generally includes a one-piece compact transducer frame 1404 having a central body portion 1402 and beam portions 1406, 1408, 1410, 1412 disposed on opposite sides 1402a, 1402c of the central body portion 1402. As best illustrated in the perspective view of FIG. 51, each of the beam portions 1406, 1408, 1410, 1412 comprises one or more load cells or transducer elements for measuring forces and/or moments.

Figure 51:
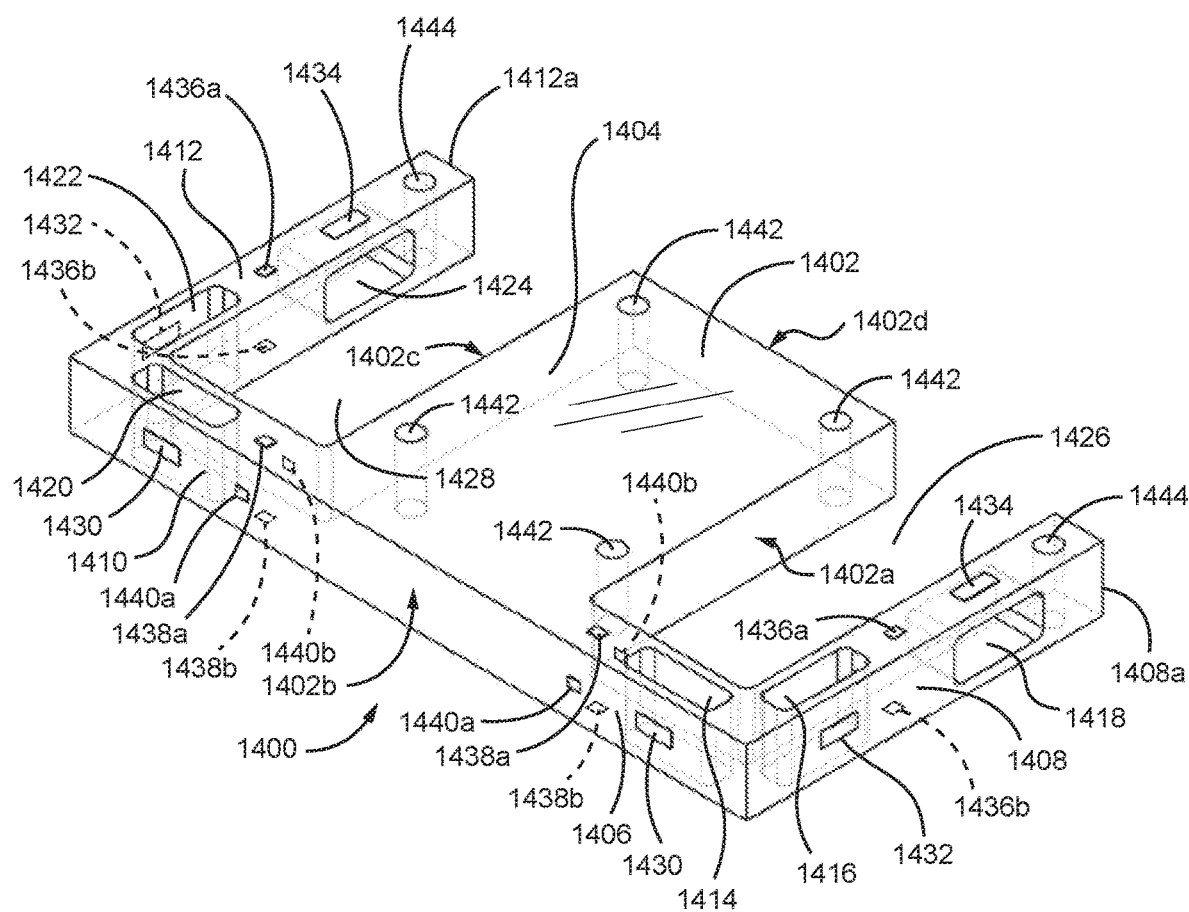
FIG. 51 is a top perspective view of a load transducer, according to a sixteenth embodiment of the invention.
Figure 52:
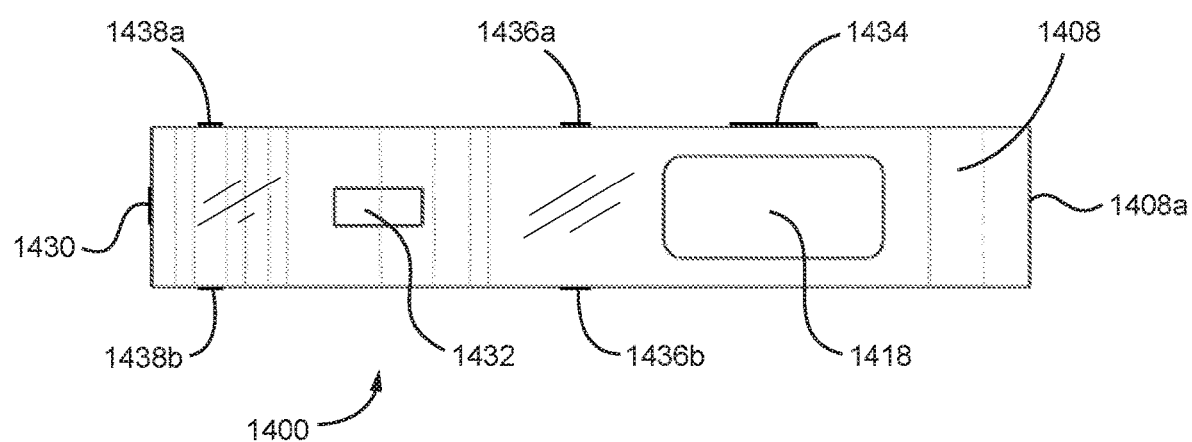
FIG. 52 is a first side view of the load transducer of FIG. 51, according to the sixteenth embodiment of the invention.
Figure 53:
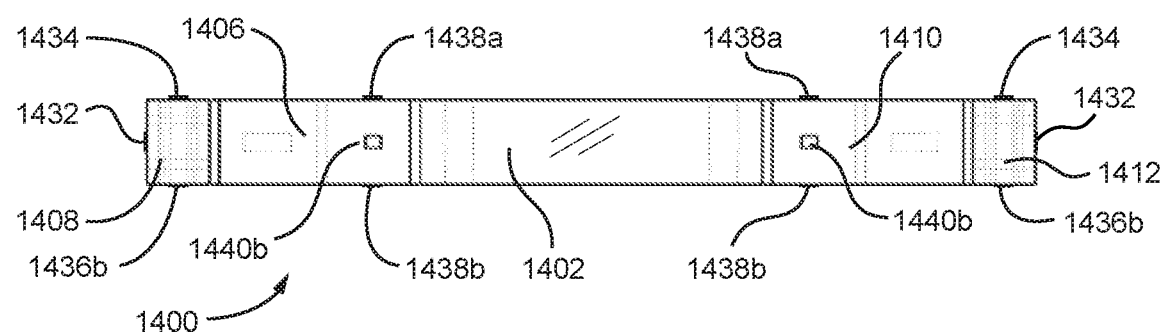
FIG. 53 is a second side view of the load transducer of FIG. 51, according to the sixteenth embodiment of the invention.

With reference again to FIG. 51, it can be seen that the illustrated central body portion 1402 is generally in the form of rectangular prism with substantially right angle corners (i.e., substantially 90 degree corners). In FIG. 51, it can be seen that the body portion 1402 comprises a first pair of opposed sides 1402a, 1402c and a second pair of opposed sides 1402b, 1402d. The side 1402a is disposed generally parallel to the side 1402c, while the side 1402b is disposed generally parallel to the side 1402d. Each of the sides 1402a, 1402b, 1402c, 1402d is disposed generally perpendicular to the planar top and bottom surfaces of the body portion 1402. Also, each of the first pair of opposed sides 1402a, 1402c is disposed generally perpendicular to each of the second pair of opposed sides 1402b, 1402d. In addition, as shown in FIG. 51, the first beam portion 1406 extends from the first side 1402a of the central body portion 1402 and the third beam portion 1410 extends from the third side 1402c of the central body portion 1402. In the illustrated embodiment, the total load applied to the load transducer 1400 is transmitted through the beam portions 1406, 1408, 1410, 1412.

Figure 54:
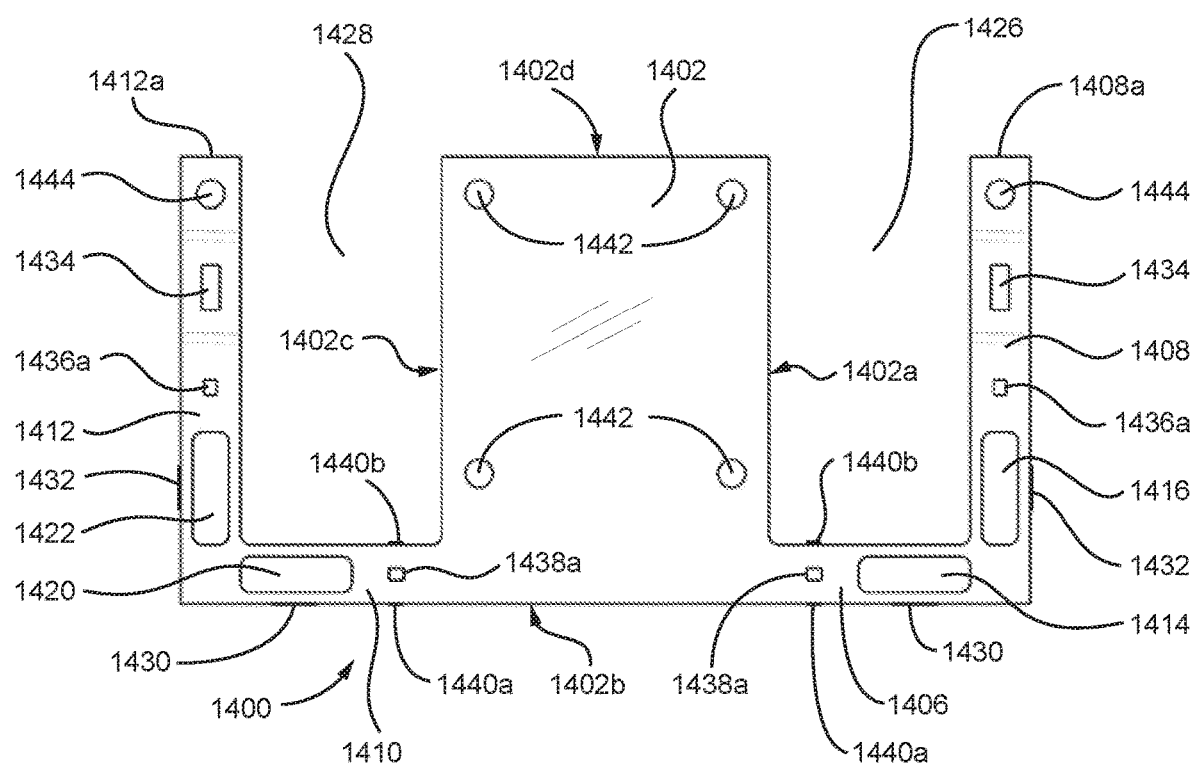
FIG. 54 is a top plan view of the load transducer of FIG. 51, according to the sixteenth embodiment of the invention.

As best shown in FIGS. 51 and 54, the proximal end of the first beam portion 1406 is rigidly connected to the first side 1402a of the central body portion 1402, and the distal end of the first beam portion 1406 is rigidly connected to the proximal end of the second beam portion 1408. As depicted in these figures, the second beam portion 1408 extends along the first side 1402a of the central body portion 1402. In the illustrative embodiment, the longitudinal axis of the first beam portion 1406 is disposed generally perpendicular to the first side 1402a of the central body portion 1402, and the longitudinal axis of the second beam portion 1408 is disposed generally parallel to the first side 1402a of the central body portion 1402. As best shown in the perspective view of FIG. 51, the top and bottom surfaces of each of the first and second beam portions 1406, 1408 are disposed substantially co-planar with the top and bottom surfaces of the central body portion 1402. Also, in the illustrative embodiment, with reference again to FIGS. 51 and 54, the first beam portion 1406 is generally perpendicular, or perpendicular to the second beam portion 1408 (i.e., together the first and second beam portions 1406, 1408 form an overall L-shaped beam arm). In addition, as shown in these figures, the second beam portion 1408 is spaced apart from the first side 1402a of the central body portion 1402 by a rectangular beam gap 1426.

Also, referring again to FIGS. 51 and 54, it can be seen that the proximal end of the third beam portion 1410 is rigidly connected to the third side 1402c of the central body portion 1402, and the distal end of the third beam portion 1410 is rigidly connected to the proximal end of the fourth beam portion 1412. As depicted in these figures, the fourth beam portion 1412 extends along the third side 1402c of the central body portion 1402. In the illustrative embodiment, the longitudinal axis of the third beam portion 1410 is disposed generally perpendicular to the third side 1402c of the central body portion 1402, and the longitudinal axis of the fourth beam portion 1412 is disposed generally parallel to the third side 1402c of the central body portion 1402. As best shown in the perspective view of FIG. 51, the top and bottom surfaces of each of the third and fourth beam portions 1410, 1412 are disposed substantially co-planar with the top and bottom surfaces of the central body portion 1402. Also, in the illustrative embodiment, with reference again to FIGS. 51 and 54, the third beam portion 1410 is generally perpendicular, or perpendicular to the fourth beam portion 1412 (i.e., together the third and fourth beam portions 1410, 1412 form an overall L-shaped beam arm). In addition, as shown in these figures, the fourth beam portion 1412 is spaced apart from the third side 1402c of the central body portion 1402 by a rectangular beam gap 1428.

In the illustrative embodiment of FIGS. 51-54, like the embodiment of FIGS. 39-41, it can be seen that the free end 1408a of the second beam portion 1408 is generally aligned, or aligned with the fourth side 1402d of the central body portion 1402 (i.e., the end face of the second beam portion 1408 is co-planar with the fourth side 1402d of the central body portion 1402). Also, as shown in FIGS. 51 and 54, the free end 1412a of the fourth beam portion 1412 is generally aligned, or aligned with the fourth side 1402d of the central body portion 1402 (i.e., the end face of the fourth beam portion 1412 is co-planar with the fourth side 1402*d* of the central body portion 1402).

In the illustrative embodiment of FIGS. 51-54, the first beam portion 1406 is provided with an aperture 1414 disposed therethrough, the second beam portion 1408 is provided with apertures 1416, 1418 disposed therethrough, the third beam portion 1410 is provided with an aperture 1420 disposed therethrough, and the fourth beam portion 1412 is provided with apertures 1422, 1424 disposed therethrough. In particular, the first and third transducer beam portions 1406, 1410 are provided with respective generally rectangular apertures 1414, 1420 disposed vertically through the beam portions 1406, 1410. The second transducer beam portion 1408 is provided with a first generally rectangular aperture 1416 disposed vertically through the beam portion 1408 and a second generally rectangular aperture 1418 disposed horizontally through the beam portion 1408. As such, the vertically extending aperture 1416 of the second beam portion 1408 extends in a direction that is generally perpendicular, or perpendicular to the extending direction of the horizontally extending aperture 1418. Similarly, the fourth transducer beam portion 1412 is provided with a first generally rectangular aperture 1422 disposed vertically through the beam portion 1412 and a second generally rectangular aperture 1424 disposed horizontally through the beam portion 1412. As such, the vertically extending aperture 1422 of the fourth beam portion 1412 extends in a direction that is generally perpendicular, or perpendicular to the extending direction of the horizontally extending aperture 1424. The apertures 1414, 1416, 1418, 1420, 1422, 1424, which are disposed through the transducer beam portions 1406, 1408, 1410, 1412, significantly increase the sensitivity of the load transducer 1400 when a load is applied thereto by reducing the cross-sectional area of the transducer beam portions 1406, 1408, 1410, 1412 at the locations of the apertures 1414, 1416, 1418, 1420, 1422, 1424.

As best shown in the perspective view of FIG. 51, the illustrated load cells are located on the transducer beam portions 1406, 1408, 1410, 1412. In the illustrated embodiment, each load cell comprises one or more strain gages 1430, 1432, 1434, 1436*a*, 1436*b*, 1438*a*, 1438*b*, 1440*a*, 1440*b*. Specifically, in the illustrated embodiment, the first transducer beam portion 1406 of the load transducer 1400 comprises a strain gage 1430 disposed on a side surface thereof that is sensitive to a first shear force component (i.e., a $F_Y$ strain gage) and substantially centered on the aperture 1414. The first transducer beam portion 1406 also comprises a first set of strain gages 1438*a*, 1438*b* that are sensitive to a first moment component (i.e., a My strain gages). The strain gages 1438*a*, 1438*b* are disposed on opposed top and bottom surfaces of the first transducer beam portion 1406, and are substantially vertically aligned with one another. The first transducer beam portion 1406 additionally comprises a second set of strain gages 1440*a*, 1440*b* that are sensitive to a second moment component (i.e., a $M_Z$ strain gages). The strain gages 1440*a*, 1440*b* are disposed on opposed side surfaces of the first transducer beam portion 1406, and are substantially horizontally aligned with one another. In the illustrated embodiment, the second transducer beam portion 1408 of the load transducer 1400 comprises a strain gage 1432 disposed on a side surface thereof that is sensitive to a second shear force component (i.e., a $F_X$ strain gage) and substantially centered on the aperture 1416. The second transducer beam portion 1408 also comprises a strain gage 1434 disposed on a top surface thereof that is sensitive to a vertical force component (i.e., a $F_Z$ strain gage) and substantially centered on the aperture 1418. In addition, the second transducer beam portion 1408 also comprises a set of strain gages 1436*a*, 1436*b* that are sensitive to a third moment component (i.e., a $M_X$ strain gages). The strain gages 1436*a*, 1436*b* are disposed on opposed top and bottom surfaces of the second transducer beam portion 1408, and are substantially vertically aligned with one another. Also, in the illustrative embodiment, the third transducer beam portion 1410 of the load transducer 1400 comprises a strain gage 1430 disposed on a side surface thereof that is sensitive to the first shear force component (i.e., a $F_Y$ strain gage) and substantially centered on the aperture 1420. The third transducer beam portion 1410 also comprises a first set of strain gages 1438*a*, 1438*b* that are sensitive to a first moment component (i.e., a $M_Y$ strain gages). The strain gages 1438*a*, 1438*b* are disposed on opposed top and bottom surfaces of the third transducer beam portion 1410, and are substantially vertically aligned with one another. The third transducer beam portion 1410 additionally comprises a second set of strain gages 1440*a*, 1440*b* that are sensitive to a second moment component (i.e., a $M_Z$ strain gages). The strain gages 1440*a*, 1440*b* are disposed on opposed side surfaces of the third transducer beam portion 1410, and are substantially horizontally aligned with one another. The fourth transducer beam portion 1412 of the load transducer 1400 comprises a strain gage 1432 disposed on a side surface thereof that is sensitive to a second shear force component (i.e., a $F_X$ strain gage) and substantially centered on the aperture 1422. The fourth transducer beam portion 1412 also comprises a strain gage 1434 disposed on a top surface thereof that is sensitive to a vertical force component (i.e., a $F_Z$ strain gage) and substantially centered on the aperture 1424. In addition, the fourth transducer beam portion 1412 also comprises a set of strain gages 1436*a*, 1436*b* that are sensitive to a third moment component (i.e., a $M_X$ strain gages). The strain gages 1436*a*, 1436*b* are disposed on opposed top and bottom surfaces of the fourth transducer beam portion 1412, and are substantially vertically aligned with one another. In the illustrated embodiment, the first shear force component is generally perpendicular to the second shear force component, and each of the first and second shear force components are generally perpendicular to the vertical force component.

In the illustrated embodiment, the strain gages 1430, 1432, 1434 are disposed on respective outer surfaces of the transducer beam portions 1406, 1408, 1410, 1412. The outer surfaces of the transducer beam portions 1406, 1408, 1410, 1412 on which the strain gages 1430, 1432, 1434 are disposed are generally opposite to the inner surfaces of the respective apertures 1414, 1416, 1418, 1420, 1422, 1424.

As shown in FIGS. 51-54, the force component strain gages of the illustrated load cells are mounted on the top and outer side surfaces of the transducer beam portions 1406, 1408, 1410, 1412 of the load transducer 1400. Alternatively, the strain gages 1430, 1432 can be mounted to the inner side surfaces of the respective first and second transducer beam portions 1406, 1408, rather than to the outer side surfaces of the respective first and second transducer beam portions 1406, 1408 as illustrated in FIGS. 51 and 54. Similarly, the strain gages 1430, 1432 can be mounted to the inner side surfaces of the respective third and fourth transducer beam portions 1410, 1412, rather than to the outer side surfaces of the respective third and fourth transducer beam portions 1410, 1412 as illustrated in FIGS. 51 and 54. In addition, the strain gages 1434 can be mounted to the bottom surfaces of the second and fourth transducer beam portions 1408, 1412, rather than to the top of the transducer beam portions 1408, 1412 as illustrated in FIGS. 51 and 54. In general, the strain gages 1430, 1432, 1434 are mounted to surfaces generally normal to the direction of applied vertical and/or shear forces (i.e., $F_X$, $F_Y$, $F_Z$). It is also noted that alternatively, strain gages 1430 can be mounted at both opposed side surfaces of first and third transducer beam portions 1406, 1410 and/or strain gages 1432 can be mounted at both opposed side surfaces of the second and fourth transducer beam portions 1408, 1412. Similarly, strain gages 1434 can be mounted at both the top surface and the bottom surface of the second and fourth transducer beam portions 1408, 1412. These strain gages 1430, 1432, 1434 measure force either by bending moment or difference of bending moments at two cross sections. As force is applied to the central body portion 1402 of the load transducer 1400, the transducer beam portions bend. This bending either stretches or compresses the strain gages 1430, 1432, 1434, which in turn changes the resistance of the electrical current passing therethrough. The amount of change in the electrical voltage or current is proportional to the magnitude of the applied force, as applied to the central body portion 1402 of the load transducer 1400.

In the illustrated embodiment, each of the strain gages 1430, 1432, 1434 comprises a full-bridge strain gage configuration (i.e., four (4) active strain gage elements wired in a Wheatstone bridge configuration), while each of the strain gages 1436a, 1436b, 1438a, 1438b, 1440a, and 1440b comprises a half-bridge strain gage configuration (i.e., two (2) active strain gage elements). Also, in the illustrative embodiment, the pair of strain gages 1436a, 1436b are wired together in one Wheatstone bridge configuration (i.e., with a total of four (4) active strain gage elements), the pair of strain gages 1438a, 1438b are wired together in another Wheatstone bridge configuration (i.e., with a total of four (4) active strain gage elements), and the pair of strain gages 1440a, 1440b are wired together in yet another Wheatstone bridge configuration (i.e., with a total of four (4) active strain gage elements).

Turning again to FIGS. 51 and 54 of the illustrated embodiment, it can be seen that the central body portion 1402 of the load transducer 1400 comprises a plurality of mounting apertures 1442 (e.g., four apertures 1442 arranged in 2×2 array) disposed therethrough for accommodating fasteners (e.g., screws) that attach the load transducer 1400 to a first object, such as a plate component of a force plate or force measurement assembly (e.g., plate component 1152 in FIGS. 42 and 43). Also, as depicted in FIGS. 51 and 54, the second and fourth transducer beam portions 1408, 1412 of the load transducer 1400 each comprise a mounting aperture 1444 (e.g., a single aperture 1444) disposed therethrough near the respective free ends 1408a, 1412a for accommodating a fastener (e.g., a screw) that attaches the load transducer 1400 to a second object, such as a mounting foot of a force plate or force measurement assembly. The load applied to the load transducer 1400 is conveyed through the plurality of beam portions 1406, 1408, 1410, 1412 of the load transducer 1400 from the first object (e.g., the plate component 1152 in FIGS. 42 and 43) to the second object (e.g., the mounting foot of the force measurement assembly).

In the illustrative embodiment of FIGS. 51-54, it can be seen that the central body portion 1402 of the load transducer 1400 comprises no other apertures besides the mounting apertures 1442. That is, the central body portion 1402 is completely solid, except for the mounting apertures 1442. Advantageously, the solid central body portion 1402 of the load transducer 1400 is structurally robust enough to support the load being applied to the object to which the load transducer 1400 is mounted (e.g., a plate component of a force measurement assembly) without undergoing excessive deformation (i.e., without undergoing non-elastic deformation).

Figure 55:
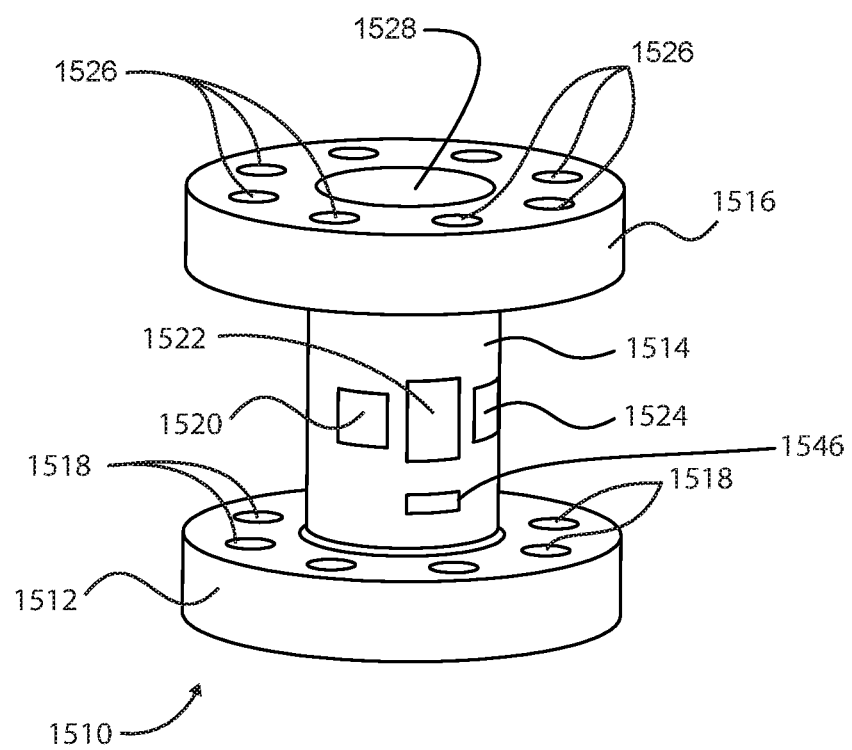
FIG. 55 is a perspective view of a load transducer, according to a seventeenth embodiment of the invention.

Referring now to the drawings, FIGS. 55-60 illustrate a load transducer 1510 according to a seventeenth exemplary embodiment of the present invention. As shown in these figures, in the illustrated embodiment, the load transducer 1510 is in the form of a pylon-type load cell. The load transducer 1510 generally includes a one-piece compact transducer frame portion having a central cylindrical body portion 1514 and a pair of flanges 1512, 1516 disposed at opposite longitudinal ends of the central cylindrical body portion 1514. In particular, the load transducer 1510 includes a bottom flange 1512 disposed at the lower longitudinal end of the cylindrical body portion 1514, and a top flange 1516 disposed at the upper longitudinal end of the cylindrical body portion 1514. As best illustrated in the perspective view of FIG. 55 and the sectional view of FIG. 60, the bottom flange 1512 comprises a plurality of circumferentially spaced-apart mounting apertures 1518 disposed therethrough (e.g., eight (8) mounting apertures 1518 disposed therethrough). Each of the mounting apertures 1518 is configured to receive a respective fastener (e.g., a threaded screw or bolt) for securing the load transducer 1510 to an object (e.g., a bottom mounting plate). Similarly, as shown in FIG. 55 and top view of FIG. 59, the top flange 1516 also comprises a plurality of circumferentially spaced-apart mounting apertures 1526 disposed therethrough (e.g., eight (8) mounting apertures 1526 disposed therethrough). Each of the mounting apertures 1526 is configured to receive a respective fastener (e.g., a threaded screw or bolt) for securing the load transducer 1510 to an object (e.g., a top plate member).

Figure 59:
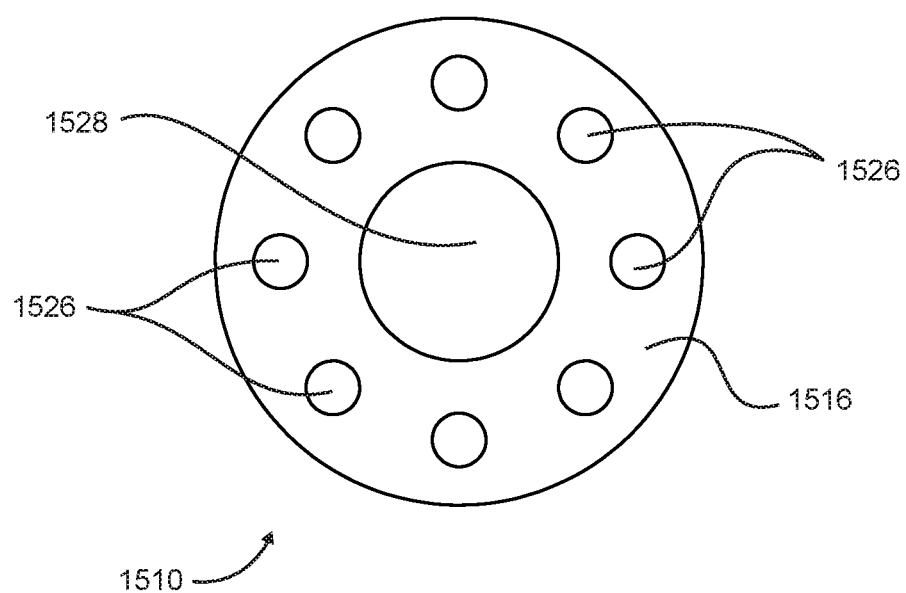
FIG. 59 is a top view of the load transducer of FIG. 55.
Figure 60:
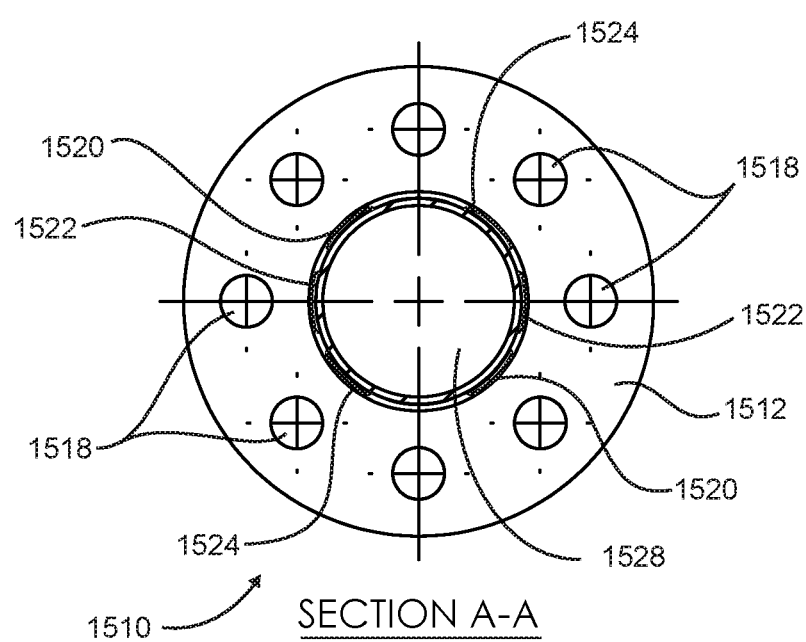
FIG. 60 is a transverse cross-sectional view of the load transducer of FIG. 55, wherein the transverse section is cut through the cutting plane line A-A in FIG. 56.

With reference to FIGS. 55, 59, and 60, it can be seen that, in the illustrative embodiment, the frame portion of the load transducer 1510 includes a central aperture 1528 disposed therethrough in a longitudinal direction of the load transducer 1510. As such, the central cylindrical body portion 1514 of the load transducer 1510 is in the form of a tubular member that undergoes elastic deformation when a load is applied to the load transducer 1510. Advantageously, adding the central aperture 1528 through the load transducer 1510 increases the sensitivity of the load transducer 1510.

In the illustrated embodiment, the frame portion of the load transducer 1510 is milled as one solid and continuous piece of a single material. That is, the frame portion of the load transducer 1510 is of unitary or one-piece construction with the central cylindrical body portion 1514 and the flanges 1512, 1516 integrally formed together. The frame portion of the load transducer 1510 is preferably machined in one piece from aluminum, titanium, steel, or any other suitable material that meets strength and weight requirements. Alternatively, the central cylindrical body portion 1514 of the load transducer 1510 may be formed separately from the flanges 1512, 1516, and then attached or joined to the flanges 1512, 1516 in any suitable manner (e.g., by welding, etc.).

Referring collectively to FIGS. 55 and 60, it can be seen that a plurality of deformation sensing elements (e.g., strain gages 1520, 1522, 1524) are disposed on the outer periphery of the central cylindrical body portion 1514 of the load transducer 1510. In particular, in the illustrative embodiment, each of a first pair of strain gages 1520 (see FIG. 60) is sensitive to a first force component (i.e., the x-component of the force, $F_X$) of the load and outputs one or more first output signals representative of the first force component ($F_X$). As best shown in the sectional view of FIG. 60, a first one of the strain gages 1520 is disposed opposite to a second one of the strain gages 1520 across the longitudinal axis of the load transducer 1510. In other words, the strain gages 1520 are spaced apart from one another about the outer periphery of the central cylindrical body portion 1514 by approximately 180 degrees.

With reference again to FIG. 60, in the illustrative embodiment, each of a second pair of strain gages 1522 (see FIG. 60) is sensitive to a torsional moment component (i.e., the z-component of the moment, $M_Z$) of the load and outputs one or more second output signals representative of the torsional moment component ($M_Z$). As best shown in the sectional view of FIG. 60, like the strain gages 1520 described above, a first one of the strain gages 1522 is disposed opposite to a second one of the strain gages 1522 across the longitudinal axis of the load transducer 1510. In other words, the strain gages 1522 are spaced apart from one another about the outer periphery of the central cylindrical body portion 1514 by approximately 180 degrees.

Turning again to FIG. 60, in the illustrative embodiment, each of a third pair of strain gages 1524 (see FIG. 60) is sensitive to a second force component (i.e., the y-component of the force, $F_Y$) of the load and outputs one or more third output signals representative of the second force component ($F_Y$). As best shown in the sectional view of FIG. 60, like the strain gages 1520 and 1522 described above, a first one of the strain gages 1524 is disposed opposite to a second one of the strain gages 1524 across the longitudinal axis of the load transducer 1510. In other words, the strain gages 1524 are spaced apart from one another about the outer periphery of the central cylindrical body portion 1514 by approximately 180 degrees.

In the illustrated embodiment, each of the strain gages 1520, 1522, 1524 comprise a half bridge (e.g., a half Wheatstone bridge). Although, in other embodiments, the strain gages 1520, 1522, 1524 may comprise a full bridge (e.g., a full Wheatstone bridge). Also, in the illustrated embodiment, each of the strain gages 1520, 1522, 1524 may produce a separate output signal (e.g., output voltage) such that the load transducer 1510 produces a total of six (6) total output signals (e.g., output voltages). Although, in other embodiments, the paired strain gages 1520, 1522, 1524 may be wired together such that the load transducer 1510 only produces a total of three (3) output signals (e.g., output voltages).

FIGS. 61-66 illustrate a load transducer 1510' according to an eighteenth exemplary embodiment of the present invention. As shown in these figures, similar to the seventeenth illustrative embodiment, the load transducer 1510' is in the form of a pylon-type load cell. As such, the load transducer 1510' is similar in many respects to the load transducer 1510 of the seventeenth embodiment described above. However, unlike the aforedescribed load transducer 1510, the load transducer 1510' has an elongated central cylindrical body portion 1514' with redundant sets of deformation sensing elements (e.g., strain gages 1530, 1532, 1534) disposed above the primary sets of deformation sensing elements (e.g., strain gages 1520, 1522, 1524). Advantageously, providing the redundant sets of deformation sensing elements (e.g., strain gages 1530, 1532, 1534) allow the load transducer 1510' to function normally even if one of the strain gages were to fail. That is, the strain gages 1530, 1532, 1534 allow for redundant measurement of the force components and torsional component in critical applications (e.g., when the load transducer 1510' is being used to control an important industrial process, etc.). Thus, advantageously, the redundant sets of deformation sensing elements (e.g., strain gages 1530, 1532, 1534) allow the load transducer 1510' to produce the same output when one of the primary deformation sensing elements (e.g., strain gages 1520, 1522, 1524) experiences a failure.

Figure 61:
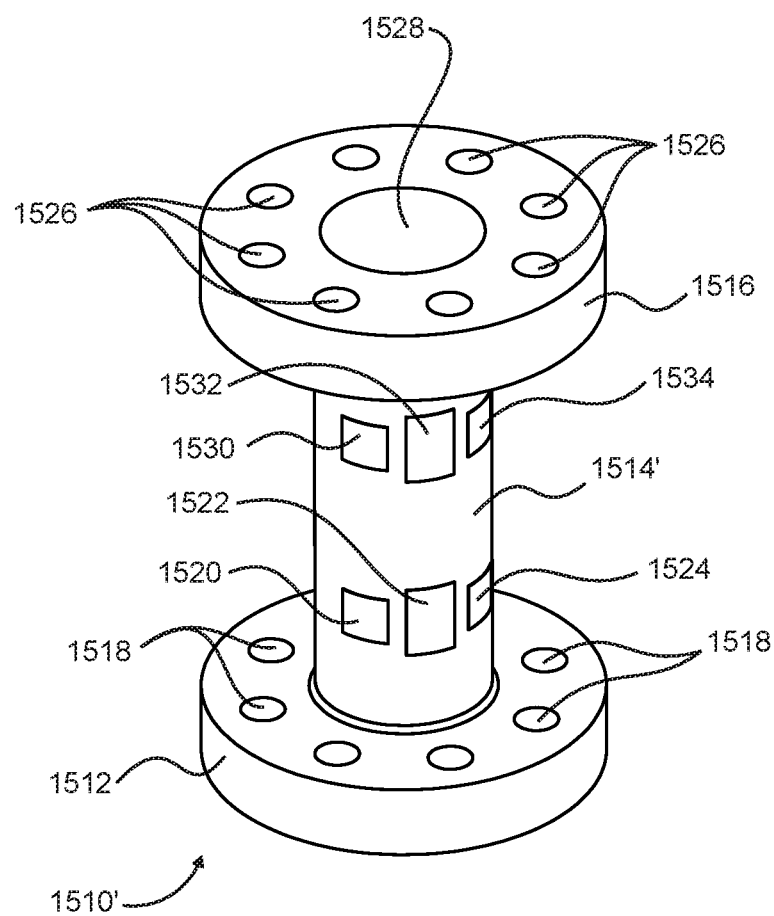
FIG. 61 is a perspective view of a load transducer, according to an eighteenth embodiment of the invention.
Figure 62:
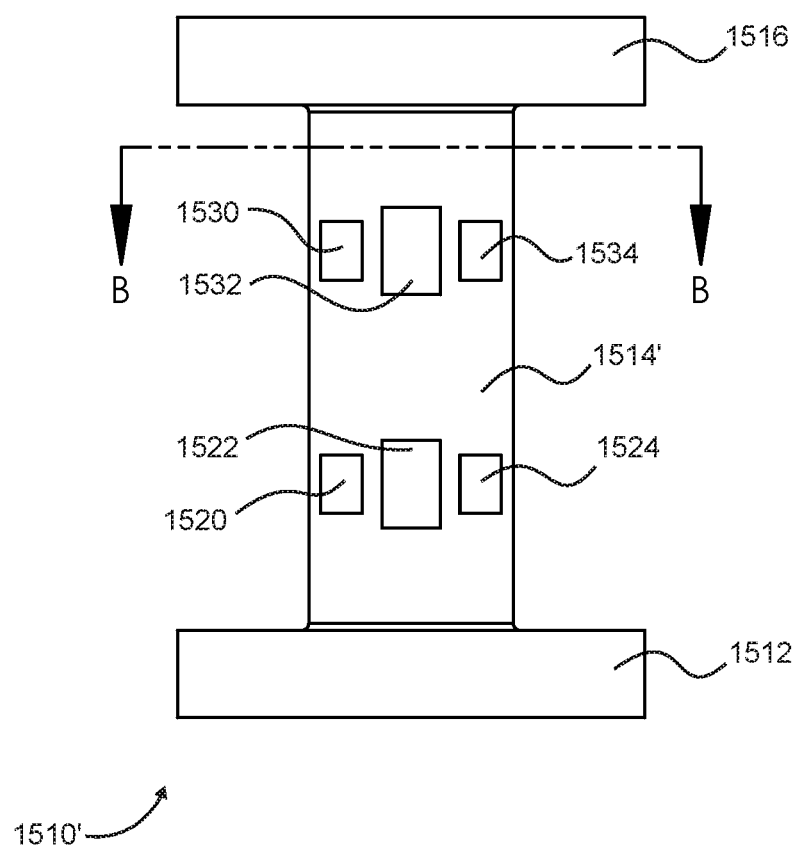
FIG. 62 is a front elevational view of the load transducer of FIG. 61.
Figure 63:
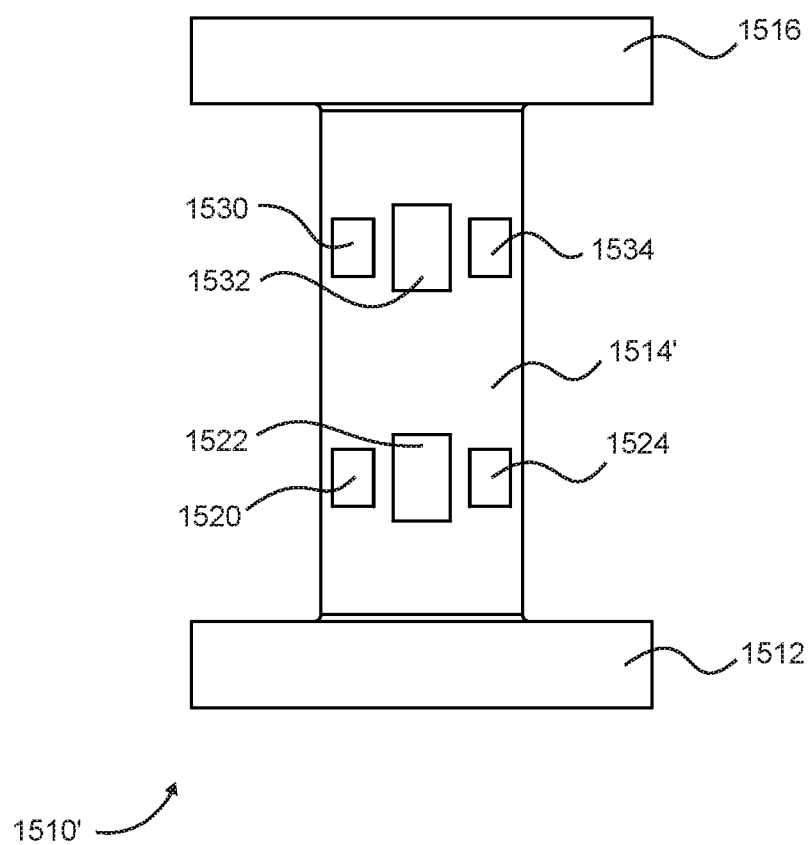
FIG. 63 is a rear elevational view of the load transducer of FIG. 61.
Figure 64:
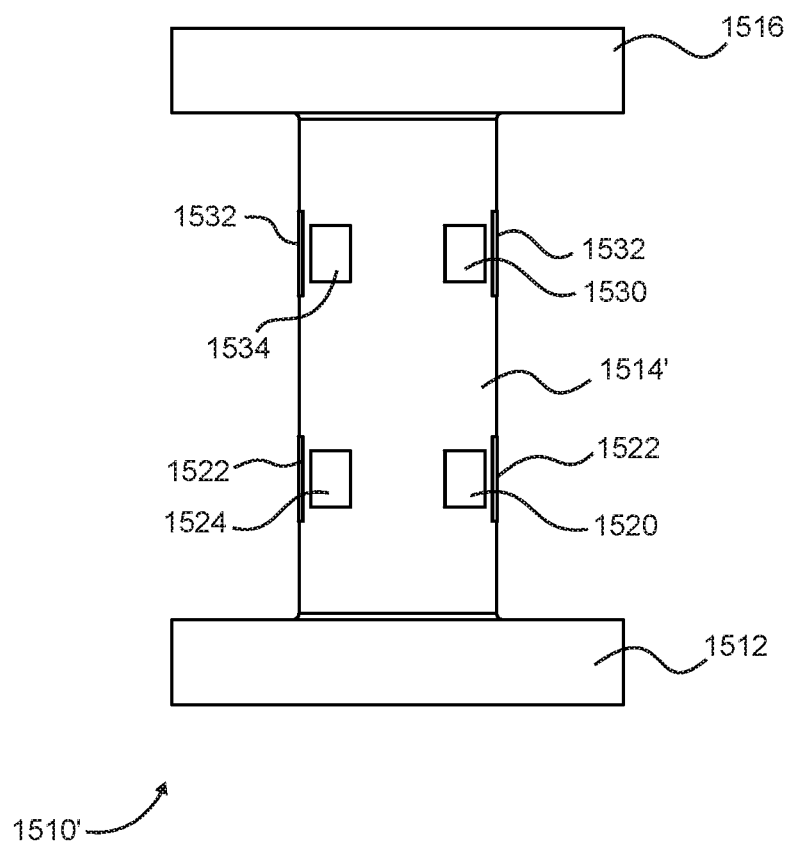
FIG. 64 is a side view of the load transducer of FIG. 61.
Figure 65:
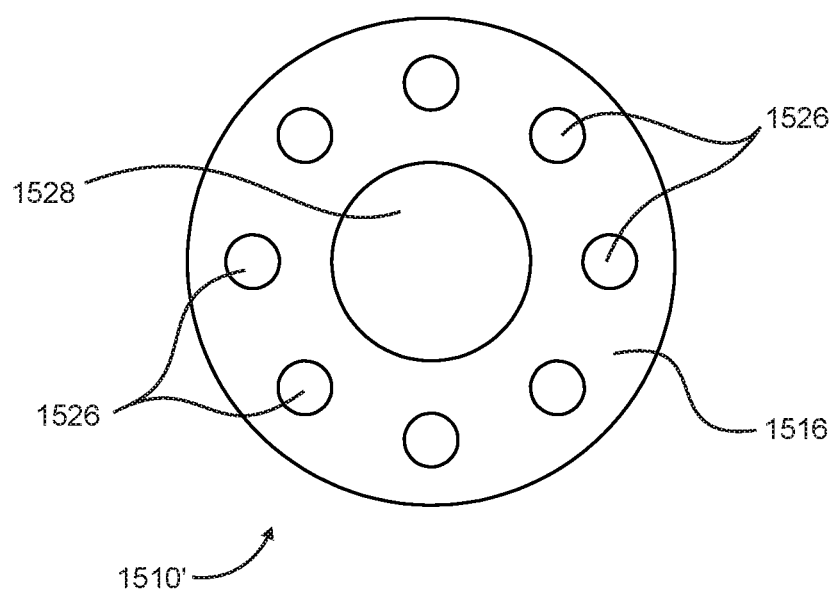
FIG. 65 is a top view of the load transducer of FIG. 61.
Figure 66:
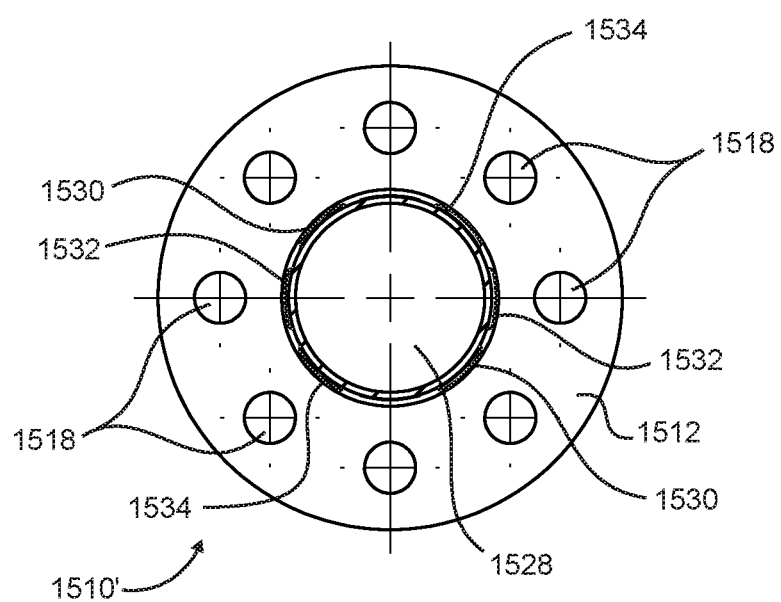
FIG. 66 is a transverse cross-sectional view of the load transducer of FIG. 61, wherein the transverse section is cut through the cutting plane line B-B in FIG. 62.

Referring collectively to FIGS. 61 and 66, it can be seen that redundant sets of deformation sensing elements (e.g., strain gages 1530, 1532, 1534) are disposed on the outer periphery of the central cylindrical body portion 1514' of the load transducer 1510' above the primary sets of deformation sensing elements (e.g., strain gages 1520, 1522, 1524). Similar to the strain gages 1520 described above, in the illustrative embodiment, each of a first pair of redundant strain gages 1530 (see FIG. 61) is sensitive to the first force component (i.e., the x-component of the force, $F_X$) of the load, and outputs one or more first output signals representative of the first force component ($F_X$). As best shown in the sectional view of FIG. 66, a first one of the strain gages 1530 is disposed opposite to a second one of the strain gages 1530 across the longitudinal axis of the load transducer 1510'. In other words, the strain gages 1530 are spaced apart from one another about the outer periphery of the central cylindrical body portion 1514 of the load transducer 1510' by approximately 180 degrees.

With reference again to FIG. 66, similar to the strain gages 1522 described above, in the illustrative embodiment, each of a second pair of redundant strain gages 1532 (see FIG. 61) is sensitive to the torsional moment component (i.e., the z-component of the moment, $M_Z$) of the load and outputs one or more second output signals representative of the torsional moment component ($M_Z$). As best shown in the sectional view of FIG. 66, like the strain gages 1522 described above, a first one of the redundant strain gages 1532 is disposed opposite to a second one of the strain gages 1532 across the longitudinal axis of the load transducer 1510'. In other words, the strain gages 1532 are spaced apart from one another about the outer periphery of the central cylindrical body portion 1514' by approximately 180 degrees.

Turning again to FIG. 66, in the illustrative embodiment, each of a third pair of redundant strain gages 1534 (see FIG. 61) is sensitive to the second force component (i.e., the y-component of the force, $F_Y$) of the load, and outputs one or more third output signals representative of the second force component ($F_Y$). As best shown in the sectional view of FIG. 66, like the strain gages 1530 and 1532 described above, a first one of the redundant strain gages 1534 is disposed opposite to a second one of the strain gages 1534 across the longitudinal axis of the load transducer 1510'. In other words, the strain gages 1534 are spaced apart from one another about the outer periphery of the central cylindrical body portion 1514' by approximately 180 degrees.

Because the other features of the load transducer 1510' have already been explained above in conjunction with the load transducer 1510, it is not necessary to reiterate these features with respect to the load transducer 1510'. That is, the features that are common to both such embodiments need not be repeated in conjunction with the description of the embodiment in FIGS. 61-66.

In the illustrated embodiments, each of the strain gages 1520, 1522, 1524, 1530, 1532, 1534 comprise a half bridge (e.g., a half Wheatstone bridge). Although, in other embodiments, the strain gages 1520, 1522, 1524, 1530, 1532, 1534 may comprise a full bridge (e.g., a full Wheatstone bridge). Also, in the illustrated embodiments, each of the strain gages 1520, 1522, 1524, 1530, 1532, 1534 may produce a separate output signal (e.g., output voltage) such that the load transducer 1510' produces a total of twelve (12) total output signals (e.g., output voltages). Although, in other embodiments, the paired strain gages 1520, 1522, 1524 may be wired together, and the paired strain gages 1530, 1532, 1534 also may be wired together, such that the load transducer 1510' only produces a total of six (6) output signals (e.g., output voltages).

Figure 67:
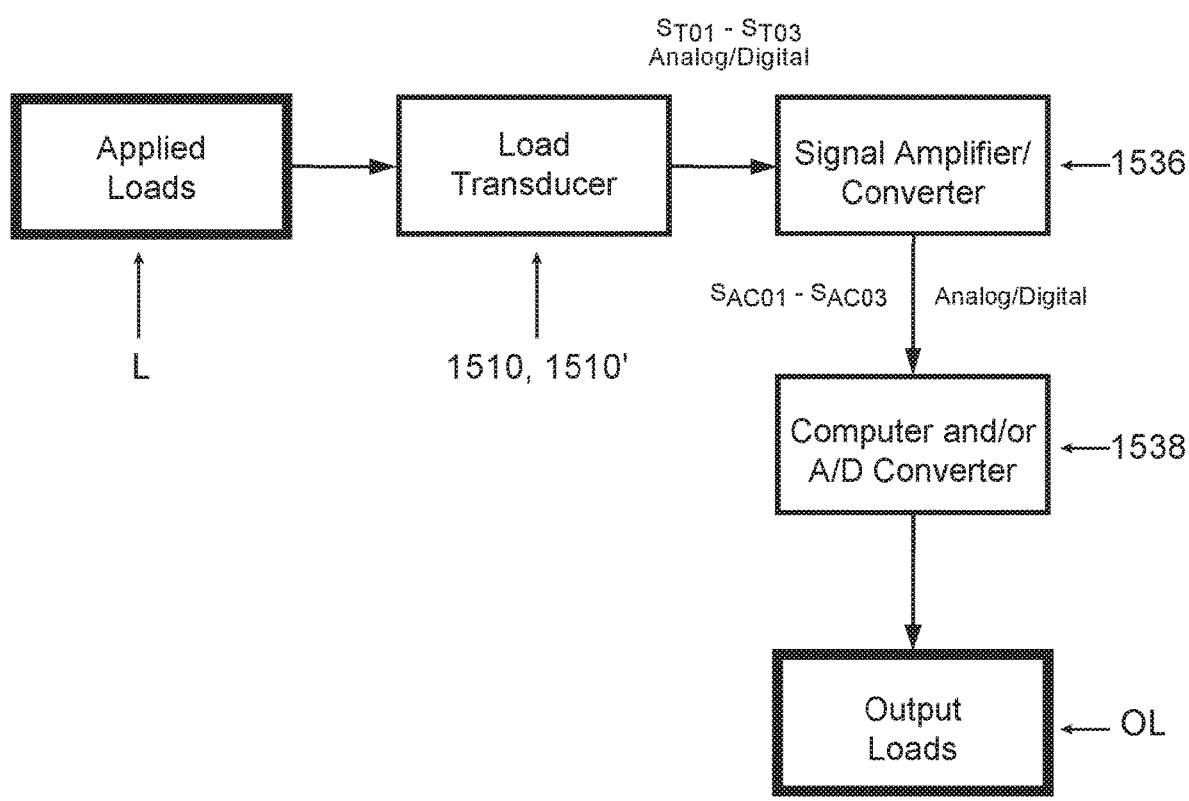
FIG. 67 is a block diagram illustrating data manipulation operations carried out by the load transducer data processing system, according to an embodiment of the invention.

FIG. 67 graphically illustrates the acquisition and processing of the load data carried out by the exemplary load transducer data processing system. Initially, as shown in FIG. 67, a load L (e.g., forces and/or moments) is applied to the load transducer 1510, 1510'. When the electrical resistance of each strain gage 1520, 1522, 1524, 1530, 1532, 1534 is altered by the application of the applied forces and/or moments, the change in the electrical resistance of the strain gages brings about consequential changes in the output voltages of the strain gage bridge circuits (e.g., a Wheatstone bridge circuits). Thus, in one embodiment, the three (3) pairs of strain gages 1520, 1522, 1524 output a total of three (3) analog output voltages (signals). In some embodiments, the three (3) output voltages from the three (3) pairs of strain gages 1520, 1522, 1524 are then transmitted to a preamplifier board (not shown) for preconditioning. The preamplifier board is used to increase the magnitudes of the analog voltage signals, and preferably, to convert the analog voltage signals into digital voltage signals as well. After which, the load transducer 1510, 1510' transmits the output signals $S_{TO1}$-$S_{TO3}$ to a main signal amplifier/converter 1536. Depending on whether the preamplifier board also includes an analog-to-digital (A/D) converter, the output signals $S_{TO1}$-$S_{TO3}$ could be either in the form of analog signals or digital signals. The main signal amplifier/converter 1536 further magnifies the transducer output signals $S_{TO1}$-$S_{TO3}$, and if the signals $S_{TO1}$-$S_{TO3}$ are of the analog-type (for a case where the preamplifier board did not include an analog-to-digital (A/D) converter), it may also convert the analog signals to digital signals. Then, the signal amplifier/converter 1536 transmits either the digital or analog signals $S_{ACO1}$-$S_{ACO3}$ to the data acquisition/data processing device 1538 (computer 1538) so that the forces and/or moments that are being applied to the load transducer 1510, 1510' can be transformed into output load values OL. The computer or data acquisition/data processing device 1538 may further comprise an analog-to-digital (A/D) converter if the signals $S_{ACO1}$-$S_{ACO3}$ are in the form of analog signals. In such a case, the analog-to-digital converter will convert the analog signals into digital signals for processing by the microprocessor of the computer 1538.

When the computer or data acquisition/data processing device 1538 receives the voltage signals $S_{ACO1}$-$S_{ACO3}$, it initially transforms the signals into output forces and/or moments by multiplying the voltage signals $S_{ACO1}$-$S_{ACO3}$ by a stored calibration matrix. After which, the force components $F_X$, $F_Y$ and the torsional moment component $M_Z$ applied to the load transducer 1510, 1510' are determined by the computer or data acquisition/data processing device 1538. The manner in which the stored calibration matrix is utilized to eliminate crosstalk between the output signals or channels will be explained in further detail hereinafter.

Figure 68:
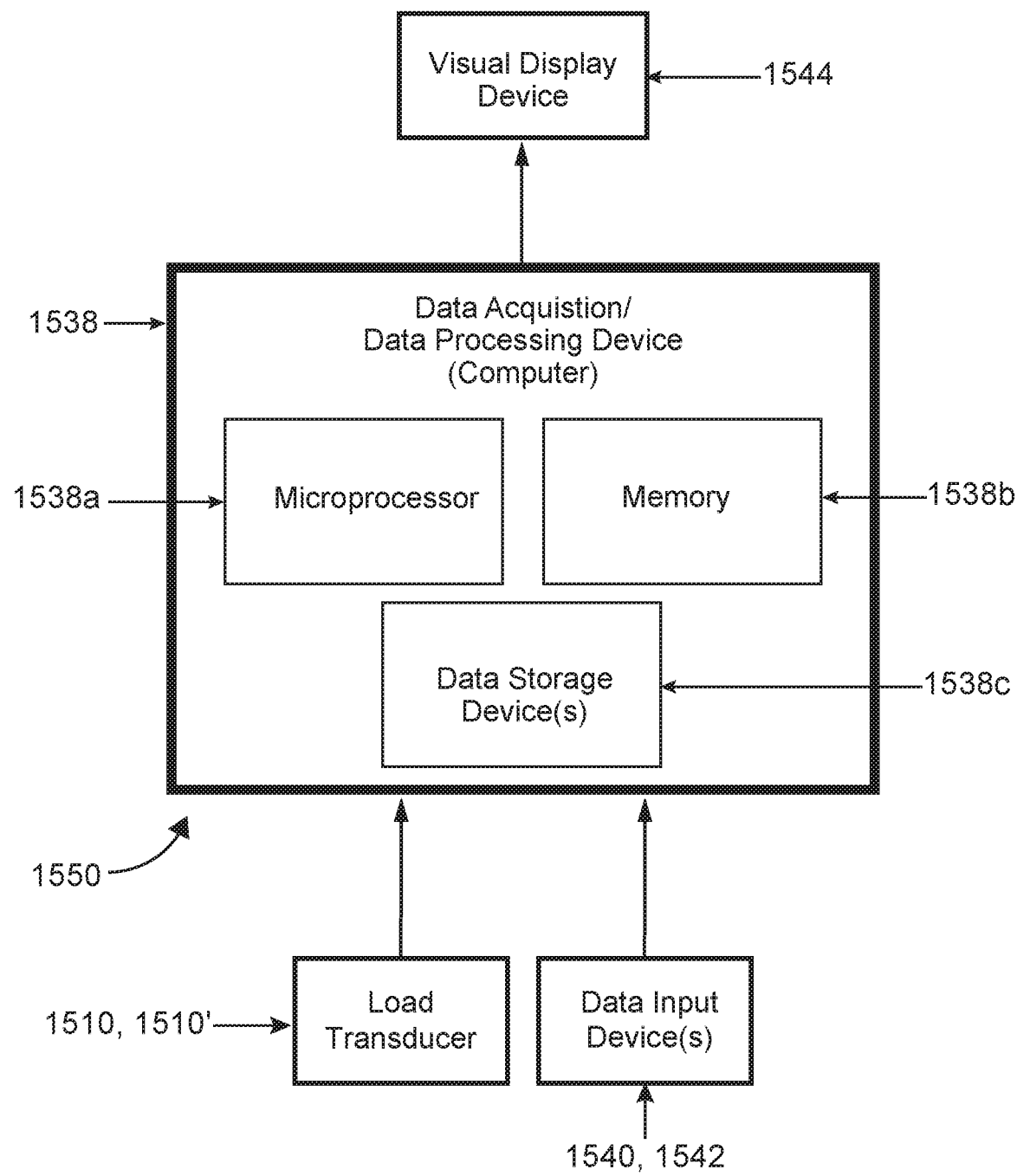
FIG. 68 is a block diagram of constituent components of the load transducer system, which utilizes the load transducer of FIG. 55 or FIG. 61, according to an embodiment of the invention.

Now, turning to FIG. 68, it can be seen that the data acquisition/data processing device 1538 (i.e., the computing device 1538) of the load transducer system 1550 comprises a microprocessor 1538a for processing data, memory 1538b (e.g., random access memory or RAM) for storing data during the processing thereof, and data storage device(s) 1538c, such as one or more hard drives, compact disk drives, floppy disk drives, flash drives, or any combination thereof. As shown in FIG. 68, one or more load transducers 1510, 1510' and a visual display device 1544 are operatively coupled to the core components 1538a, 1538b, 1538c of the data acquisition/data processing device 1538 such that data is capable of being transferred between these devices 1510, 1510', 1538, and 1544. Also, as illustrated in FIG. 68, a plurality of data input devices 1540, 1542 such as a keyboard 1540 and mouse 1542 are operatively coupled to the core components 1538a, 1538b, 1538c of the data acquisition/data processing device 1538 so that a user is able to enter data into the data acquisition/data processing device 1538. In some embodiments, the data acquisition/data processing device 1538 can be in the form of a laptop computer, while in other embodiments, the data acquisition/data processing device 1538 can be embodied as a desktop computer.

As will be described hereinafter, in the illustrative embodiment, the data acquisition/data processing device 1538 is configured to utilize the stored calibration matrix in order to substantially eliminate crosstalk between the transducer output signals $S_{TO1}$-$S_{TO3}$ so that the respective transducer output signals are generally representative only of a respective one of the force or moment components ($F_X$, $F_Y$, $M_Z$).

Figure 69:
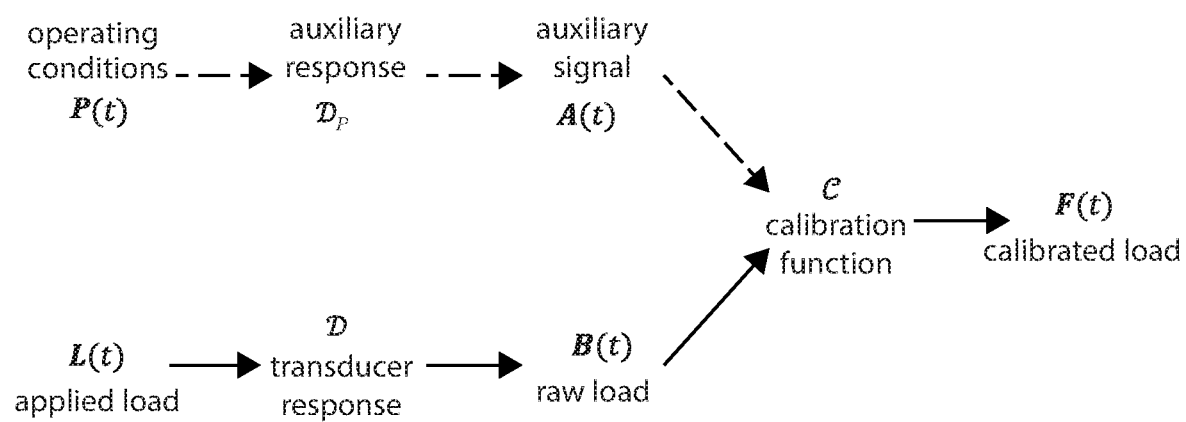
FIG. 69 is a signal flow diagram for the load transducer system described herein, which utilizes the load transducer of FIG. 55 or FIG. 61, according to an embodiment of the invention.

For example, initially referring to the signal flow diagram depicted in FIG. 69, the load L(t) applied to the transducer causes the deformation of the transducer strain gages. The response of the transducer to such deformation is denoted by the operator $\mathcal{D}$ in FIG. 69. The strain signals from the strain gages are digitized into time-dependent raw load signals B(t). Inherently, the strain signals are also a function of the applied load: B(t)≡B(L(t), t).

The transducer's operating conditions P(t) other than mechanical loads, such as temperatures, can have an effect on the transducer response $\mathcal{D}$. They can also be collected and digitized into time-dependent auxiliary signals A(t), subject to their own auxiliary response $\mathcal{D}_P$. In addition to temperature, operating conditions P(t) that can affect the transducer response include the ambient pressure in the environment containing the load transducer, magnetic fields present in the environment, and non-inertial conditions (i.e., accelerations other than gravitational acceleration).

When the transducer has a generally linear response to the applied load, and when the operating conditions P(t) are presumed to have a negligible effect on the transducer response, the calibrated load F(t) may be determined from the following equation:

$$F(t)=C \cdot B(t) \quad (1)$$

where:
F(t): calibrated load;
C: calibration function; and
B(t): raw load.

Thus, using equation (1) above, the raw loads are calibrated using the calibration function C to obtain the calibrated load F. The calibration function is the outcome of a transducer calibration process.

In general, crosstalk in the raw load B is the linear dependence of any one component of the raw load on more than one component of the applied load L. Given a transducer with a linear response $\mathcal{D}$ such that rank($\mathcal{D}$)≥1 (or $l_n$≥1), there exists a linear transformation CB such that CB≈L: it recovers and separates the individual components of the applied load so that they become linearly independent. The linear independence of the components of F is equivalent to lack of cross-talk.

For example, in one embodiment, a 2-axis sensor with two raw load signal components and two calibrated load signal components is provided. Due to the design of the transducer, each of the raw load signals is a linear combination of both components of the load that are being sensed, as described by the following two equations:

$$B_1(t) = 100F_1(t) + 100F_2(t) \quad (2)$$

$$B_2(t) = -100F_1(t) + 100F_2(t) \quad (3)$$

The response $\mathcal{D}$ of this transducer is linear and given by the following matrix:

$$\mathcal{D} = \begin{bmatrix} 100 & 100 \\ -100 & 100 \end{bmatrix} \quad (4)$$

Because both $B_1$ and $B_2$ carry a measure of $F_1$ and $F_2$, there is crosstalk. The following matrix separates these signals:

$$C = \mathcal{D}^{-1} = \begin{bmatrix} 0.005 & -0.005 \\ 0.005 & 0.005 \end{bmatrix} \quad (5)$$

Generally, for non-rectangular C and $\mathcal{D}$, it holds that $\mathcal{D} \cdot C \approx I$, where I is an identity matrix. In other words, $\mathcal{D}$ is a pseudoinverse of C.

Also, in the illustrative embodiment, data acquisition/data processing device 1538 is additionally configured to determine one or more deformation compensation parameters for the load transducer system 1550 and to correct the one or more respective output forces or moments using the one or more deformation compensation parameters. For example, with combined reference to FIGS. 55 and 60, suppose that it is desired to determine the x-component of the force ($F_X$) using the load transducer 1510. As explained above, the pair of strain gages 1520 is sensitive to the x-component of the force ($F_X$). However, because the transducer frame of the load transducer 1510 is not perfectly symmetrical (e.g., due to machining imperfections) and the strain gages 1520, 1522, 1524 are not perfectly positioned on the transducer frame of the load transducer 1510, the strain gages 1522, 1524, which are not designed to be sensitive to the x-component of the force ($F_X$), will output a non-zero signal when only a force in the x-direction is applied to the pylon-type load transducer 1510. The data acquisition/data processing device 1538 may correct the load transducer output by using the following equation:

$$F_x = (S_x \cdot A) + (S_y \cdot B) + (S_T \cdot C) \quad (6)$$

where:

$F_x$: x-component of the force, which is the desired measured quantity;

$S_x$: signal from strain gages 1520 that are sensitive to the x-component of the force;

A: calibration coefficient for the x-component of the force;

$S_y$: signal from strain gages 1524 that are sensitive to the y-component of the force;

B: calibration coefficient for the y-component of the force;

$S_T$: signal from strain gages 1522 that are sensitive to the torsional moment component ($M_Z$); and C: calibration coefficient for the torsional moment component ($M_Z$).

As such, the data acquisition/data processing device 1538 uses the deformation output signals $S_y$, $S_T$ from the strain gages 1522, 1524 in order to correct the x-component of the force. That is, the terms ($S_y \cdot B$) and ($S_T \cdot C$) in equation (6) are deformation compensation parameters that are used to correct the x-component of the force so that the imperfections in the machining of the frame portion of the load transducer 1510 and the imperfect placement of the strain gages may compensated for in the determination of the output force ($F_X$), thereby resulting in a more accurate determination of the output force ($F_X$).

In addition, in the illustrative embodiment, the data acquisition/data processing device 1538 is further configured to determine one or more temperature compensation parameters for the load transducer system 1550, and to correct the transducer output signals $S_{TO1}$-$S_{TO3}$ using the one or more temperature compensation parameters. The data acquisition/data processing device 1538 is further configured to determine the respective force or moment components ($F_X$, $F_Y$, $M_Z$) from the respective transducer output signals $S_{TO1}$-$S_{TO3}$.

Figure 56:
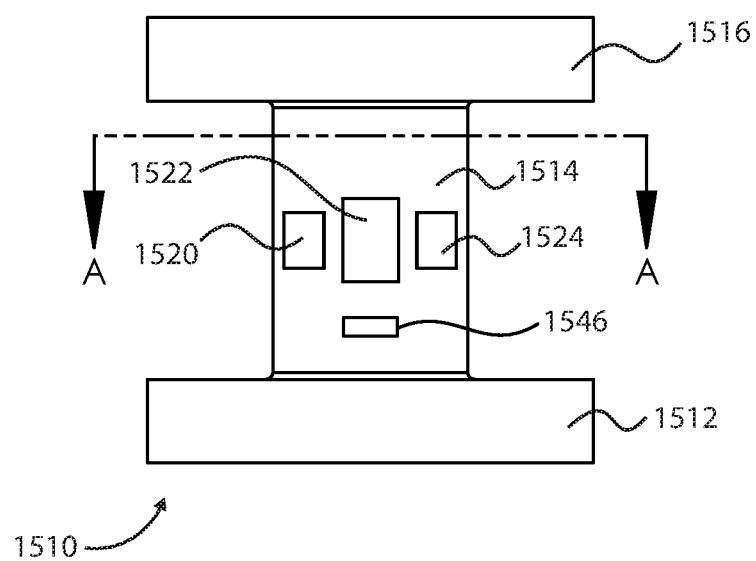
FIG. 56 is a front elevational view of the load transducer of FIG. 55.
Figure 57:
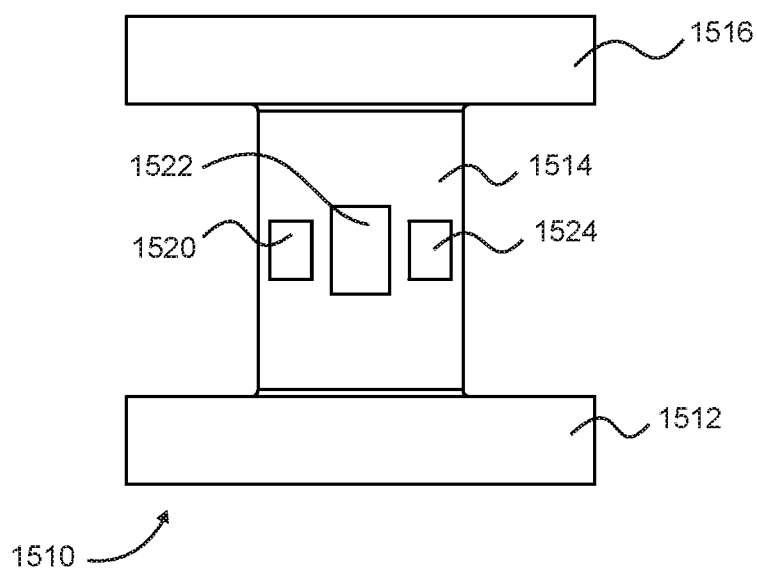
FIG. 57 is a rear elevational view of the load transducer of FIG. 55.
Figure 58:
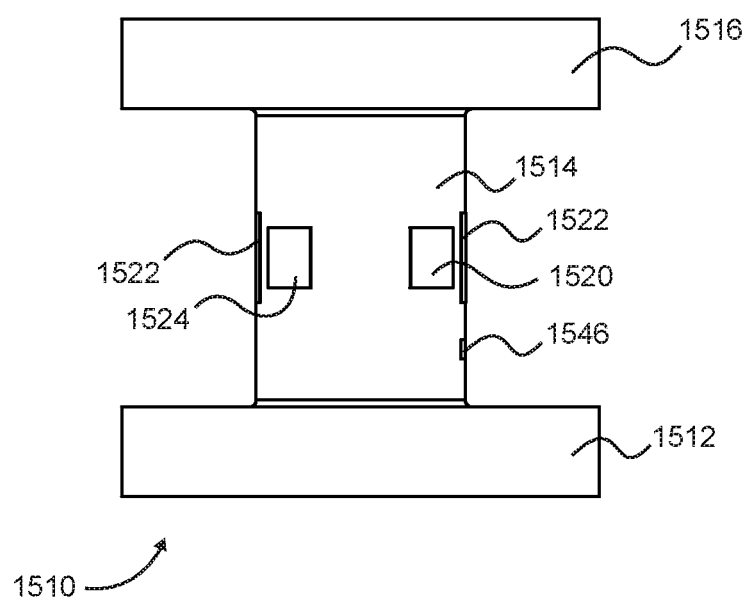
FIG. 58 is a side view of the load transducer of FIG. 55.

In one or more embodiments, the load transducer 1510 further comprises one or more temperature sensing elements 1546 disposed thereon (see FIGS. 55, 56, and 58). For example, in some embodiments, the one or more temperature sensing elements 1546 may comprise one or more thermistors. In other embodiments, one or more of the strain gages 1520, 1522, 1524 may be used as the temperature sensing elements so that additional temperature sensing elements are not required. In these one or more embodiments, the one or more temperature sensing elements are configured to output one or more temperature output signals indicative of a temperature of at least a portion of the load transducer 1510. The one or more temperature sensing elements are operatively coupled to the data acquisition/data processing device 1538. The data acquisition/data processing device 1538 is configured to receive the one or more respective temperature output signals from the one or more temperature sensing elements, and to determine the one or more temperature compensation parameters based upon the one or more respective temperature output signals for correcting the force and/or moment components ($F_X$, $F_Y$, $M_Z$).

In one or more alternative embodiments, rather than using temperature sensing elements to determine the temperature compensation parameters, the data processing device is configured to determine the one or more temperature compensation parameters based upon the one or more excitation current values associated with the one or more deformation sensing elements (e.g., strain gages 1520, 1522, 1524) of the load transducer 1510. In these one or more alternative embodiments, the one or more excitation current values may be determined by measuring the excitation current of the strain gage bridge circuits of the load transducer 1510 (e.g., the current flowing through a particular one of the strain gages). The resistance of the strain gages 1520, 1522, 1524 changes in accordance with the ambient temperature of the environment in which the load transducer 1510 is disposed.

In the illustrative embodiment, the data acquisition/data processing device 1538 may utilize the one or more temperature compensation parameters (as determined from either one or more temperature sensing elements or the one or more excitation current values) to correct for temperature-induced effects on the zero drift of the load transducer 1510. Also, in the illustrative embodiment, the data acquisition/data processing device 1538 may utilize the one or more temperature compensation parameters to correct for temperature-induced effects on the sensitivity of the load transducer 1510.

Further, in the illustrative embodiment, the data acquisition/data processing device 1538 may be additionally configured to determine a position of the applied load using the load transducer system 1550, and to correct the one or more output forces or moments based upon the position of the applied load. In particular, as will be explained hereinafter, in one or more embodiments, the data acquisition/data processing device 1538 is configured to correct the one or more output forces or moments of the load transducer system 1550 by utilizing a mathematical relationship (e.g., a polynomial function) that is based upon the position of the applied load.

In one or more embodiments, to correct for errors correlated to the point of application of the load, a nonlinear calibration function is utilized. There is a general form of such calibration function that is easy to compute and is a good representation of the nonlinearities typical of transducers. First, the linear calibration function based on the calibration matrix $\mathbb{C}$, as usually used for calibration of load sensors, is $$\mathcal{C} = \mathbb{C} B. \tag{7}$$

The generalized form of the calibration function uses a generalization of the calibration matrix to a multivariate polynomial matrix $\mathbb{C}(B)$ of degree N on the elements of the raw load vector B:

$$\mathcal{C} = \mathbb{C}_{(B)} B, \tag{8}$$

where each i, j-th element of the polynomial matrix $\mathbb{C}(B)$ is a general multivariate polynomial of degree N in each element of B. Given a b-dimensional B, and $$c_{i,j,1}, \ldots, c_{i,j,\binom{b+N}{b}}$$

are in coefficients, and the multivariate polynomial matrix's elements are of the following degree-lexicographically ordered form, where the lexicographic order is on the elements of B:

$$\mathbb{C}_{i,j} = c_{i,j,1} + c_{i,j,2} B_1 + \ldots + c_{i,j,(b+2)} B_1^2 + \tag{9}$$
$$\ldots + c_{i,j,(Nb+1)} B_b^N + \ldots + c_{i,j,\binom{b+N}{b}} (B_1^N \ldots B_b^N)$$

There are $$l \cdot c \cdot \binom{b+N}{b}$$

polynomial coefficients in the polynomial matrix $\mathbb{C}(B)$, where l is the dimension of the calibrated load vector F.

In practice, it is often sufficient to use a specialized form of multivariate polynomials, with some classes of the monomials having zero coefficients. For example, a multivariate polynomial might include all single-variable terms up to N-th order, i.e. terms of the form $B_i^n$, where n≤N, then all mixed terms of up to q variables up to M-th order, i.e. of the form $B_{i_1}^{m_1} \cdots B_{i_q}^{m_q}$, where $m_q$ and $i_q$ are the exponents and component indices in the q-th element of the term.

The multivariate polynomial calibration matrix elements can determined during the calibration process, by solving a linear system of equations $\mathbb{C}(B_l) B_l = L_l$ for each l-th applied calibration load $L_l$. The unknowns are the values of coefficients $c_{i,j,k}$, where i covers the indices of the applied load, j covers the indices of the raw load, and k covers the indices of the multivariate polynomial of the chosen dimension N. In practical applications, where the number of polynomial coefficients to be determined is much smaller than the number of applied calibration points, the resulting coefficient vectors building up $\mathbb{C}$ are linear combinations of basis vectors, and further constraints are used to select a single scalar for each coefficient. Such constraint can be e.g. a minimal-norm criterion for the vector of coefficients of $\mathbb{C}$.

In one or more embodiments, to correct for errors correlated to the operating conditions P, a nonlinear calibration function is utilized. The auxiliary signal A, representing the operating conditions, can include elements that are measures of any of the following: (i) temperature at one or more locations within the load sensor, (ii) resistance of one or more strain gage bridges, measured across their excitation voltage inputs, (iii) resistance of one or more strain gage half-bridges, either individual or forming a full bridge, measured across their excitation voltage inputs, (iv) atmospheric pressure, (v) components of magnetic field measured using a Hall sensor at one or more locations within the load sensor, and (vi) components of magnetic field measured using sense coils and represented by the voltages induced in these coils.

The generalized form of the calibration function uses a generalization of the calibration matrix to a multivariate polynomial matrix $\mathbb{C}(A)$ of degree N on the elements of auxiliary signal vector A, used to calibrate the raw load vector B:

$$\mathcal{C} = \mathbb{C}_{(A)} B, \tag{10}$$

where each i, j-th element of the polynomial matrix $\mathbb{C}(A)$ is a general multivariate polynomial of degree N in each element of A. Given an α-dimensional A, and its coefficients $$c_{i,j,1}, \ldots, c_{i,j,\binom{a+N}{a}},$$

the multivariate polynomial matrix's elements are of the following degree-lexicographically ordered form, where the lexicographic order is on the elements of A:

$$\mathbb{C}_{i,j} = c_{i,j,1} + c_{i,j,2} A_1 + \ldots + c_{i,j,(a+2)} A_1^2 + \tag{11}$$
$$\ldots + c_{i,j,(Na+1)} A_a^N + \ldots + c_{i,j,\binom{a+N}{a}} (A_1^N \ldots A_b^N).$$

There are $$l \cdot c \cdot \binom{a+N}{a}$$

in the polynomial matrix $\mathbb{C}(A)$, where l is the dimension of the calibrated load vector F. The multivariate polynomial matrix of a sufficient degree corrects for both zero drift and the sensitivity of the transducer.

In practice, it is often sufficient to use a specialized form of multivariate polynomials, with some classes of the monomials having zero coefficients. For example, a multivariate polynomial might include all single-variable terms up to N-th order, i.e. terms of the form $A_i^n$, where n≤N, then all mixed terms of up to q variables up to M-th order, i.e. of the form $A_{i_1}^{m_1} \cdot \ldots \cdot A_{i_q}^{m_q}$, where $m_q$ and $i_q$ are the exponents and component indices in the q-th element of the term.

The multivariate polynomial calibration matrix elements can be determined during the calibration process, by solving a linear system of equations $\mathbb{C}(A_l)B_l=L_l$ for each l-th applied calibration load $L_l$, under some conditions that resulted in $A_l$. The unknowns are the values of coefficients $c_{i,j,k}$, where i covers the indices of the applied load, j covers the indices of the raw load, and k covers the indices of the multivariate polynomial of the chosen dimension N. In practical applications, where the number of polynomial coefficients to be determined is much smaller than the number of applied calibration points, the resulting coefficient vectors building up $\mathbb{C}$ are linear combinations of basis vectors, and further constraints are used to select a single scalar for each coefficient. Such constraint can be e.g. a minimal-norm criterion for the vector of coefficients of $\mathbb{C}$.

In one or more further embodiments, the load accuracy and operating conditions corrections may be applied with their multivariate polynomial matrices separated, first applying the load accuracy correction calibration, and then the operating conditions correction:

$$\mathcal{C} = \mathbb{C}_{1(A)} \mathbb{C}_{2(B)} B. \quad (12)$$

Alternatively, the load accuracy and operating condition corrections can be expressed using a single multivariate polynomial matrix on the coefficients of both the auxiliary and raw load vectors:

$$\mathcal{C} = \mathbb{C}_{(A, B)} B. \quad (13)$$

The multivariate polynomial calibration matrix $\mathbb{C}$'s elements can be determined during the calibration process, by solving a linear system of equations $\mathbb{C}((A, B)_l)B_l=L_l$ for each l-th applied calibration load $L_l$, under some conditions where $(A, B)_l$ is the concatenation of the raw load and auxiliary signal vectors. The unknowns are the values of coefficients $c_{i,j,k}$, where i covers the indices of the applied load, j covers the indices of the concatenation of the raw load and auxiliary signal vectors, and k covers the indices of the multivariate polynomial of the chosen dimension N. In practical applications, where the number of polynomial coefficients to be determined is much smaller than the number of applied calibration points, the resulting coefficient vectors building up $\mathbb{C}$ are linear combinations of basis vectors, and further constraints are used to select a single scalar for each coefficient. Such constraint can be e.g. a minimal-norm criterion for the vector of coefficients of $\mathbb{C}$.

Figure 70:
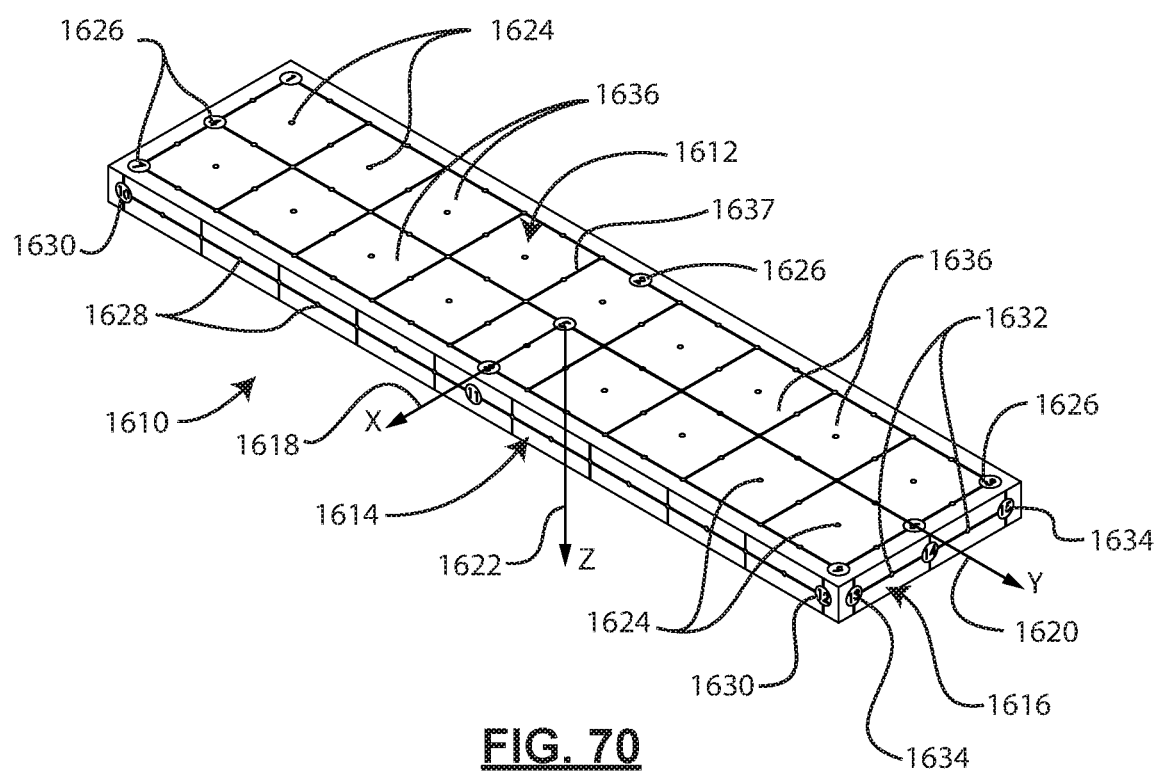
FIG. 70 is a perspective view of a top plate component of a force measurement assembly, according to an embodiment of the invention, wherein load calibration points disposed in grid arrangements are illustrated on the top and side surfaces of the top plate component.

One or more further illustrative embodiments will be described with reference to FIGS. 70-74. In these one or more further illustrative embodiments, a force measurement system, which may be in the form of the force measurement system depicted in FIG. 42 with force measurement assembly 1150 and data acquisition/data processing device 1174, is configured to more accurately determine the forces and/or moments of a load applied to a particular region of the force measurement assembly. Initially, referring to FIG. 70, an exemplary top plate component 1610 of the force measurement system is illustrated with coordinate measurement axes 1618, 1620, 1622 and a plurality of calibration points 1624, 1628, 1632 depicted on the top plate component 1610. In the illustrative embodiment, the top plate component 1610 of the force measurement system depicted in FIG. 70 may have six outputs ($F_x$, $F_y$, $F_z$, $M_x$, $M_y$, $M_z$) and the illustrated XYZ coordinate system. As shown in FIG. 70, the X and Y axes 1618, 1620 are coplanar to the top surface 1612 and perpendicular to each other. Also, as shown in the illustrative embodiment of FIG. 70, the Z axis 1622 points down into the top plate component 1610. The origin is located at the center of the top surface 1612 of the top plate component 1610 of the force measurement assembly.

In the illustrative embodiment, the force measurement assembly with top plate component 1610 is provided with two or more or more load-sensing cells (e.g., the two load transducers 1100 in FIG. 42) disposed underneath the top plate component 1610. As will be described in detail hereinafter, the load-sensing cells or load transducers of the force measurement assembly are calibrated by applying known loads at known locations so as to convert the raw signal output into a calibrated output. For a six-component force measurement assembly with the top plate component 1610 depicted in FIG. 70, at least six calibration points are needed to solve for all unknown variables using a least-squares fit. This collection of calibrations points is called a calibration matrix. This calibration matrix is multiplied by the raw signal output to provide the six calibrated outputs of the force measurement assembly.

Figure 71:
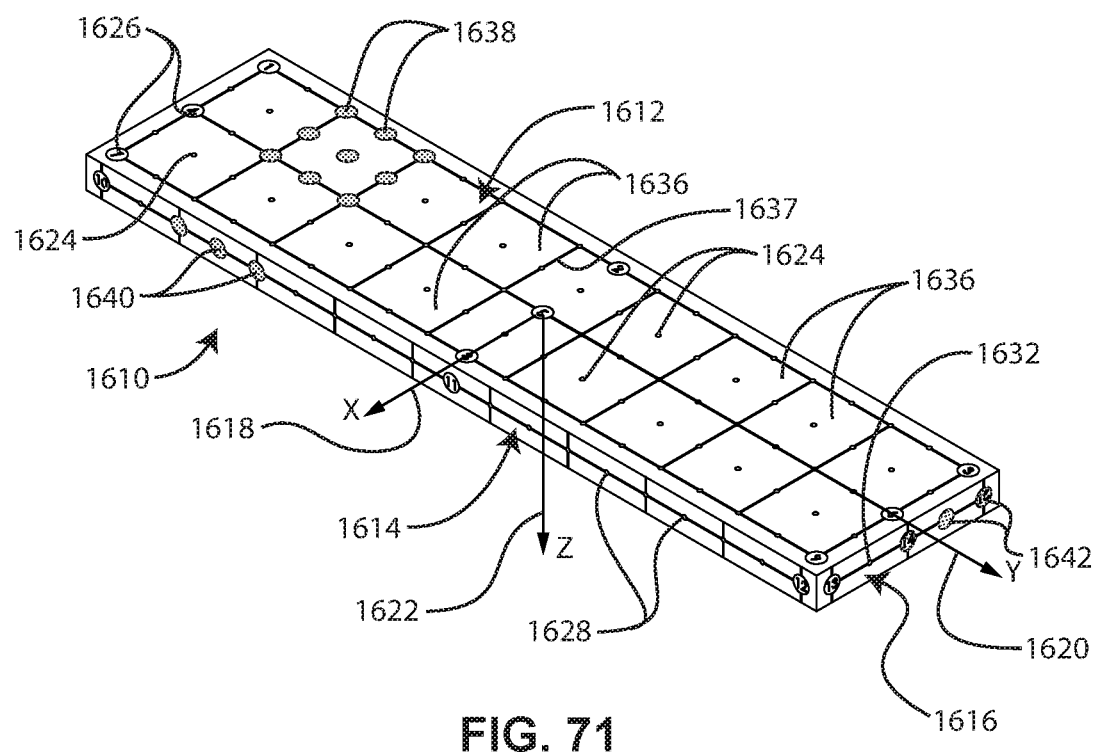
FIG. 71 is a perspective view of a top plate component of a force measurement assembly, according to an embodiment of the invention, wherein the load calibration points for a particular one of the load regions are illustrated in emphasized form on the top and side surfaces of the top plate component.

Now, with reference to the flowchart illustrated in FIG. 72, an illustrative calibration procedure for the force measurement assembly with the top plate component 1610 depicted in FIGS. 70 and 71 will be described. The calibration process begins at step 1644, and then one or more pluralities of points are selected on one or more surfaces of the force measurement assembly for applying one or more known loads in step 1646. In particular, referring again to FIG. 70, a first plurality of vertical force calibration points 1624 arranged in a grid pattern may be selected on the top surface 1612 of the top plate component 1610 (e.g., 5×19 array of grid points totaling 95 overall points on the top surface 1612). A second plurality of first shear force calibration points 1628 arranged in a linear pattern may be selected on the first side surface 1614 of the top plate component 1610 (e.g., 19 shear points for the shear force in the x-direction). A third plurality of second shear force calibration points 1632 arranged in a linear pattern may be selected on the second side surface 1616 of the top plate component 1610 (e.g., 5 shear points for the shear force in the y-direction).

Turning again to FIG. 72, after the calibration points are selected in step 1646, one or more known loads are applied at the pluralities of points 1624, 1628, 1632 on the surfaces 1612, 1614, 1616 of the top plate component 1610 of the force measurement assembly in step 1648. For example, in the illustrative embodiment, one or more calibration weights with known weights are applied at each of the points 1624, 1628, 1632 on the surfaces 1612, 1614, 1616 of the top plate component 1610. Then, in step 1650, after each known load is applied, the raw load data for each of the points 1624, 1628, 1632 on the surfaces 1612, 1614, 1616 of the top plate component 1610 of the force measurement assembly is stored using the data processing device (e.g., using the data acquisition/data processing device 1174 in FIG. 42).

Next, in step 1652, a global calibration matrix for the force measurement assembly is generated, by using the data processing device 1174, using the stored raw load data for the pluralities of points 1624, 1628, 1632 on the surfaces 1612, 1614, 1616 of the top plate component 1610 of the force measurement assembly. As shown by equation (14)

below, in general, the calibration matrix is multiplied by the raw signal output to provide the six calibrated outputs of the force measurement assembly.

$$\begin{bmatrix} F_x \\ F_y \\ F_z \\ M_x \\ M_y \\ M_z \end{bmatrix} = [C] \begin{bmatrix} S_{F_x} \\ S_{F_y} \\ S_{F_z} \\ S_{M_x} \\ S_{M_y} \\ S_{M_z} \end{bmatrix} \tag{14}$$

where:
$F_x$, $F_y$, $F_z$: forces along each axis;
$M_x$, $M_y$, $M_z$: moments about each axis;
C: calibration matrix; and
$S_{F_x}$, $S_{F_y}$, $S_{F_z}$, $S_{M_x}$, $S_{M_y}$, $S_{M_z}$: raw output signals from each channel.

Because all values except for the C matrix are known, equation (14) can be solved as shown below:

$$[C] = \begin{bmatrix} F_x \\ F_y \\ F_z \\ M_x \\ M_y \\ M_z \end{bmatrix} \begin{bmatrix} S_{F_x} \\ S_{F_y} \\ S_{F_z} \\ S_{M_x} \\ S_{M_y} \\ S_{M_z} \end{bmatrix}^T \left( \begin{bmatrix} S_{F_x} \\ S_{F_y} \\ S_{F_z} \\ S_{M_x} \\ S_{M_y} \\ S_{M_z} \end{bmatrix} \begin{bmatrix} S_{F_x} \\ S_{F_y} \\ S_{F_z} \\ S_{M_x} \\ S_{M_y} \\ S_{M_z} \end{bmatrix}^T \right)^{-1} \tag{15}$$

By simplifying equation (15), the following equation is obtained:

$$[C] = [F][S]^T \{[S][S]^T\}^{-1} \tag{16}$$

where:
C: calibration matrix;
F: known loads;
S: raw output signals;
$[S]^T$: transpose of the S matrix; and
$\{[S][S]^T\}^{-1}$: inverse of the raw signals post-multiplied by its transpose.

In order to achieve an error of less than 1% in the computation of the global calibration matrix, a minimum of fifteen (15) calibration points need to be taken on the top plate component 1610 of FIG. 70 for the six-component force measurement assembly. For example, referring again to FIG. 70, the nine points 1626 (points 1-9 in FIG. 70) may be used on the top surface 1612 of the top plate component 1610 to form a 3×3 grid for the computation of the global calibration matrix, rather all 95 points described above. In addition, for the shear forces, two 1×3 grids of points 1630, 1634 (points 10-15 in FIG. 70) may be used on the sides 1614, 1616 of the top plate component 1610 for the computation of the global calibration matrix, rather all 24 side points described above. Then, as described above, a known load is applied at each point 1626, 1630, 1634 and the load value, point of application and vector of application are stored. When data has been stored for all 15 points, there will be a 15×6 matrix of known loads, F, and an 8×15 matrix of raw signal output, S. Using the F and S matrices and equation (16) above, a 6×8 global calibration matrix, $C_G$, is then generated by the data processing device 1174. After the global calibration matrix, $C_G$, has been generated by the data processing device 1174 in step 1652, the global calibration matrix is stored in non-volatile memory (e.g., in the memory 1174b or on the data storage device(s) 1174c of the data processing device 1174) in step 1654 of the calibration process. The global calibration matrix, $C_G$, is used to convert the raw signal output from the force measurement assembly into calibrated data and determine the values of unknown loads.

Figure 72:
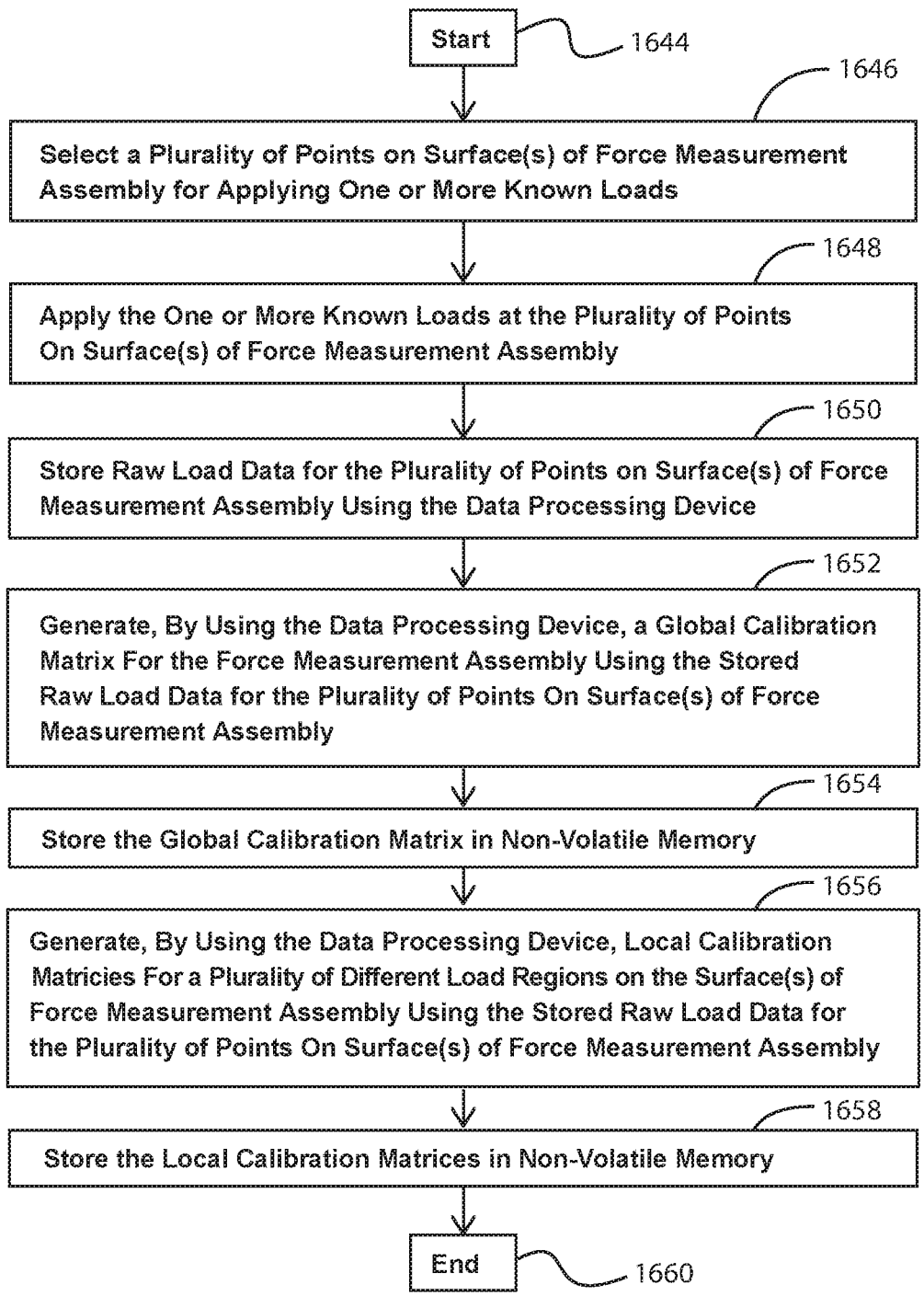
FIG. 72 is a flowchart illustrating a calibration procedure for a force measurement assembly carried out by the force measurement system illustrated in FIGS. 42, 70, and 71, according to an embodiment of the invention.

Referring again to the illustrative embodiment of FIG. 72, after the global calibration matrix $C_G$ has been generated by the data processing device 1174, in step 1656, the data processing device 1174 further generates local calibration matrices for a plurality of different load regions 1636 on the surface 1612 of the top plate component 1610 of the force measurement assembly in FIG. 70 to further reduce measurement errors when unknown forces and moments are determined using the force measurement assembly. In the illustrative embodiment, a local calibration matrix $C_{Li}$ may be determined for each of the eighteen (18) load regions 1636 in FIG. 70 (i.e., local calibration matrices, $C_{Li}$, are determined, where i=1:18 in the illustrative embodiment). When the local calibration matrices $C_{Li}$ are determined during the calibration process of the force measurement assembly as in step 1656 of FIG. 72, the area on the top and sides of the top plate component 1610 may be divided into 18 subsets (an example of a subset is shown using larger, hatched points in FIG. 71). As shown in FIG. 71, the example subset includes nine (9) calibration points 1638 disposed on the top surface 1612 of the top plate component 1610, three (3) calibration points 1640 disposed on the first side surface 1614 of the top plate component 1610, and three (3) calibration points 1642 disposed on the second side surface 1616 of the top plate component 1610. As shown in FIG. 71, the three (3) calibration points 1640 disposed on the first side surface 1614 of the top plate component 1610 and the three (3) calibration points 1642 disposed on the second side surface 1616 of the top plate component 1610 are aligned with the nine (9) calibration points 1638 disposed on the top surface 1612 of the top plate component 1610. By applying known loads at each of the fifteen (15) points corresponding to each of the load regions 1636 in FIGS. 70 and 71, a local calibration matrix $C_{Li}$ is computed for each of the load regions 1636. Using the F and S matrices and equation (16) above, a 6×8 local calibration matrix $C_{Li}$ is then generated by the data processing device 1174 for each of the load regions 1636 in FIGS. 70 and 71. After each of the local calibration matrices $C_{Li}$ have been generated by the data processing device 1174 in 1656, the local calibration matrices $C_{Li}$ are stored in non-volatile memory (e.g., in the memory 1174b or on the data storage device(s) 1174c of the data processing device 1174) in step 1658 of the calibration process, and then, the process is concluded in step 1660. The local calibration matrices $C_{Li}$ are used to convert the raw signal output from the force measurement assembly into calibrated data and determine the values of unknown loads lying in the specific load regions 1636 of the top plate component 1610.

Next, with reference to the flowchart illustrated in FIG. 73, a first illustrative load correction procedure for the force measurement assembly with the top plate component 1610 depicted in FIGS. 70 and 71 will be described. In this first load correction procedure, precomputed local calibration matrices are used to correct the unknown load applied to the top plate component 1610 of the force measurement assembly. The first illustrative load correction process begins at step 1662, and then an unknown load is applied on the surface of the force measurement assembly (e.g., on the top surface 1612 of the top plate component 1610 of the force measurement assembly) in step 1664 of FIG. 73. After the unknown load is applied in step 1664, the data processing device (e.g., the data acquisition/data processing device 1174 in FIG. 42) determines, in step 1666, a location of the applied load on the surface of the top plate component 1610 of the force measurement assembly using the stored global calibration matrix $C_G$, which was determined in the calibration process explained above. When the unknown load is applied to the surface of the top plate component 1610, the global calibration matrix $C_G$ determines the location of loading. Initially, the data acquisition/data processing device 1174 utilizes the global calibration matrix $C_G$ to determine the applied forces and moments ($F_x$, $F_y$, $F_z$, $M_x$, $M_y$, $M_z$). Then, the data acquisition/data processing device 1174 uses equations (17) and (18) below to determine the center of pressure (COP) or point of application of the applied load:

$$x = -M_y/F_z \quad (17)$$

$$y = M_x/F_z \quad (18)$$

where:

x, y: coordinates of the point of application for the force (i.e., center of pressure) on the top plate component 1610;

$F_z$: z-component of the resultant force acting on the top plate component 1610;

$M_x$: x-component of the resultant moment acting on the top plate component 1610; and $M_y$: y-component of the resultant moment acting on the top plate component 1610.

Figure 73:
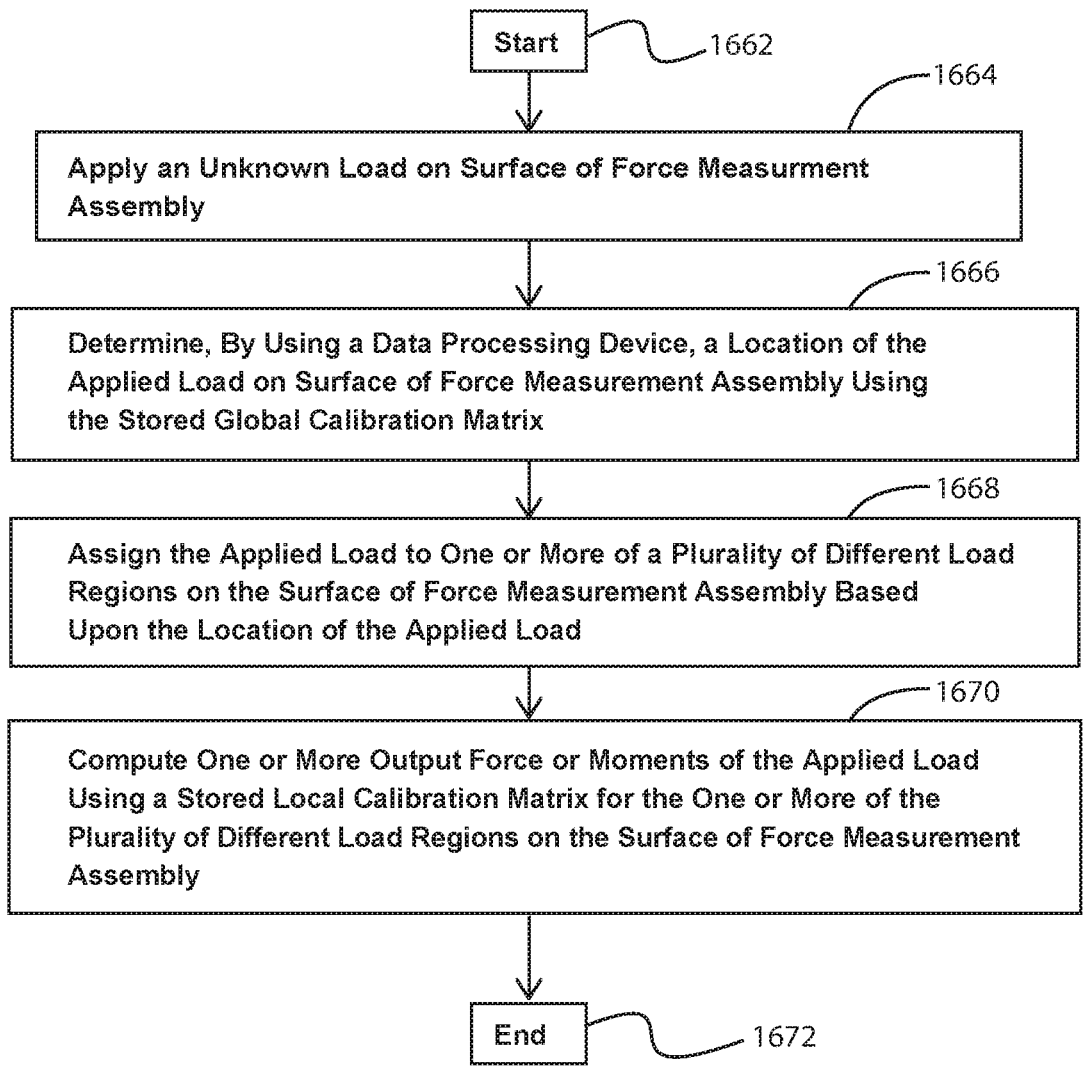
FIG. 73 is a flowchart illustrating a first load correction procedure for a force measurement assembly carried out by the force measurement system illustrated in FIGS. 42, 70, and 71, according to an embodiment of the invention.

Then, in the illustrative embodiment, once equations (17) and (18) are used to determine the location of force application, the applied load is assigned to one or more of the load regions 1636 on the surface of the top plate component 1610 based upon the location of the applied load in step 1668 of FIG. 73. In the illustrative embodiment, the data processing device 1174 is configured to assign the applied load to one or more of the plurality of load regions 1636 based upon the location of the applied load by using one or more mathematical inequalities. In applying the mathematical inequalities, an iterative process may be utilized by the data processing device 1174 in which it is determined whether the load coordinates x, y lie between a predetermined range of x and y values (e.g., initially determine $-10 < x < 10$ and $10 < y < 10$). In the illustrative embodiment, the upper and lower limits of the mathematical inequalities utilized by the data processing device 1174 may get progressively smaller during the iterative process in order to determine the load regions or regions 1636 in which the applied load is located.

After the applied load is assigned to one or more of the load regions 1636 on the top surface 1612 of the top plate component 1610 of the force measurement assembly, a corresponding local calibration matrix $C_{Li}$ is selected by the data processing device 1174 to refine the calibrated outputs. When the applied load lies within a single load region 1636 on the top surface 1612 of the top plate component 1610 of the force measurement assembly, the corresponding single local calibration matrix $C_{Li}$ is utilized by the data processing device 1174. Although, in the illustrative embodiment, when multiple local calibration matrices $C_{Li}$ are equidistant from the location of force application (e.g., when the x and y coordinates of the point of application for the force lies on one of the boundaries 1637 between the load regions 1636 in FIGS. 70 and 71), the calibrated values from each local calibration matrix $C_{Li}$ are averaged before being output.

Referring again to FIG. 73, after the local calibration matrix or matrices $C_{Li}$ corresponding to the load are selected, one or more output forces or moments of the applied load are computed by the data processing device 1174 using the selected local calibration matrix or matrices for the one or more of the load regions 1636 on the surface of force measurement assembly in step 1670. In particular, the one or more output forces or moments of the applied load are computed using equation (14) above by the data processing device 1174, wherein the selected local calibration matrix or averaged local calibration matrix (when the x and y coordinates of the point of application for the force lies on one of the boundaries 1637 between the load regions 1636) is used for the calibration matrix C in equation (14). After the corrected output forces and/or moments of the applied load are determined by the data processing device 1174 in step 1670, the load correction process concludes at step 1672 in FIG. 73.

In one or more alternative embodiments, rather than determining a corrected applied load using a local calibration matrix, the corrected applied load may be determined by applying a mathematical correction factor that is not in the form of a matrix. For example, once the position of the applied load is determined using the global calibration matrix, a correction factor may be applied to the entries of the global calibration matrix based upon the position of the applied load. In particular, as one such example, a global calibration matrix and a resulting calibrated output may initially be determined ($F_{x,g}$=20.1 lbf (89.41 N)). Then, the center of pressure (COP) location and the localized calibration data is used to determine a new value that is more accurate for that region of the force plate ($F_{x,l}$=20.2 lbf (89.85 N)). After which, the local value for $F_z$ is divided by the global value of $F_z$ to get a "correction factor", in this case $CF_{Fx}$=1.005, and then that value is stored as a "correction factor" for $F_z$ in that region of the force plate. In equation form, the correction may be represented as:

$$CF = \frac{F_l}{F_g} \quad (19)$$

where:

CF: correction Factor;

$F_l$: calibrated force output calculated by the local calibration matrix; and $F_g$: Calibrated force output calculated by the global calibration matrix.

Equation (19) may be expanded to show all the different variables as follows:

$$CF_{Fx} = \frac{F_{x,l}}{F_{x,g}}, \; CF_{Fy} = \frac{F_{y,l}}{F_{y,g}}, \; CF_{Fz} = \frac{F_{z,l}}{F_{z,g}} \quad (20)$$

$$CF_{Mx} = \frac{M_{x,l}}{M_{x,g}}, \; CF_{My} = \frac{M_{y,l}}{M_{y,g}}, \; CF_{Mz} = \frac{M_{z,l}}{M_{z,g}} \quad (21)$$

Advantageously, the calculation of the correction factor in the manner above simplifies the calculation of the calibrated output when the force plate is in use.

Figure 74:
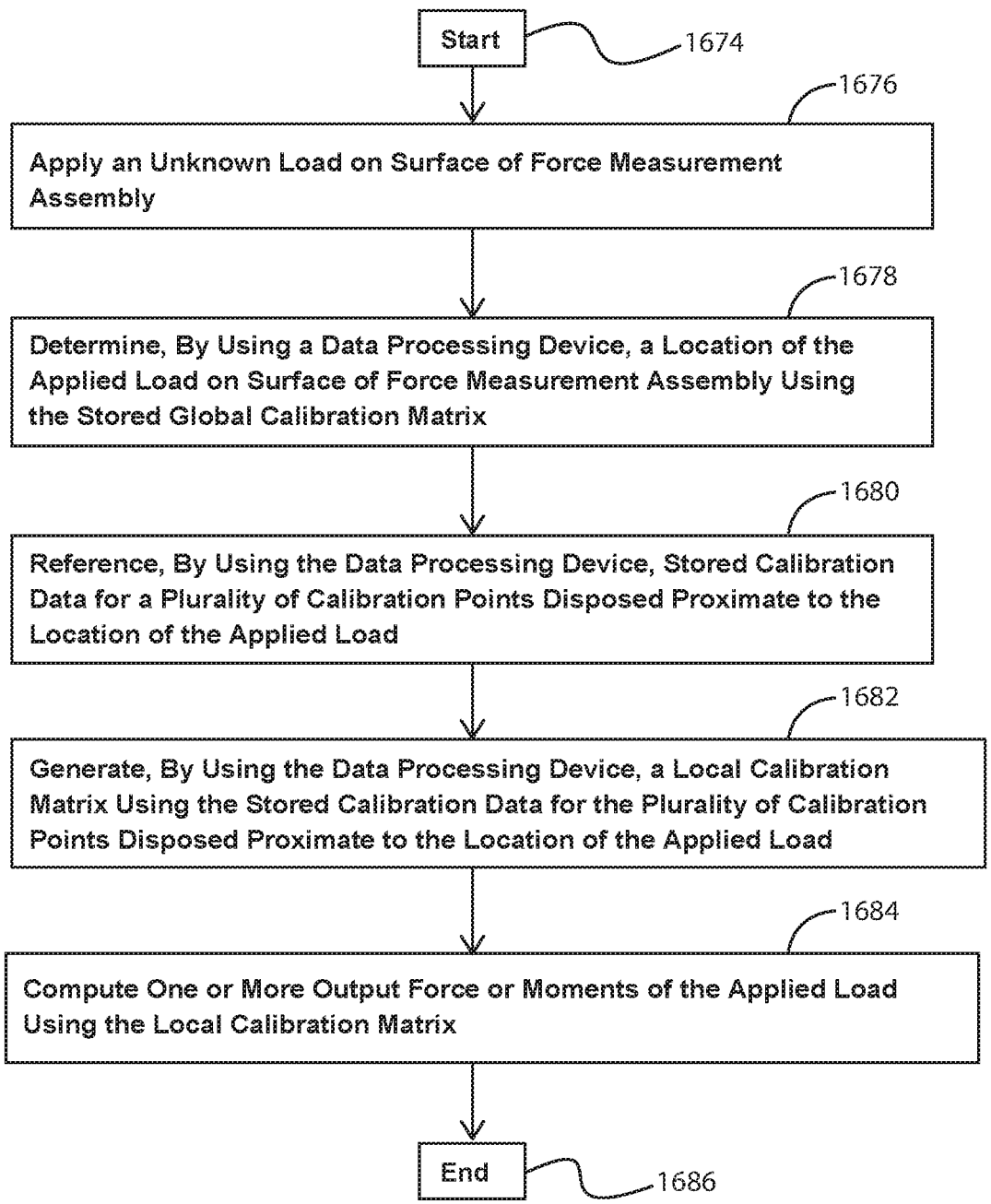
FIG. 74 is a flowchart illustrating a second load correction procedure for a force measurement assembly carried out by the force measurement system illustrated in FIGS. 42, 70, and 71, according to an embodiment of the invention.

Now, with reference to the flowchart illustrated in FIG. 74, a second illustrative load correction procedure for the force measurement assembly with the top plate component 1610 depicted in FIGS. 70 and 71 will be described. In this second load correction procedure, the local calibration matrix is computed during the load computational process using the stored calibration data for a plurality of calibration points (i.e., the local calibration matrix is computed "on the fly" during the load computational process), rather than being precomputed. The second illustrative load correction process begins at step 1674, and then an unknown load is applied on the surface of the force measurement assembly (e.g., on the top surface 1612 of the top plate component 1610 of the force measurement assembly) in step 1676 of FIG. 74. After the unknown load is applied in step 1676, the data processing device (e.g., the data acquisition/data processing device 1174 in FIG. 42) determines, in step 1678, a location of the applied load on the surface of the top plate component 1610 of the force measurement assembly using the stored global calibration matrix $C_G$, which was determined in the calibration process explained above. When the unknown load is applied to the surface of the top plate component 1610, the global calibration matrix $C_G$ determines the location of loading. Initially, the data acquisition/data processing device 1174 utilizes the global calibration matrix $C_G$ to determine the applied forces and moments ($F_x$, $F_y$, $F_z$, $M_x$, $M_y$, $M_z$). Then, the data acquisition/data processing device 1174 uses equations (17) and (18) above to determine the center of pressure (COP) or point of application of the applied load.

Then, in the illustrative embodiment, once equations (17) and (18) are used to determine the location of force application, the data acquisition/data processing device 1174 references stored calibration data for a plurality of calibration points disposed proximate to the location of the applied load in step 1680. That is, in the illustrative embodiment, after the global calibration matrix $C_G$ specifies an initial estimation of the location of force application, a subset of data is created quasi-instantaneously from the raw load data acquired in step 1650. In the illustrative embodiment, the subset of data created from the raw load data is centered (as close as the data will allow) about the location of force application.

After creating the subset of data centered about the location of force application from the raw load data in step 1680 (i.e., the stored calibration data for the plurality of calibration points), the data acquisition/data processing device 1174 generates a local calibration matrix $C_L$ using the stored calibration data for the plurality of calibration points disposed proximate to the location of the applied load (i.e., the data acquisition/data processing device 1174 generates a local calibration matrix $C_L$ "on the fly" customized for that particular force plate location) in step 1682. Referring again to FIG. 74, after the local calibration matrix $C_L$ disposed proximate to the location of the applied load is determined, one or more output forces or moments of the applied load are computed by the data processing device 1174 using the local calibration matrix $C_L$ determined in step 1682. In particular, the one or more output forces or moments of the applied load are computed using equation (14) above by the data processing device 1174, wherein the local calibration matrix $C_L$ is used for the calibration matrix C in equation (14). After the corrected output forces and/or moments of the applied load are determined by the data processing device 1174 in step 1684, the load correction process concludes at step 1686 in FIG. 74.

One or more further illustrative embodiments will be described with reference to FIGS. 75-80. In these one or more further illustrative embodiments, a force measurement system, which may be in the form of the force measurement system 1700, 1700' depicted in FIGS. 75 and 76 includes a force measurement assembly 1710, 1710' and a data processing device 1716, wherein the data processing device 1716 is configured to determine a center of pressure for the subject 1728 using the output forces and/or moments from the force measurement assembly 1710, 1710'. The center of pressure for the subject 1728 may be computed in the manner described above. In these one or more further illustrative embodiments, the force measurement system 1700, 1700' further includes an inertial measurement unit 1727 and/or camera 1729 configured to generate output data for determining one or more parameters indicative of the body sway of the subject 1728 and a mobile device 1726 having a built-in data processor (see FIGS. 75 and 76). The data processor of the mobile device 1726 is operatively coupled to the inertial measurement unit 1727 and/or camera 1729, the data processor being configured to receive the output data from the inertial measurement unit 1727 and/or camera 1729, and to determine the one or more parameters indicative of the body sway of the subject 1728. In these one or more further illustrative embodiments, a fall risk of the subject 1728 may be assessed based upon a combination of the computed center of pressure and the one or more parameters indicative of the body sway determined for the subject 1728. Also, in these one or more further illustrative embodiments, the center of pressure for the subject 1728 determined by the data processing device 1716 may be independently computed from the one or more parameters indicative of the body sway for the subject 1728 determined by the mobile device 1726.

Figure 75:
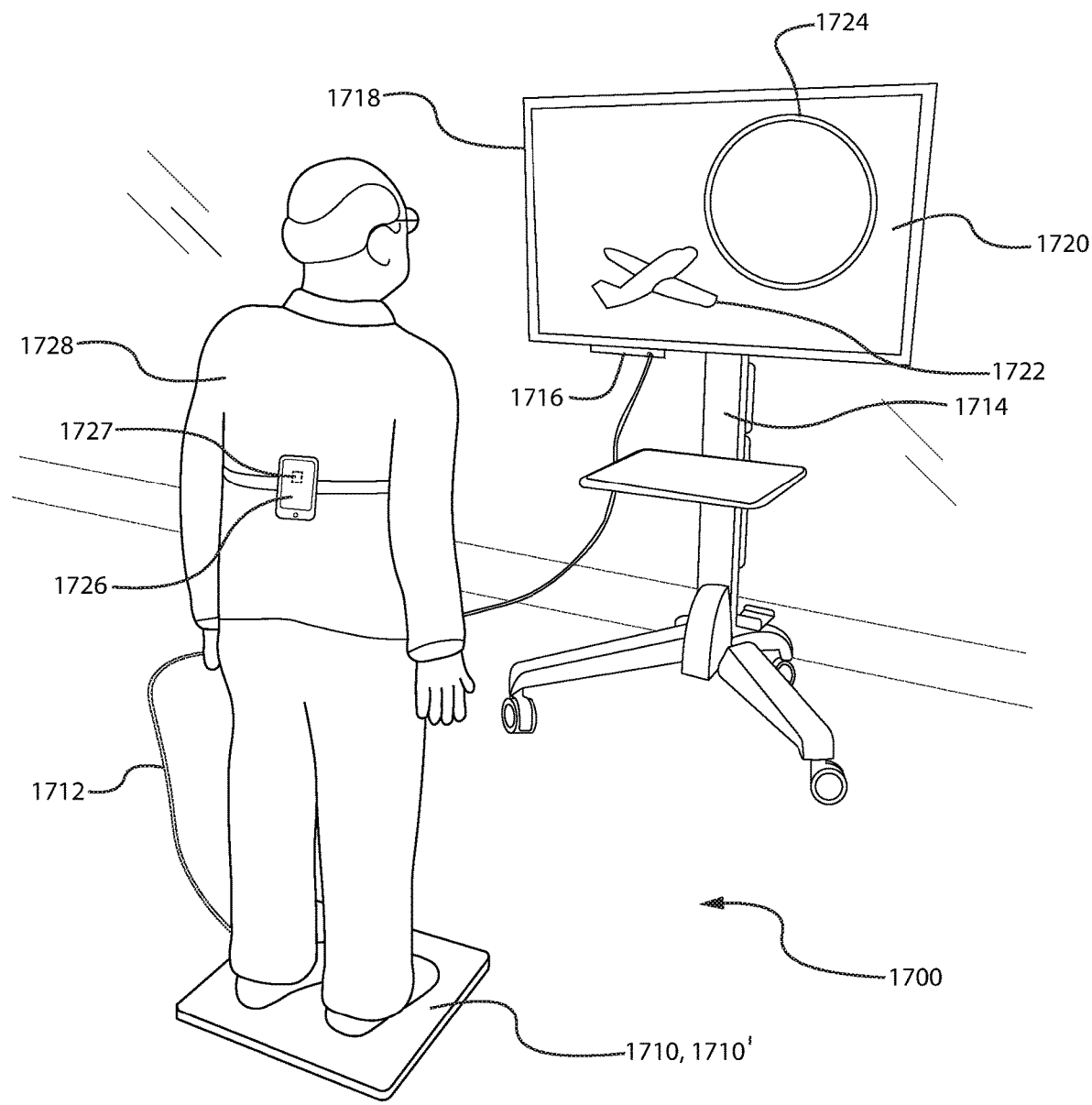
FIG. 75 is a diagrammatic perspective view of a first exemplary force measurement system for measuring the center of pressure and body sway of a subject, according to a further embodiment of the invention.
Figure 76:
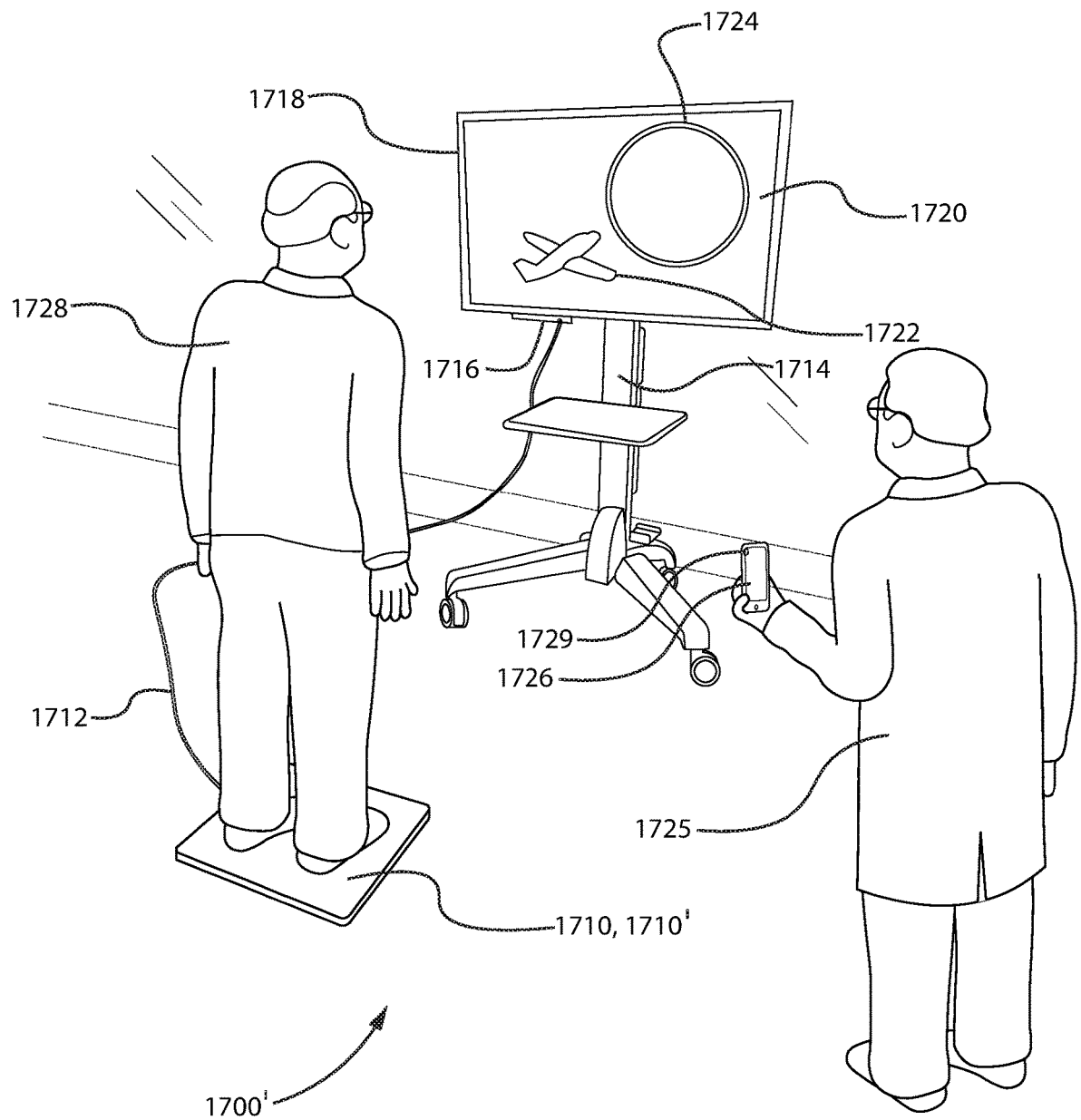
FIG. 76 is a diagrammatic perspective view of a second exemplary force measurement system for measuring the center of pressure and body sway of a subject, according to yet a further embodiment of the invention.

In the illustrative embodiment of FIGS. 75 and 76, the force measurement system 1700, 1700' further comprises a visual display device 1718 operatively coupled to the data processing device 1716 (e.g., a computing device or a small-form-factor personal computer, such as the Intel® NUC). The small-form-factor personal computer 1716 is one illustrative form of a data processing device and/or data processing and data acquisition device. In FIGS. 75 and 76, the small-form-factor personal computer 1716 may be mounted on the back of the visual display device 1718 (e.g., mounted on the back panel of a touchscreen visual display device with output screen 1720). In one or more embodiments, the screen images described hereinafter are displayed on the output screen 1720 of the visual display device 1718 so that the subject 1728 is able to interact with one or more visual objects in the screen images.

In the illustrative embodiment of FIGS. 75 and 76, the visual display device 1718 is disposed on an adjustable height stand or cart 1714 so that the height of the visual display device 1718 is selectively adjustable by a user. Advantageously, prior to a testing session of the subject 1728, the height of the stand 1714 may be adjusted such that the approximate center of the visual display device 1718 is generally horizontally aligned with the eyes of the standing subject (i.e., so the subject is generally looking at the central portion of the visual display device 1718 during the testing).

Referring again to FIGS. 75 and 76, it can be seen that the illustrative force measurement systems 1700, 1700' include a force measurement assembly 1710, 1710' for determining the center of pressure of the subject 1728. In particular, the force measurement assembly 1710, 1710' may comprise a static force plate that is configured to rest on the floor of the room in which the system 1700, 1700' is disposed (see FIGS. 75 and 76). As will be described in further detail hereinafter, the force plate 1710, 1710' comprises a plurality of force transducers or load cells for measuring the forces and/or moments generated on the plate surface thereof by the feet of the subject 1728. As such, the center of pressure (COP), center of gravity (COG), and/or sway angle of the subject 1728 may be determined while the subject 1728 undergoes testing on the force measurement assembly 1710, 1710'.

In addition, as illustrated in FIGS. 75 and 76, the force measurement assembly 1710, 1710' is operatively coupled to the data processing device 1716 by virtue of an electrical cable 1712. In one embodiment, the electrical cable 1712 is used for data transmission, as well as for providing power to the force measurement assembly 1710, 1710'. Various types of data transmission cables can be used for cable 1712. For example, the cable 1712 can be a Universal Serial Bus (USB) cable or an Ethernet cable. Preferably, the electrical cable 1712 contains a plurality of electrical wires bundled together, with at least one wire being used for power and at least another wire being used for transmitting data. The bundling of the power and data transmission wires into a single electrical cable 1712 advantageously creates a simpler and more efficient design. In addition, it enhances the safety of the training environment for the subject 1728. However, it is to be understood that the force measurement assembly 1710, 1710' can be operatively coupled to the data processing device 1716 using other signal transmission means, such as a wireless data transmission system. If a wireless data transmission system is employed, it is preferable to provide the force measurement assembly 1710, 1710' with a separate power supply in the form of an internal power supply or a dedicated external power supply.

Figure 77:
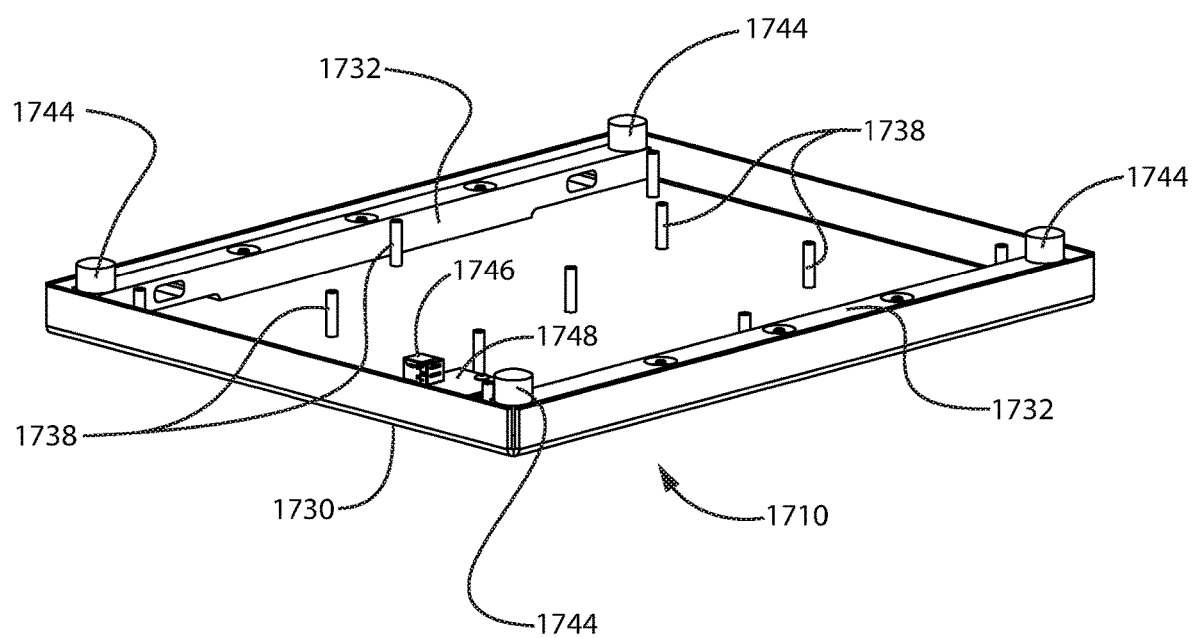
FIG. 77 is a bottom, assembled perspective view of a first type of force measurement assembly used in the force measurement systems of FIGS. 75 and 76.
Figure 78:
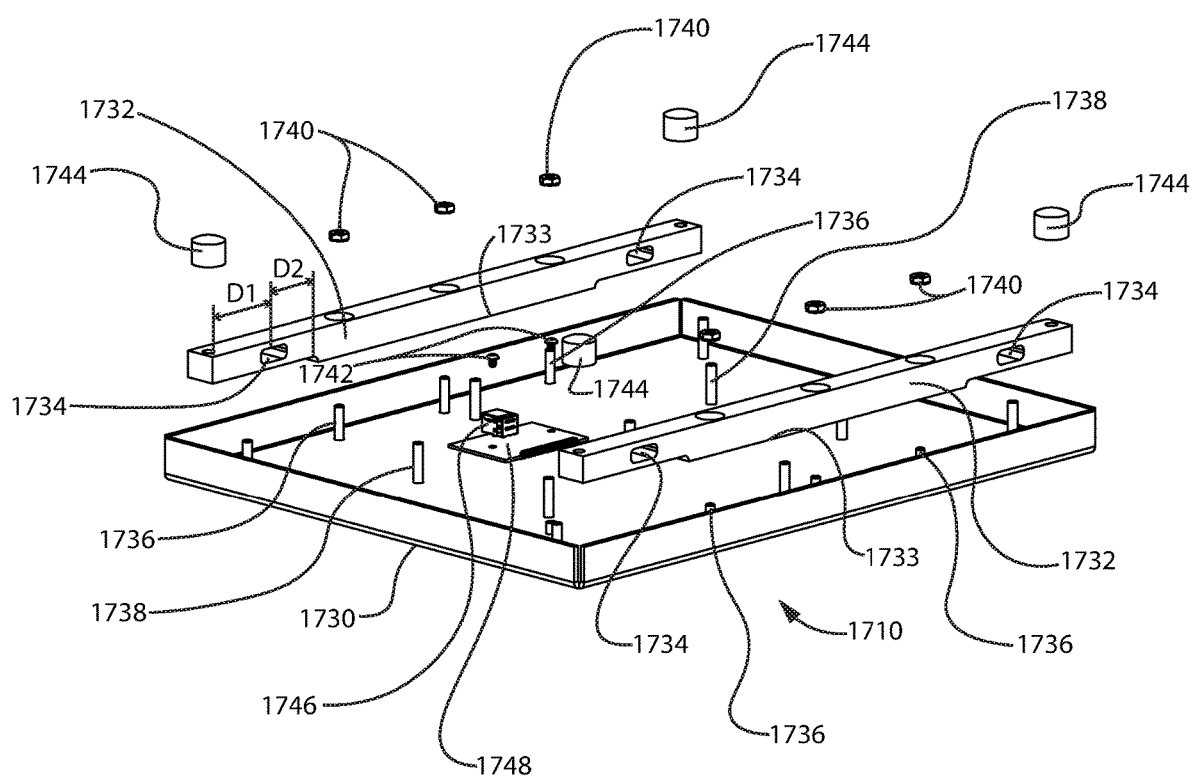
FIG. 78 is a bottom, exploded perspective view of the force measurement assembly of FIG. 77.

Now, with reference to FIGS. 77 and 78, a first illustrative type of force measurement assembly 1710 that may be used in the force measurement systems 1700, 1700' of FIGS. 75 and 76 will be described. As shown in FIGS. 77 and 78, the force measurement assembly 1710 of the illustrated embodiment is in the form of a force plate assembly with a single, continuous measurement surface that measures the vertical force (i.e., $F_Z$) exerted thereon by the subject 1728. The center of pressure (COP) for the subject 1728 may be computed based upon the fraction of the vertical force that is measured by the load cells in each of the corners of the force measurement assembly 1710. The force plate assembly 1710 includes a plate component 1730 supported on a plurality of force transducer beams 1732. As shown in FIGS. 77 and 78, the plate component 1730 comprises a top measurement surface (i.e., a planar top surface) and a plurality of side surfaces extending downward from the top measurement surface. In FIGS. 77 and 78, it can be seen that the bottom surface of the plate component 1730 comprises a first plurality of beam fastener standoffs 1736 and a second plurality of cover fastener standoffs 1738 extending downward from the bottom surface of the plate component 1730. The first plurality of beam fastener standoffs 1736 are used to secure the force transducer beams 1732 to the plate component 1730 (i.e., the first plurality of beam fastener standoffs 1736 together with the securement nuts 1740 secure the force transducer beams 1732 to the underside of the plate component 1730). The second plurality of cover fastener standoffs 1738 are used to secure the bottom cover (not shown) of the force plate assembly 1710 to the underside of the plate component 1730.

In the illustrative embodiment of FIGS. 77 and 78, each of the force transducer beams 1732 is generally in the form of a linear force transducer beam with load cells disposed at the opposite ends of the beam 1732. Each of the load cells measures the vertical force (i.e., $F_Z$) exerted on the plate component 1730 by the subject 1728. Also, as best shown in FIG. 78, each of the load cells is provided with a generally rectangular aperture 1734 disposed through the beam 1732. The apertures 1734 significantly increase the sensitivity of the force transducer beam 1732 when a load is applied thereto by reducing the cross-sectional area of the transducer beam 1732 at the locations of the apertures 1734. Referring again to FIG. 78, it can be seen that each of the force transducer beams 1732 comprises a raised portion or standoff portion 1733 so as to ensure that the total load applied to the plate component 1730 is transmitted through the load cells of the force transducer beams 1732. While not explicitly shown in the figures, it is to be understood that each of the load cells of the force transducer beams 1732 include strain gages mounted on the outer surfaces of the force transducer beams 1732 and centered on the apertures 1734 as described above for the preceding load transducer embodiments (see e.g., FIGS. 26, 29, 33, 39).

Referring again to FIGS. 77 and 78, it can be seen that the force measurement assembly 1710 further includes a pre-amplifier board 1748 for digitizing and conditioning the force output signal from the load cells, and one or more Universal Serial Bus (USB) ports 1746 for operatively coupling the force measurement assembly 1710 to the data processing device 1716 (i.e., the electrical cable 1712 may have a USB plug that is inserted into one of the USB ports 1746). As shown in the exploded view of FIG. 78, the pre-amplifier board 1748 may be secured to the plate component 1730 of the force measurement assembly 1710 by means of securement screws 1742. In one or more embodiments, the pre-amplifier board 1748 also may compute the output forces, the output moments, and/or the center of pressure, and then the data processing device 1716 may perform the remainder of the computations that use the output forces, the output moments, and/or the center of pressure.

Also, as shown in FIGS. 77 and 78, the force measurement assembly 1710 is provided with a plurality of support feet 1744 disposed thereunder. Preferably, each of the four (4) corners of the force measurement assembly 1710 is provided with a support foot 1744 (e.g., mounted on the bottom corner of each force transducer beam 1732. In particular, in the illustrated embodiment, each support foot 1744 is attached to an aperture in a respective corner of one of the force transducer beams 1732 by means of a fastener (e.g., a screw).

With reference again to FIG. 78, it can be seen that the load cells with apertures 1734 are located predetermined distances from the foot members 1744 at the ends of the force transducer beams 1732 so that the load measurement (i.e., of the vertical force $F_Z$) is not affected by stress concentrations on the force transducer beams 1732 resulting from moments developed at the locations of the foot members 1744. For example, as shown in FIG. 78, the center of the load cell aperture 1734 at the left end of the rearward force transducer beam 1732 is located a predetermined distance D1 (e.g., approximately 48 millimeters) from the end of the beam 1732, and the center of the load cell aperture 1734 is located a predetermined distance D2 (e.g., approximately 35 millimeters) from the end of the raised portion or standoff portion 1733 of the beam 1732. In the illustrative embodiment, the distances D1, D2 have been optimized to avoid the edge effects associated with the foot member 1744 (i.e., the accuracy of the load cell output is not adversely affected by any moment that develops at the foot member 1744 as long as the load cell is located a sufficient distance D1 away from the end of the beam 1732 with the foot member 1744). Also, in the illustrative embodiment, the distances D1, D2 have been optimized to maximize the natural frequency of the force measurement assembly 1710. A larger value of D1 minimizes the edge effects because load cell is further away from the end of the beam 1732. However, a larger value of D1 results in a longer beam 1732 that reduces the natural frequency of the force measurement assembly 1710, and thus results in more noise. As such, the distances D1, D2 are optimized so as to result in an overall beam length that minimizes edge effects, while simultaneously minimizing noise in the load measurement.

In other embodiments, a foot member with a rounded bottom surface can also be used to eliminate the development of a moment at the end of the force transducer beam 1732 (the foot member with a rounded bottom surface allows the force transducer beam 1732 to behave like a cantilever beam). However, the optimization of the distances D1, D2 advantageously eliminates the need for a foot with a rounded bottom surface so that foot members 1744 with the flat bottom surfaces illustrated in FIGS. 77 and 78 may be used.

Next, with reference to FIGS. 79 and 80, a second illustrative type of force measurement assembly 1710' that may be used in the force measurement systems 1700, 1700' of FIGS. 75 and 76 will be described. With reference to these figures, it can be seen that, in some respects, the second illustrative embodiment is similar to that of the first illustrative embodiment of the force measurement assembly 1710 described above. Moreover, some parts are common to both such embodiments. For the sake of brevity, the description of the parts that the second embodiment of the force measurement assembly has in common with the first embodiment will not be repeated with regard to the second embodiment because these components have already been explained in detail above. Furthermore, in the interest of clarity, these components will be denoted using the same reference characters that were used in the first embodiment.

Figure 79:
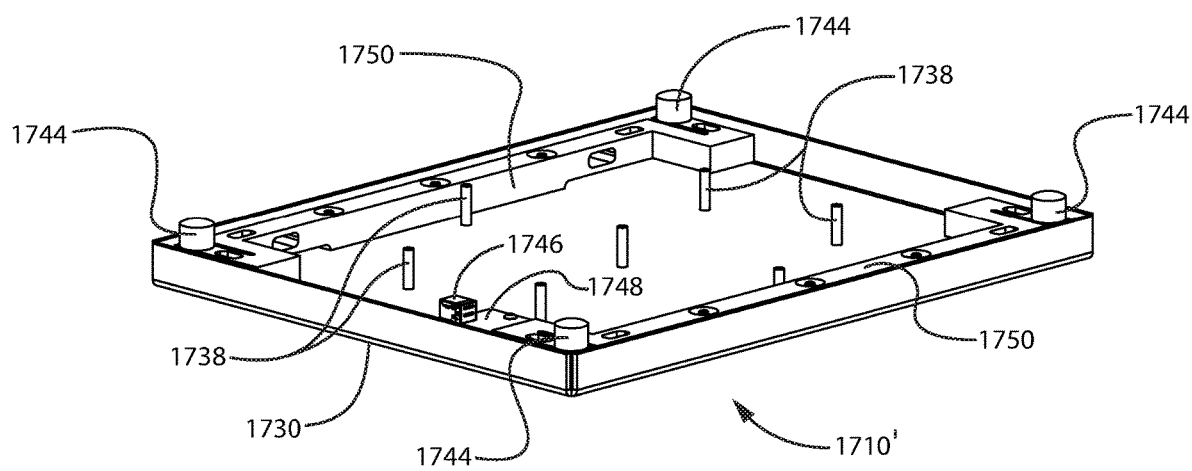
FIG. 79 is a bottom, assembled perspective view of a second type of force measurement assembly used in the force measurement systems of FIGS. 75 and 76.
Figure 80:
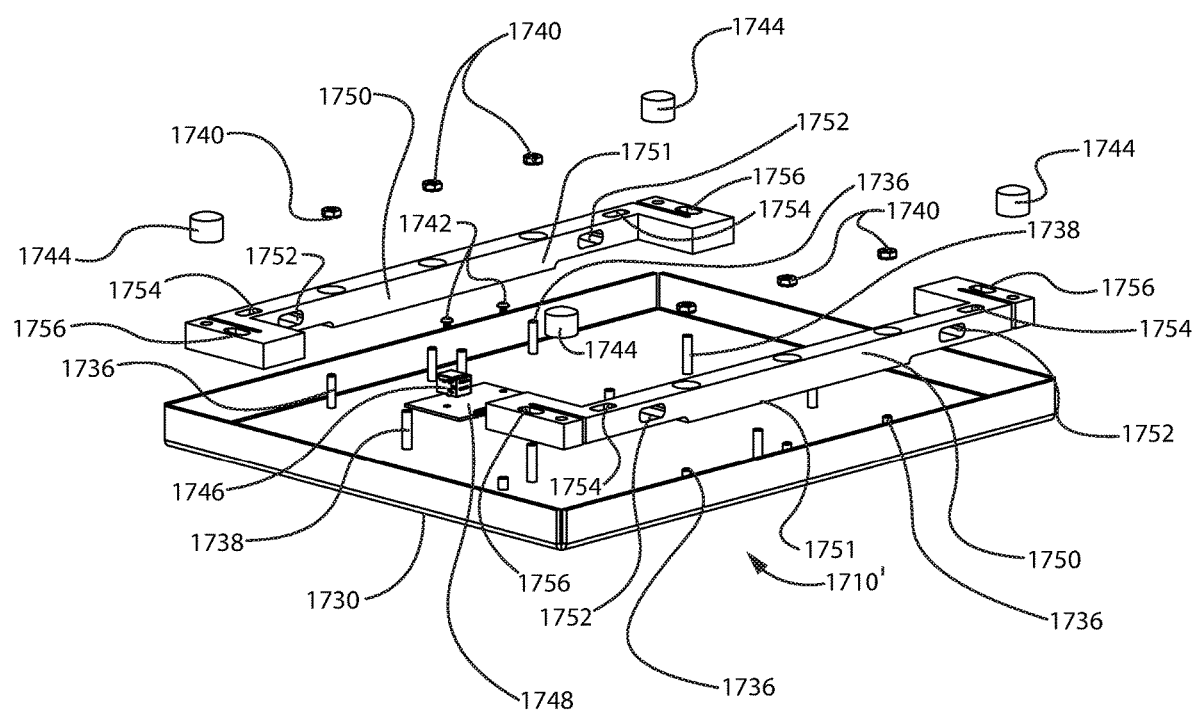
FIG. 80 is a bottom, exploded perspective view of the force measurement assembly of FIG. 79.

Turning to FIGS. 79 and 80, it can be seen that the second illustrative type of force measurement assembly 1710' utilizes a different type of force transducer beam 1750 than the force measurement assembly 1710 described above. More specifically, rather than using a force transducer beam that measures only a single force component, the force measurement assembly 1710' utilizes a multi-component force transducer beam 1750 that measures both the vertical force and the shear forces. In the illustrative embodiment of FIGS. 79 and 80, each of the force transducer beams 1750 has a linear middle portion with generally U-shaped opposed end portions. In the illustrative embodiment, the generally U-shaped end portions of the force transducer beams 1750 each contain three (3) load cells. Also, as best shown in FIG. 80, each of the load cells is provided with generally rectangular apertures 1752, 1754, 1756 disposed through the beam 1750. The first aperture 1752 is associated with the load cell that measures the vertical force (i.e., $F_Z$). The second aperture 1754 is associated with the load cell that measures the first shear force (i.e., $F_X$), while the third aperture 1756 is associated with the load cell that measures the second shear force (i.e., $F_Y$). The apertures 1752, 1754, 1756 significantly increase the sensitivity of the force transducer beam 1750 when a load is applied thereto by reducing the cross-sectional area of the transducer beam 1750 at the locations of the apertures 1752, 1754, 1756. Referring again to FIG. 80, it can be seen that each of the force transducer beams 1750 comprises a raised portion or standoff portion 1751 so as to ensure that the total load applied to the plate component 1730 is transmitted through the load cells of the force transducer beams 1750. While not explicitly shown in the figures, it is to be understood that each of the load cells of the force transducer beams 1750 include strain gages mounted on the outer surfaces of the force transducer beams 1750 and centered on the apertures 1752, 1754, 1756 as described above for the preceding load transducer embodiments (see e.g., FIGS. 26, 29, 33, 39).

In the force measurement systems 1700, 1700' of FIGS. 75 and 76, the mobile device with the data processor is in the form of a smartphone 1726. However, in other embodiments, the mobile device also may be in the form of a tablet computing device, a laptop computing device, or a smartwatch. For example, in the illustrative embodiment, the inertial measurement unit 1727 and/or camera 1729 of the force measurement systems 1700, 1700' may comprise the built-in inertial measurement unit and/or camera of the smartphone 1726. In another illustrative embodiment, rather than a mobile computing device, another type of computing device is used. For example, the other type of computing device may be a desktop computing device, a tower computing device, a server computing device, or a small-form-factor personal computer.

In the illustrative embodiment of FIG. 75, the mobile device 1726 (e.g., the smartphone) comprises the inertial measurement unit 1727 configured to generate the output data for determining the one or more parameters indicative of the body sway of the subject 1728 (i.e., the built-in inertial measurement unit 1727 of the smartphone 1726 is utilized). In this illustrative embodiment, the data processor of the mobile device 1726 is configured to determine the one or more parameters indicative of the body sway of the subject 1728 based upon the output data from the inertial measurement unit 1727 of the mobile device 1726. In the illustrative embodiment, the inertial measurement unit 1727 comprises at least one of an accelerometer configured to detect linear acceleration and a gyroscope configured to detect angular velocity.

For example, as part of the sway analysis, the inertial measurement unit 1727 (i.e., IMU 1727) is capable of measuring gravitational and motion components. The gravitational component makes it possible to define a true vertical vector. The body sway is the angle and translation made by the IMU 1727 around that true vertical. The calculation for the body sway can be done by a principal component analysis (PCA) to approximate the area of body sway excursion (i.e., the body sway envelope) as follows:

$$\sigma_{xy}^2 = \frac{1}{N-1} \sum_{i=1}^{N} (x_i - \bar{x})(y_i - \bar{y}) \qquad (22)$$

$$\tan\theta = \frac{\sigma_{xy}^2}{\sigma_0^2 - \sigma_{yy}^2} \qquad (23)$$

where θ in equation (23) above is the body sway angle. In the illustrative embodiment, the computation of the principal component analysis (PCA) set forth in equation (22) may be computed for each joint of the subject 1728.

In one alternative embodiment, the inertial measurement unit that is configured to generate the output data for determining the one or more parameters indicative of the body sway of the subject 1728 is located remotely from the mobile device 1726, rather than being a part of mobile device 1726. In this alternative embodiment, the data processor of the mobile device 1726 is configured to determine the one or more parameters indicative of the body sway of the subject 1728 based upon the output data from the remotely located inertial measurement unit. In this alternative embodiment, the data processor of the mobile device 1726 may be operatively coupled to the remotely located inertial measurement unit by a wireless connection.

In the illustrative embodiment of FIG. 76, the mobile device 1726 (e.g., the smartphone) comprises the camera 1729 configured to generate the output data for determining the one or more parameters indicative of the body sway of the subject 1728 (i.e., the built-in camera 1729 of the smartphone 1726 is utilized). For example, the mobile device 1726 (e.g., the smartphone) may be held by a remote observer 1725, and the camera 1729 of the mobile device 1726 may be focused on the subject 1728. As the subject's body moves due to his or her sway, the image of the subject 1728 is captured by the camera 1729 so that the one or more parameters indicative of the body sway of the subject 1728 may be determined from the image data of the camera 1729.

In the illustrative embodiment of FIG. 76, the data processor of the mobile device 1726 may be configured to determine the one or more parameters indicative of the body sway of the subject 1728 based upon the output data from the camera 1729 using pose estimation. For example, as part of the sway analysis, the camera 1729 is capable of capturing image data of the subject 1728. Then, the data processor of the mobile device 1726 receives the image data of the subject 1728 from the camera 1729. After receiving the image data, the data processor of the mobile device 1726 may then extract features from the image data for providing inputs to a convolutional neural network (CNN). After this step, the data processor of the mobile device 1726 may generate one or more keypoints using a keypoint subnet, and determine one or more poses of the subject 1728 based upon the position of the keypoints.

In one alternative embodiment, the camera that is configured to generate the output data for determining the one or more parameters indicative of the body sway of the subject 1728 is located remotely from the mobile device 1726, rather than being a part of mobile device 1726. In this alternative embodiment, the data processor of the mobile device 1726 is configured to determine the one or more parameters indicative of the body sway of the subject 1728 based upon the output data from the remotely located camera. In this alternative embodiment, the data processor of the mobile device 1726 may be operatively coupled to the remotely located camera by a wireless connection.

Also, in the illustrative embodiment, using the pose estimation described above, the data processor of the mobile device 1726 may determine a displacement curve for any of the keypoints of the user (e.g., a displacement curve for the shoulder joint, elbow joint, knee joint, ankle joint, etc.).

In the illustrative embodiments of FIGS. 75 and 76, the one or more parameters indicative of the body sway of the subject 1728 determined by the data processor of the mobile device 1726 are selected from the group consisting of: (i) a sway angle of the subject, (ii) sway coordinates of the subject, (iii) a sway envelope of the subject.

In the illustrative embodiments of FIGS. 75 and 76, the data processing device 1716 and/or the mobile device 1726 is programmed to determine a mathematical relationship between the center of pressure and the one or more parameters indicative of the body sway for the subject 1728 over a predetermined time period. For example, with regard to the body sway of the subject 1728, the motion of the subject 1728 is modeled as an inverted pendulum with an imaginary vertical line extending lengthwise along the body of the subject 1728. Using the inverted pendulum model, the mathematical relationship that is determined between the center of pressure and the one or more parameters indicative of the body sway for the subject 1728 may be a comparison between the location of one or more coordinate points on the imaginary vertical line extending along the subject 1728 (e.g., one or points proximate to, or higher than the center of gravity (COG) of the subject 1728) and the center of pressure of the subject 1728. Also, in the illustrative embodiments of FIGS. 75 and 76, the data processing device 1716 and/or the mobile device 1726 is programmed to determine the fall risk of the subject 1728 based upon the mathematical relationship between the center of pressure and the one or more parameters indicative of the body sway over the predetermined time period. For example, using the inverted pendulum model, the data processing device 1716 and/or the mobile device 1726 may estimate the fall risk of the subject 1728 by determining if the one or more coordinate points on the imaginary vertical line extending along the subject 1728 (e.g., one or points proximate to, or higher than the center of gravity (COG) of the subject 1728) lags behind the center of pressure of the subject 1728 (a large lag value indicates that the subject 1728 is likely to fall).

In the illustrative embodiments of FIGS. 75 and 76, the output forces and/or moments determined by the data processing device 1716 from the force measurement assembly 1710, 1710' include a shear force in a fore/aft direction of the subject 1728, and the data processing device 1716 is further configured to determine a center of pressure for the subject 1716 using the output forces and/or moments from the force measurement assembly. In these illustrative embodiments, the data processing device 1716 is additionally configured to determine the fall risk of the subject 1728 based upon a combination of the center of pressure and the shear force in the fore/aft direction of the subject 1728. For example, the data processing device 1716 may evaluate the maximum sway range of the center of pressure of the subject 1728 and the magnitude of the shear force in a fore/aft direction of the subject 1728 in order to assess the fall risk of the subject 1728. If both the value of the maximum sway range of the center of pressure of the subject 1728 and the value of the shear force in a fore/aft direction of the subject 1728 are large in magnitude, then the data processing device 1716 may conclude the subject is highly likely to sustain a fall. If at least one of the maximum sway range of the center of pressure of the subject 1728 and the shear force in a fore/aft direction of the subject 1728 is large in magnitude, then the data processing device 1716 may conclude the subject is likely to sustain a fall. If both the value of the maximum sway range of the center of pressure of the subject 1728 and the value of the shear force in a fore/aft direction of the subject 1728 are small in magnitude, then the data processing device 1716 may conclude the subject is unlikely to sustain a fall.

In one variation of the illustrative embodiments of FIGS. 75 and 76, the data processing device 1716 and/or the mobile device 1726 is further programmed to determine the fall risk of the subject based upon a relationship between the one or more parameters indicative of the body sway for the subject 1728 determined by the mobile device 1726 and the shear force in the fore/aft direction of the subject 1728 determined by the data processing device 1716 from the output data of the force measurement assembly 1710, 1710'. For example, the data processing device 1716 and/or the mobile device 1726 may evaluate the magnitude of the maximum sway angle for the subject 1728 and the magnitude of the shear force in a fore/aft direction of the subject 1728 in order to assess the fall risk of the subject 1728. If both the value of the maximum sway angle of the subject 1728 and the value of the shear force in a fore/aft direction of the subject 1728 are large in magnitude, then the data processing device 1716 and/or the mobile device 1726 may conclude the subject is highly likely to sustain a fall. If at least one of the maximum sway angle of the subject 1728 and the shear force in a fore/aft direction of the subject 1728 is large in magnitude, then the data processing device 1716 and/or the mobile device 1726 may conclude the subject is likely to sustain a fall. If both the value of the maximum sway angle of the subject 1728 and the value of the shear force in a fore/aft direction of the subject 1728 are small in magnitude, then the data processing device 1716 and/or the mobile device 1726 may conclude the subject is unlikely to sustain a fall.

Referring again to FIG. 75, in the illustrative embodiment, the visual display device 1718 of the illustrative force measurement systems 1700, 1700' may be configured to display at least one manipulatable element (e.g., an airplane 1722) of an interactive game on the output screen so that the at least one manipulatable element is visible to the subject 1728. In the illustrative embodiment, the data processing device 1716 and/or the mobile device 1726 is programmed to control the movement of the at least one manipulatable element (e.g., an airplane 1722) of the interactive game displayed on the visual display device 1718 by using the center of pressure and the one or more parameters indicative of the body sway for the subject 1728 (e.g., if the user leans forward, the airplane decreases in altitude, while, if the user leans backward, the airplane increases in altitude). In the exemplary interactive game, the fore/aft leaning of the subject 1728 could guide the airplane 1722 through rings or hoops 1724 located at different altitudes in the sky. In the illustrative embodiment, the data processing device 1716 and/or the mobile device 1726 may be further programmed to determine the fall risk of the subject 1728 based upon the performance of the subject 1728 while playing the interactive game (e.g., in the airplane game, the fall risk of the subject 1728 may increase as the number of rings or hoops missed by the subject 1728 increases).

In an alternative embodiment, rather than using the mobile device 1726 to determine the one or more parameters indicative of the body sway for the subject 1728, other suitable means may be used for determining the one or more body sway parameters. For example, to measure the body sway of the subject 1728, one end of an extendable elongated attachment member (e.g., a string) may be attached to the belt of the subject 1728, and the other fixed end of the extendable elongated attachment member (e.g., the string) may be attached to a goniometer (e.g., similar to an extendable dog leash). As another example, to measure the body sway of the subject 1728, a distance measuring laser targeting the mid-portion of the subject 1728 may be used. Also, rather than using a distance measuring laser, an infrared detector or ultrasonic detector may be used to measure the distance to the mid-portion of the subject 1728.

Any of the features or attributes of the above described embodiments and variations can be used in combination with any of the other features and attributes of the above described embodiments and variations as desired. For example, any of the features or functionality described in conjunction with embodiments illustrated in FIGS. 55-74 (e.g., temperature compensation, crosstalk elimination, or load correction based on the position of the applied load) may be utilized in the embodiments of FIGS. 1-54.

It is apparent from the above detailed description that the present invention provides a low profile six-component load transducer 10, 10', 100, 200, 300, 400, 500, 600, 700, 800 which has a significant allowable offset for the line of action of the force. In that, for a given allowable maximum load, this load transducer has a much higher moment capacity than currently available load transducers and the offset value can be as high as five times the diameter (or width dimension) of the transducer. Therefore, the load transducer 10, 10', 100, 200, 300, 400, 500, 600, 700, 800 according to the present invention is able to withstand and measure moments which are approximately ten times higher than that of a similarly sized and rated conventional load cell.

Also, it is readily apparent that the embodiments of the load transducer 900, 1000, 1000', 1100, 1200, 1300, 1300', 1400 and the force measurement assemblies 1040, 1150, 1340 using the same offer numerous advantages and benefits. In particular, the load transducer 900, 1000, 1000', 1100, 1200, 1300, 1300', 1400 described herein is capable of being interchangeably used with a myriad of different force plate sizes so that load transducers that are specifically tailored for a particular force plate size are unnecessary. Moreover, the universal load transducer 900, 1000, 1000', 1100, 1200, 1300, 1300', 1400 described herein is compact and uses less stock material than conventional load transducers, thereby resulting in lower material costs. Also, advantageously, the load transducer 1100, 1200, 1300, 1300' described herein is easily machined using a single block of raw material (i.e., a single block of aluminum) with very little waste because there are only narrow gaps between the central body portion and the transducer beam portions. Furthermore, the aforedescribed force measurement assemblies 1040, 1150, 1340 utilize the compact and universal load transducer 900, 1000, 1000', 1100, 1200, 1300, 1300', 1400 thereon so as to result in a more lightweight and portable force measurement assembly.

In addition, it is readily apparent that the embodiments of the load transducer system 1550 described above offer numerous advantages and benefits. In particular, the load transducer system 1550 is capable of correcting the output signal of a load transducer 1510, 1510' so as to reduce or eliminate the effects of crosstalk among the channels of the load transducer 1510, 1510'. Moreover, the load transducer system 1550 is capable of correcting the output signal of a load transducer 1510, 1510' so as to reduce or eliminate the effects of changes in temperature on the output of the load transducer 1510, 1510'. Furthermore, the load transducer system 1550 is capable of accurately determining the applied load regardless of the location of the applied load being measured by the load transducer 1510, 1510'.

Further, it is readily apparent that the embodiments of the force measurement system and the calibration method used therewith described above offer numerous advantages and benefits. In particular, the force measurement system allows for more versatile transducer designs and minimizes measurement errors. Moreover, the force measurement system is capable of correcting for load measurement errors resulting from loads applied near the periphery of the force measurement assembly. Furthermore, the load calibration process used with the force measurement system results in more accurate load measurements by correcting the computed load based upon the applied position of the load. In addition, a force measurement system is described above that is capable of assessing the fall risk of a subject based upon a combination of balance parameters.

From the foregoing disclosure and detailed description of certain preferred embodiments, it is also apparent that various modifications, additions and other alternative embodiments are possible without departing from the true scope and spirit of the present invention. The embodiments discussed were chosen and described to provide the best illustration of the principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled.

The invention claimed is:

1. A force measurement system, comprising:
 a force measurement assembly configured to receive a subject, the force measurement assembly including:
  a top surface for receiving at least one portion of the body of the subject; and
  at least one force transducer, the at least one force transducer configured to sense one or more measured quantities and output one or more signals that are representative of forces and/or moments being applied to the top surface of the force measurement assembly by the subject;
 a data processing device operatively coupled to the force measurement assembly, the data processing device configured to receive the one or more signals that are representative of the forces and/or moments being applied to the top surface of the force measurement assembly by the subject, and to convert the one or more signals into output forces and/or moments, the data processing device further configured to determine a center of pressure for the subject using the output forces and/or moments from the force measurement assembly; and
 a mobile device configured to determine one or more parameters indicative of the body sway for the subject;
 wherein a fall risk of the subject is assessed based upon a combination of the center of pressure and the one or more parameters indicative of the body sway determined for the subject.

2. The force measurement system according to claim 1, wherein the mobile device is selected from the group consisting of: (i) a smartphone, (ii) a tablet computing device, (iii) a laptop computing device, and (iv) a smartwatch.

3. The force measurement system according to claim 1, wherein the data processing device and/or the mobile device is programmed to determine a mathematical relationship between the center of pressure and the one or more parameters indicative of the body sway for the subject over a predetermined time period, and the data processing device and/or the mobile device is further programmed to determine the fall risk of the subject based upon the mathematical relationship between the center of pressure and the one or more parameters indicative of the body sway over the predetermined time period.

4. The force measurement system according to claim 1, wherein the output forces and/or moments determined by the data processing device from the force measurement assembly include a shear force in a fore/aft direction of the subject, and the data processing device and/or the mobile device is further programmed to determine the fall risk of the subject based upon a relationship between the one or more parameters indicative of the body sway for the subject and the shear force in the fore/aft direction of the subject.

5. The force measurement system according to claim 1, further comprising a visual display device having an output screen, the visual display device operatively coupled to the data processing device and/or the mobile device;
 wherein the data processing device and/or the mobile device is programmed to control the movement of at least one manipulatable element of an interactive game displayed on the visual display device by using the center of pressure and the one or more parameters indicative of the body sway for the subject, and the data processing device and/or the mobile device is further programmed to determine the fall risk of the subject based upon the performance of the subject while playing the interactive game.

6. The force measurement system according to claim 1, wherein the center of pressure for the subject determined by the data processing device is independently computed from the one or more parameters indicative of the body sway for the subject determined by the mobile device.

7. The force measurement system according to claim 1, wherein the at least one force transducer of the force measurement assembly comprises a force transducer beam with at least one load cell and at least one foot member disposed near an end of the force transducer beam, the at least one load cell configured to measure at least one component of the forces and/or moments being applied to the top surface of the force measurement assembly by the subject, and the at least one load cell being located a predetermined distance from the at least one foot member so that the measurement is not affected by a stress concentration on the force transducer beam.

8. The force measurement system according to claim 1, wherein the mobile device further comprises a camera, and wherein the mobile device is configured to determine the one or more parameters indicative of the body sway for the subject based upon output data from the camera.

9. The force measurement system according to claim 8, wherein the data processor is configured to determine the one or more parameters indicative of the body sway of the subject by using a convolutional neural network (CNN) to process the output data from the camera of the mobile device.

10. The force measurement system according to claim 1, wherein the mobile device further comprises an inertial measurement unit, and wherein the mobile device is configured to determine the one or more parameters indicative of the body sway for the subject based upon output data from the inertial measurement unit.

11. The force measurement system according to claim 10, wherein the inertial measurement unit of the mobile device comprises at least one of an accelerometer configured to detect linear acceleration and a gyroscope configured to detect angular velocity.

12. The force measurement system according to claim 1, wherein the one or more parameters indicative of the body sway of the subject determined by the mobile device are selected from the group consisting of: (i) a sway angle of the subject, (ii) sway coordinates of the subject, (iii) a sway envelope of the subject.

13. A force measurement system, comprising:
 a force measurement assembly configured to receive a subject, the force measurement assembly including:
  a top surface for receiving at least one portion of the body of the subject; and
  at least one force transducer, the at least one force transducer configured to sense one or more measured quantities and output one or more signals that are representative of forces and/or moments being applied to the top surface of the force measurement assembly by the subject;
 a data processing device operatively coupled to the force measurement assembly, the data processing device configured to receive the one or more signals that are representative of the forces and/or moments being applied to the top surface of the force measurement assembly by the subject, and to convert the one or more signals into output forces and/or moments, the data processing device further configured to determine a center of pressure for the subject using the output forces and/or moments from the force measurement assembly;

an inertial measurement unit or camera configured to generate output data for determining one or more parameters indicative of the body sway of the subject; and a computing device having a data processor, the data processor including at least one hardware component, the data processor being operatively coupled to the inertial measurement unit or camera, the data processor configured to receive the output data from the inertial measurement unit or camera, and to determine the one or more parameters indicative of the body sway of the subject;

wherein a fall risk of the subject is assessed based upon a combination of the center of pressure and the one or more parameters indicative of the body sway determined for the subject.

14. The force measurement system according to claim 13, wherein the inertial measurement unit configured to generate the output data for determining the one or more parameters indicative of the body sway of the subject is located remotely from the computing device; and wherein the data processor of the computing device is configured to determine the one or more parameters indicative of the body sway of the subject based upon the output data from the remotely located inertial measurement unit.

15. The force measurement system according to claim 14, wherein the data processor of the computing device is operatively coupled to the remotely located inertial measurement unit by a wireless connection.

16. The force measurement system according to claim 13, wherein the camera configured to generate the output data for determining the one or more parameters indicative of the body sway of the subject is located remotely from the computing device; and wherein the data processor of the computing device is configured to determine the one or more parameters indicative of the body sway of the subject based upon the output data from the remotely located camera.

17. The force measurement system according to claim 16, wherein the data processor of the computing device is operatively coupled to the remotely located camera by a wireless connection.

18. A force measurement system, comprising:

a force measurement assembly configured to receive a subject, the force measurement assembly including:
  a top surface for receiving at least one portion of the body of the subject; and
  at least one force transducer, the at least one force transducer configured to sense one or more measured quantities and output one or more signals that are representative of forces and/or moments being applied to the top surface of the force measurement assembly by the subject; and a data processing device operatively coupled to the force measurement assembly, the data processing device configured to receive the one or more signals that are representative of the forces and/or moments being applied to the top surface of the force measurement assembly by the subject, and to convert the one or more signals into output forces and/or moments, the output forces and/or moments determined by the data processing device from the force measurement assembly including a shear force in a fore/aft direction of the subject, the data processing device further configured to determine a center of pressure for the subject using the output forces and/or moments from the force measurement assembly, and the data processing device additionally configured to determine the fall risk of the subject based upon a combination of the center of pressure and the shear force in the fore/aft direction of the subject.

\* \* \* \* \*